US010611843B2

(12) United States Patent
Fournier et al.

(10) Patent No.: US 10,611,843 B2
(45) Date of Patent: Apr. 7, 2020

(54) ANTI-CD303 MONOCLONAL ANTIBODIES

(71) Applicant: Laboratoire Francais du Fractionnement et des Biotechnologies, Les Ulis (FR)

(72) Inventors: Nathalie Fournier, Erquinghem-Lys (FR); Alexandre Fontayne, La Madeleine (FR); Christophe de Romeuf, Lambersart (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 110 days.

(21) Appl. No.: 15/563,138

(22) PCT Filed: Mar. 31, 2016

(86) PCT No.: PCT/EP2016/056995
§ 371 (c)(1),
(2) Date: Sep. 29, 2017

(87) PCT Pub. No.: WO2016/156450
PCT Pub. Date: Oct. 6, 2016

(65) Prior Publication Data
US 2018/0086834 A1 Mar. 29, 2018

(30) Foreign Application Priority Data

Mar. 31, 2015 (FR) ...................... 15 52757

(51) Int. Cl.
| C07K 16/00 | (2006.01) |
| C07K 16/46 | (2006.01) |
| C07K 16/28 | (2006.01) |
| C07H 21/04 | (2006.01) |
| C12P 21/06 | (2006.01) |
| C12N 15/87 | (2006.01) |
| C12N 1/20 | (2006.01) |
| C12N 15/74 | (2006.01) |
| C12N 15/79 | (2006.01) |

(52) U.S. Cl.
CPC .......... *C07K 16/2851* (2013.01); *C12N 15/79* (2013.01); *C07K 2317/14* (2013.01); *C07K 2317/24* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/732* (2013.01); *C07K 2317/734* (2013.01); *C07K 2317/76* (2013.01); *C07K 2317/77* (2013.01); *C07K 2317/92* (2013.01); *C12N 2510/00* (2013.01)

(58) Field of Classification Search
None
See application file for complete search history.

(56) References Cited

U.S. PATENT DOCUMENTS

2016/0319025 A1* 11/2016 Nakao ................ C07K 16/2851

FOREIGN PATENT DOCUMENTS

| EP | 1176195 A1 | 1/2002 |
| EP | 2537864 A1 | 12/2012 |
| WO | 9004036 A1 | 4/1990 |
| WO | 9517085 A1 | 6/1995 |
| WO | 9951642 A1 | 10/1999 |
| WO | 2000026357 A2 | 5/2000 |
| WO | 2000042072 A2 | 7/2000 |
| WO | 2001026455 A1 | 4/2001 |
| WO | 2001036487 A2 | 5/2001 |
| WO | 2001077181 A2 | 10/2001 |
| WO | 2002060919 A9 | 1/2003 |
| WO | 2004050847 A2 | 6/2004 |
| WO | 2004063351 A2 | 7/2004 |
| WO | 2004074455 A2 | 9/2004 |
| WO | 2004029207 A3 | 10/2004 |
| WO | 2005033281 A2 | 4/2005 |
| WO | 2007048077 A2 | 4/2007 |
| WO | 2007106078 A2 | 9/2007 |
| WO | 2008028686 A2 | 3/2008 |
| WO | 2010045193 A1 | 4/2010 |
| WO | 2010106180 A2 | 9/2010 |
| WO | 2011114063 A2 | 9/2011 |
| WO | 2012041768 A1 | 4/2012 |
| WO | 2012080642 A1 | 6/2012 |
| WO | 2013061010 A1 | 5/2013 |

(Continued)

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Pellerin et al. Anti-BDCA2 monoclonal antibody inhibits plasmacytoid dendritic cell activation through Fc-dependent and Fc-independent mechanisms. EMBO Mol Med (Apr. 2015) 7: 464-476 (Year: 2015).*

(Continued)

*Primary Examiner* — Maher M Haddad
(74) *Attorney, Agent, or Firm* — Potomac Law Group, PLLC

(57) ABSTRACT

The invention relates to chimeric or humanised anti-CD303 antibodies to nucleic acids coding for the heavy and light chains of these antibodies, expression vectors, host cells, transgenic non-human animals or transgenic plants expressing said antibodies, as well as to the uses thereof in the treatment or prevention of blastic plasmacytoid dendritic cell neoplasms (BPDCN) or inflammatory diseases, in particular autoimmune diseases, involving plasmacytoid dendritic cells.

18 Claims, 28 Drawing Sheets

Specification includes a Sequence Listing.

(56) References Cited

FOREIGN PATENT DOCUMENTS

| | | |
|---|---|---|
| WO | 2012175751 A3 | 8/2013 |
| WO | 2013117871 A2 | 8/2013 |
| WO | 2014093396 A1 | 6/2014 |
| WO | 2015098813 A1 | 7/2015 |

OTHER PUBLICATIONS

Almagro et al., "Humanization of antibodies," Frontiers in Bioscience, vol. 13, pp. 1619-1633, Jan. 2008.
Brochet et al., "IMGT/V-QUEST: the highly cutomized and integrated system for IG and TR standardized V-J and V-D-J sequence analysis," Nucleic Acids Research, vol. 36, pp. W503-W508, May 2008.
Cao, "Pivotal Functions of Plasmacytoid Dendritic Cells in Systemic Autoimmune Pathogenesis," J. Clin. Cell Immunol., vol. 5, No. 2, p. 212, Apr. 2014.
Cardarelli et al., "A nonfucosylated human antibody to CD19 with potent B-cell depletive activity for therapy of B-cell malignancies," Cancer Immunol. Immunother., vol. 59, pp. 257-265, Aug. 2009.
Cardarelli et al., "In vitro and in vivo Characterization of MDX-1401 for Therapy of Malignant Lymphoma," Clinical Cancer Research, vol. 15, pp. 3376-3383, Apr. 2009.
Cibelli et al., "Cloned Transgenic Calves Produced from Nonquiescent Fetal Fibroblasts," Science, vol. 280, pp. 1256-1258, May 1998.
Dall'Acqua et al., "Increasing the Affinity of a Human IgG1 for the Neonatal Fc Receptor: Biological Consequences," The Journal of Immunology, vol. 169, pp. 5171-5180, 2002.
Dall'Acqua et al., "Modulation of the Effector Functions of a Human IgG1 through Engineering of Its Hinge Region," The Journal of Immunology, vol. 177, pp. 1129-1138, 2006.
Dall'Acqua et al., Properties of Human IgG1s Engineered for Enhanced Binding to the Neonatal Fc Receptor (FcRn), The Journal of Biological Chemistry, vol. 281, No. 33, pp. 23514-23524, Aug. 2006.
Edelman et al., "The Covalent Structure of an Entire yG Immunoglobulin Molecule," Proc. Natl. Acad. USA, vol. 63, pp. 78-85, 1969.
Ehrenmann et al., "IMGT/3Dstructure-DB and IMGT/DomainGapAlign: a database and a tool for immunoglobulins or antibodies, T cell receptors, MHC, IgSF, and MhcSF," Nucleic Acids Research, vol. 38, Database issue, pp. D301-D307, Nov. 2009.
Ehrenmann et al., "IMGT/DomainGapAlign: IMGT Standardized Analysis of Amino Acid Sequences of Variable, Constant, and Groove Domains (IG, TR, Mh, IgSF, MhSF)," Cold Spring Harbor Protocols, pp. 100-112, 2011.
Fischer et al., "Production of antibodies in plants and their use for global health," Vaccine, vol. 21, pp. 820-825, 2003.
Forthal et al., "Fc-Glycosation Influences Fcy Receptor Binding and Cell-Mediated Anti-HIV Activity of Monoclonal Antibody 2G12," The Journal of Immunology, vol. 185, pp. 6876-6882, Nov. 2010.
Gordon et al..., "Genetic transformation of mouse embryos by microinjection of purified DNA," Proc. Natl. Acad. Sci. USA, vol. 77, No. 12, pp. 7380-7384, Dec. 1980.
Herbst et al., "B-Cell Depletion In Vitro and In Vivo with an Afucosylated Anti-CD19 Antibody," The Journal of Pharmacology and Experimental Therapeutics, vol. 335, No. 1, pp. 213-222, Oct. 2010.
Hinton et al., "Engineered Human IgG Antibodies with Longer Serum Half-lives inn Primates," The Journal of Biological Chemistry, vol. 279, No. 8, pp. 6213-6216, Feb. 2004.
Hogan et al., "Manipulating the Mouse Embryo—A Laboratory Manual," Cold Spring Harbor Press, 2nd edition, pp. 1-113, 1994.
Idusogie et al., "Engineered Antibodies with Increased Activity to Recruit Complement," The Journal of Immunology, vol. 166, pp. 2571-2575, 2001.
Imai-Nishiya et al., "Double knockdown of alpha I,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnology, vol. 7, p. 84, Nov. 2007.
Jones et al., "Replacing the complementarity—determining the regions in a human antibody with those from a mouse," Nature, vol. 329, pp. 522-525, May 1986.
Kanda et al., "Establishment of a GDP-mannose 4,6-dehydratase (GMD) knockout host cell line: A new strategy for generating completely non-fucosylated recombinant therapeutics," Journal of Biotechnology, vol. 130, pp. 300-310, 2007.
Lazar et al., "Engineered antibody Fc variants with enhanced effector function," PNAS, vol. 103, No. 11, pp. 4005-4010, Mar. 2006.
Lefranc et al., "IMGT unique numbering for immunoglobulin and T cell receptor variable domains and Ig superfamily V-like domains," Developmental & Comparative Immunology, vol. 27, pp. 55-77, 2003.
Ma et al., "The Production of Recombinant Pharmaceutical Proteins in Plants," Nature Review Genetics, vol. 4, No. 10, pp. 794-805, Oct. 2003.
Maeda et al., "A Novel Plasmacytoid Dendritic Cell Line, CAL-1, Established from a Patient with Blastic Natural Cell Killer Lymphoma," International Journal of Hematology, vol. 81, pp. 148-154, Feb. 2005.
Moore et al., "Engineered Fc variant antibodies with enhanced ability to recruit complement and mediate effector functions," mAbs, 2:2, pp. 181-189, Mar./Apr. 2010.
Mori et al., "Engineering Chinese Hamster Ovary Cells to Maximize Effector Function of Produced Antibodies Using FUT8 siRNA," Biotechnology and Bioengineering, vol. 88, No. 7, pp. 901-908, Dec. 2004.
Needleman et al., "A General Method Applicable to the Search for Similarities in the Amino Acid Sequence of Two Proteins," J. Mol. Biol., vol. 48, pp. 443-453, 1970.
Olivier et al., "EB66 cell line, a duck embryonic stem cell-derived substrate for the industrial production of therapeutic monoclonal antibodies with enhanced ADCC activity," mAbs, 2:4, pp. 405-415, Jul./Aug. 2010.
Riechmann et al., "Reshaping human antibodies for therapy," Nature, vol. 332, pp. 323-327, Mar. 1988.
Ryan et al., "Knockout-Transgenic Mouse Model of Sickle Cell Disease," Science, vol. 278, pp. 873-876, Oct. 1997.
Schillberg et al., "Opportunities for recombinant antigen and antibody expression in transgenic plants—technology assessment," Vaccine, vol. 23, pp. 1764-1769, 2005.
Shields et al., "High Resolution Mapping of the Binding Site on Human IgG1 for FcyRI, FcyRII, FcyRIII, and FcRn and Design of IgG1 Variants with Improved Binding to the FcyR," The Journal of Biological Chemistry, vol. 276, No. 9, pp. 6591-6604, Mar. 2001.
Shields et al., "Lack of Fucose on Human IgG1 N-Linked Oligosaccharide Improves Binding to Human FcyRIII and Antibody-dependent Cellular Toxicity," The Journal of Biological Chemistry, vol. 277, No. 30, pp. 26733-26740, Jul. 2002.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278, No. 5, pp. 3466-3473, Jan. 2003.
Stoger et al., "Practical considerations for pharmaceutical antibody production in different crop systems," Molecular Breeding, vol. 9, pp. 149-158, 2002.
Suzuki et al., "A Nonfucosylated Anti-HER2 Antibody Augments Antibody-Dependent Cellular Cytotoxicity in Breast Cancer Patients," Clinical Cancer Research, vol. 13, pp. 1875-1882, Mar. 2007.
Umana et al., "Engineered glycoforms of an antineuro-blastoma IgG1 with optimized antibody-dependent cellular cytotoxic activity," Nature Biotechnology, vol. 17, pp. 176-180, Feb. 1999.
Urlaub et al., "Deletion of the Diploid Dihydrofolate Reductase Locus from Cultured Mammalian Cells," Cell, vol. 33, pp. 405-412, pp. 405-412, Jun. 1983.
Verhoeyen et al., "Engineering of Antibodies," BioEssays, vol. 8, No. 2, pp. 74-78, Feb./Mar. 1988.

(56) References Cited

OTHER PUBLICATIONS

Verhoeyen et al., "Reshaping Human Antibodies: Grafting an Antilysozyme Activity," Science, vol. 239, pp. 1534-1536, Mar. 1988.
Wollenberg et al., "Plasmacytoid Dendritic Cells: A New Cutaneous Dendritic Cell Subset with Distinct Role in Inflammatory Skin Diseases," The Journal of Investigative Dermatology, vol. 119, No. 5, pp. 1096-1102, Nov. 2002.
Dzionek et al., "BDCA-2, a novel plasmacytoid dendritic cell-specific type II C-type lectin, mediates antigen capture and is a potent inhibitor of interferon alpha/beta induction," The Journal of Experimental Medicine; vol. 194, No. 12, pp. 1823-1834, Dec. 2001.
International Search Report issued for application No. PCT/EP2016/056995 dated Aug. 10, 2016.
Jahn et al., "BDCA-2 signaling inhibits TLR-9-agonist-induced plasmacytoid dendritic cell activation and antigen presentation," Cellular Immunology, vol. 265, No. 1. pp. 15-22, Jan. 2010 (Abstract).
Monnet et al., "Selection of IgG variants with increased FcRn binding using random and directed mutagenesis: impact on effector functions," Frontiers in Immunology, vol. 6, No. 39, pp. 1-14, Feb. 2015.
Yamane-Ohnuke et al., "Production of therapeutic antibodies with controlled fucosylation," MABS, vol. 1, No. 3, pp. 230-236, May 2009.

\* cited by examiner

ANTI-CD303 MONOCLONAL ANTIBODIES

FIELD OF THE INVENTION

The present invention is in to the field of therapeutic antibodies for treating or preventing hematopoietic tumors of the CD4+CD56+ phenotype or inflammatory diseases, notably autoimmune diseases, involving plasmacytoid dendritic cells (pDCs). It relates to five monoclonal antibodies directed against the CD303 antigen, and to functional fragments and derivatives thereof, to the nucleic acids encoding the heavy and/or light chain of the antibody, to expression vectors, host cells, transgenic non-human animals or transgenic plants expressing said antibodies, and to therapeutic uses of said antibodies.

PRIOR ART

Dendritic cells (called "DCs" throughout the present description) are antigen-presenting cells (APCs) of the immune system. Under certain conditions, DCs have cytoplasmic projections similar to the dendrites of neurons.

Dendritic cells have two main functions:
they trigger the adaptive immune response directed against "non-self" (foreign) antigens, by presenting these foreign antigens to T lymphocytes; and
they maintain central tolerance to "self", by educating T cells in the thymus, by the so-called "negative selection" process.

DCs are capable of differentiating into various subpopulations, according to the stimuli they receive. There are three major types of DCs: conventional DCs, plasmacytoid DCs (called "pDCs") and inflammatory DCs.

Conventional DCs present self or non-self-antigens in lymphoid organs or in the periphery. Inflammatory DCs, probably derived from blood monocytes, appear only in the event of stimulation following inflammation or infection.

Plasmacytoid DCs (pDCs) are circulating, round and without dendrites in the basal state, but acquire dendrites after activation, generally by a viral antigen. After stimulation, they produce a large amount of type I interferons (IFNs), and are chiefly involved in the antiviral response or in autoimmune diseases. Phenotypically, they are notably characterized by the following markers: CD4+, CD11c−, Lin−, CD303+, CD304+.

pDCs can be the cause of hematopoietic tumors in which they acquire an additional marker (CD56). This is referred to as blastic plasmacytoid dendritic cell neoplasm (BPDCN). These tumors are also referred to as CD4+CD56+ hematopoietic tumors. These hematopoietic tumors are rare (1% of acute leukemias) and appear as cutaneous nodules associated with lymphadenopathy or swelling of the spleen and with frequent cytopenia. The cutaneous manifestations are very quickly followed by infiltration of the bone marrow. It is now accepted that the hematopoietic cells at the origin of these tumors are pDCs.

The current treatments for these blastic plasmacytoid dendritic cell neoplasms are based on chemotherapy. Although relatively effective at first, this treatment is characterized by frequent and early relapses (about 9 months), median overall survival being only about 13 months. Another treatment is based on allografting of hematopoietic cells, but it does not enable long-term survival either.

It has been proposed in WO2012/080642 to use anti-BDCA-2 (i.e., anti-CD303) antibodies to treat these neoplasms by tumor cell depletion.

pDCs are also involved in certain inflammatory diseases, and notably in certain autoimmune diseases, in particular via their secretion of type I IFN.

One treatment is based on the use of anti-IFNα antibody. However, this treatment leads to systemic neutralization of IFNα, thus potentially increasing the risk of opportunistic infections. It has thus also been proposed in WO01/365487 and WO2012/080642 to use anti-BDCA-2 (anti-CD303) antibodies (in particular antibody AC144) to treat autoimmune diseases, by removing the pDCs responsible for local inflammation.

However, in order for these treatments to be effective, it is necessary to have suitable monoclonal antibodies that allow, in humans, the most efficient as possible removal of pDCs. To that end, chimeric or humanized antibodies with high affinity for the CD303 antigen and effector capabilities (ADCC, CDC, phagocytosis, signaling via cross-linking of CD303 by Fc receptors, in particular Fcγ receptor III (FcγRIII, also called CD16) and/or apoptosis) enabling them to remove pDCs in physiological conditions are necessary. The anti-CD303 antibodies available to date being inadequate, there thus exists a need for new anti-CD303 antibodies having the desired properties.

WO2014/09339 describes humanized anti-CD303 antibodies, defined by the sequences of their heavy and light chains, and notably antibody BIIB059, which is the one having the best affinity for the CD303 antigen. Antibody BIIB059 was produced in CHO cells and characterized in terms of certain properties.

SUMMARY OF THE INVENTION

In the context of the present invention, the inventors generated five chimeric monoclonal antibodies having such properties. At least two of these chimeric antibodies (122A2 and 102E9) have a capacity to bind to the ectodomain of the human CD303 antigen that is greater than that of the antibody (BIIB059) described in WO2014/09339 (in particular 122A2). Moreover, humanized antibodies derived from these two chimeric antibodies were generated and characterized. These humanized antibodies can be produced with higher productivity than the original chimeric antibodies and, among those derived from chimeric antibody 122A2, certain have a capacity to bind to the ectodomain of the human CD303 antigen that is even higher than that of the original chimeric antibody and thus higher than that of the antibody (BIIB059) described in WO2014/09339. The chimeric and humanized antibodies produced in YB2/0 cells also have high affinity for FcγRIIIa (CD16a), and are capable of inducing strong ADCC responses, even at low antigen density. The antibodies also have CDC activity and are capable of inhibiting the secretion of IFN-α and of TNF-α.

In a first aspect, the present invention thus relates to a monoclonal antibody directed against the ectodomain of the human CD303 antigen (SEQ ID NO: 130), or a functional fragment or a derivative thereof, characterized in that:
  a) it competes for binding to the human CD303 antigen with at least one antibody selected from:
    i) An antibody which heavy chain variable region comprises SEQ ID NO: 43 and which light chain variable region comprises SEQ ID NO: 48;
    ii) An antibody which heavy chain variable region comprises SEQ ID NO: 44 and which light chain variable region comprises SEQ ID NO: 49;

iii) An antibody which heavy chain variable region comprises SEQ ID NO: 45 and which light chain variable region comprises SEQ ID NO: 50;

iv) An antibody which heavy chain variable region comprises SEQ ID NO: 46 and which light chain variable region comprises SEQ ID NO: 51;

v) An antibody which heavy chain variable region comprises SEQ ID NO: 47 and which light chain variable region comprises SEQ ID NO: 52; and the light and heavy chain constant regions are constant regions from a non-murine species.

The present invention also relates to a monoclonal antibody directed against the ectodomain of the human CD303 antigen (SEQ ID NO: 130), or a functional fragment or a derivative thereof, characterized in that:

a) it has improved affinity for FcγRIIIa (CD16a) compared to antibodies directed against the ectodomain of the human CD303 antigen, produced in CHO cells; and b) the light and heavy chain constant regions are constant regions from a non-murine species.

The present invention also relates to a nucleic acid encoding the heavy and/or light chain of an antibody, functional fragment or derivative thereof according to the invention.

The present invention also relates to a vector comprising a nucleic acid according to the invention.

The present invention also relates to a host cell, a transgenic non-human animal or a transgenic plant comprising at least one nucleic acid according to the invention or a vector according to the invention.

The present invention also relates to an antibody, functional fragment or derivative thereof according to the invention, for use as a medicinal product.

The antibody, functional fragment or derivative thereof according to the invention is advantageously used in the treatment or prevention of hematopoietic tumors expressing the CD303 antigen or in the treatment or prevention of inflammatory diseases, notably autoimmune diseases.

DETAILED DESCRIPTION OF THE INVENTION

Antibody, Functional Fragment or Derivative

Figures 1A, 1B:
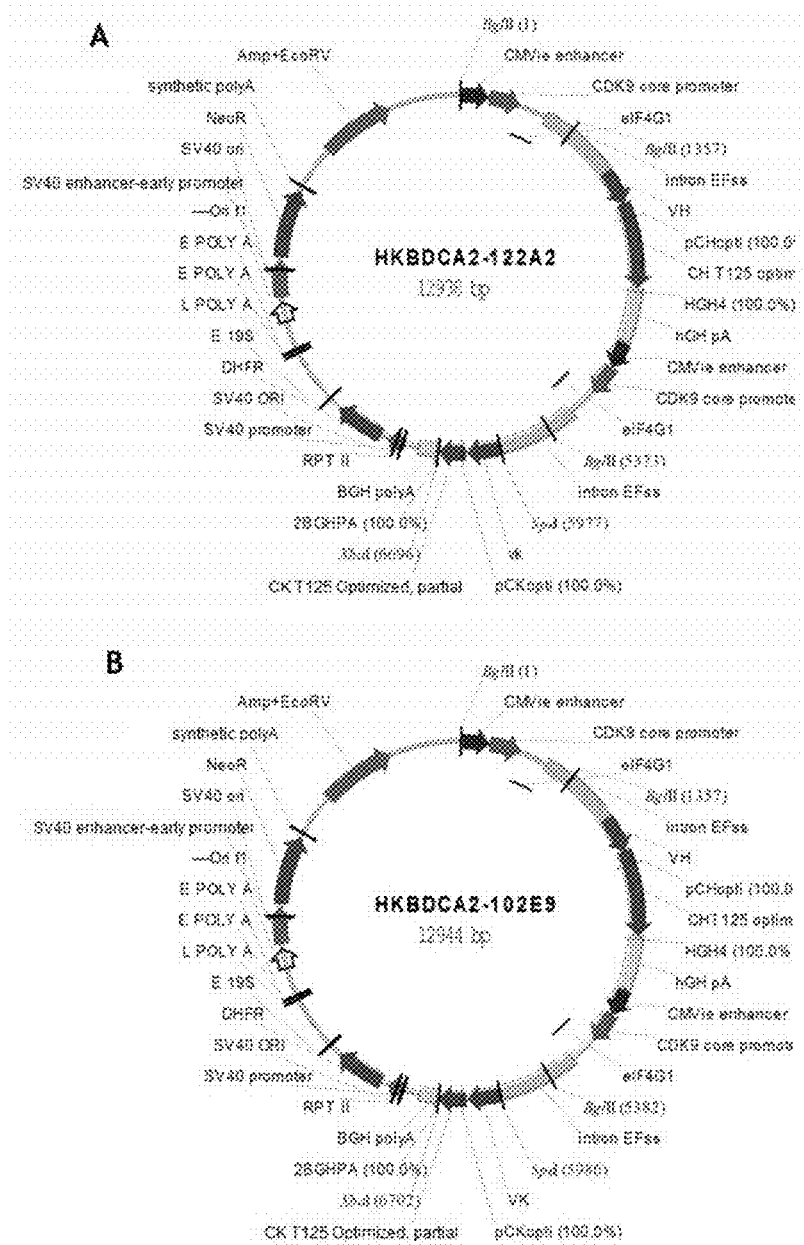
FIG. 1. Maps of the expression vectors for chimeric antibodies 122A2 (A), 102E9 (B), 104C12 (C), 114D11 (D), and 104E10 (E), and of the antibody BIIB059 expression vector (F).
Figures 1C, 1D:
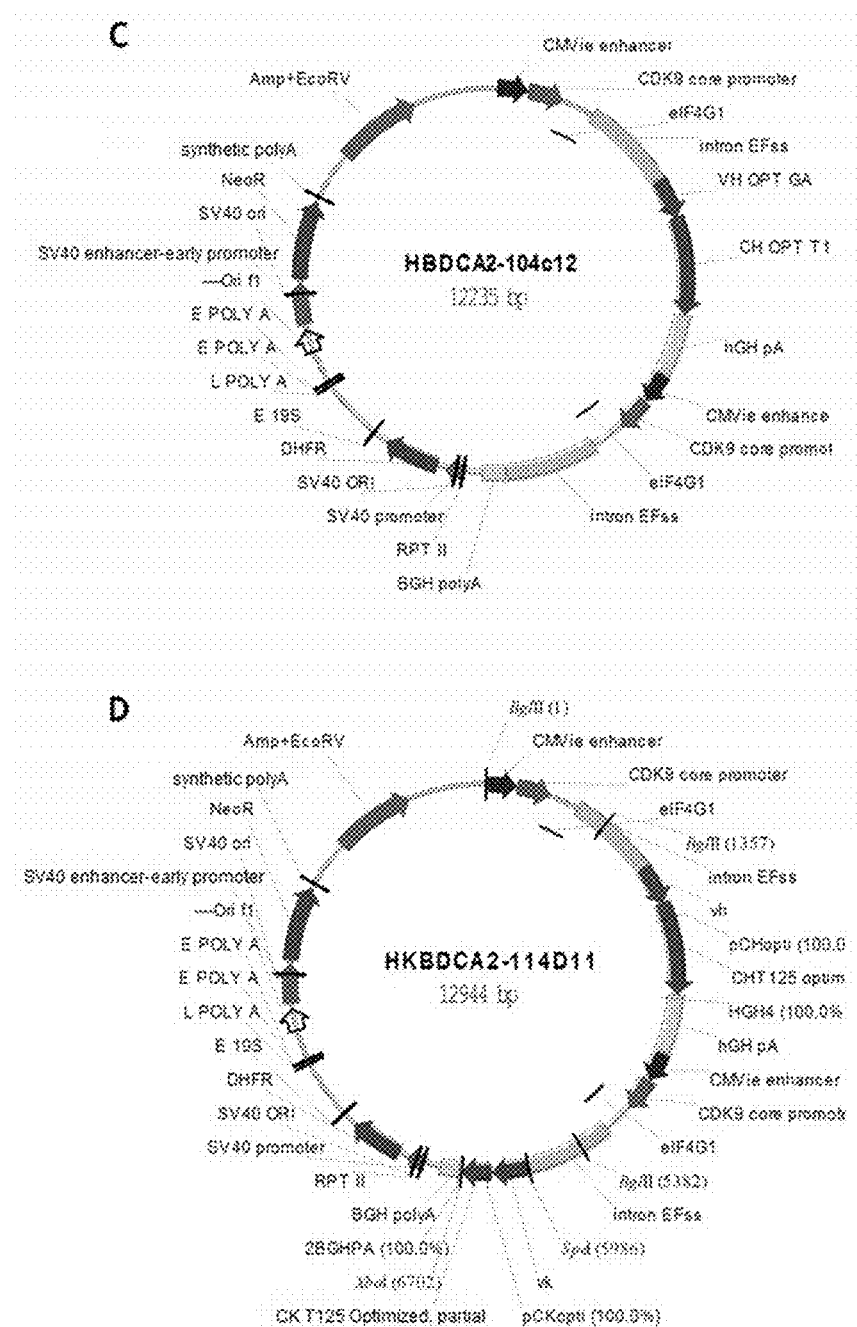

The present invention relates to a monoclonal antibody directed against the ectodomain of the human CD303 antigen (SEQ ID NO: 130), or a functional fragment or a derivative thereof, characterized in that:
a) it competes for binding to the human CD303 antigen with at least one antibody selected from:
  i) An antibody which heavy chain variable region comprises SEQ ID NO: 43 and which light chain variable region comprises SEQ ID NO: 48;
  ii) An antibody which heavy chain variable region comprises SEQ ID NO: 44 and which light chain variable region comprises SEQ ID NO: 49;
  iii) An antibody which heavy chain variable region comprises SEQ ID NO: 45 and which light chain variable region comprises SEQ ID NO: 50;
  iv) An antibody which heavy chain variable region comprises SEQ ID NO: 46 and which light chain variable region comprises SEQ ID NO: 51;
  v) An antibody which heavy chain variable region comprises SEQ ID NO: 47 and which light chain variable region comprises SEQ ID NO: 52; and
b) the light and heavy chain constant regions are constant regions from a non-murine species.

Advantageously, the heavy chains comprise three CDR-H (heavy-chain CDR according to IMGT nomenclature) having the following amino acid sequences, or sequences having at least 80% identity with the following sequences, and the light chains comprise three CDR-L (light-chain CDR according to IMGT nomenclature) having the following amino acid sequences, or sequences having at least 80% identity with the following sequences:
  i) CDR1-H-family 1: SEQ ID NO: 1, CDR2-H-family 1: SEQ ID NO: 2, CDR3-H-family 1: SEQ ID NO: 3, CDR1-L-family 1: SEQ ID NO: 4, CDR2-L-family 1: SEQ ID NO: 5, CDR3-L-family 1: SEQ ID NO: 6; or
  ii) CDR1-H-family 2: SEQ ID NO: 7, CDR2-H-family 2: SEQ ID NO: 8, CDR3-H-family 2: SEQ ID NO: 9, CDR1-L-family 2: SEQ ID NO: 10, CDR2-L-family 2: SEQ ID NO: 11, CDR3-L-family 2: SEQ ID NO: 12.

Table 1 below summarizes the amino acid sequences of the CDR-IMGT of the two families of antibodies according to the invention:

TABLE 1

CDR amino acid sequences of the two families of antibodies according to the invention according to IMGT nomenclature. In each sequence, X may represent any amino acid.

|  | Family 1 | Family 2 |
| --- | --- | --- |
| CDR1-H | GYTFTDYS (SEQ ID NO: 1) | GYTFTDXS (SEQ ID NO: 7) |
| CDR2-H | ISXYYGDX (SEQ ID NO: 2) | INTETGXP (SEQ ID NO: 8) |
| CDR3-H | ARNXXXYXXXY (SEQ ID NO: 3) | XRNGYYVGYYAXDY (SEQ ID NO: 9) |
| CDR1-L | QDIXNY (SEQ ID NO: 4) | SSVXY (SEQ ID NO: 10) |
| CDR2-L | YTS (SEQ ID NO: 5) | STS (SEQ ID NO: 11) |
| CDR3-L | QQGXTLPWT (SEQ ID NO: 6) | QQRRSYPXT (SEQ ID NO: 12) |

Advantageously, the heavy chains of an antibody, functional fragment or derivative thereof according to the invention comprise three CDR-H (heavy-chain CDR according to IMGT nomenclature) having the following amino acid sequences, or sequences having at least 80% identity with the following sequences, and the light chains comprise three CDR-L (light-chain CDR according to IMGT nomenclature) having the following amino acid sequences, or sequences having at least 80% identity with the following sequences:
  i) CDR1-H-122A2: SEQ ID NO: 13, CDR2-H-122A2: SEQ ID NO: 14, CDR3-H-122A2: SEQ ID NO: 15, CDR1-L-122A2: SEQ ID NO: 16, CDR2-L-122A2: SEQ ID NO: 17, CDR3-L-122A2: SEQ ID NO: 18;
  ii) CDR1-H-102E9: SEQ ID NO: 19, CDR2-H-102E9: SEQ ID NO: 20, CDR3-H-102E9: SEQ ID NO: 21, CDR1-L-102E9: SEQ ID NO: 22, CDR2-L-102E9: SEQ ID NO: 23, CDR3-L-102E9: SEQ ID NO: 24;
  iii) CDR1-H-104C12: SEQ ID NO: 25, CDR2-H-104C12: SEQ ID NO: 26, CDR3-H-104C12: SEQ ID NO: 27, CDR1-L-104C12: SEQ ID NO: 28, CDR2-L-104C12: SEQ ID NO: 29, CDR3-L-104C12: SEQ ID NO: 30;
  iv) CDR1-H-114D11: SEQ ID NO: 31, CDR2-H-114D11: SEQ ID NO: 32, CDR3-H-114D11: SEQ ID NO: 33, CDR1-L-114D11: SEQ ID NO: 34, CDR2-L-114D11: SEQ ID NO: 35, CDR3-L-114D11: SEQ ID NO: 36; or
  v) CDR1-H-104E10: SEQ ID NO: 37, CDR2-H-104E10: SEQ ID NO: 38, CDR3-H-104E10: SEQ ID NO: 39, CDR1-L-104E10: SEQ ID NO: 40, CDR2-L-104E10: SEQ ID NO: 41, CDR3-L-104E10: SEQ ID NO: 42.

Advantageously, the heavy chains of an antibody, functional fragment or derivative thereof according to the invention comprise a variable region having a sequence selected from SEQ ID NOs: 43 to 47 or a sequence having at least 80% identity with one of SEQ ID NOs: 43 to 47.

Additionally or alternatively, the light chains of an antibody, functional fragment or derivative thereof according to the invention comprise a variable region having a sequence selected from SEQ ID NOs: 48 to 52 or a sequence having at least 80% identity with one of SEQ ID NOs: 48 to 52.

In a preferred embodiment, the antibody, functional fragment or derivative thereof according to the invention has heavy and light chains which variable regions have the following amino acid sequences or sequences having at least 80% identity with the following sequences:
  i) Antibody 122A2: heavy chain: SEQ ID NO: 43, light chain: SEQ ID NO: 48,
  ii) Antibody 102E9: heavy chain: SEQ ID NO: 44, light chain: SEQ ID NO: 49,
  iii) Antibody 104C12: heavy chain: SEQ ID NO: 45, light chain: SEQ ID NO: 50,
  iv) Antibody 114D11: heavy chain: SEQ ID NO: 46, light chain: SEQ ID NO: 51, or
  v) Antibody 104E10: heavy chain: SEQ ID NO: 47, light chain: SEQ ID NO: 52.

Table 2 below summarizes the murine VH, JH and VL and JL gene segments used by the various antibodies according to the invention and the percent identity.

TABLE 2

Murine VH, JH and VL and JL segments used by the various antibodies according to the invention, as defined by IMGT.

| Antibody | VH | JH | VL | JL |
|---|---|---|---|---|
| 122A2 | IGHV1S137*01 (94.9%) | IGHJ2*02 (85%) | IGKV10-96*01 (98.9%) | IGKJ1*01 (100%) |
| 102E9 | IGHV9-2-1*01 (93.9%) | IGHJ4*01 (100%) | IGKV4-57*01 (95.7%) | IGKJ1*02 (100%) |
| 104C12 | IGHV1S137*01 (91.8%) | IGHJ3*01 (100%) | IGKV10-96*02 (89.5%) | IGKJ1*02 (100%) |
| 114D11 | IGHV9-2-1*01 (94.9%) | IGHJ4*01 (94.1%) | IGKV4-57*01 (97.9%) | IGKJ1*02 (100%) |
| 104E10 | IGHV9-2-1*01 (98%) | IGHJ4*01 (100%) | IGKV4-57*01 (96.8%) | IGKJ1*02 (100%) |

Table 3 below summarizes the amino acid sequences of the CDRs and the variable regions of the heavy and light chains of the anti-CD303 antibodies generated by the inventors:

TABLE 3

Amino acid sequences of the heavy- and light-chain CDR1, CDR2, and CDR3 according to IMGT nomenclature, and of the VH and VL fragments of the antibodies according to the invention.

Antibody 122A2

Heavy chain

| | |
|---|---|
| CDR1-H-IMGT-122A2 | GYTFTDYS (SEQ ID NO: 13) |

TABLE 3-continued

Amino acid sequences of the heavy- and light-chain CDR1, CDR2, and CDR3 according to IMGT nomenclature, and of the VH and VL fragments of the antibodies according to the invention.

| | |
|---|---|
| CDR2-H-IMGT-122A2 | ISTYYGDS (SEQ ID NO: 14) |
| CDR3-H-IMGT-122A2 | ARNGNFYVMDY (SEQ ID NO: 15) |
| VH-122A2 | QVQLQQSGAELVRPGVSVKISCKGSGYTFTDYSMHW VKQSHAKSLEWIGVISTYYGDSNYNQKFKGKATMTV DKSSTTAYMELARLTSEDSAIYYCARNGNFYVMDYW GQGTSVTVSS (SEQ ID NO: 43) |

Light chain

| | |
|---|---|
| CDR1-L-IMGT-122A2 | QDISNY (SEQ ID NO: 16) |
| CDR2-L-IMGT-122A2 | YTS (SEQ ID NO: 17) |
| CDR3-L-IMGT-122A2 | QQGNTLPWT (SEQ ID NO: 18) |
| VL-122A2 | DIQMTQTTSSLSASLGDRVTISCRASQDISNYLNW YQQKPDGTVKLLIYYTSRLHSGVPSRFSGSGSGTD YSLTISNLDQEDIATYFCQQGNTLPWTFGGGTKLE IK (SEQ ID NO: 48) |

Antibody 102E9

Heavy chain

| | |
|---|---|
| CDR1-H-IMGT-102E9 | GYTFTDYS (SEQ ID NO: 19) |
| CDR2-H-IMGT-102E9 | INTETGEP (SEQ ID NO: 20) |
| CDR3-H-IMGT-102E9 | TRNGYYVGYYAMDY (SEQ ID NO: 21) |
| VH-102E9 | QIHLVQSGPDLKKPGETVKISCKASGYTFTDYSMHW VKQAPGKGLKWMGWINTETGEPTYADDFKGRFAFSL ESSASTAFLQINNLKNEDTSTYFCTRNGYYVGYYAM DYWGQGTSVTVSS (SEQ ID NO: 44) |

Light chain

| | |
|---|---|
| CDR1-L-IMGT-102E9 | SSVIY (SEQ ID NO: 22) |
| CDR2-L-IMGT-102E9 | STS (SEQ ID NO: 23) |
| CDR3-L-IMGT-102E9 | QQRRSYPFT (SEQ ID NO: 24) |
| VL-102E9 | QIVLTQSPAIMSASPGEKVTITCSASSSVIYIHWF QQKPGTSPKLWIYSTSYLASGVPARFSGSGSGTSY SLTISRMEAEDAATYYCQQRRSYPFTFGGGTKLEI K (SEQ ID NO: 49) |

Antibody 104C12

Heavy chain

| | |
|---|---|
| CDR1-H-IMGT-104C12 | GYTFTDYS (SEQ ID NO: 25) |
| CDR2-H-IMGT-104C12 | ISPYYGDT (SEQ ID NO: 26) |
| CDR3-H-IMGT-104C12 | ARNDDYYRFAY (SEQ ID NO: 27) |
| VH-104C12 | QVQLQQSGAELVGPGVSVKISCKGSGYTFTDYSMH WVKQSHAKSLEWIGVISPYYGDTNYNQKFKGKATM TVDKSSTAYMELASLTSEDSAIYFCARNDDYYRF AYWGQGTLVTVSA (SEQ ID NO: 45) |

Light chain

| | |
|---|---|
| CDR1-L-IMGT-104C12 | QDINNY (SEQ ID NO: 28) |

TABLE 3-continued

Amino acid sequences of the heavy- and light-chain CDR1, CDR2, and CDR3 according to IMGT nomenclature, and of the VH and VL fragments of the antibodies according to the invention.

| | |
|---|---|
| CDR2-L-IMGT-104C12 | YTS (SEQ ID NO: 29) |
| CDR3-L-IMGT-104C12 | QQGKTLPWT (SEQ ID NO: 30) |
| VL-104C12 | DLQMTQTPSSLSASLGDRVTISCRASQDINNYLSWYQEKPDGTFKLLIYYTSRLHSGVPSRFSGSGSGTDYSLTVRNLEQEDIGTYFCQQGKTLPWTFGGGTKLEIR (SEQ ID NO: 50) |

Antibody 114D11

Heavy chain

| | |
|---|---|
| CDR1-H-IMGT-114D11 | GYTFTDSS (SEQ ID NO: 31) |
| CDR2-H-IMGT-114D11 | INTETGGP (SEQ ID NO: 32) |
| CDR3-H-IMGT-114D11 | ARNGYYVGYYALDY (SEQ ID NO: 33) |
| VH-114D11 | QIQLVQSGPELKKPGETVKISCKASGYTFTDSSMHWVQQAPNKGLKWMGWINTETGGPTYADDFKGRFAFSLETSARTAYLQINNLKNEDTATYFCARNGYYVGYYALDYWGQGTSVTVSS (SEQ ID NO: 46) |

Light chain

| | |
|---|---|
| CDR1-L-IMGT-114D11 | SSVFY (SEQ ID NO: 34) |
| CDR2-L-IMGT-114D11 | STS (SEQ ID NO: 35) |
| CDR3-L-IMGT-114D11 | QQRRSYPYT (SEQ ID NO: 36) |
| VL-114D11 | QIVLTQSPAIMSASPGEKVTITCSASSSVFYMHWFQQKPGTSPKLWIYSTSNLASGVPARFSGSGSGTSYSLTISRMEAEDAATYYCQQRRSYPYTFGGGTKLEIK (SEQ ID NO: 51) |

Antibody 104E10

Heavy chain

| | |
|---|---|
| CDR1-H-IMGT-104E10 | GYTFTDYS (SEQ ID NO: 37) |
| CDR2-H-IMGT-104E10 | INTETGEP (SEQ ID NO: 38) |
| CDR3-H-IMGT-104E10 | ARNGYYVGYYAMDY (SEQ ID NO: 39) |
| VH-104E10 | QIQLVQSGPELKKPGETVKISCKASGYTFTDYSMHWVKQAPGKGLKWMGWINTETGEPTYADDFKGRFAFSLETSATTAYLQINNFKNEDTATYFCARNGYYVGYYAMDYWGQGTSVTVSS (SEQ ID NO: 47) |

Light chain

| | |
|---|---|
| CDR1-L-IMGT-104E10 | SSVIY (SEQ ID NO: 40) |
| CDR2-L-IMGT-104E10 | STS (SEQ ID NO: 41) |
| CDR3-L-IMGT-104E10 | QQRRSYPYT (SEQ ID NO: 42) |
| VL-104E10 | QIVLTQSPAIMSASPGEKVTMTCSASSSVIYMHWFQQKPGTSPKLWIYSTSNLASGVPARFSGSGSGTSYSLTISRMEAEDAATYYCQQRRSYPYTFGGGTKLEIK (SEQ ID NO: 52) |

The human CD303 antigen is C-type lectin domain family 4, member C (CLEC4), also called DLEC; HECL; BDCA2; CLECSF7; CLECSF11; or PRO34150 (see the Entrez Gene website for the CLEC4 gene). It is a type II transmembrane glycoprotein of 213 amino acids, comprising a short cytoplasmic domain with no evident signaling motif (amino acids 1-21), a transmembrane region (amino acids 22-41), a neck domain (amino acids 42-82), and a carbohydrate recognition domain (CRD; amino acids 83-213) (Dzionek et al.—2001). The mRNA sequence encoding this protein may be found in the 14 Feb. 2002 version of the GenBank database under accession number AF293615.1 (SEQ ID NO: 129), while the amino acid sequence is accessible in the 14 Feb. 2002 version of the GenBank database under accession number AAL37036.1 (SEQ ID NO: 130).

By "antibody" or "immunoglobulin" is meant a molecule comprising at least one binding domain for a given antigen and a constant domain comprising an Fc fragment capable of binding to Fc receptors (FcR). In most mammals, like humans and mice, an antibody consists of four polypeptide chains: two heavy chains and two light chains bound together by a variable number of disulfide bridges providing flexibility to the molecule. Each light chain consists of a constant domain (CL) and a variable domain (VL); the heavy chains consisting of a variable domain (VH) and three or four constant domains (CH1 to CH3 or CH1 to CH4) according to the isotype of the antibody. In a few rare mammals, such as camels and llamas, the antibodies consist of only two heavy chains, each heavy chain comprising a variable domain (VH) and a constant region.

The variable domains are involved in antigen recognition, while the constant domains are involved in the biological, pharmacokinetic and effector properties of the antibody.

The variable region differs from one antibody to another. Indeed, the genes encoding antibody heavy and light chains are respectively generated by recombination of three and two distinct gene segments called VH, DH and JH-CH for the heavy chain and VL and JL-CL for the light chain. The CH and CL segments do not participate in recombination and form the constant regions of the heavy and light chains, respectively. Recombinations of the VH-DH-JH and VL-JL segments form the variable regions of the heavy and light chains, respectively. The VH and VL regions each have three hypervariable zones or complementarity-determining regions (CDRs) called CDR1, CDR2 and CDR3, with CDR3 being the most variable since it is located in the recombination zone. These three CDRs, and particularly CDR3, are found in the portion of the antibody that will be in contact with the antigen and are thus very important for antigen recognition. Thus, antibodies retaining the three CDRs and each of the heavy and light chains of an antibody mostly retain the antigen specificity of the original antibody. In a certain number of cases, an antibody retaining only one of the CDRs, and notably CDR3, also retains the specificity of the original antibody. CDR1, CDR2 and CDR3 are each preceded by FR1, FR2 and FR3, respectively, corresponding to framework regions (FRs) that vary the least from one VH or VL segment to another. CDR3 is also followed by a framework region, FR4.

An antibody's CDRs are defined by the amino acid sequence of its heavy and light chains compared to criteria known to a person skilled in the art. Various methods for determining CDRs have been proposed, and the portion of the amino acid sequence of a heavy or light chain variable region of an antibody defined as a CDR varies according to the method chosen. The first determination method is that proposed by Kabat et al. (1991). In this method, CDRs are defined by looking for the amino acids responsible for antibody-antigen binding. A second method was proposed by the IMGT, based on determining hypervariable regions. In this method, a unique numbering has been defined to compare variable regions regardless of the antigen receptor, chain type or species (Lefranc et al. 2003). This numbering provides a standardized definition of framework regions ((FR1-IMGT: positions 1 to 26, FR2-IMGT: 39 to 55, FR3-IMGT: 66 to 104 and FR4-IMGT: 118 to 128) and complementarity-determining regions (CDR1-IMGT: positions 27 to 38, CDR2-IMGT: positions 56 to 65 and CDR3-IMGT: positions 105 to 117). Finally, there is also a numbering called "common" in which the sequence of a particular CDR corresponds to the common sequence between the Kabat numbering and the IMGT numbering. Throughout the present description, the CDR sequences are indicated by the IMGT numbering. In particular, the CDRs have been determined by using the IMGT/V-QUEST program available at http://www.imgt.org/IMGT_vquest/share/textes/ and described in Brochet et al.—2008. Unlike the variable domains, whose sequence strongly varies from one antibody to another, the constant domains are characterized by an amino acid sequence that is very similar from one antibody to another, typical of the species and the isotype, with optionally a few somatic mutations. The Fc fragment naturally consists of the heavy chain constant region excluding the CH1 domain, i.e., the lower hinge region and the constant domains CH2 and CH3 or CH2 to CH4 (depending on the isotype). In human IgG1, the complete Fc fragment consists of the C-terminal portion of the heavy chain starting from the cysteine residue at position 226 (C226), the numbering of amino acid residues in the Fc fragment being throughout the present description that of the EU index described in Edelman et al.—1969 and Kabat et al.—1991. The corresponding Fc fragments of other types of immunoglobulins may easily be identified by a person skilled in the art by sequence alignments.

The Fc fragment is glycosylated in the CH2 domain with the presence, on each of the two heavy chains, of an N-glycan bound to the asparagine residue at position 297 (Asn297).

The following binding domains, located in the Fc, are important for the biological properties of the antibody:
  the neonatal Fc receptor (FcRn) binding domain, involved in the pharmacokinetic properties (in vivo half-life) of the antibody:
    Different data suggest that certain residues located at the interface of the CH2 and CH3 domains are involved in FcRn binding.
  the complement C1q protein binding domain, involved in the complement-dependent cytotoxicity (CDC) response: located in the CH2 domain;
  the Fc receptor (FcR) binding domain, involved in responses of the phagocytosis or antibody-dependent cell cytotoxicity (ADCC) type: located in the CH2 domain.

In the context of the invention, the Fc fragment of an antibody may be natural, as defined above, or else may be modified in various ways, provided that it comprises a functional FcR (FcγR for IgGs) binding domain, and preferably a functional FcRn binding domain. The modifications may include deletion of certain portions of the Fc fragment, provided that the latter contains a functional FcR (FcγR for IgGs) binding domain, and preferably a functional FcRn binding domain. The modifications may further include various amino acid substitutions able to affect the biological properties of the antibody, provided that the latter contains a functional FcR binding domain, and preferably a functional FcRn binding domain. In particular, when the antibody is an IgG, it may comprise mutations intended to increase FcγRIIIa (CD16a)-binding, as described in WO00/42072, Shields et al.—2001, Lazar et al.—2006, WO2004/029207, WO2004/063351, WO2004/074455. Mutations for increasing FcRn binding and thus in vivo half-life may also be present, as described for example in Shields et al.—2001, Dall'Acqua et al.—2002, Hinton et al.—2004, Dall'Acqua et al.—2006(a), WO00/42072, WO02/060919, WO2010/045193, or WO2010/106180. Other mutations, such as those for decreasing or increasing binding to complement proteins and thus the CDC response, may optionally be present (see WO99/51642, WO2004/074455, Idusogie et al.—2001, Dall'Acqua et al.—2006(b), and Moore et al.—2010).

In the context of the present invention, the preferred mutants comprising mutations for increasing FcRn binding and thus in vivo half-life are mutants comprising the following combinations of mutations in their Fc fragment, described in WO2010/106180:
  N315D/A330V/N361D/A378V/N434Y,
  P230S/N315D/M428L/N434Y,
  E294del/T307P/N434Y,
  T307A/N315D/A330V/E382V/N389T/N434Y,
  V259I/N315D/N434Y, or
  T256N/A378V/S383N/N434Y,
where the numbering of the amino acids in the Fc fragment is that of the EU index described in Kabat et al., Sequences of Proteins of Immunological Interest, $5^{th}$ Ed. Public Health Service, National Institutes of Health, Bethesda, Md. (1991), which is incorporated herein by reference. "EU index" or "EU index of Kabat" refers to the numbering of the amino acids of human IgG1 antibody.

Alternatively, just as fragments or derivatives without the Fc fragment of the antibody may be useful in the context of the invention, notably for the treatment of inflammatory, notably autoimmune, diseases involving pDCs, the antibody according to the invention may also have a mutated Fc fragment free of effector functions. Examples of mutations leading to a mutated Fc fragment free of effector functions are the single amino acid deletions at position 293 (Del293) or 294 (Del294) of the Fc fragment, where the numbering of the amino acids in the Fc fragment is that of the EU index of Kabat (WO2012/175751).

By "monoclonal antibody" or "monoclonal antibody composition" is meant a composition comprising antibody molecules having an identical and unique antigen specificity. The antibody molecules present in the composition are likely to vary in terms of their post-translational modifications, and notably in terms of their glycosylation structures or their isoelectric point, but have all been encoded by the same heavy and light chain sequences and thus have, before any post-translational modification, the same protein sequence. Certain differences in protein sequences, related to post-translational modifications (such as for example cleavage of the heavy chain C-terminal lysine, deamidation of asparagine residues and/or isomerization of aspartate residues), may nevertheless exist between the various antibody molecules present in the composition.

The percent identities referred to in the context of the disclosure of the present invention are determined on the basis of a global alignment of sequences to be compared, i.e., on an alignment of the sequences taken in their entirety over their entire length using any algorithm well-known to a person skilled in the art, such as the algorithm of Needleman and Wunsch (1970). This sequence comparison may be performed using any software well-known to a person skilled in the art, for example the Needle software by using the "Gap open" parameter equal to 10.0, the "Gap extend"

parameter equal to 0.5 and a "Blosum 62" matrix. The Needle software is for example available on the website ebi.ac.uk under the name "Align".

When the CDR or variable region of an antibody according to the invention has an amino acid sequence that is not 100% identical to one of those described above and in the sequence listing (reference sequences) but that has at least 80%, preferably at least 85%, at least 90%, at least 95%, at least 96%, at least 97%, at least 98%, at least 99% identity with one such reference sequence, it may have insertions, deletions or substitutions with regard to the reference sequence. When it is a matter of substitutions, the substitution is preferably made with an "equivalent" amino acid, i.e., any amino acid whose structure is similar to that of the original amino acid and therefore unlikely to change the biological activity of the antibody. Examples of such substitutions are presented in Table 4 below:

TABLE 4

Substitutions with equivalent amino acids

| Original amino acid | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

The antibodies may be of several isotypes, according to the nature of their constant region: the γ, α, μ, ε and δ constant regions correspond to immunoglobulins IgG, IgA, IgM, IgE and IgD, respectively. Advantageously, the monoclonal antibody present in a composition used as a medicinal product in the context of the invention is of isotype IgG. Indeed, this isotype shows a capacity to generate antibody-dependent cell cytotoxicity (ADCC) activity in the greatest number of individuals (humans). The γ constant regions comprise several subtypes: γ1, γ2, γ3, these three types of constant regions having the feature of binding human complement, and γ4, thus creating the subtypes IgG1, IgG2, IgG3, and IgG4. Advantageously, the monoclonal antibody present in a composition used as a medicinal product in the context of the invention is of isotype IgG1 or IgG3, preferably IgG1.

The antibody, functional fragment or derivative thereof according to the invention is advantageously a chimeric or humanized antibody, in particular a chimeric antibody whose heavy and light chain constant region is of human origin.

By "chimeric" antibody is meant an antibody that contains a natural variable region (light chain and heavy chain) derived from an antibody of a given species in combination with the light and heavy chain constant regions of an antibody of a species heterologous to said given species. Advantageously, if the monoclonal antibody composition for use as a medicinal product according to the invention comprises a chimeric monoclonal antibody, the latter comprises human constant regions. From a non-human antibody, a chimeric antibody can be prepared by using the genetic recombination techniques well-known to a person skilled in the art. For example, the chimeric antibody can be prepared by cloning the heavy and light chains of a recombinant DNA comprising a promoter and a sequence encoding the variable region of the non-human antibody, and a sequence encoding the constant region of a human antibody. For methods for preparing chimeric antibodies, reference may be made, for example, to the document by Verhoeyen et al.—1988.

By "humanized" antibody is meant an antibody that contains CDRs derived from an antibody of non-human origin, the other portions of the antibody molecule being derived from one (or from several) human antibodies. Moreover, certain residues of the framework regions (FR) may be modified to retain binding affinity (Jones et al.—1986; Verhoeyen et al. 1988; Riechmann et al.—1988). The humanized antibodies according to the invention can be prepared by techniques known to a person skilled in the art such as CDR grafting, resurfacing, superhumanization, human string content, FR libraries, guided selection, FR shuffling and humaneering technologies, as summarized in the review by Almagro et al.—2008.

In addition to the five chimeric antibodies comprising the CDR or variable region sequences described above, the inventors also generated humanized antibodies derived from two of the five anti-CD303 antibodies obtained initially. To that end, for each of the two antibodies, several mutated heavy chain variable region sequences (mutations directed at making the sequence more similar to a human sequence) and several mutated light chain variable region sequences were generated and combined with each other in pairs to try to obtain humanized antibodies having the strongest possible capacity to bind to the human CD303 antigen (SEQ ID NO: 130) (advantageously at least 70% of the binding capacity of the murine or chimeric antibody, more advantageously similar to the binding capacity of the murine or chimeric antibody, even more advantageously higher than the binding capacity of the murine or chimeric antibody).

For antibody 122A2, the amino acid sequences of the heavy and light chain variable regions (humanized, i.e., mutated) that were tested are presented in Table 5 below:

TABLE 5

Amino acid sequences of the heavy and light chain variable regions (humanized, i.e., mutated) that were tested for the humanization of antibody 122A2.

| 122A2 - humanized heavy chain VH | Mutations relative to the chimeric VH sequence | Sequence |
| --- | --- | --- |
| 122A2-VHha | L12V/R14K/V17A/S45A/ A76V/T85S/A92S/E97D/ S99T/I101V/S123L | QVQLQQSGAEVVKPGASVKISCKGSGYTFTDYSM HWVKQAHAKSLEWIGVISTYYGDSNYNQKFKGKV TMTVDKSSSTAYMELSRLTSDDTAVYYCARNGNFY VMDYWGQGTLVTVSS (SEQ ID NO: 131) |

TABLE 5-continued

Amino acid sequences of the heavy and light chain variable regions (humanized, i.e., mutated) that were tested for the humanization of antibody 122A2.

| | | |
|---|---|---|
| 122A2-VHhb | L12V/R14K/V17A/K43R/ S45A/A76V/K82T/ T85S/A925/T95R/E97D/ S99T/I101V/S123L | QVQLQQSGAEVVKPGASVKISCKGSGYTFTDYSM HWVRQAHAKSLEWIGVISTYYGDSNYNQKFKGKV TMTVDTSSSTAYMELSRLRSDDTAVYYCARNGNFY VMDYWGQGTLVTVSS (SEQ ID NO: 132) |
| 122A2-VHhc | L12V/R14K/V17A/K43R/ S45A/H46P/A47G/ K48Q/S49G/A76V/T85S/ A92S/E97D/S99T/I101Y/ S123L | QVQLQQSGAEVVKPGASVKISCKGSGYTFTDYSM HWVRQAPGQGLEWIGVISTYYGDSNYNQKFKGKV TMTVDKSSSTAYMELSRLTSDDTAVYYCARNGNFY VMDYWGQGTLVTVSS (SEQ ID NO: 133) |

| 122A2 - humanized light chain VL | Mutations relative to the chimeric VL sequence | Sequence |
|---|---|---|
| 122A2-VKha | T7S/S22T/R24Q/S69T/ F103Y | DIQMTQSTSSLSASLGDRVTITCQASQDISNYLNWY QQKPDGTVKLLIYYTSRLHTGVPSRFSGSGSGTDY SLTISNLDQEDIATYYCQQGNTLPWTFGGGTKLEI K (SEQ ID NO: 134) |
| 122A2-VKhb | T7S/T8P/L15V/S22T/ R24Q/S69T/F103Y | DIQMTQSPSSLSASVGDRVTITCQASQDISNYLNWY QQKPDGTVKLLIYYTSRLHTGVPSRFSGSGSGTDY SLTISNLDQEDIATYYCQQGNTLPWTFGGGTKLEI K (SEQ ID NO: 135) |
| 122A2-VKhc | T7S/S22T/R24Q/R66N/ S69T/D95Q/F103Y | DIQMTQSTSSLSASLGDRVTITCQASQDISNYLNWY QQKPDGTVKLLIYYTSNLHTGVPSRFSGSGSGTDY SLTISNLQQEDIATYYCQQGNTLPWTFGGGTKLEI K (SEQ ID NO: 136) |
| 122A2-VKhd | T7S/T8P/L15V/S22T/ R24Q/R66N/S69T/D95Q/ F103Y | DIQMTQSPSSLSASVGDRVTITCQASQDISNYLNWY QQKPDGTVKLLIYYTSNLHTGVPSRFSGSGSGTDY SLTISNLQQEDIATYYCQQGNTLPWTFGGGTKLEI K (SEQ ID NO: 137) |

Humanized antibodies 122A2 are thus advantageously selected from those whose heavy chains comprise a variable region having an amino acid sequence selected from SEQ ID NOs: 131 to 133, advantageously from those whose heavy chains comprise a variable region having an amino acid sequence selected from SEQ ID NO: 131 and 132.

Humanized antibodies 122A2 are also advantageously selected from those whose light chains comprise a variable region having an amino acid sequence selected from SEQ ID NOs: 134 to 137, advantageously from those whose light chains comprise a variable region having an amino acid sequence selected from SEQ ID NO: 134 and 135.

The various humanized antibodies 122A2 generated by the inventors have heavy and light chains comprising variable regions having the amino acid sequences described in Table 6 below. The preferred humanized antibodies 122A2 (because they exhibit antigen-binding equal to or higher than that of the original chimeric antibody) are those whose heavy and light chains comprise variable regions having the amino acid sequences comprising those described for antibodies 122A2H5, 122A2H9, 122A2H6, 122A2H10, 122A2H14, 122A2H7, 122A2H11 and 122A2H15 in Table 6 below (shown in bold in Table 6 below). The most-preferred humanized antibodies 122A2 are those exhibiting higher antigen-binding than that of the original chimeric antibody: 122A2H5, 122A2H9, 122A2H6, 122A2H10, 122A2H14, 122A2H7, and in particular 122A2H5, 122A2H9, 122A2H7, and 122A2H10.

TABLE 6

Amino acid sequences comprised in the VH and VL domains of the humanized antibodies derived from chimeric antibody 122A2. The sequences corresponding to the preferred antibodies (because they exhibit antigen-binding equal to or higher than that of the original chimeric antibody in ELISA) are shown in bold.

| Humanized antibody derived from 122A2 | Amino acid sequence comprised in the VH domain | Amino acid sequence comprised in the VL (VK) domain |
|---|---|---|
| 122A2H5 | 122A2-VHha (SEQ ID NO: 131) | 122A2-VKha (SEQ ID NO: 134) |
| 122A2H9 | 122A2-VHha (SEQ ID NO: 131) | 122A2-VKhb (SEQ ID NO: 135) |
| 122A2H13 | 122A2-VHha (SEQ ID NO: 131) | 122A2-VKhc (SEQ ID NO: 136) |
| 122A2H17 | 122A2-VHha (SEQ ID NO: 131) | 122A2-VKhd (SEQ ID NO: 137) |
| 122A2H6 | 122A2-VHhb (SEQ ID NO: 132) | 122A2-VKha (SEQ ID NO: 134) |
| 122A2H10 | 122A2-VHhb (SEQ ID NO: 132) | 122A2-VKhb (SEQ ID NO: 135) |
| 122A2H14 | 122A2-VHhb (SEQ ID NO: 132) | 122A2-VKhc (SEQ ID NO: 136) |
| 122A2H18 | 122A2-VHhb (SEQ ID NO: 132) | 122A2-VKhd (SEQ ID NO: 137) |
| 122A2H7 | 122A2-VHhc (SEQ ID NO: 133) | 122A2-VKha (SEQ ID NO: 134) |
| 122A2H11 | 122A2-VHhc (SEQ ID NO: 133) | 122A2-VKhb (SEQ ID NO: 135) |
| 122A2H15 | 122A2-VHhc (SEQ ID NO: 133) | 122A2-VKhc (SEQ ID NO: 136) |
| 122A2H19 | 122A2-VHhc (SEQ ID NO: 133) | 122A2-VKhd (SEQ ID NO: 137) |

For antibody 102E9, the amino acid sequences of the heavy and light chain variable regions (humanized, i.e., mutated) that were tested are presented in Table 7 below:

TABLE 7

Amino acid sequences of the heavy and light chain variable regions (humanized, i.e., mutated) that were tested for the humanization of antibody 102E9.

| 102E9 - humanized heavy chain VH | Mutations relative to the chimeric VH sequence* | Sequence |
|---|---|---|
| 102E9-VHha | D11E/T18S/K48Q/A77V/ E81D/S82T/A84V/F88Y/ N93S/F103Y | QIHLVQSGPELKKPGESVKISCKASGYTFTDYSM HWVKQAPGQGLKWMGWINTETGEPTYADDFK GRFVFSLDTSVSTAYLQINSLKNEDTSTYYCTRN GYYVGYYAMDYWGQGTSVTVSS (SEQ ID NO: 138) |
| 102E9-VHhb | D11E/T18S/K43R/K48Q/ D69Q/A77V/E81D/S82T/ A84V/F88Y/N93S/F103Y | QIHLVQSGPELKKPGESVKISCKASGYTFTDYSM HWVRQAPGQGLKWMGWINTETGEPTYAQDFK GRFVFSLDTSVSTAYLQINSLKNEDTSTYYCTRN GYYVGYYAMDYWGQGTSVTVSS (SEQ ID NO: 139) |
| 102E9-VHhc | P95/D11E/T18S/K43R/ K48Q/D69Q/A77V/E81D/ S82T/A84V/F88Y/N93S/ F103Y | QIHLVQSGSELKKPGESVKISCKASGYTFTDYSMH WVRQAPGQGLKWMGWINTETGEPTYAQDFKG RFVFSLDTSVSTAYLQINSLKNEDTSTYYCTRNGY YVGYYAMDYWGQGTSVTVSS (SEQ ID NO: 140) |

| 102E9 - humanized light chain VL | Mutations relative to the chimeric VL sequence | Sequence |
|---|---|---|
| 102E9-VKha | V3Q/A9S/I10F/M11L/ K18R/T48K/S49A/A74S/ S86E/S88T/R93S/A99F | QIQLTQSPSFLSASPGERVTITCSASSSVIYIHWFQ QKPGKAPKLWIYSTSYLASGVPSRFSGSGSGTEY TLTISSMEAEDFATYYCQQRRSYPFTFGGGTKLEI K (SEQ ID NO: 141) |
| 102E9-VKhb | V3Q/A9S/I10F/M11L/ K18R/S49A/A74S/S88T/ A99F | QIQLTQSPSFLSASPGERVTITCSASSSVIYIHWFQ QKPGTAPKLWIYSTSYLASGVPSRFSGSGSGTSY TLTISRMEAEDFATYYCQQRRSYPFTFGGGTKLE IK (SEQ ID NO: 142) |
| 102E9-VKhc | V3Q/A9S/I10F/M11L/ E17D/K18R/T48K/S49A/ A74S/S86E/S88T/R93S/ E95Q/A99F | QIQLTQSPSFLSASPGDRVTITCSASSSVIYIHWFQ QKPGKAPKLWIYSTSYLASGVPSRFSGSGSGTEY TLTISSMQAEDFATYYCQQRRSYPFTFGGGTKLE IK (SEQ ID NO: 143) |

*The position of the amino acid residues corresponds to IMGT unique numbering.

Humanized antibodies 102E9 are thus advantageously selected from those whose heavy chains comprise a variable region having an amino acid sequence selected from SEQ ID NOs: 138 to 140, advantageously from those whose heavy chains comprise a variable region having the amino acid sequence SEQ ID NO: 139.

Humanized antibodies 102E9 are also advantageously selected from those whose light chains comprise a variable region having an amino acid sequence selected from SEQ ID NOs: 141 to 143, advantageously from those whose light chains comprise a variable region having the amino acid sequence SEQ ID NO: 142.

The various humanized antibodies 102E9 generated by the inventors have heavy and light chains comprising variable regions having the amino acid sequences described in Table 8 below. The preferred humanized antibodies 102E9 (because they exhibit binding on the level of the chimeric antibody similar to that of the original chimeric antibody: at least 70% of the binding of the chimeric antibody in ELISA) are those whose heavy and light chains comprise variable regions having the amino acid sequences comprising those described for antibodies 102E9H6, 102E9H7, 102E9H9, and 102E9H10 in Table 8 below (shown in bold in Table 8 below), more advantageously those whose heavy and light chains comprise variable regions having the amino acid sequences comprising those described for antibody 102E9H10 in Table 8 below.

TABLE 8

Amino acid sequences comprised in the VH and VL domains of the humanized antibodies derived from chimeric antibody 102E9. The sequences corresponding to the preferred antibodies (because they exhibit binding on the level of the chimeric antibody similar to that of the original chimeric antibody: at least 70% of the binding of the chimeric antibody in ELISA) are shown in bold.

| Humanized antibody derived from 102E9 | Amino acid sequence comprised in the VH domain | Amino acid sequence comprised in the VL (VK) domain |
|---|---|---|
| 102E9H5 | 102E9-VHha (SEQ ID NO: 138) | 102E9-VKha (SEQ ID NO: 141) |
| 102E9H9 | 102E9-VHha (SEQ ID NO: 138) | 102E9-VKhb (SEQ ID NO: 142) |
| 102E9H13 | 102E9-VHha (SEQ ID NO: 138) | 102E9-VKhc (SEQ ID NO: 143) |
| 102E9H6 | 102E9-VHhb (SEQ ID NO: 139) | 102E9-VKha (SEQ ID NO: 141) |
| 102E9H10 | 102E9-VHhb (SEQ ID NO: 139) | 102E9-VKhb (SEQ ID NO: 142) |
| 102E9H14 | 102E9-VHhb (SEQ ID NO: 139) | 102E9-VKhc (SEQ ID NO: 143) |
| 102E9H7 | 102E9-VHhc (SEQ ID NO: 140) | 102E9-VKha (SEQ ID NO: 141) |
| 102E9H11 | 102E9-VHhc (SEQ ID NO: 140) | 102E9-VKhb (SEQ ID NO: 142) |
| 102E9H15 | 102E9-VHhc (SEQ ID NO: 140) | 102E9-VKhc (SEQ ID NO: 143) |

An antibody, functional fragment or derivative thereof according to the invention, which is chimeric with human constant regions, or else humanized, will advantageously comprise a human heavy chain constant region having the amino acid sequence SEQ ID NO: 53 or SEQ ID NO: 144 (which corresponds to the human heavy chain constant region sequence SEQ ID NO: 53 with an additional C-terminal lysine residue). Additionally or alternatively, an antibody, functional fragment or derivative thereof according to the invention, which is chimeric with human, or else humanized, constant regions will advantageously comprise a human light chain constant region having the amino acid sequence SEQ ID NO: 54. Preferred human heavy chain (SEQ ID NO: 53 or SEQ ID NO: 144) or light chain (SEQ ID NO: 54) constant region sequences, of isotype IgG1, are presented in Table 9 below.

TABLE 9

Preferred human heavy chain (SEQ ID NO: 53 or SEQ ID NO: 144) or light chain (SEQ ID NO: 54) constant region sequences. Human heavy chain constant region SEQ ID NO: 144 corresponds to human heavy chain constant region SEQ ID NO: 53 with an additional C-terminal lysine residue.

| | |
|---|---|
| Preferred human heavy chain constant region (IgG1) | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHTC PPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKS LSLSPG (SEQ ID NO: 53) |
| Preferred human heavy chain constant region (IgG1) | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHTC PPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKS LSLSPGK (SEQ ID NO: 144) |
| Preferred human light chain constant region (IgG1) | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 54) |

Thus, the heavy and light chains of the chimeric or humanized antibodies, functional fragments or derivatives thereof according to the invention advantageously comprise the sequences described in Table 10 below (or consist essentially of or consist of such sequences).

TABLE 10

Heavy and light chain amino acid sequences of the chimeric or humanized antibodies according to the invention.

| Antibody | Heavy chain | Light chain |
|---|---|---|
| Chimeric antibodies | | |
| 122A2 | Fusion SEQ ID NO: 43-SEQ ID NO: 53 (SEQ ID NO: 55) | Fusion SEQ ID NO: 48-SEQ ID NO: 54 (SEQ ID NO: 60) |
| 102E9 | Fusion SEQ ID NO: 44-SEQ ID NO: 53 (SEQ ID NO: 56) | Fusion SEQ ID NO: 49-SEQ ID NO: 54 (SEQ ID NO: 61) |
| 104C12 | Fusion SEQ ID NO: 45-SEQ ID NO: 53 (SEQ ID NO: 57) | Fusion SEQ ID NO: 50-SEQ ID NO: 54 (SEQ ID NO: 62) |
| 114D11 | Fusion SEQ ID NO: 46-SEQ ID NO: 53 (SEQ ID NO: 58) | Fusion SEQ ID NO: 51-SEQ ID NO: 54 (SEQ ID NO: 63) |
| 104E10 | Fusion SEQ ID NO: 47-SEQ ID NO: 53 (SEQ ID NO: 59) | Fusion SEQ ID NO: 52-SEQ ID NO: 54 (SEQ ID NO: 64) |
| 122A2 | Fusion SEQ ID NO: 43-SEQ ID NO: 144 (SEQ ID NO: 145) | Fusion SEQ ID NO: 48-SEQ ID NO: 54 (SEQ ID NO: 60) |
| 102E9 | Fusion SEQ ID NO: 44-SEQ ID NO: 144 (SEQ ID NO: 146) | Fusion SEQ ID NO: 49-SEQ ID NO: 54 (SEQ ID NO: 61) |
| 104C12 | Fusion SEQ ID NO: 45-SEQ ID NO: 144 (SEQ ID NO: 147) | Fusion SEQ ID NO: 50-SEQ ID NO: 54 (SEQ ID NO: 62) |
| 114D11 | Fusion SEQ ID NO: 46-SEQ ID NO: 144 (SEQ ID NO: 148) | Fusion SEQ ID NO: 51-SEQ ID NO: 54 (SEQ ID NO: 63) |
| 104E10 | Fusion SEQ ID NO: 47-SEQ ID NO: 144 (SEQ ID NO: 149) | Fusion SEQ ID NO: 52-SEQ ID NO: 54 (SEQ ID NO: 64) |
| Humanized antibodies | | |
| 122A2H5 | Fusion SEQ ID NO: 131-SEQ ID NO: 144 | Fusion SEQ ID NO: 134-SEQ ID NO: 54 (SEQ ID NO: 153) |
| 122A2H9 | (SEQ ID NO: 150) | Fusion SEQ ID NO: 135-SEQ ID NO: 54 (SEQ ID NO: 154) |

TABLE 10-continued

Heavy and light chain amino acid sequences of the chimeric or humanized antibodies according to the invention.

| Antibody | Heavy chain | Light chain |
|---|---|---|
| 122A2H13 | | Fusion SEQ ID NO: 136-SEQ ID NO: 54 (SEQ ID NO: 155) |
| 122A2H17 | | Fusion SEQ ID NO: 137-SEQ ID NO: 54 (SEQ ID NO: 156) |
| 122A2H6 | Fusion SEQ ID NO: 132-SEQ ID NO: 144 | Fusion SEQ ID NO: 134-SEQ ID NO: 54 (SEQ ID NO: 153) |
| 122A2H10 | (SEQ ID NO: 151) | Fusion SEQ ID NO: 135-SEQ ID NO: 54 (SEQ ID NO: 154) |
| 122A2H14 | | Fusion SEQ ID NO: 136-SEQ ID NO: 54 (SEQ ID NO: 155) |
| 122A2H18 | | Fusion SEQ ID NO: 137-SEQ ID NO: 54 (SEQ ID NO: 156) |
| 122A2H7 | Fusion SEQ ID NO: 133-SEQ ID NO: 144 | Fusion SEQ ID NO: 134-SEQ ID NO: 54 (SEQ ID NO: 153) |
| 122A2H11 | (SEQ ID NO: 152) | Fusion SEQ ID NO: 135-SEQ ID NO: 54 (SEQ ID NO: 154) |
| 122A2H15 | | Fusion SEQ ID NO: 136-SEQ ID NO: 54 (SEQ ID NO: 155) |
| 122A2H19 | | Fusion SEQ ID NO: 137-SEQ ID NO: 54 (SEQ ID NO: 156) |
| 102E9H5 | Fusion SEQ ID NO: 138-SEQ ID NO: 144 | Fusion SEQ ID NO: 141-SEQ ID NO: 54 (SEQ ID NO: 160) |
| 102E9H9 | (SEQ ID NO: 157) | Fusion SEQ ID NO: 142-SEQ ID NO: 54 (SEQ ID NO: 161) |
| 102E9H13 | | Fusion SEQ ID NO: 143-SEQ ID NO: 54 (SEQ ID NO: 162) |
| 102E9H6 | Fusion SEQ ID NO: 139-SEQ ID NO: 144 | Fusion SEQ ID NO: 141-SEQ ID NO: 54 (SEQ ID NO: 160) |
| 102E9H10 | (SEQ ID NO: 158) | Fusion SEQ ID NO: 142-SEQ ID NO: 54 (SEQ ID NO: 161) |
| 102E9H14 | | Fusion SEQ ID NO: 143-SEQ ID NO: 54 (SEQ ID NO: 162) |
| 102E9H7 | Fusion SEQ ID NO: 140-SEQ ID NO: 144 | Fusion SEQ ID NO: 141-SEQ ID NO: 54 (SEQ ID NO: 160) |
| 102E9H11 | (SEQ ID NO: 159) | Fusion SEQ ID NO: 142-SEQ ID NO: 54 (SEQ ID NO: 161) |
| 102E9H15 | | Fusion SEQ ID NO: 143-SEQ ID NO: 54 (SEQ ID NO: 162) |

The heavy and/or light chain of the antibody, functional fragment or derivative thereof according to the invention advantageously further comprises at least one heterologous signal peptide of sequence SEQ ID NO: 65 (MRWSWI-FLLLLSITSANA, signal peptide MB7). Indeed, this peptide has been shown to improve the expression and secretion of recombinant proteins in higher eukaryotic cell lines (see WO2011/114063). Thus, the heavy chains of the antibodies, functional fragments or derivatives thereof according to the invention advantageously comprise an amino acid sequence selected from SEQ ID NOs: 66 to 70, consisting of the N- to C-terminal fusion of the amino acid sequence of signal peptide MB7 (SEQ ID NO: 65) to one of the amino acid sequences of the VH region of the antibodies according to the invention (SEQ ID NOs: 43 to 47), or consist essentially of or consist of such sequences. Additionally or alternatively, the light chains of the antibodies, functional fragments or derivatives thereof according to the invention advantageously comprise an amino acid sequence selected from SEQ ID NOs: 71 to 75, consisting of the N- to C-terminal fusion of the amino acid sequence of signal peptide MB7 (SEQ ID NO: 65) to one of the amino acid sequences of the VL region of the antibodies according to the invention (SEQ ID NOs: 48 to 52), or consist essentially of or consist of such sequences.

By adding the preferred heavy and light chain constant regions, the preferred complete amino acid sequences of the antibodies according to the invention are obtained, as described in Table 11 below. For the heavy chain, the constant region may further contain an additional C-terminal lysine residue. Thus, the heavy and light chains of the chimeric or humanized antibodies, functional fragments or derivatives thereof according to the invention advantageously comprise the sequences described in Table 11 below (or consist essentially of or consist of such sequences).

TABLE 11

Heavy and light chain amino acid sequences of the chimeric and humanized antibodies according to the invention, with signal peptide MB7.

| Antibody | Heavy chain | Light chain |
|---|---|---|
| Chimeric antibodies | | |
| 122A2 | Fusion SEQ ID NO: 65-SEQ ID NO: 43-SEQ ID NO: 53 (SEQ ID NO: 76) | Fusion SEQ ID NO: 65-SEQ ID NO: 48-SEQ ID NO: 54 (SEQ ID NO: 81) |

TABLE 11-continued

Heavy and light chain amino acid sequences of the chimeric and humanized antibodies according to the invention, with signal peptide MB7.

| Antibody | Heavy chain | Light chain |
|---|---|---|
| 102E9 | Fusion SEQ ID NO: 65-SEQ ID NO: 44-SEQ ID NO: 53 (SEQ ID NO: 77) | Fusion SEQ ID NO: 65-SEQ ID NO: 49-SEQ ID NO: 54 (SEQ ID NO: 82) |
| 104C12 | Fusion SEQ ID NO: 65-SEQ ID NO: 45-SEQ ID NO: 53 (SEQ ID NO: 78) | Fusion SEQ ID NO: 65-SEQ ID NO: 50-SEQ ID NO: 54 (SEQ ID NO: 83) |
| 114D11 | Fusion SEQ ID NO: 65-SEQ ID NO: 46-SEQ ID NO: 53 (SEQ ID NO: 79) | Fusion SEQ ID NO: 65-SEQ ID NO: 51-SEQ ID NO: 54 (SEQ ID NO: 84) |
| 104E10 | Fusion SEQ ID NO: 65-SEQ ID NO: 47-SEQ ID NO: 53 (SEQ ID NO: 80) | Fusion SEQ ID NO: 65-SEQ ID NO: 52-SEQ ID NO: 54 (SEQ ID NO: 85) |
| 122A2 | Fusion SEQ ID NO: 65-SEQ ID NO: 43-SEQ ID NO: 144 (SEQ ID NO: 163) | Fusion SEQ ID NO: 65-SEQ ID NO: 48-SEQ ID NO: 54 (SEQ ID NO: 81) |
| 102E9 | Fusion SEQ ID NO: 65-SEQ ID NO: 44-SEQ ID NO: 144 (SEQ ID NO: 164) | Fusion SEQ ID NO: 65-SEQ ID NO: 49-SEQ ID NO: 54 (SEQ ID NO: 82) |
| 104C12 | Fusion SEQ ID NO: 65-SEQ ID NO: 45-SEQ ID NO: 144 (SEQ ID NO: 165) | Fusion SEQ ID NO: 65-SEQ ID NO: 50-SEQ ID NO: 54 (SEQ ID NO: 83) |
| 114D11 | Fusion SEQ ID NO: 65-SEQ ID NO: 46-SEQ ID NO: 144 (SEQ ID NO: 166) | Fusion SEQ ID NO: 65-SEQ ID NO: 51-SEQ ID NO: 54 (SEQ ID NO: 84) |
| 104E10 | Fusion SEQ ID NO: 65-SEQ ID NO: 47-SEQ ID NO: 144 (SEQ ID NO: 167) | Fusion SEQ ID NO: 65-SEQ ID NO: 52-SEQ ID NO: 54 (SEQ ID NO: 85) |
| Humanized antibodies | | |
| 122A2H5 | Fusion SEQ ID NO: 65-SEQ ID NO: 131-SEQ ID NO: 144 (SEQ ID NO: 168) | Fusion SEQ ID NO: 65-SEQ ID NO: 134-SEQ ID NO: 54 (SEQ ID NO: 171) |
| 122A2H9 | | Fusion SEQ ID NO: 65-SEQ ID NO: 135-SEQ ID NO: 54 (SEQ ID NO: 172) |
| 122A2H13 | | Fusion SEQ ID NO: 65-SEQ ID NO: 136-SEQ ID NO: 54 (SEQ ID NO: 173) |
| 122A2H17 | | Fusion SEQ ID NO: 65-SEQ ID NO: 137-SEQ ID NO: 54 (SEQ ID NO: 174) |
| 122A2H6 | Fusion SEQ ID NO: 65-SEQ ID NO: 132-SEQ ID NO: 144 (SEQ ID NO: 169) | Fusion SEQ ID NO: 65-SEQ ID NO: 134-SEQ ID NO: 54 (SEQ ID NO: 171) |
| 122A2H10 | | Fusion SEQ ID NO: 65-SEQ ID NO: 135-SEQ ID NO: 54 (SEQ ID NO: 172) |
| 122A2H14 | | Fusion SEQ ID NO: 65-SEQ ID NO: 136-SEQ ID NO: 54 (SEQ ID NO: 173) |
| 122A2H18 | | Fusion SEQ ID NO: 65-SEQ ID NO: 137-SEQ ID NO: 54 (SEQ ID NO: 174) |
| 122A2H7 | Fusion SEQ ID NO: 65-SEQ ID NO: 133-SEQ ID NO: 144 (SEQ ID NO: 170) | Fusion SEQ ID NO: 65-SEQ ID NO: 134-SEQ ID NO: 54 (SEQ ID NO: 171) |
| 122A2H11 | | Fusion SEQ ID NO: 65-SEQ ID NO: 135-SEQ ID NO: 54 (SEQ ID NO: 172) |
| 122A2H15 | | Fusion SEQ ID NO: 65-SEQ ID NO: 136-SEQ ID NO: 54 (SEQ ID NO: 173) |
| 122A2H19 | | Fusion SEQ ID NO: 65-SEQ ID NO: 137-SEQ ID NO: 54 (SEQ ID NO: 174) |
| 102E9H5 | Fusion SEQ ID NO: 65-SEQ ID NO: 138-SEQ ID NO: 144 (SEQ ID NO: 175) | Fusion SEQ ID NO: 65-SEQ ID NO: 141-SEQ ID NO: 54 (SEQ ID NO: 178) |
| 102E9H9 | | Fusion SEQ ID NO: 65-SEQ ID NO: 142-SEQ ID NO: 54 (SEQ ID NO: 179) |
| 102E9H13 | | Fusion SEQ ID NO: 65-SEQ ID NO: 143-SEQ ID NO: 54 (SEQ ID NO: 180) |

TABLE 11-continued

Heavy and light chain amino acid sequences of the chimeric and humanized antibodies according to the invention, with signal peptide MB7.

| Antibody | Heavy chain | Light chain |
| --- | --- | --- |
| 102E9H6 | Fusion SEQ ID NO: 65-SEQ ID NO: 139-SEQ ID NO: 144 (SEQ ID NO: 176) | Fusion SEQ ID NO: 65-SEQ ID NO: 141-SEQ ID NO: 54 (SEQ ID NO: 178) |
| 102E9H10 | | Fusion SEQ ID NO: 65-SEQ ID NO: 142-SEQ ID NO: 54 (SEQ ID NO: 179) |
| 102E9H14 | | Fusion SEQ ID NO: 65-SEQ ID NO: 143-SEQ ID NO: 54 (SEQ ID NO: 180) |
| 102E9H7 | Fusion SEQ ID NO: 65-SEQ ID NO: 140-SEQ ID NO: 144 (SEQ ID NO: 177) | Fusion SEQ ID NO: 65-SEQ ID NO: 141-SEQ ID NO: 54 (SEQ ID NO: 178) |
| 102E9H11 | | Fusion SEQ ID NO: 65-SEQ ID NO: 142-SEQ ID NO: 54 (SEQ ID NO: 179) |
| 102E9H15 | | Fusion SEQ ID NO: 65-SEQ ID NO: 143-SEQ ID NO: 54 (SEQ ID NO: 180) |

The antibody, functional fragment or derivative thereof according to the invention may be produced from any host cell, any transgenic non-human animal or any transgenic plant described in the present description, and notably below in the section concerning the nucleic acids, vectors, host cells, transgenic non-human animals and transgenic plants according to the invention.

By "functional fragment" is meant an antibody fragment retaining the antigen-binding domain and thus having the same antigen specificity as the original antibody, such as the fragments Fv, ScFv, Fab, F(ab')$_2$, Fab', scFv-Fc or diabodies. A functional antibody fragment according to the invention is thus advantageously selected from the fragments Fv, ScFv, Fab, F(ab')$_2$, Fab', scFv-Fc or diabodies.

By "derivative" of an antibody is meant a fusion protein consisting of a carrier peptide and at least one CDR of the original antibody allowing it to retain its ability to recognize CD303.

The antibody, functional fragment or derivative thereof according to the invention advantageously has a low fucose content, of less than or equal to 65%.

By "fucose content" is meant the percentage of fucosylated forms within N-glycans attached to the Asn297 residue of the Fc fragment of each heavy chain of each antibody. By "low fucose content" is meant a fucose content of less than or equal to 65%. Indeed, it is known today that the fucose content of an antibody composition plays a crucial role in the capacity of said composition to induce a strong ADCC response via FcγRIII. Advantageously, the fucose content is less than or equal to 65%, preferably less than or equal to 60%, 55% or 50%, even less than or equal to 45%, 40%, 35%, 30%, 25% or 20%. However, it is not necessary that the fucose content is nil, and it may for example be greater than or equal to 5%, 10%, 15% or 20%. The fucose content may for example be between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 15% and 65%, between 15% and 60%, between 15% and 55%, between 15% and 50%, between 15% and 45%, between 15% and 40%, between 15% and 35%, between 15% and 30%, between 15% and 25%, between 15% and 20%, between 20% and 65%, between 20% and 60%, between 20% and 55%, between 20% and 50%, between 20% and 45%, between 20% and 40%, between 20% and 35%, between 20% and 30%, between 20% and 25%.

The antibody, functional fragment or derivative thereof according to the invention may moreover have different types of glycosylation (N-glycans of the oligomannose or biantennary complex type, with a variable proportion of bisecting N-acetylglucosamine (GlcNAc) residues, or of galactose residues in the case of N-glycans of the biantennary complex type), provided that they have a low fucose content. Thus, oligomannose-type N-glycans may be obtained by culturing in the presence of various glycosylation inhibitors, such as α1,2-mannosidase I inhibitors (such as deoxymannojirimycin (DMM)) or α-glucosidase inhibitors (such as castanospermine (Cs)); or by producing the antibody in the CHO cell line Lec1. Production in the milk of transgenic goats also leads to an antibody whose majority N-glycan is of the oligomannose type, with as minority forms fucosylated biantennary complex forms with one or two galactoses, without bisecting GlcNAc and without sialylation (G1F or G2F) (see WO2007/048077). N-glycans of the biantennary complex type may be obtained in most mammalian cells, but also in bacteria, yeasts or plants whose glycosylation machinery has been modified. To limit the fucose content, cell lines naturally having low activity of the enzyme 1,6-fucosyltransferase (FUT8) responsible for the addition of fucose on the GlcNAc bound to the Fc fragment; such as the YB2/0 cell line, duck embryonic cell line EB66®, rat hepatoma cell lines H4-II-E (DSM ACC3129) and H4-II-Es (DSM ACC3130) or the lines NM-H9D8-E6 (DSM ACC 2807) and NM H9D8-E6Q12 (DSM ACC 2856) may be used. Lines mutant for other genes and whose expression or overexpression leads to a low fucose content may also be used, such as the CHO cell line Lec13, a mutant of the CHO line having decreased synthesis of GDP-fucose. It is also possible to select a line of interest and to decrease or abolish (notably by using interfering RNAs or by mutation or deletion of the gene expressing the protein of interest) the expression of a protein involved in the N-glycan fucosylation pathway (notably FUT8, see Yamane-Ohnuki et al.—2004; but also GMD, a gene involved in GDP-fucose transport, see Kanda et al.—2007). Another alternative consists in selecting a cell line of interest and in overexpressing a protein that interferes in some way with the fucosylation of N-glycans, such as the GnTIII (β(1,4)-N-acetylglucosaminetransferase III) protein. In particular, antibodies having low fucosylated N-glycans were notably obtained by:

- Production in YB2/0 (see EP1176195A1, WO01/77181, Shinkawa et al.—2003), CHO Lec13 (see Shields et al.—2002), EB66® (Olivier et al.—2010), the rat hepatoma cell lines H4-II-E (DSM ACC3129), H4-II-Es (DSM ACC3130) (see WO2012/041768) and the human lines NM-H9D8 (DSM ACC2806), NM-H9D8-E6 (DSM ACC 2807) and NM H9D8-E6Q12 (DSM ACC 2856) (see WO2008/028686).

- Production in a wild-type CHO cell line in the presence of small interfering RNAs directed against FUT8 (Mori et al.—2004, Suzuki et al.—2007, Cardarelli et al.—2009, Cardarelli et al.—2010, Herbst et al.—2010) or GMD (gene encoding the GDP-fucose transporter in the Golgi apparatus, see Imai-Nishiya et al.—2007).

- Production in a CHO cell line in which both alleles of the FUT8 gene encoding 1,6-fucosyltransferase have been deleted (Yamane-Ohnuki et al.—2004), or in which both alleles of the GMD gene encoding the GDP-fucose transporter in the Golgi apparatus have been deleted (Kanda et al.—2007).

- Production in a CHO cell line in which the gene encoding the GnTIII (β(1,4)-N-acetylglucosaminetransferase III) enzyme was overexpressed transgenically (Umana et al.—1999). In addition to low fucosylation, the N-glycans obtained are characterized by a high bisecting GlcNAc content.

- Production in transgenic plants (*N. benthamiana*), with a strong reduction of the β1,2-xylose and α1,3-fucose residue contents by means of the use of small interfering RNAs (Forthal et al.—2010).

Oligomannose-type N-glycans have a reduced in vivo half-life compared to biantennary complex-type N-glycans. Consequently, advantageously, the antibodies according to the invention have, on their Fc-fragment N-glycosylation sites, biantennary complex-type glycan structures with a low fucose content as defined above.

In particular, the monoclonal antibody according to the invention may have a content of G0+G1+G0F+G1F forms greater than 60% and a low fucose content as defined above. It may also have a content of G0+G1+G0F+G1F forms greater than 65% and a low fucose content as defined above. It may also have a content of G0+G1+G0F+G1F forms greater than 70% and a low fucose content as defined above. It may also have a content of G0+G1+G0F+G1F forms greater than 75% and a low fucose content as defined above. It may also have a content of G0+G1+G0F+G1F forms greater than 80% and a low fucose content as defined above. It may also have a content of G0+G1+G0F+G1F forms greater than 60%, 65%, 70%, 75% or 80% and a content of G0F+G1F forms of less than 50%. The forms G0, G1, G0F and G1F are as defined below:

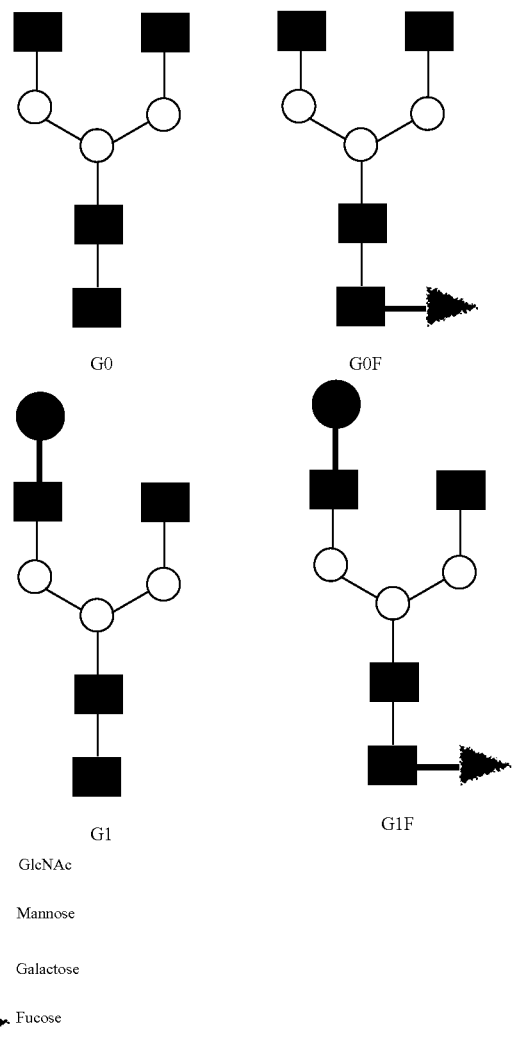

■ GlcNAc
○ Mannose
● Galactose
▶ Fucose

Such antibody compositions may notably be obtained by production in YB2/0 cells, in CHO Lec13 cells, in wild-type CHO cell lines cultured in the presence of small interfering RNAs directed against FUT8 or GMD, or in CHO cell lines in which both alleles of the FUT8 gene encoding 1,6-fucosyltransferase or both alleles of the GMD gene encoding the GDP-fucose transporter in the Golgi apparatus have been deleted.

However, in another embodiment, the antibody, functional fragment or derivative thereof according to the invention has a high oligomannose-type N-glycans content.

By "oligomannose-type N-glycans" is meant N-glycans whose pentasaccharide core, consisting of two N-acetylglucosamine (GlcNAc) residues (one of them being bound to the Asn297 residue of the Fc fragment of the antibody) and three mannose residues, is supplemented by one to six additional mannoses bound to the terminal mannose residues of the pentasaccharide core. The oligomannose-type N-glycans are not fucosylated.

By "oligomannose-type N-glycans content" is meant the percentage of oligomannose forms within N-glycans attached to the Asn297 residue of the Fc fragment of each heavy chain of each antibody. By "high oligomannose-type N-glycans content" is meant an oligomannose-type N-glycans content of greater than or equal to 30%, advantageously greater than or equal to 35%, greater than or equal to 40%, greater than or equal to 45%, greater than or equal to 50%, greater than or equal to 55%, greater than or equal to 60%, greater than or equal to 65%, greater than or equal to 70%, greater than or equal to 75%, greater than or equal to 80%, greater than or equal to 85%, greater than or equal to 90%, or even greater than or equal to 95%.

In addition or alternatively to a low fucose content, the antibody, functional fragment or derivative thereof according to the invention has a high galactose content.

By "galactose content" or "galactosylation level" of the antibody is meant a percentage calculated from an analytical chromatogram of the N-glycans released from the antibody, according to the following formula:

$$\text{galactose content} = \frac{\sum_{i=1}^{n} (\text{number of Gal}) \times (\% \text{ relative area})}{\sum_{i=1}^{n} (\text{number of } A) \times (\% \text{ relative area})} \times 100$$

wherein:
- "n" is the number of N-glycan peaks analyzed on a chromatogram, for example a normal-phase high-performance liquid chromatography (NP-HPLC) spectrum,
- "number of Gal" is the number of galactoses on the antenna of the glycan corresponding to the peak,
- "number of A" is the number of N-acetyl-glucosamine antennas of the glycan form corresponding to the peak, and
- "% relative area" is the percentage of the area under the corresponding peak.

By "high galactose content" is meant a galactose content of greater than or equal to 30%, advantageously greater than or equal to 50%, advantageously greater than or equal to 55%, greater than or equal to 60%, greater than or equal to 65%, greater than or equal to 70%, greater than or equal to 75%, greater than or equal to 80%, greater than or equal to 85%, greater than or equal to 90%, greater than or equal to 95%, or even equal to 100%.

The present invention also relates to a monoclonal antibody directed against the ectodomain of the human CD303 antigen (SEQ ID NO: 130), or a functional fragment or a derivative thereof, characterized in that:
a) it has improved affinity for FcγRIIIa (CD16a) compared to antibodies directed against the ectodomain of the human CD303 antigen, produced in CHO cells; and
b) the light and heavy chain constant regions are constant regions from a non-murine species.

The affinity of the Fc fragment of an antibody for FcγRIIIa (CD16a) may be measured by several methods, including surface plasmon resonance (SPR, notably using a BIAcore 2000 device—Pharmacia Biosensor, Upsala, Sweden) and Scatchard analysis. Eight genes encoding FcγR have been identified in humans, but only five encode expressed receptors (FcγRIa, FcγRIIa, FcγRIIb, FcγRIIIa, FcγRIIIb). All are effector cell-activating receptors, except for FcγRIIb, which is an immune cell activation-inhibiting receptor. FcγRIa is characterized by high affinity for immunoglobulins (Kd of $5 \cdot 10^{-7}$ to $10^{-10}$ M) while FcγRIIa, FcγRIIb, FcγRIIIa, FcγRIIIb are characteristic of low-affinity receptors (Kd below $10^{-7}$ M). The antibodies according to the invention have improved affinity for FcγRIIIa (CD16a) compared to antibodies directed against the ectodomain of the human CD303 antigen produced in CHO cells. In the context of this comparison, reference is preferably made to a wild-type CHO cell line producing in normal conditions antibodies in which the Fc fragment is highly fucosylated (at least 80%, preferably at least 90% of the oligosaccharides attached to the Fc fragment are fucosylated), such as one of the following lines: CHO-K-1 (ATCC® CCL-61™), CHO Pro-5 (ATCC® CRL-1781™), CHO dhfr-(ATCC® CRL-9096™), CHO-DP12 (ATCC® CRL-12444™ or ATCC® CRL-12445™), CHO DUKX-B11 (ATCC CRL-9010), and CHO DG-44 (Urlaub et al., Cell 33[2], 405-412, 1983). The antibodies according to the invention which have improved affinity for FcγRIIIa (CD16a) compared to antibodies directed against the ectodomain of the human CD303 antigen produced in CHO cells (as defined above) have the advantage that this improved affinity enables them not to be displaced, or to be less displaced, from FcγRIIIa (CD16a) by polyclonal IgG antibodies, notably the IgG present in serum. Such antibodies advantageously have high affinity for FcγRIIIa (CD16a), i.e., affinity at least equal to $2 \cdot 10^6$ M$^{-1}$, at least equal to $2 \cdot 10^7$M$^{-1}$, $2 \cdot 10^8$M$^{-1}$ or $2 \cdot 10^9$M$^{-1}$, as determined by Scatchard analysis or BIAcore (label-free surface plasmon resonance-based) technology.

High affinity for FcγRIIIa (CD16a), significantly improved compared to antibodies produced in CHO cells, may be obtained in the various ways described above for the antibody, functional fragment or derivative thereof according to the invention defined by its capacity to compete for binding to the CD303 ectodomain with the specific antibodies developed by the inventors and by the fact that the constant regions of its light and heavy chains are constant regions from a non-murine species. In particular, high affinity for FcγRIIIa (CD16a), significantly improved compared to antibodies produced in CHO cells, may be obtained by:
- The presence of mutations in the Fc fragment that increase FcγRIIIa (CD16a)-binding, as described above (in particular mutations that increase the FcγRIIIa (CD16a)-binding described in WO00/42072, Shields et al.—2001, Lazar et al.—2006, WO2004/029207, WO2004/063351, WO2004/074455); and/or
- Controlling the glycosylation of the antibody, notably:
  - Low fucose content, within biantennary complex forms and/or via a high oligomannose-type N-glycans content, as described above, and/or
  - High galactose content, as described above.

Such an antibody according to the invention may in addition have any characteristic or combination of characteristics described above for the antibody, functional fragment or derivative thereof according to the invention defined by its capacity to compete for binding to the CD303 ectodomain with the specific antibodies developed by the inventors and by the fact that the constant regions of its light and heavy chains are constant regions from a non-murine species.

Nucleic Acids, Vectors, Host Cells, Transgenic Non-Human Animals and Transgenic Plants The present invention also relates to a nucleic acid (also called nucleic or nucleotide sequence) encoding the heavy and/or light chain of an antibody, functional fragment or derivative thereof according to the invention as described above.

All the different nucleic sequences, because of degeneration of the genetic code, encoding a particular amino acid sequence are within the scope of the invention.

In particular, the sequence of a nucleic acid according to the invention may be optimized to promote the expression thereof in a host cell, a transgenic non-human animal or a transgenic plant of interest. Indeed, there are in general several three-nucleotide combinations encoding the same amino acid (except for methionine and tryptophan), called synonymous codons. However, some of these combinations are in general used preferentially by a cell or a given organism (this is referred to as genetic code usage bias). This preference depends notably on the producing organism from which the cell is derived. Consequently, when a protein derived from one or more organisms is produced in a heterologous organism or a cell of such a heterologous organism, it may be useful to modify the nucleic sequence encoding the protein to use mainly the preferred codons of the heterologous organism. Data are available in the literature concerning the use of codons preferred by different species and a person skilled in the art knows how to optimize the expression of a given protein in a heterologous organism or a cell of a heterologous organism.

A nucleic acid according to the invention advantageously comprises at least one of SEQ ID NOs: 86 to 95 (chimeric antibodies), as described in Table 12 below, which encode the amino acid sequences of the VH and VL regions of the antibodies according to the invention and have been optimized for expression in *Rattus norvegicus* cells.

TABLE 12

Preferred nucleotide sequences, optimized for expression in *Rattus norvegicus* cells, encoding the VH and VL regions of the antibodies, functional fragments or derivatives thereof according to the invention.

| Antibody | VH | VL |
|---|---|---|
| 122A2 | CAGGTCCAGCTGCAGCAGTCTGGGGCT GAGCTGGTGAGGCCTGGGGTCTCAGTG AAGATTTCCTGCAAGGGTTCTGGCTACA CATTCACTGATTATTCTATGCACTGGGT GAAGCAGAGTCATGCAAAGAGTCTAGAG TGGATTGGAGTTATTAGTACTTACTATG GTGATTCTAACTATAACCAGAAGTTCAA GGGCAAGGCCACAATGACTGTAGACAAA TCCTCCACCACAGCCTATATGGAACTTG CCAGACTGACATCTGAGGATTCTGCCAT CTATTACTGTGCAAGAAATGGTAATTTC TATGTTATGGACTACTGGGGTCAAGGAA CCTCAGTCACCGTCTCCTCA (SEQ ID NO: 86) | GATATCCAGATGACACAGACTACAT CCTCCCTGTCTGCCTCTCTGGGAGA CAGAGTCACCATCAGTTGCAGGGCA AGTCAGGACATTAGCAATTATTTAA ACTGGTATCAGCAGAAACCAGATGG AACTGTTAAACTCCTGATCTACTAC ACATCAAGATTACACTCAGGAGTCC CATCAAGGTTCAGTGGCAGTGGGT CTGGAACAGATTATTCTCTCACCAT TAGCAACCTGGACCAAGAAGATATT GCCACTTACTTTTGCCAACAGGGTA ATACGCTTCCTTGGACGTTCGGTGG AGGCACCAAGCTGGAAATCAAA (SEQ ID NO: 91) |
| 102E9 | CAGATCCATTTGGTGCAGTCTGGACCTG ACCTGAAGAAGCCTGGAGAGACAGTCAA GATCTCCTGCAAGGCTTCTGGTTATACC TTCACAGACTATTCAATGCACTGGGTGA AGCAGGCTCCAGGAAAGGGTTTAAAGTG GATGGGCTGGATAAACACTGAGACTGGT GAACCAACATATGCAGATGACTTCAAGG GACGGTTTGCCTTCTCTTTGGAAAGTTC TGCCAGCACTGCCTTTTTGCAGATCAAC AACCTCAAAAATGAGGACACGTCTACAT ATTTCTGTACTAGAAATGGTTACTACGT GGGTTACTATGCTATGGACTACTGGGGT CAAGGAACCTCAGTCACCGTCTCCTCA (SEQ ID NO: 87) | CAAATTGTTCTCACCCAGTCTCCAG CAATCATGTCTGCATCTCCAGGGGA GAAGGTCACCATAACCTGCAGTGCC AGCTCAAGTGTAATTTACATTCACT GGTTCCAGCAGAAGCCAGGCACTTC TCCCAAACTCTGGATTTATAGCACA TCCTACCTGGCTTCTGGAGTCCCTG CTCGCTTCAGTGGCAGTGGATCTG GGACCTCTTACTCTCTCACAATCAG CCGAATGGAGGCTGAAGATGCTGC CACTTATTACTGCCAGCAGAGGAGA AGTTACCCGTTCACGTTCGGAGGG GGGACCAAGCTGGAAATAAAA (SEQ ID NO: 92) |
| 104C12 | CAGGTCCAGCTGCAGCAGTCTGGGGCT GAGCTGGTGGGGCCTGGGGTCTCAGTG AAGATTTCCTGCAAGGGTTCTGGCTACA CATTCACTGATTATTCTATGCACTGGGT AAAGCAGAGTCATGCAAAGAGTCTAGAG TGGATTGGAGTTATTAGTCCTTACTATG GTGATACTAACTACAACCAGAAGTTCAA GGGCAAGGCCACAATGACTGTAGACAAA TCCTCCAGCACAGCCTATATGGAACTTG CCAGTCTGACATCTGAGGATTCTGCCAT CTATTTCTGTGCAAGAAATGATGATTAC TACAGGTTTGCTTACTGGGGCCAAGGA CTCTGGTCACTGTCTCTGC (SEQ ID NO: 88) | GATCTCCAGATGACACAGACTCCAT CCTCCCTGTCTGCCTCTCTGGGAGA CAGAGTCACCATCAGTTGCAGGGCA AGTCAGGACATTAACAATTATTTAA GCTGGTATCAGGAGAAACCAGATG GAACTTTTAAACTCCTGATCTACTA CACATCAAGATTACACTCAGGAGTC CCATCAAGGTTCAGTGGCAGTGGG TCTGGAACAGATTATTCTCTCACCG TTCGCAACCTGGAACAGGAAGATAT TGGCACTTACTTTTGCCAACAGGGT AAAACGCTTCCGTGGACGTTCGGTG GAGGCACCAAGCTGGAAATCAG (SEQ ID NO: 93) |
| 114D11 | CAGATCCAGTTGGTGCAGTCTGGACCTG AGCTGAAGAAGCCTGGAGAGACAGTCAA GATCTCCTGCAAGGCTTCTGGTTATACC TTCACAGACTCTTCAATGCACTGGGTGC AGCAGGCTCCAAACAAGGGTTTAAAGTG GATGGGCTGGATAAACACTGAGACTGGT GGGCCAACGTATGCAGATGATTTCAAGG GACGGTTTGCCTTCTCTTTGGAAACCTC TGCCAGAACTGCCTATTTGCAGATCAAC AACCTCAAAAATGAGGACACGGCTACAT ATTTCTGTGCTAGAAATGGATACTACGT GGGGTACTATGCTCTGGACTACTGGGG TCAAGGAACCTCAGTCACCGTCTCCTCA (SEQ ID NO: 89) | CAAATTGTTCTCACCCAGTCTCCAG CAATCATGTCTGCATCTCCAGGGGA GAAGGTCACCATAACCTGCAGTGCC AGCTCAAGTGTATTTACATGCACT GGTTCCAGCAGAAGCCAGGCACTTC TCCCAAACTCTGGATTTATAGCACA TCCAACCTGGCTTCTGGAGTCCCTG CTCGCTTCAGTGGCAGTGGATCTG GGACCTCTTACTCTCTCACAATCAG CCGAATGGAGGCTGAAGATGCTGC CACTTATTACTGCCAGCAAAGGAGA AGTTACCCGTACACGTTCGGAGGG GGGACCAAGCTGGAAATAAAA (SEQ ID NO: 94) |
| | CAGATCCAGTTGGTGCAGTCTGGACCTG | CAAATTGTTCTCACCCAGTCTCCAG |

TABLE 12-continued

Preferred nucleotide sequences, optimized for expression in *Rattus norvegicus* cells, encoding the VH and VL regions of the antibodies, functional fragments or derivatives thereof according to the invention.

| Antibody | VH | VL |
|---|---|---|
| 104E10 | AGCTGAAGAAGCCTGGAGAGACAGTCAA GATCTCCTGCAAGGCTTCTGGTTATACC TTCACAGACTATTCAATGCACTGGGTGA AGCAGGCTCCAGGAAAGGGTTTAAAGTG GATGGGCTGGATAAACACTGAGACTGGT GAGCCAACATATGCAGATGACTTCAAGG GACGGTTTGCCTTCTCTTTGGAAACCTC TGCCACCACTGCCTATTTGCAGATCAAC AACTTCAAAAATGAGGACACGGCTACAT ATTTCTGTGCTAGAAATGGTTACTACGT GGGATATTATGCTATGGACTACTGGGGT CAAGGAACCTCAGTCACCGTCTCCTCA (SEQ ID NO: 90) | CAATCATGTCTGCATCTCCAGGGGA GAAGGTCACCATGACCTGCAGTGCC AGTTCAAGTGTAATTTACATGCACT GGTTCCAGCAGAAGCCAGGCACTTC TCCCAAACTCTGGATTTATAGCACA TCCAACCTGGCTTCTGGAGTCCCTG CTCGCTTCAGTGGCAGTGGATCTG GGACATCTTACTCTCTCACAATCAG CCGAATGGAGGCTGAAGATGCTGC CACTTATTACTGCCAGCAAAGGAGA AGTTACCCGTACACGTTCGGAGGG GGGACCAAGCTGGAAATAAAA (SEQ ID NO: 95) |

A nucleic acid according to the invention may also advantageously comprise at least one of SEQ ID NOs: 181 to 187 (humanized antibodies derived from antibody 122A2), as described in Table 13 below, which encode the amino acid sequences of the VH and VL regions of the humanized antibodies according to the invention and have been optimized for expression in *Rattus norvegicus* cells.

TABLE 13

Preferred nucleotide sequences for humanized antibodies derived from antibody 122A2, optimized for expression in *Rattus norvegicus* cells, encoding the VH and VL regions of the antibodies, functional fragments or derivatives thereof according to the invention.

122A2 - humanized heavy chain VH Sequence

| | |
|---|---|
| 122A2-VHha | caggtccagctgcagcagtctggcgccgaagtggtcaagcctggcgcctccgtgaagatcagct gcaagggcagcggctacaccttcaccgactacagcatgcactgggtcaagcaggcccacgcca agagcctggaatggatcggcgtgatcagcacctactacggcgacagcaactacaaccagaagt tcaagggcaaagtcaccatgaccgtggacaagagcagctccaccgcctacatggaactgagca ggctgaccagcgacgacaccgccgtgtactactgcgccagaaacggcaacttctacgtgatgg actactggggccagggcaccctggtcaccgtgtcatct (SEQ ID NO: 181) |
| 122A2-VHhb | caggtccagctgcagcagtctggcgccgaagtggtcaagcctggcgcctccgtgaagatcagct gcaagggcagcggctacaccttcaccgactacagcatgcactgggtccgacaggcccacgcca agagcctggaatggatcggcgtgatcagcacctactacggcgacagcaactacaaccagaagt tcaagggcaaagtcaccatgaccgtggacaccagcagctccaccgcctacatggaactgagca ggctgagaagcgacgacaccgccgtgtactactgcgccagaaacggcaacttctacgtgatgg actactggggccagggcaccctggtcaccgtgtcatct (SEQ ID NO: 182) |
| 122A2-VHhc | caggtccagctgcagcagtctggcgccgaagtggtcaagcctggcgcctccgtgaagatcagct gcaagggcagcggctacaccttcaccgactacagcatgcactgggtccgacaggcccctggac agggcctggaatggatcggcgtgatcagcacctactacggcgacagcaactacaaccagaagt tcaagggcaaagtcaccatgaccgtggacaagagcagctccaccgcctacatggaactgagca ggctgaccagcgacgacaccgccgtgtactactgcgccagaaacggcaacttctacgtgatgg actactggggccagggcaccctggtcaccgtgtcatct (SEQ ID NO: 183) |

122A2 - humanized light chain VL Sequence

| | |
|---|---|
| 122A2-VKha | gacatccagatgacccagagcaccagcagcctgagcgcctctctgggcgacagagtgaccatc acctgtcaggccagccaggacatcagcaactacctgaactggtatcagcagaaacccgacggc accgtgaagctgctgatctactacaccagcaggctgcacaccggcgtgcccagcagattctctg gctctggcagcggcaccgactacagcctgaccatctccaacctggaccaggaagatattgcca cctactactgccagcagggcaacaccctgccctggacattcggcggaggcaccaagctggaaa tcaag (SEQ ID NO: 184) |
| 122A2-VKhb | gacatccagatgacccagagccctagcagcctgagcgcctctctgtgggcgacagagtgaccatc acctgtcaggccagccaggacatcagcaactacctgaactggtatcagcagaaacccgacggc accgtgaagctgctgatctactacaccagcaggctgcacaccggcgtgcccagcagattctctg gctctggcagcggcaccgactacagcctgaccatctccaacctggaccaggaagatattgcca cctactactgccagcagggcaacaccctgccctggacattcggcggaggcaccaagctggaaa tcaag (SEQ ID NO: 185) |
| 122A2-VKhc | gacatccagatgacccagagcaccagcagcctgagcgcctctctgggcgacagagtgaccatc acctgtcaggccagccaggacatcagcaactacctgaactggtatcagcagaaacccgacggc |

TABLE 13-continued

Preferred nucleotide sequences for humanized antibodies derived from antibody 122A2, optimized for expression in *Rattus norvegicus* cells, encoding the VH and VL regions of the antibodies, functional fragments or derivatives thereof according to the invention.

| | |
|---|---|
| | accgtgaagctgctgatctactacaccagcaacctgcacaccggcgtgcccagcagattcagc<br>ggctctggctctggcaccgactacagcctgaccatctccaacctccagcaggaagatattgcca<br>cctactactgccagcagggcaacaccctgccctggacattcggcggaggcaccaagctggaaa<br>tcaag (SEQ ID NO: 186) |
| 122A2-VKhd | gacatccagatgacccagagccctagcagcctgagcgcctctgtgggcgacagagtgaccatc<br>acctgtcaggccagccaggacatcagcaactacctgaactggtatcagcagaaacccgacggc<br>accgtgaagctgctgatctactacaccagcaacctgcacaccggcgtgcccagcagattcagc<br>ggctctggctctggcaccgactacagcctgaccatctccaacctccagcaggaagatattgcca<br>cctactactgccagcagggcaacaccctgccctggacattcggcggaggcaccaagctggaaa<br>tcaag (SEQ ID NO: 187) |

A nucleic acid according to the invention may also advantageously comprise at least one of SEQ ID NOs: 188 to 193 (humanized antibodies derived from antibody 102E9), as described in Table 14 below, which encode the amino acid sequences of the VH and VL regions of the humanized antibodies according to the invention and have been optimized for expression in *Rattus norvegicus* cells.

TABLE 14

Preferred nucleotide sequences for humanized antibodies derived from antibody 102E9, optimized for expression in *Rattus norvegicus* cells, encoding the VH and VL regions of the antibodies, functional fragments or derivatives thereof according to the invention.

| 102E9 - humanized heavy chain VH | Sequence |
|---|---|
| 102E9-VHha | cagatccatctggtgcagagcggccctgagctgaagaaacccggcgagagcgtgaagatcagc<br>tgcaaggccagcggctacaccttcaccgactacagcatgcactgggtcaagcaggccccaggc<br>cagggcctgaagtggatgggctggatcaacaccgagacaggcgagcccacctacgccgacgac<br>ttcaagggcagattcgtgttcagcctggacaccagcgtgtccaccgcctacctgcagatcaaca<br>gcctgaagaacgaggacacctccacctactactgcacccggaacggctactacgtggggtact<br>acgccatggactactggggccagggcacctccgtgaccgtgtcatct (SEQ ID NO: 188) |
| 102E9-VHhb | cagatccatctggtgcagagcggccctgagctgaagaaacccggcgagagcgtgaagatcagc<br>tgcaaggccagcggctacaccttcaccgactacagcatgcactgggtccgacaggcccctgga<br>cagggcctgaagtggatgggctggatcaacaccgagacaggcgagcccacctacgcccaggac<br>ttcaagggcagattcgtgttcagcctggacaccagcgtgtccaccgcctacctgcagatcaaca<br>gcctgaagaacgaggacacctccacctactactgcacccggaacggctactacgtggggtact<br>acgccatggactactggggccagggcacctccgtgaccgtgtcatct (SEQ ID NO: 189) |
| 102E9-VHhc | cagatccatctggtgcagagcggcagcgagctgaagaaacccggcgagagcgtgaagatcagc<br>tgcaaggccagcggctacaccttcaccgactacagcatgcactgggtccgacaggcccctgga<br>cagggcctgaagtggatgggctggatcaacaccgagacaggcgagcccacctacgcccaggac<br>ttcaagggcagattcgtgttcagcctggacaccagcgtgtccaccgcctacctgcagatcaaca<br>gcctgaagaacgaggacacctccacctactactgcacccggaacggctactacgtggggtact<br>acgccatggactactggggccagggcacctccgtgaccgtgtcatct (SEQ ID NO: 190) |

| 102E9 - humanized light chain VL | Sequence |
|---|---|
| 102E9-VKha | cagatccagctgacccagagccctagcttcctgagcgcctctcctggcgagagagtgaccatca<br>cctgtagcgccagcagctccgtgatctacatccactggttccagcagaagcccggcaaggcccc<br>taagctgtggatctacagcaccagctacctggccagcggcgtgccaagcagattcagcggctct<br>ggctctggcaccgagtacaccctgaccatcagctccatggaagccgaggacttcgccacctact<br>actgccagcagaggcggagctacccccttcaccttcggcggaggcaccaagctggaaatcaag<br>(SEQ ID NO: 191) |
| 102E9-VKhb | cagatccagctgacccagagccctagcttcctgagcgcctctcctggcgagagagtgaccatca<br>cctgtagcgccagcagctccgtgatctacatccactggttccagcagaagcccggcaccgcccc<br>taagctgtggatctacagcaccagctacctggccagcggcgtgccaagcagattcagcggctct<br>ggcagcggcacctcctacaccctgaccatcagcaggatggaagccgaggacttcgccacctac<br>tactgccagcagaggcggagctacccccttcaccttcggcggaggcaccaagctggaaatcaag<br>(SEQ ID NO: 192) |
| 102E9-VKhc | cagatccagctgacccagagccctagcttcctgagcgcctctcctggcgacagagtgaccatca<br>cctgtagcgccagcagctccgtgatctacatccactggttccagcagaagcccggcaaggcccc<br>taagctgtggatctacagcaccagctacctggccagcggcgtgccaagcagattcagcggctct<br>ggctctggcaccgagtacaccctgaccatcagctccatgcaggccgaggacttcgccacctact<br>actgccagcagaggcggagctacccccttcaccttcggcggaggcaccaagctggaaatcaag<br>(SEQ ID NO: 193) |

The nucleic sequences encoding the preferred heavy or light chain constant regions were also optimized for expression in *Rattus norvegicus* cells and are preferably those described in Table 15 below.

TABLE 15

Preferred nucleotide sequences encoding the preferred human heavy or light chain constant regions.

| | |
|---|---|
| Preferred human heavy chain constant region | GCCTCCACCAAGGGCCCATCCGTGTTCCCCCTGGCCCCATCCAGCAAGTCT ACCTCCGGAGGCACAGCCGCCCTGGGCTGTCTGGTGAAGGACTACTTCCC CGAGCCAGTGACCGTGTCCTGGAACTCCGGAGCCCTGACATCCGGCGTGC ACACCTTCCCCGCCGTGCTGCAGTCCAGCGGCCTGTACTCTCTGTCTTCCG TGGTGACCGTGCCATCCAGCTCCCTGGGAACCCAGACATACATCTGCAACG TGAACCACAAGCCTAGCAACACCAAGGTGGACAAGAAGGTGGAGCCTAAG AGCTGTGACAAGACACACACATGCCCTCCTTGTCCAGCCCCTGAGCTGCTG GGCGGCCCCTCCGTGTTCCTGTTCCCCCCCAAGCCTAAGGATACCCTGATG ATCAGCAGAACCCCCGAGGTGACCTGCGTGGTGGTGGACGTGTCCCACGA GGATCCCGAGGTGAAGTTCAACTGGTACGTGGACGGCGTGGAGGTGCACA ACGCTAAGACCAAGCCCAGAGAGGAGCAGTACAACAGCACATACAGAGTG GTGTCTGTGCTGACCGTGCTGCACCAGGACTGGCTGAACGGGAAGGAGTA CAAGTGCAAGGTGTCCAACAAGGCCCTGCCTGCCCCTATCGAGAAGACCAT CTCTAAGGCTAAGGGGCAGCCCCGGGAGCCACAGGTGTACACCCTGCCAC CCAGCCGCGACGAGCTGACCAAGAACCAGGTGTCCCTGACATGCCTGGTG AAGGGATTCTACCCCAGCGACATCGCCGTGGAGTGGGAGAGCAACGGCCA GCCCGAGAACAACTACAAGACAACCCCTCCCGTGCTGGACAGCGATGGATC CTTCTTCCTGTACTCCAAGCTGACCGTGGACAAGAGCAGGTGGCAGCAGG GAAACGTGTTCTCTTGTTCCGTGATGCACGAGGCTCTGCACAACCACTACA CCCAGAAGTCCCTGAGCCTGTCTCCAGGCAAG (SEQ ID NO: 96) |
| Preferred human light chain constant region | CGAACTGTGGCTGCACCAAGTGTCTTCATCTTTCCTCCGAGTGATGAGCAG CTGAAGAGCGGGACAGCTTCTGTGGTGTGTCTGCTGAATAACTTCTACCC AAGAGAAGCAAAGGTCCAGTGGAAGGTGGACAACGCCCTGCAGTCTGGCA ACTCACAGGAGTCTGTCACTGAGCAGGATTCCAAGGACAGCACTTACAGCC TGTCCAGCACCCTCACTCTGTCCAAAGCCGACTACGAAAAGCATAAGGTGT ATGCTTGTGAGGTGACCCACCAGGGACTGAGCAGCCCTGTGACGAAGTCC TTCAACCGGGGCGAGTGC (SEQ ID NO: 97) |

Thus, a nucleic acid encoding the heavy and/or light chain of an antibody according to the invention preferably comprises (or consists essentially of, or consists of) at least one nucleic sequence described in Table 16 below, consisting of the 5' to 3' fusion:

- Of one of SEQ ID NOs: 86 to 90 encoding the VH region of the preferred chimeric antibodies according to the invention and of SEQ ID NO: 96 encoding the preferred human heavy chain constant region (see SEQ ID NOs: 98 to 102);
- Of one of SEQ ID NOs: 91 to 95 encoding the VL region of the preferred chimeric antibodies according to the invention and of SEQ ID NO: 97 encoding the preferred human light chain constant region (see SEQ ID NOs: 103 to 107);
- Of one of SEQ ID NOs: 181 to 183 encoding the VH region of the preferred humanized antibodies derived from chimeric antibody 122A2 according to the invention and of SEQ ID NO: 96 encoding the preferred human heavy chain constant region (see SEQ ID NOs: 194 to 196);
- Of one of SEQ ID NOs: 184 to 187 encoding the VL region of the preferred humanized antibodies derived from chimeric antibody 122A2 according to the invention and of SEQ ID NO: 97 encoding the preferred human light chain constant region (see SEQ ID NO: 197 to 200);
- Of one of SEQ ID NOs: 188 to 190 encoding the VH region of the preferred humanized antibodies derived from chimeric antibody 102E9 according to the invention and of SEQ ID NO: 96 encoding the preferred human heavy chain constant region (see SEQ ID NO: 201 to 203);
- Of one of SEQ ID NOs: 191 to 193 encoding the VL region of the preferred humanized antibodies derived from chimeric antibody 102E9 according to the invention and of SEQ ID NO: 97 encoding the preferred human light chain constant region (see SEQ ID NO: 204 to 206).

TABLE 16

Preferred nucleotide sequences of the heavy and light chains of the antibodies according to the invention.

| Antibody | Heavy chain | Light chain |
|---|---|---|
| Chimeric antibodies | | |
| 122A2 | Fusion SEQ ID NO: 86-SEQ ID NO: 96 (SEQ ID NO: 98) | Fusion SEQ ID NO: 91-SEQ ID NO: 97 (SEQ ID NO: 103) |
| 102E9 | Fusion SEQ ID NO: 87-SEQ ID NO: 96 (SEQ ID NO: 99) | Fusion SEQ ID NO: 92-SEQ ID NO: 97 (SEQ ID NO: 104) |
| 104C12 | Fusion SEQ ID NO: 88-SEQ ID NO: 96 | Fusion SEQ ID NO: 93-SEQ ID NO: 97 |

TABLE 16-continued

Preferred nucleotide sequences of the heavy and light chains of the antibodies according to the invention.

| Antibody | Heavy chain | Light chain |
|---|---|---|
| 114D11 | (SEQ ID NO: 100)<br>Fusion SEQ ID NO: 89-SEQ ID NO: 96<br>(SEQ ID NO: 101) | (SEQ ID NO: 105)<br>Fusion SEQ ID NO: 94-SEQ ID NO: 97<br>(SEQ ID NO: 106) |
| 104E10 | Fusion SEQ ID NO: 90-SEQ ID NO: 96<br>(SEQ ID NO: 102) | Fusion SEQ ID NO: 95-SEQ ID NO: 97<br>(SEQ ID NO: 107) |
| | Humanized antibodies | |
| 122A2H5 | Fusion SEQ ID NO: 181-SEQ ID NO: 96<br>(SEQ ID NO: 194) | Fusion SEQ ID NO: 184-SEQ ID NO: 97<br>(SEQ ID NO: 197) |
| 122A2H9 | | Fusion SEQ ID NO: 185-SEQ ID NO: 97<br>(SEQ ID NO: 198) |
| 122A2H13 | | Fusion SEQ ID NO: 186-SEQ ID NO: 97<br>(SEQ ID NO: 199) |
| 122A2H17 | | Fusion SEQ ID NO: 187-SEQ ID NO: 97<br>(SEQ ID NO: 200) |
| 122A2H6 | Fusion SEQ ID NO: 182-SEQ ID NO: 96<br>(SEQ ID NO: 195) | Fusion SEQ ID NO: 184-SEQ ID NO: 97<br>(SEQ ID NO: 197) |
| 122A2H10 | | Fusion SEQ ID NO: 185-SEQ ID NO: 97<br>(SEQ ID NO: 198) |
| 122A2H14 | | Fusion SEQ ID NO: 186-SEQ ID NO: 97<br>(SEQ ID NO: 199) |
| 122A2H18 | | Fusion SEQ ID NO: 187-SEQ ID NO: 97<br>(SEQ ID NO: 200) |
| 122A2H7 | Fusion SEQ ID NO: 183-SEQ ID NO: 96<br>(SEQ ID NO: 196) | Fusion SEQ ID NO: 184-SEQ ID NO: 97<br>(SEQ ID NO: 197) |
| 122A2H11 | | Fusion SEQ ID NO: 185-SEQ ID NO: 97<br>(SEQ ID NO: 198) |
| 122A2H15 | | Fusion SEQ ID NO: 186-SEQ ID NO: 97<br>(SEQ ID NO: 199) |
| 122A2H19 | | Fusion SEQ ID NO: 187-SEQ ID NO: 97<br>(SEQ ID NO: 200) |
| 102E9H5 | Fusion SEQ ID NO: 188-SEQ ID NO: 96<br>(SEQ ID NO: 201) | Fusion SEQ ID NO: 191-SEQ ID NO: 97<br>(SEQ ID NO: 204) |
| 102E9H9 | | Fusion SEQ ID NO: 192-SEQ ID NO: 97<br>(SEQ ID NO: 205) |
| 102E9H13 | | Fusion SEQ ID NO: 193-SEQ ID NO: 97<br>(SEQ ID NO: 206) |
| 102E9H6 | Fusion SEQ ID NO: 189-SEQ ID NO: 96<br>(SEQ ID NO: 202) | Fusion SEQ ID NO: 191-SEQ ID NO: 97<br>(SEQ ID NO: 204) |
| 102E9H10 | | Fusion SEQ ID NO: 192-SEQ ID NO: 97<br>(SEQ ID NO: 205) |
| 102E9H14 | | Fusion SEQ ID NO: 193-SEQ ID NO: 97<br>(SEQ ID NO: 206) |
| 102E9H7 | Fusion SEQ ID NO: 190-SEQ ID NO: 96<br>(SEQ ID NO: 203) | Fusion SEQ ID NO: 191-SEQ ID NO: 97<br>(SEQ ID NO: 204) |
| 102E9H11 | | Fusion SEQ ID NO: 192-SEQ ID NO: 97<br>(SEQ ID NO: 205) |
| 102E9H15 | | Fusion SEQ ID NO: 193-SEQ ID NO: 97<br>(SEQ ID NO: 206) |

A nucleic acid encoding the heavy and/or light chain of the antibody, functional fragment or derivative thereof according to the invention advantageously comprises a nucleic sequence encoding heterologous signal peptide MB7 (MRWSWIFLLLLSITSANA, SEQ ID NO: 65), and notably the nucleic sequence SEQ ID NO: 108 (ATGAGGTGGTC-CTGGATCTTCCTGCTGCTGCTGAGCATCACCA-GCGCCAACGCC). Indeed, this peptide has been shown to improve the expression and secretion of recombinant proteins in higher eukaryotic cell lines (see WO2011/114063).

Thus, a nucleic acid encoding the heavy chain of the antibodies, functional fragments or derivatives thereof according to the invention advantageously comprises (or consists essentially of, or consists of) a nucleic sequence selected from SEQ ID NOs: 109 to 113 (chimeric antibodies), SEQ ID NOs: 207 to 209 (humanized antibodies derived from chimeric antibody 122A2) and SEQ ID NOs: 214 to 216 (humanized antibodies derived from chimeric antibody 102E9), consisting of the 5' to 3' fusion of the nucleic sequence encoding signal peptide MB7 (SEQ ID NO: 108) to one of the nucleic sequences encoding the VH region of the antibodies according to the invention (SEQ ID NOs: 86 to 90 for the chimeric antibodies, SEQ ID NOs: 181 to 183 for the humanized antibodies derived from chimeric antibody 122A2, and SEQ ID NOs: 188 to 190 for the humanized antibodies derived from chimeric antibody 102E9).

Additionally or alternatively, a nucleic acid encoding the light chain of the antibodies, functional fragments or derivatives thereof according to the invention advantageously comprises (or consists essentially of, or consists of) a nucleic sequence selected from SEQ ID NOs: 114 to 118, (chimeric antibodies), SEQ ID NOs: 210 to 213 (humanized antibodies derived from chimeric antibody 122A2) and SEQ ID NOs: 217 to 219 (humanized antibodies derived from chimeric antibody 102E9), consisting of the 5' to 3' fusion of the nucleic sequence encoding signal peptide MB7 (SEQ ID NO: 108) to one of the amino acid sequences of the VL region of the antibodies according to the invention (SEQ ID NOs: 91 to 95 for the chimeric antibodies, SEQ ID NOs: 184 to 187 for the humanized antibodies derived from chimeric antibody 122A2, and SEQ ID NOs: 191 to 193 for the humanized antibodies derived from chimeric antibody 102E9).

By adding the preferred heavy and light chain constant regions, the preferred complete amino acid sequences of the antibodies according to the invention are obtained, as described in Table 17 below.

Thus, a nucleic acid encoding the heavy and/or light chain of a chimeric or humanized antibody, a functional fragment or a derivative thereof according to the invention advantageously comprises at least one sequence described in Table 17 below (or consists essentially of, or consists of, such sequences).

TABLE 17

Nucleic sequences encoding the heavy and light chains of the antibodies according to the invention, with signal peptide MB7.

| Antibody | Heavy chain | Light chain |
|---|---|---|
| Chimeric antibodies | | |
| 122A2 | Fusion SEQ ID NO: 108-SEQ ID NO: 86-SEQ ID NO: 96 (SEQ ID NO: 119) | Fusion SEQ ID NO: 108-SEQ ID NO: 91-SEQ ID NO: 97 (SEQ ID NO: 124) |
| 102E9 | Fusion SEQ ID NO: 108-SEQ ID NO: 87-SEQ ID NO: 96 (SEQ ID NO: 120) | Fusion SEQ ID NO: 108-SEQ ID NO: 92-SEQ ID NO: 97 (SEQ ID NO: 125) |
| 104C12 | Fusion SEQ ID NO: 108-SEQ ID NO: 88-SEQ ID NO: 96 (SEQ ID NO: 121) | Fusion SEQ ID NO: 108-SEQ ID NO: 93-SEQ ID NO: 97 (SEQ ID NO: 126) |
| 114D11 | Fusion SEQ ID NO: 108-SEQ ID NO: 89-SEQ ID NO: 96 (SEQ ID NO: 122) | Fusion SEQ ID NO: 108-SEQ ID NO: 94-SEQ ID NO: 97 (SEQ ID NO: 127) |
| 104E10 | Fusion SEQ ID NO: 108-SEQ ID NO: 90-SEQ ID NO: 96 (SEQ ID NO: 123) | Fusion SEQ ID NO: 108-SEQ ID NO: 95-SEQ ID NO: 97 (SEQ ID NO: 128) |
| Humanized antibodies | | |
| 122A2H5 | Fusion SEQ ID NO: 108-SEQ ID NO: 181-SEQ ID NO: 96 (SEQ ID NO: 207) | Fusion SEQ ID NO: 108-SEQ ID NO: 184-SEQ ID NO: 97 (SEQ ID NO: 210) |
| 122A2H9 | | Fusion SEQ ID NO: 108-SEQ ID NO: 185-SEQ ID NO: 97 (SEQ ID NO: 211) |
| 122A2H13 | | Fusion SEQ ID NO: 108-SEQ ID NO: 186-SEQ ID NO: 97 (SEQ ID NO: 212) |
| 122A2H17 | | Fusion SEQ ID NO: 108-SEQ ID NO: 187-SEQ ID NO: 97 (SEQ ID NO: 213) |
| 122A2H6 | Fusion SEQ ID NO: 108-SEQ ID NO: 182-SEQ ID NO: 96 (SEQ ID NO: 208) | Fusion SEQ ID NO: 108-SEQ ID NO: 184-SEQ ID NO: 97 (SEQ ID NO: 210) |
| 122A2H10 | | Fusion SEQ ID NO: 108-SEQ ID NO: 185-SEQ ID NO: 97 (SEQ ID NO: 211) |
| 122A2H14 | | Fusion SEQ ID NO: 108-SEQ ID NO: 186-SEQ ID NO: 97 (SEQ ID NO: 212) |
| 122A2H18 | | Fusion SEQ ID NO: 108-SEQ ID NO: 187-SEQ ID NO: 97 (SEQ ID NO: 213) |
| 122A2H7 | Fusion SEQ ID NO: 108-SEQ ID NO: 183-SEQ ID NO: 96 (SEQ ID NO: 209) | Fusion SEQ ID NO: 108-SEQ ID NO: 184-SEQ ID NO: 97 (SEQ ID NO: 210) |
| 122A2H11 | | Fusion SEQ ID NO: 108-SEQ ID NO: 185-SEQ ID NO: 97 (SEQ ID NO: 211) |
| 122A2H15 | | Fusion SEQ ID NO: 108-SEQ ID NO: 186-SEQ ID NO: 97 (SEQ ID NO: 212) |
| 122A2H19 | | Fusion SEQ ID NO: 108-SEQ ID NO: 187-SEQ ID NO: 97 (SEQ ID NO: 213) |
| 102E9H5 | Fusion SEQ ID NO: 108-SEQ ID NO: 188-SEQ ID NO: 96 (SEQ ID NO: 214) | Fusion SEQ ID NO: 108-SEQ ID NO: 191-SEQ ID NO: 97 (SEQ ID NO: 217) |
| 102E9H9 | | Fusion SEQ ID NO: 108-SEQ ID NO: 192-SEQ ID NO: 97 (SEQ ID NO: 218) |
| 102E9H13 | | Fusion SEQ ID NO: 108-SEQ ID NO: 193-SEQ |

TABLE 17-continued

Nucleic sequences encoding the heavy and light chains of the antibodies according to the invention, with signal peptide MB7.

| Antibody | Heavy chain | Light chain |
|---|---|---|
| | | ID NO: 97 (SEQ ID NO: 219) |
| 102E9H6 | Fusion SEQ ID NO: 108-SEQ ID NO: 189-SEQ ID NO: 96 (SEQ ID NO: 215) | Fusion SEQ ID NO: 108-SEQ ID NO: 191-SEQ ID NO: 97 (SEQ ID NO: 217) |
| 102E9H10 | | Fusion SEQ ID NO: 108-SEQ ID NO: 192-SEQ ID NO: 97 (SEQ ID NO: 218) |
| 102E9H14 | | Fusion SEQ ID NO: 108-SEQ ID NO: 193-SEQ ID NO: 97 (SEQ ID NO: 219) |
| Chimeric antibodies | | |
| 102E9H7 | Fusion SEQ ID NO: 108-SEQ ID NO: 190-SEQ ID NO: 96 (SEQ ID NO: 216) | Fusion SEQ ID NO: 108-SEQ ID NO: 191-SEQ ID NO: 97 (SEQ ID NO: 217) |
| 102E9H11 | | Fusion SEQ ID NO: 108-SEQ ID NO: 192-SEQ ID NO: 97 (SEQ ID NO: 218) |
| 102E9H15 | | Fusion SEQ ID NO: 108-SEQ ID NO: 193-SEQ ID NO: 97 (SEQ ID NO: 219) |

The present invention also relates to a vector comprising a nucleic acid according to the invention. Such a vector comprises the elements necessary for the expression of said nucleic sequence, and notably a promoter, a transcription initiation codon, termination sequences, and suitable transcription regulatory sequences. These elements vary according to the host used for the expression and are easily selected by persons skilled in the art based on their general knowledge. In particular, for a vector designed for expression in eukaryotic cells, the vector advantageously comprises a Kozak consensus sequence, i.e., a conserved sequence found at the translation start site of eukaryotic messenger RNA, around the AUG start codon (generally GCCGCC(A/G)CC ATGG, the translation initiation codon being underlined). The vector can notably be a plasmid or viral vector. It is used to clone or express the nucleic acids according to the invention. Examples of preferred vectors able to be used in the context of the invention include:

A vector as described in WO2013/061010 (particularly preferred), comprising at least one transcription unit comprising the following regulatory elements: the hCMVie virus enhancer, said enhancer having the nucleotide sequence SEQ ID NO: 220, or a nucleic acid having at least 70% sequence identity with SEQ ID NO: 220 and essentially having transcription activation properties, and the cyclin-dependent kinase 9 (CDK9) promoter region, said promoter region having the nucleotide sequence SEQ ID NO: 221, or a nucleic acid having at least 70% sequence identity with SEQ ID NO: 221 and essentially having a promoter activity. Advantageously, the transcription unit comprised in the vector further comprises at least one of the following two additional components:
  a 5' untranslated region (5' UTR) situated downstream of the promoter region, in particular selected from:
    the HTLV-1 virus Long Terminal Repeat (LTR) regulatory (R) region having the nucleotide sequence SEQ ID NO: 222, or a nucleic acid having at least 70% sequence identity with SEQ ID NO: 222,
    the NF-κB Repressing Factor (NRF) gene 5' UTR having the nucleotide sequence SEQ ID NO: 223, or a nucleic acid having at least 70% sequence identity with SEQ ID NO: 223,
    the eukaryotic Initiation Factor 4GI (eIF4GI) gene 5' UTR having the nucleotide sequence SEQ ID NO: 224, or a nucleic acid having at least 70% sequence identity with SEQ ID NO: 224,
    said nucleic acids having at least 70% sequence identity with said SEQ ID NOs: 222, 223, 224 essentially having mRNA stabilization and translation facilitator properties.
  an intron situated downstream of the promoter region and upstream of the translation initiation site, in particular selected from:
    the Elongation Factor 1α (EF1α) gene intron having the nucleotide sequence SEQ ID NO: 225, or a nucleic acid having at least 70% sequence identity with SEQ ID NO: 225,
    the murine ROSA intron having the nucleotide sequence SEQ ID NO: 226, or a nucleic acid having at least 70% sequence identity with SEQ ID NO: 226,
    the HTLV-1 virus 5' LTR intron having the nucleotide sequence SEQ ID NO: 227, or a nucleic acid having at least 70% sequence identity with SEQ ID NO: 227,
    the pCI-neo intron having the nucleotide sequence SEQ ID NO: 228, or a nucleic acid having at least 70% sequence identity with SEQ ID NO: 228,
    the ubiquitin gene intron having the nucleotide sequence SEQ ID NO: 229, or a nucleic acid having at least 70% sequence identity with SEQ ID NO: 229,
    the human ROSA intron having the nucleotide sequence SEQ ID NO: 230, or a nucleic acid having at least 70% sequence identity with SEQ ID NO: 230.

Advantageously, the transcription unit comprised in the vector comprises the hCMVie virus enhancer, the CDK9 promoter region, the eIF4GI gene 5' UTR and the EF1a gene intron, and has the nucleotide sequence SEQ ID NO: 231 ("HKgenEFss" vector).

A vector as described in WO2013/117871, comprising at least one transcription unit comprising the following regulatory elements:
- the hCMVie virus enhancer, said enhancer having the nucleotide sequence SEQ ID NO: 232, or a nucleic acid having at least 70% sequence identity with SEQ ID NO: 232 and essentially having transcription activation properties,
- the β-actin promoter region, said promoter region having the nucleotide sequence SEQ ID NO: 233, or a nucleic acid having at least 70% sequence identity with SEQ ID NO: 233 and essentially having a promoter activity, and
- a nucleic acid situated downstream of said promoter region and upstream of the translation initiation site, said nucleic acid comprising at least one 5' untranslated region (5' UTR) selected from the following:
  - the HTLV-1 virus 5' Long Terminal Repeat (LTR) regulatory (R) region having the nucleotide sequence SEQ ID NO: 234, or a nucleic acid having at least 70% sequence identity with SEQ ID NO: 234,
  - the NF-κB Repressing Factor (NRF) gene 5' UTR having the nucleotide sequence SEQ ID NO: 235, or a nucleic acid having at least 70% sequence identity with SEQ ID NO: 235,
  - the eukaryotic Initiation Factor 4GI (eIF4GI) gene 5' UTR having the nucleotide sequence SEQ ID NO: 236, or a nucleic acid having at least 70% sequence identity with SEQ ID NO: 236,
  - said nucleic acids having at least 70% sequence identity with one of the sequences represented by SEQ ID NO: 234, SEQ ID NO: 235 or SEQ ID NO: 236 essentially having mRNA stabilization and translation facilitator properties.

The transcription unit comprised in the vector may further comprise an intron, in particular selected from the following:
- the Elongation Factor 1α (EF1α) gene intron having the nucleotide sequence SEQ ID NO: 237, or a nucleic acid having at least 70% sequence identity with SEQ ID NO: 237,
- the murine ROSA intron having the nucleotide sequence SEQ ID NO: 238, or a nucleic acid having at least 70% sequence identity with SEQ ID NO: 238,
- the human ROSA intron having the nucleotide sequence SEQ ID NO: 239, or a nucleic acid having at least 70% sequence identity with SEQ ID NO: 239,
- said intron being located:
  (i) downstream of the 5' UTR and upstream of the translation initiation site, or
  (ii) downstream of the promoter and upstream of the 5' UTR, or
  (iii) after the translation initiation site and within a coding sequence, or
  (iv) between the stop codon of the coding sequence and the polyadenylation signal.
  Advantageously, the transcription unit comprised in the vector comprises the hCMVie virus enhancer, the β-actin promoter region, the HTLV-1 virus 5' UTR (U1) and the eIF4GI gene 5' UTR (U3), and has the nucleotide sequence SEQ ID NO: 240.

The present invention also relates to a host cell, a transgenic non-human animal or a transgenic plant comprising at least one nucleic acid according to the invention or a vector according to the invention.

The host cell may be of prokaryotic or eukaryotic origin, and may in particular be selected from bacterial, insect, plant, yeast or mammalian cells. The antibody, functional fragment or derivative according to the invention may then be produced by culturing the host cell under suitable conditions. A host cell according to the invention can notably be obtained by transforming a cell line by the expression vector(s) for the heavy and light chains of an antibody, functional fragment or derivative thereof according to the invention, and separating the various cell clones obtained. The transformed cell line is preferably of eukaryotic origin, and may in particular be selected from insect, plant, yeast or mammalian cells. Suitable cell lines for antibody production notably include lines selected from: SP2/0; YB2/0; IR983F; human myeloma Namalwa; PERC6; CHO cell lines, notably CHO-K-1, CHO-Lec10, CHO-Lec1, CHO-Lec13, CHO Pro-5, CHO dhfr-, CHO-DP12, CHO DUKX-B11, CHO DG-44, or the CHO cell line deleted for both alleles encoding the FUT8 gene and/or the GMD gene; Wil-2; Jurkat; Vero; Molt-4; COS-7; 293-HEK; BHK; K6H6; NSO; SP2/0-Ag 14, P3X63Ag8.653, duck embryonic cell line EB66® (Valneva); rat hepatoma cell lines H4-II-E (DSM ACC3129) and H4-II-Es (DSM ACC3130) (see WO2012/041768), NM-H9D8 (DSM ACC2806), NM-H9D8-E6 (DSM ACC 2807) and NM H9D8-E6Q12 (DSM ACC 2856) (see WO2008/028686).

A transgenic non-human animal according to the invention may be obtained by directly injecting the gene(s) of interest (here, the rearranged genes encoding the heavy and light chains of the antibody) into a fertilized egg (Gordon et al.—1980). A transgenic non-human animal may also be obtained by introducing the gene(s) of interest (here, the rearranged genes encoding the heavy and light chains of the antibody) into an embryonic stem cell and preparing the animal by a chimera aggregation method or a chimera injection method (see Manipulating the Mouse Embryo, A Laboratory Manual, Second edition, Cold Spring Harbor Laboratory Press (1994); Gene Targeting, A Practical Approach, IRL Press at Oxford University Press (1993)). A transgenic non-human animal may also be obtained by a cloning technique in which a nucleus, into which the gene(s) of interest (here, the rearranged genes encoding the heavy and light chains of the antibody) has/have been introduced, is transplanted into an enucleated egg (Ryan et al.—1997; Cibelli et al.—1998, WO00/26357). A transgenic non-human animal producing an antibody of interest can be prepared by the methods above. The antibody may then be accumulated in the transgenic animal and harvested, notably from the animal's milk or eggs. For producing antibodies in the milk of transgenic non-human animals, preparation methods are notably described in WO90/04036, WO95/17085, WO01/26455, WO2004/050847, WO2005/033281, WO2007/048077. Methods for purifying proteins of interest from milk are also known (see WO01/26455, WO2007/106078). The transgenic non-human animals of interest notably include mice, rabbits, rats, goats, bovines (notably cows), and poultry (notably chicken). A transgenic plant according to the invention may be selected from any plant allowing antibody production. Numerous antibodies have already been produced in transgenic plants and the technologies required for obtaining a transgenic plant expressing an antibody of interest and for recovering the antibody are well-known to a person skilled in the art (see Stoger et al.—2002, Fisher et al.—2003, My et al.—2003, Schillberg et al.—2005). It is also possible to influence the glycosylation obtained in the plants in order to obtain glycosylation similar to that of natural human antibodies (without xylose), but with, in addition, slight fucosylation, for example by means of small interfering RNAs (Forthal et al.—2010).

Therapeutic Uses of the Antibodies

The present invention also relates to an antibody, functional fragment or derivative thereof according to the invention, for use as a medicinal product.

In a first embodiment, the antibody, functional fragment or derivative thereof according to the invention is advantageously used in the treatment or prevention of hematopoietic tumors expressing the CD303 antigen. It is notably the case of blastic plasmacytoid dendritic cell neoplasms (BPDCN), of phenotype CD4+, CD11c−, Lin−, CD303+, CD304+, CD56+.

In a second embodiment, the antibody, functional fragment or derivative thereof according to the invention is advantageously used in the treatment or prevention of inflammatory diseases, notably autoimmune diseases. The antibody, functional fragment or derivative thereof according to the invention is advantageously used in the treatment or prevention of diseases involving pDCs, and more particularly diseases involving IFN-α secretion by pDCs. In particular, the antibody, functional fragment or derivative thereof according to the invention is advantageously used in the treatment or prevention of the following diseases, for which a role for pDCs has been established (see Wollenberg et al.—2002 and Cao-2014): atopic dermatitis, contact dermatitis, psoriasis, systemic lupus erythematosus, dermatomyositis, Sjögren's syndrome, type 1b diabetes, autoimmune thrombocytopenia (or thrombopenia) (notably idiopathic thrombocytopenic purpura, or ITP), systemic scleroderma (also called progressive systemic scleroderma or systemic sclerosis), rheumatoid arthritis.

The present invention also concerns:

the use of an antibody, functional fragment or derivative thereof according to the invention for preparing a medicinal product for treating or preventing hematopoietic tumors expressing the CD303 antigen, and notably blastic plasmacytoid dendritic cell neoplasms (BPDCN), of phenotype CD4+, CD11c−, Lin−, CD303+, CD304+, CD56+.

the use of an antibody, functional fragment or derivative thereof according to the invention for preparing a medicinal product for treating or preventing inflammatory diseases, notably autoimmune diseases, and in particular the diseases mentioned above.

The present invention also concerns:

the use of an antibody, functional fragment or derivative thereof according to the invention in the treatment or prevention of hematopoietic tumors expressing the CD303 antigen, and notably blastic plasmacytoid dendritic cell neoplasms (BPDCN), of phenotype CD4+, CD11c−, Lin−, CD303+, CD304+, CD56+.

the use of an antibody, functional fragment or derivative thereof according to the invention in the treatment or prevention of inflammatory diseases, notably autoimmune diseases, and in particular the diseases mentioned above.

The present invention also concerns:

a method for treating or preventing a hematopoietic tumor expressing the CD303 antigen in a patient, and notably a blastic plasmacytoid dendritic cell neoplasm (BPDCN), of phenotype CD4+, CD11c−, Lin−, CD303+, CD304+, CD56+, comprising administering to said patient an effective amount of an antibody, functional fragment or derivative thereof according to the invention.

a method for treating or preventing inflammatory disease in a patient, notably autoimmune disease, and in particular one of the diseases mentioned above, comprising administering to said patient an effective amount of an antibody, functional fragment or derivative thereof according to the invention.

By "treatment" is meant an improvement, observed at the clinical or biochemical level, of the patient's disease.

By "prevention" is meant the fact of preventing or delaying the onset of, or of decreasing the intensity of, the clinical or biochemical manifestations associated with the disease. Persons skilled in the art know, on the basis of their general knowledge, how to determine which clinical or biochemical manifestations are associated with a given disease and which are likely to be improved (treatment) or prevented, delayed or decreased in intensity (prevention). In the context of hematopoietic tumors expressing the CD303 antigen, and notably blastic plasmacytoid dendritic cell neoplasms (BPDCN), a biological parameter of interest may be the number of blasts. In the context of inflammatory diseases, a biological parameter of interest may be the number of pDCs or the number of local or systemic molecules contributing to the inflammation (inflammatory cytokines and notably INFα).

The following examples aim at illustrating the present invention.

EXAMPLES

Example 1: Preparation and Structure of Five Chimeric Antibodies and a Humanized Antibody of the Prior Art Five chimeric monoclonal antibodies with murine variable regions and human constant regions of IgG1 type were generated and their structures characterized. In addition, humanized antibody B11B059, the sequences of which are described in the application WO2014/09339, was reproduced for comparison with the chimeric antibodies according to the invention.

Materials and Methods

Sequencing of the Heavy and Light Chains from Murine Hybridomas

Total RNA from each hybridoma was extracted using the NucleoSpin RNA II Kit (column purification) from Macherey-Nagel.

The mRNA was converted to cDNA and the heavy and light chains of the antibody were amplified using the GeneRacer Kit (Invitrogen) and cloned into an M13 vector. Bacteria were then transformed by the M13 vector and clones positive for the M13 sequences were sequenced.

Determination of the Heavy Chain VH, DH, JH Segments and the Light Chain VL and JL Segments The variable portion, the V and J segments used by the heavy and light chains and the sequences of the heavy and light chain CDRs were determined by using IMGT's Domain Gap Align tool (see Ehrenmann et al.—2010 and Ehrenmann et al.—2011) available at the following address: http://www.imgt.org/3Dstructure-DB/cgi/DomainGapAlign.cgi.

Construction of Expression Vectors for the Chimeric Antibodies

The sequences of the variable regions, VH and VL, of the five murine antibodies were optimized for preferential use of codons from *Rattus norvegicus*. A sequence encoding heterologous signal peptide MB7 was in addition introduced at the 5' end of the sequence encoding the variable region, VH or VL, of each antibody.

The sequences of the human constant portions were extracted from the expression vector CHK622-21 for a human anti-Rhesus D antibody (T125) by ApaI/AscI digestion for the H chain (IgG1m1.17) and DraIII/XbaI for the Kappa chain.

Lastly, the variable and constant portions of the same chain were introduced simultaneously into the generic HKgenEFss vector by ligation with KAPA T4 ligase, generating the vectors HKBDCA-2-122A2, HKBDCA-2-102E9, HKBDCA-2-104C12, HKBDCA-2-114D11, and HKBDCA-2-104E10 (see FIGS. 1A to 1E).

Production of Chimeric Antibodies

Vectors HKBDCA-2-122A2, HKBDCA-2-102E9, HKBDCA-2-104C12, HKBDCA-2-114D11, and HKBDCA-2-104E10 (see FIGS. 1A to 1E) were transfected into YB2/0 cells, and a clone producing each antibody was selected to produce the chimeric antibodies.

Production of an Antibody Corresponding to the Antibody (B11B059) Described in WO2014/09339

Based on the sequences described in said patent application, the sequences of the heavy (H) chain and of the light (K) chain were synthesized by adding a Kozak sequence and restriction sites on each side of the two H and K sequences, to allow cloning by digestion/ligation.

Figures 1E, 1F:
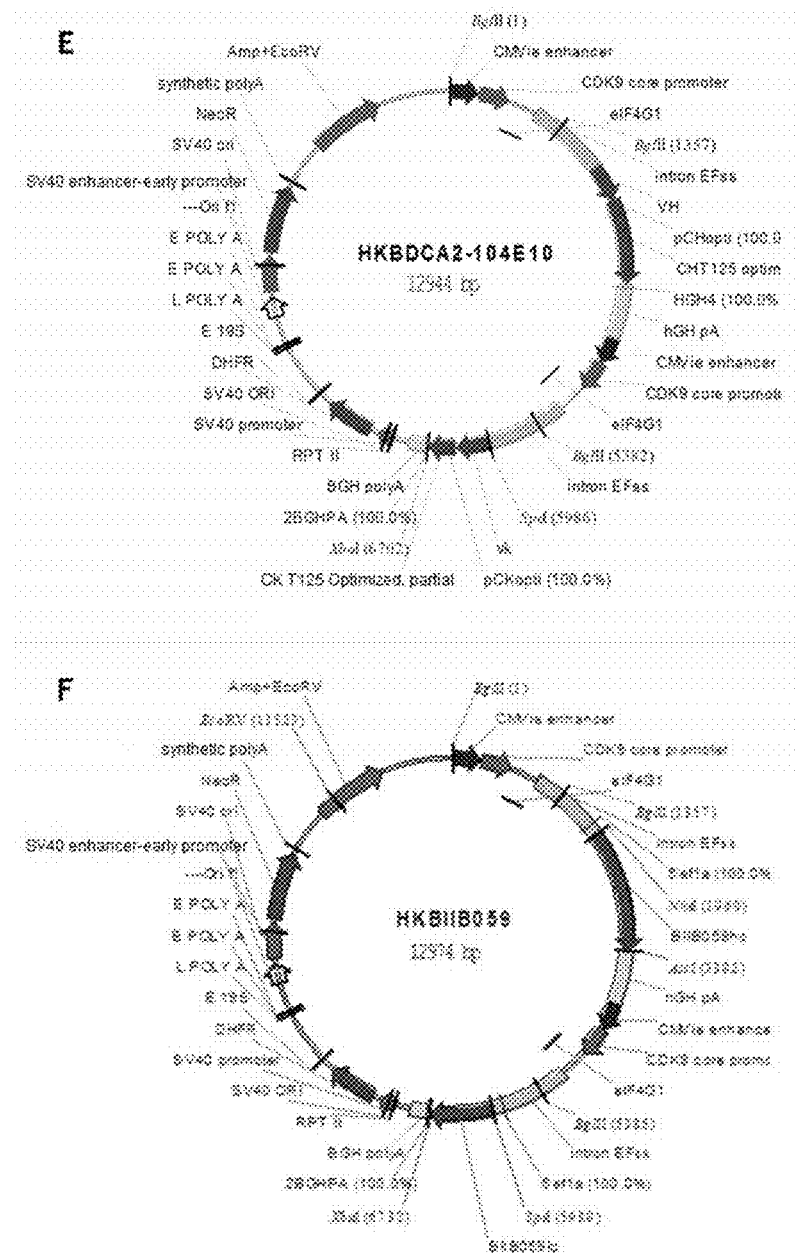

The expression vector used to produce humanized antibody B11B059 is a bicistronic vector, HKgenEFss, of 10,835 bp, which makes it possible to optimally produce the antibody in CHO cells (FIG. 1F). Cloning of the heavy and light chains is carried out in two sequential steps. The first step consists in inserting by digestion/ligation the H chain between the NheI/AscI cloning sites to produce an intermediate vector containing only this chain. During the second step, the K chain is inserted, by the same technique, between the SpeI/XbaI cloning sites. The ligation enzyme is KAPA T4 DNA Ligase (Kapa Biosystems). However, a dephosphorylation step before insertion of the K chain is necessary to prevent the linearized plasmid from circularizing, due to the blunt ends generated by the SpeI/XbaI restriction sites.

Humanized antibody B11B059 is produced by transient transfection from the CHO cell line, in order to meet the conditions of the application WO2014/09339. This line is cultured in ProCHO4 medium, supplemented with 4 mM glutamine. In the laboratory, the line is maintained at 2·10⁵ to 3·10⁵ cells/mL, every 2 days. The solutions used for the transfection are buffer (OptiPRO) and transfection agent (Freestyle Max Reagent).

Once produced, antibody BIIB059 was purified by affinity chromatography.

Results

The data concerning the heavy chain VH, DH, JH segments and the light chain VL and JL segments of the five antibodies are presented in Table 2 above. It is noted that:

The two antibodies of family 1 (122A2 and 104C12) share the use of the same VH segment (IGHV1S137*01), as well as the use of the VL (IGKV10-96*01/IGKV10-96*02) and JL (IGKJ1*01/IGKJ1*02) segments of the same family, as illustrated in Table 18 below. These two antibodies thus have a similar structure.

The three antibodies of family 2 (102E9, 114D11 and 104E10) share the use of the same VH, JH, VL and JL segments, as illustrated in Table 18 below. These three antibodies thus have a similar structure.

TABLE 18

The VH JH, VL and JL segments used by the various antibodies.
The identical segments within the same family are in bold.

| Antibody | VH | JH | VL | JL |
|---|---|---|---|---|
| Family 1 | | | | |
| 122A2 | **IGHV1S137*01** | IGHJ2*02 | **IGKV10-96*01** | **IGKJ1*01** |
| 104C12 | **IGHV1S137*01** | IGHJ3*01 | **IGKV10-96*02** | **IGKJ1*02** |
| Family 2 | | | | |
| 102E9 | **IGHV9-2-1*01** | **IGHJ4*01** | **IGKV4-57*01** | **IGKJ1*02** |
| 114D11 | **IGHV9-2-1*01** | **IGHJ4*01** | **IGKV4-57*01** | **IGKJ1*02** |
| 104E10 | **IGHV9-2-1*01** | **IGHJ4*01** | **IGKV4-57*01** | **IGKJ1*02** |

Furthermore, the data concerning the amino acid sequences of the CDRs and of the variable regions of the five antibodies are presented in Table 3 above. It is noted that:

The two antibodies of family 1 (122A2 and 104C12) have the same CDR1-H and CDR2-L sequences, and in addition have highly similar CDR2-H, CDR1-L and CDR3-L sequences (a difference of only one or two amino acids). Even the CDR3-H sequences have high homology (5/11 amino acids in common), as illustrated in Table 19 below. That confirms that these two antibodies have a very similar structure.

The three antibodies of family 2 (102E9, 114D11 and 104E10) have the same CDR2-L sequences, and in addition have highly similar CDR1-H, CDR2-H, CDR1-L and CDR3-L sequences (only one amino acid of difference). Even the CDR3-H sequences have high homology (12/14 amino acids in common), as illustrated in Table 19 below. That confirms that these three antibodies have a structure that is truly highly similar.

TABLE 19

Sequence homology between the CDRs of antibodies of the same family.

| Family 1 | | | | | | |
|---|---|---|---|---|---|---|
| Antibody | CDR1-H | CDR2-H | CDR3-H | CDR1-L | CDR2-L | CDR3-L |
| 122A2 | GYTFTDYS | ISTYYGDS | ARNGNFYVMDY | QDISNY | YTS | QQGNTLPWT |
| 104C12 | GYTFTDYS | ISPYYGDT | ARNDDYYRFAY | QDINNY | YTS | QQGKTLPWT |

| Family 2 | | | | | | |
|---|---|---|---|---|---|---|
| Antibody | CDR1-H | CDR2-H | CDR3-H | CDR1-L | CDR2-L | CDR3-L |
| 102E9 | GYTFTDYS | INTETGEP | TRNGYYVGYYAMDY | SSVIY | STS | QQRRSYPFT |
| 114D11 | GYTFTDSS | INTETGGP | ARNGYYVGYYALDY | SSVFY | STS | QQRRSYPYT |
| 104E10 | GYTFTDYS | INTETGEP | ARNGYYVGYYAMDY | SSVIY | STS | QQRRSYPYT |

The identical amino acids within the same family are in bold.

The data concerning the amino acid sequences of the constant regions of the five antibodies are presented in Table 9 above.

Moreover, the nucleic acid sequences of the variable regions (VH and VL) and of the constant regions of each antibody are presented in Tables 12 and 15 above. Lastly, the maps of the expression vectors for the five antibodies are presented in FIGS. 1A to 1E.

Conclusions

Five chimeric monoclonal antibodies, with murine variable regions and human constant regions of IgG1 type, and directed against the CD303 antigen, were generated and their structures characterized. It turns out that two antibodies (122A2 and 104C12) have similar structures and form an antibody subfamily (family 1), and that the other three antibodies (102E9, 114D11 and 104E10) are also very similar structurally and form another antibody subfamily (family 2).

A humanized antibody having the sequences of the antibody (B11B059) described in the application WO2014/09339 was also produced in CHO cells (as in the application WO2014/09339).

These antibodies were then characterized in terms of their biological properties (see Example 2).

Example 2: Biological Properties of the Five Chimeric Antibodies and of an Antibody Corresponding to the Antibody (BIIB059) Described in the Application WO2014/09339

The five chimeric monoclonal antibodies, with murine variable regions and human constant regions of IgG1 type, and directed against the CD303 antigen, generated in Example 1 were tested for various biological properties. In certain cases, these properties were compared to those of an antibody corresponding to the antibody (B11B059) described in the application WO2014/09339 (same sequences and same production line).

Materials and Methods

Tested Antibodies

Tested antibodies are those prepared as described in Example 1.

Antigen-Binding

Binding to CD303+ cells (Fcγ chain-CD303 Jurkat, CAL-1, and CAL-1 overexpressing CD303)

Various types of cells expressing CD303 at various antigen densities were used:
1. Fcγ chain-CD303 Jurkat cells, which express about 25,000-35,000 CD303 molecules/cell;
2. CAL-1 cells, as described in Maeda T et al. (Int J Hematol. 2005 February; 81(2):148-54), which express about 3,000-6,000 CD303 molecules/cell;
3. CAL-1 cells transfected with a CD303 expression vector, selected for their high CD303 expression, about 40,000-50,000 CD303 molecules/cell.

The CD303-expressing cells and the antibodies are prepared in diluent (PBS+1% FCS). $1 \cdot 10^5$ cells are incubated at 4° C. for 30 minutes with 100 µL of antibody (anti-CD303 or negative control) at various concentrations (0-40 µg/mL, final concentration). After washing with the diluent, the antibodies are visualized by addition of a phycoerythrin (PE)-coupled goat anti-mouse IgG F(ab')$_2$ fragment (100 µL diluted to 1:100 in the diluent) for 45 minutes at 4° C. The cells are then washed and analyzed by flow cytometry (FC500, Beckman Coulter).

FcγRIIIa (CD16a)-Binding

NK cells were isolated from peripheral blood mononuclear cells (PBMCs), then incubated with varying concentrations of the antibodies tested (0 to 100 µg/mL) simultaneously incubated with the phycoerythrin-coupled murine antibody (3G8-PE, Beckman Coulter) at 10 µL/test.

After washing, the binding of 3G8-PE to CD16 expressed by the NK cells was evaluated by flow cytometry. Mean fluorescence intensity (MFI) values are expressed as a percentage, 100% being the value obtained with the 3G8-PE antibody alone, and 0% the value obtained in the absence of 3G8-PE.

IC50 values (concentration of anti-CD303 antibody necessary to induce 50% inhibition of 3G8-binding) are calculated using the PRISM software.

ADCC

Fcγ chain-CD303 Jurkat cells (35,000 cells/well) are incubated in a 96-well flat-bottom plate with NK cells and increasing concentrations of anti-CD303 antibody for 4 hours at 37° C. After incubation, the supernatant is collected. Lysis of the target cells induced by the anti-CD303 antibodies is measured chromogenically by quantifying the intracellular lactate dehydrogenase (LDH) enzyme released into the supernatant by the lysed target cells (Cytotoxicity Detection Kit (LDH), Roche Diagnostics).

The percentage of lysis is calculated according to the following formula:

$$\% \text{ lysis} = [(ER-SR)/(100-SR)] - [(NC-SR)/(100-SR)]$$

Where ER and SR represent the experimental release (ER) and the spontaneous release (SR) of LDH, respectively, and NC represents the natural cytotoxicity of the NK cells.

The results (% lysis) are expressed as a function of antibody dilution factor. For each antibody, the "50% activity" value corresponds to the antibody dilution factor necessary to induce 50% of the plateau value obtained for this antibody. This value was calculated with the PRISM software.

Inhibition of IFN-α Secretion

Preparation of the Cells

Peripheral blood mononuclear cells (PBMCs) are isolated from peripheral blood of healthy donors by Ficoll density gradient. The pDCs are purified by negative depletion (Miltenyi Biotec—Plasmacytoid Dendritic Cell Isolation Kit, human). The cells are counted and resuspended at $2 \cdot 10^5$ cells/mL in diluent (RPMI 1640+10% fetal calf serum (FCS)).

IFN-α Secretion by Purified pDCs

This suspension (205 µL/well) is then transferred to a 24-well flat-bottom culture plate. CpG ODN (10 µM, 50 µL), IL-3 (100 ng/mL, 50 µL), antibody (100 µg/mL, 50 µL) and diluent (100 µL) are added. The plate is then incubated overnight at 37° C., 7% $CO_2$.

IFN-α Assay

The culture supernatants of each well are collected and assayed by flow cytometry by using the FlowCytomix Human IFN-α Kit (Bender MedSystems BMS216FF+Basic kit BMS8420FF).

The percentage of inhibition of each sample is evaluated in relation to the negative control (CPG-activated pDCs without anti-CD303 monoclonal antibody).

The samples leading to less than 20% inhibition are considered non-inhibitors, those leading to between 20% and 75% inhibition are considered weak inhibitors, those leading to greater than 75% inhibition are considered strong inhibitors.

Inhibition of TNF-α Secretion
Preparation of the Cells

Peripheral blood mononuclear cells (PBMCs) are isolated from peripheral blood of healthy donors by Ficoll density gradient. The pDCs are purified by negative depletion (Miltenyi Biotec—Plasmacytoid Dendritic Cell Isolation Kit, human). The cells are counted and resuspended at $2 \cdot 10^5$ cells/mL in diluent (RPMI 1640+10% fetal calf serum (FCS)).

TNF-α Secretion by Purified pDCs

This suspension (205 μL/well) is then transferred to a 24-well flat-bottom culture plate. CpG ODN (10 μM, 50 μL), IL-3 (100 ng/mL, 50 μL), antibody (100 μg/mL, 50 μL) and diluent (100 μL) are added. The plate is then incubated overnight at 37° C., 7% $CO_2$.

TNF-α Assay

The culture supernatants of each well are collected and assayed by flow cytometry by using the FlowCytomix Human IFN-α Kit (Bender MedSystems BMS216FF+Basic kit BMS8420FF).

The percentage of inhibition of each sample is evaluated in relation to the negative control (CPG-activated pDCs without anti-CD303 monoclonal antibody).

The samples leading to less than 20% inhibition are considered non-inhibitors, those leading to between 20% and 75% inhibition are considered weak inhibitors, those leading to greater than 75% inhibition are considered strong inhibitors.

Measurement of Complement-Dependent Cytotoxicity (CDC) Activity

Fcγ chain-CD303 Jurkat cells are incubated with increasing concentrations of anti-CD303 antibody (0 to 5,000 ng/mL) and in the presence of baby rabbit serum as source of (1:10 dilution).

After 2 hours of incubation at 37° C., the amount of intracellular lactate dehydrogenase (LDH) enzyme released into the supernatant by the lysed target cells is measured with the Cytotoxicity Detection Kit (LDH) (Roche Diagnostics, product no. 11644793001).

Results
Antigen-Binding
Binding to Fcγ Chain-CD303 Jurkat Cells

Figures 2A, 2B:
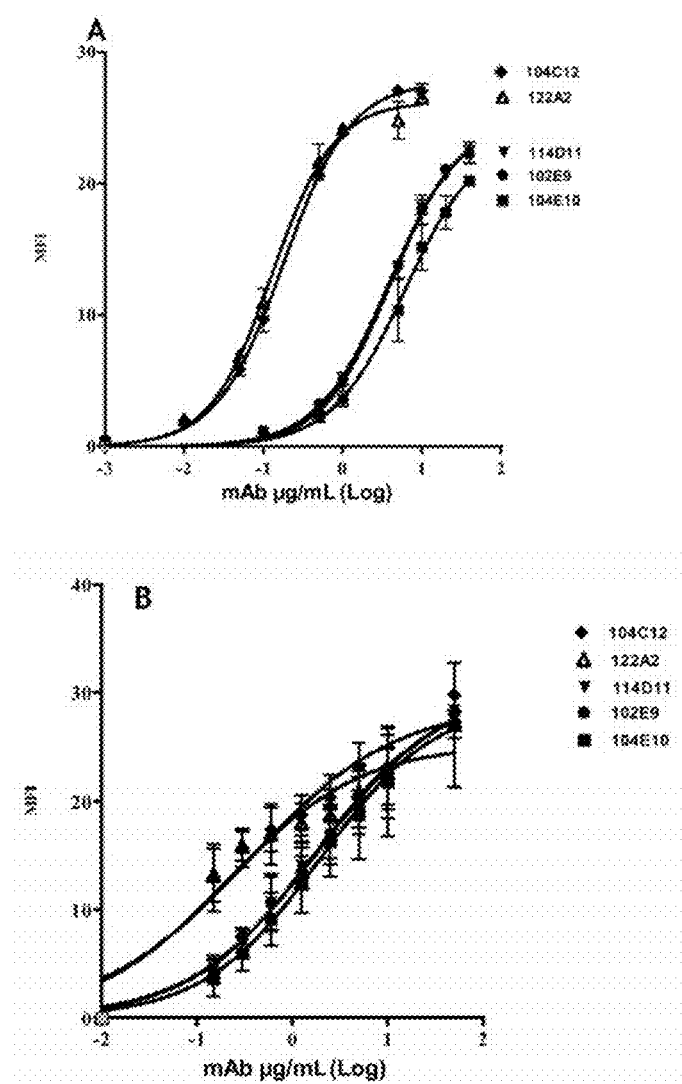
FIG. 2. Antigen-binding of the antibodies according to the invention. (A) Mean fluorescence intensity (MFI) of Fcγ chain-CD303 Jurkat cells (expressing about 25,000-35,000 CD303 molecules/cell) labeled with the antibodies according to the invention, at different antibody concentrations (represented in logarithmic units). (B) Mean fluorescence intensity (MFI) of CAL-1 cells (cell line established from a BPDCN patient) labeled with the chimeric antibodies according to the invention, at different antibody concentrations (represented in logarithmic units). (C) Mean fluorescence intensity (MFI) of CAL-1 cells (cell line established from a BPDCN patient, expressing about 3,000-6,000 CD303 molecules/cell) labeled with one of chimeric antibodies 122A2 and 102E9, with humanized antibody BIIB059 or with an irrelevant antibody. (D) Mean fluorescence intensity (MFI) of CAL-1 cells transfected with a CD303 expression vector and selected for their high expression of CD303, about 40,000-50,000 CD303 molecules/cell, labeled with one of chimeric antibodies 122A2 and 102E9, with humanized antibody BIIB059 or with an irrelevant antibody.

The results of the tests for binding of the antibodies according to the invention to their CD303 antigen on Fcγ chain-CD303 Jurkat cells are presented in FIG. 2A and in Table 20 below.

TABLE 20

Binding of the antibodies according to the invention to their CD303 antigen on Fcγ chain-CD303 Jurkat cells.

|  | 104C12 | 122A2 | 114D11 | 102C9 | 104E10 |
|---|---|---|---|---|---|
| Bmax (MFI) | 27.74 | 26.21 | 24.69 | 24.95 | 23.73 |
| EC50 (μg/mL) | 0.1781 | 0.1284 | 3.980 | 3.870 | 6.064 |

Bmax: maximum binding expressed as mean fluorescence intensity (MFI).
EC50 (μg/mL): antibody concentration in μg/mL to obtain 50% of the maximum binding obtained for this antibody.

These relative Kd results and the Bmax values calculated after dose-response modeling make it possible to classify the antibodies into two groups: A first group that contains the antibodies 104C12 (Bmax: MFI=27.7; Kd=0.17 μg/mL) and 122A2 (Bmax: MFI=26.2 Kd=0.13 μg/mL) which are comparable and exhibit higher relative affinity than the antibodies of the second group: 114D11 (Bmax: MFI=24.7; Kd=3.9 μg/mL), 104E10 (Bmax: MFI=23.7; Kd=6 μg/mL) and 102E9 (Bmax: MFI=24.9; Kd=3.8 μg/mL).

These results show that all the chimeric antibodies generated efficiently bind the CD303 antigen expressed on the surface of Jurkat cells, for which they are specific.

Binding to CAL-1 Cells

The results of the tests for binding of the chimeric antibodies according to the invention to their CD303 antigen on CAL-1 cells are presented in FIG. 2B and in Table 21 below.

TABLE 21

Binding of the chimeric antibodies according to the invention to their CD303 antigen on CAL-1 cells.

|  | 104C12 | 122A2 | 114D11 | 102E9 | 104E10 |
|---|---|---|---|---|---|
| Bmax (MFI) | 29.02 | 25.22 | 30.14 | 30.47 | 29.2 |
| EC50 (μg/mL) | 0.3447 | 0.2075 | 1.704 | 1.813 | 1.932 |

Bmax: maximum binding expressed as mean fluorescence intensity (MFI).
EC50 (μg/mL): antibody concentration in μg/mL to obtain 50% of the maximum binding obtained for this antibody.

These relative Kd results and the Bmax values calculated after dose-response modeling make it possible to classify the antibodies into two groups: A first group that contains the antibodies 104C12 (Bmax: MFI=29.02 Kd=0.34 μg/mL) and 122A2 (Bmax: MFI=25.2 Kd=0.20 μg/mL) which are comparable and exhibit higher relative affinity than the antibodies of the second group: 114D11 (Bmax: MFI=30.1; Kd=1.7 μg/mL), 104E10 (Bmax: MFI=29.2; Kd=1.93 μg/mL) and 102E9 (Bmax: MFI=30.47; Kd=1.81 μg/mL).

These results notably correlate with the results for binding to Jurkat-CD303 cells.

In another experiment, the CAL-1 cell-binding of chimeric antibodies 122A2 and 102E9 and of humanized antibody B11B059 was tested. The results are presented in FIG. 2C and in Table 22 below.

TABLE 22

Binding of the chimeric antibodies according to the invention, 122A2 and 102E9, and of humanized antibody BIIB059 to their CD303 antigen on CAL-1 cells.

|  | 122A2 | 102E9 | BIIB059 |
|---|---|---|---|
| Bmax | 13.2 | 14.7 | 11.8 |
| EC50 (μg/mL) | 0.06 | 0.44 | 0.6 |
| Relative EC50 (122A2 = 1) | 1 | 6.9 | 9.3 |

Bmax: maximum binding expressed as mean fluorescence intensity (MFI).
EC50 (μg/mL): antibody concentration in μg/mL to obtain 50% of the maximum binding obtained for this antibody.

These data show that the two chimeric antibodies according to the invention, 122A2 and 102E9 (and in particular chimeric antibody 122A2), bind more strongly than humanized antibody 6116059 to the CD303 antigen on the surface of CAL-1 cells.

Binding to CAL-1 Cells Overexpressing the CD303 Antigen

Figures 2C, 2D:
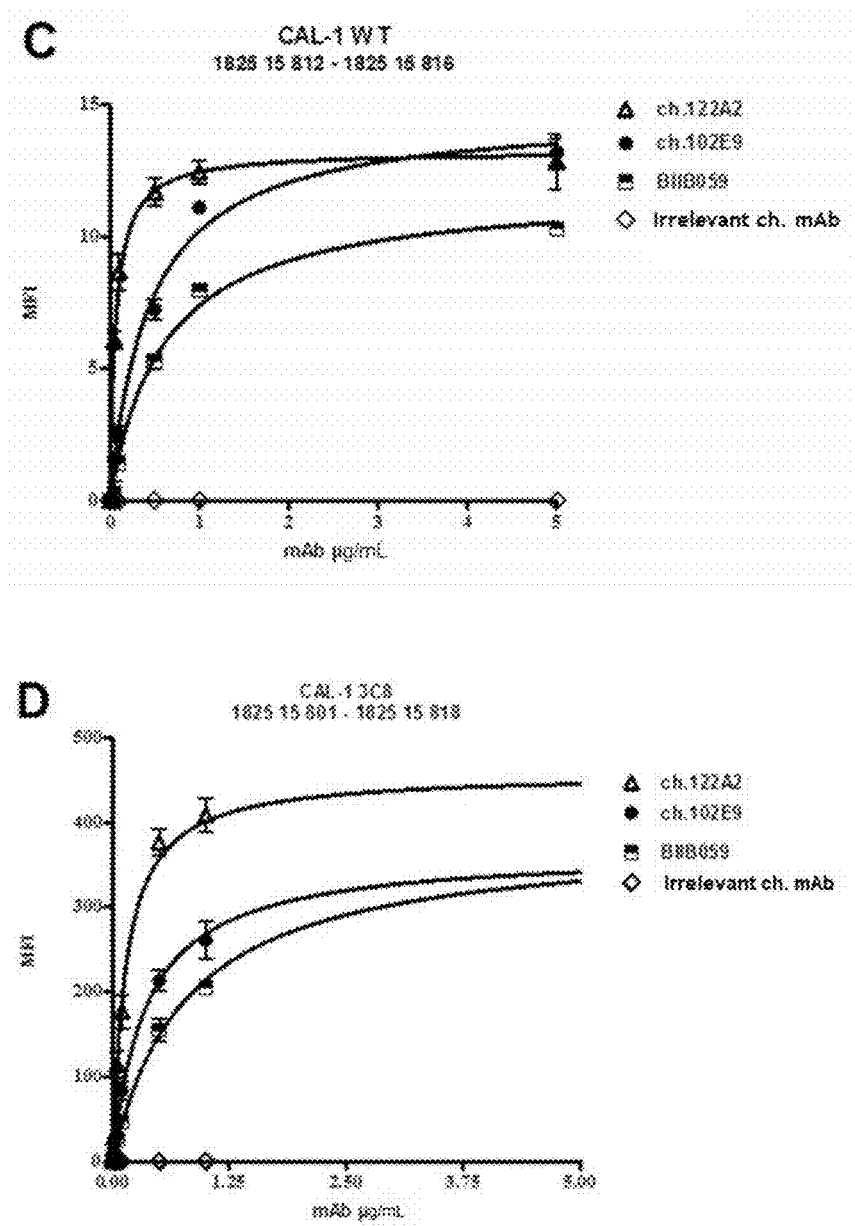

The results of the tests for binding of the chimeric antibodies 122A2 and 102E9 according to the invention and of humanized antibody 6116059 to their CD303 antigen on CAL-1 cells transfected with a CD303 expression vector and expressing about 40,000-50,000 CD303 molecules/cell (or about 10 times more than wild-type CAL-1 cells) are presented in FIG. 2D and in Table 23 below.

TABLE 23

Binding of the chimeric antibodies according to the invention, 122A2 and 102E9, and of humanized antibody BIIB059 to their CD303 antigen on CAL-1 cells transfected with a CD303 expression vector and expressing about 40,000-50,000 CD303 molecules/cell (or about 10 times more than wild-type CAL-1 cells).

|  | 122A2 | 102E9 | BIIB059 |
|---|---|---|---|
| Bmax | 458.1 | 366.2 | 382.2 |
| EC50 (µg/mL) | 0.142 | 0.3629 | 0.7841 |
| Relative EC50 (122A2 = 1) | 1 | 2.56 | 5.52 |

Bmax: maximum binding expressed as mean fluorescence intensity (MFI).
EC50 (µg/mL): antibody concentration in µg/mL to obtain 50% of the maximum binding obtained for this antibody.

These data again show that the two chimeric antibodies according to the invention, 122A2 and 102E9 (and in particular chimeric antibody 122A2), bind more strongly than humanized antibody 6116059 to the CD303 antigen on the surface of CAL-1 cells transfected with a CD303 expression vector and expressing about 40,000-50,000 CD303 molecules/cell.

FcγRIIIa (CD16a)-Binding

Figures 3A, 3B:
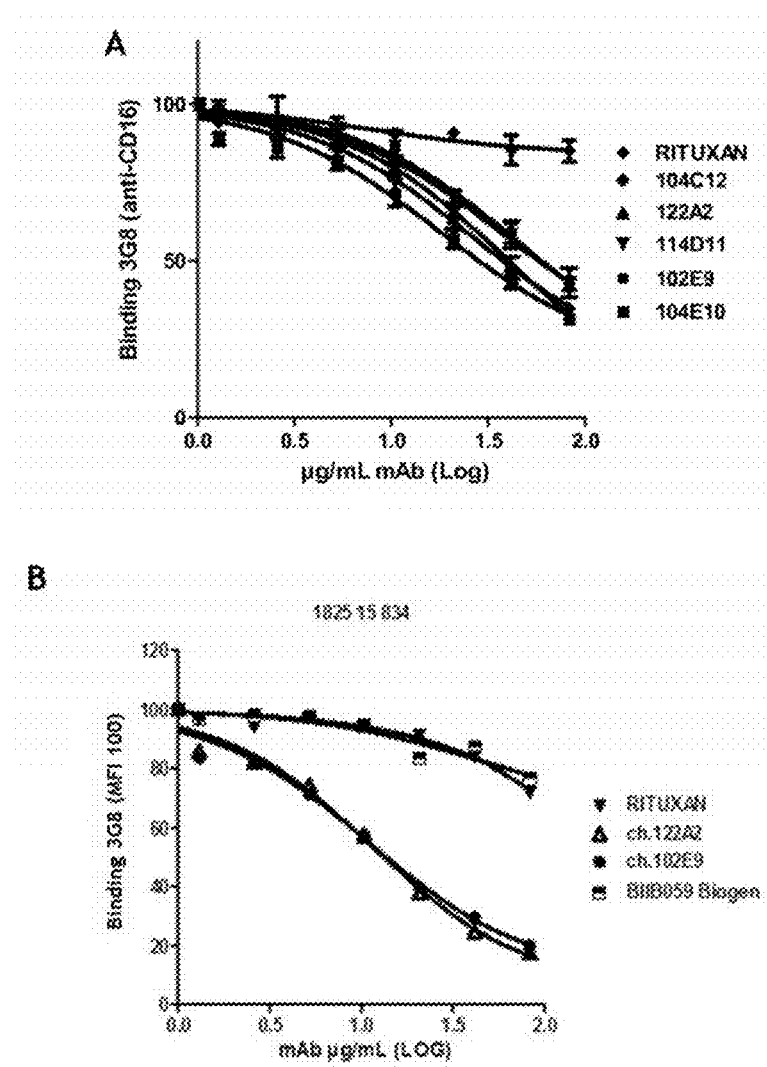
FIG. 3. FcγRIIIa (CD16a)-binding. (A) The CD16-binding of the antibodies according to the invention was studied in a competition experiment using a phycoerythrin-coupled murine anti-CD16 antibody, 3G8. The binding of anti-CD16 3G8 to CD16 (mean fluorescence intensity values) is measured as a function of the increasing concentration of antibodies according to the invention added (μg/mL). (B) The CD16-binding of chimeric antibodies ch.122A2 and ch.102E9 according to the invention, of the chimeric antibody Rituxan and of the humanized antibody (31113059) described in the application WO2014/09339 was studied in a competition experiment using a phycoerythrin-coupled murine anti-CD16 antibody, 3G8. The binding of anti-CD16 3G8 to CD16 (mean fluorescence intensity values) is measured as a function of the increasing concentration of antibodies according to the invention added (μg/mL).

The results of the tests for binding to FcγRIIIa (CD16a) of the five chimeric antibodies according to the invention are presented in FIG. 3A, and show that the chimeric antibodies according to the invention are all capable of efficiently binding CD16a, with an optimized binding affinity. They have an IC50 value below that of the antibody produced in CHO cells (Rituxan), in a range of 18.08 to 45.02 µg/mL, even below 18 µg/mL, as illustrated in Table 24 below.

TABLE 24

IC50 values (concentration of anti-CD303 antibody necessary to induce 50% inhibition of 3G8-binding) of the control (Rituxan) and of the chimeric antibodies of the invention.

|  | RITUXAN | 104C12 | 122A2 | 114D11 | 102E9 | 104E10 |
|---|---|---|---|---|---|---|
| IC50 (µg/mL) | >80 | 26.75 | 40.44 | 45.02 | 36.99 | 18.08 |

The results of the tests for FcγRIIIa (CD16a)-binding of the two chimeric antibodies according to the invention, 122A2 and 102E9, and of humanized antibody 8116059 are presented in FIG. 3B and in Table 25 below, and show that the two chimeric antibodies according to the invention, 122A2 and 102E9, bind to FcγRIIIa (CD16a) much more strongly than the antibodies Rituxan and 8116059.

TABLE 25

IC50 values (concentration of anti-CD303 antibody necessary to induce 50% inhibition of 3G8-binding) of the control (Rituxan), of the chimeric antibodies of the invention 122A2 and 102E9, and of humanized antibody BIIB059.

| Antibody | IC50 µg/mL (50%) |
|---|---|
| Rituxan | >83 |
| 122A2 | 13 |
| 102E9 | 13 |
| BIIB059 | >83 |

ADCC

Figure 4A:
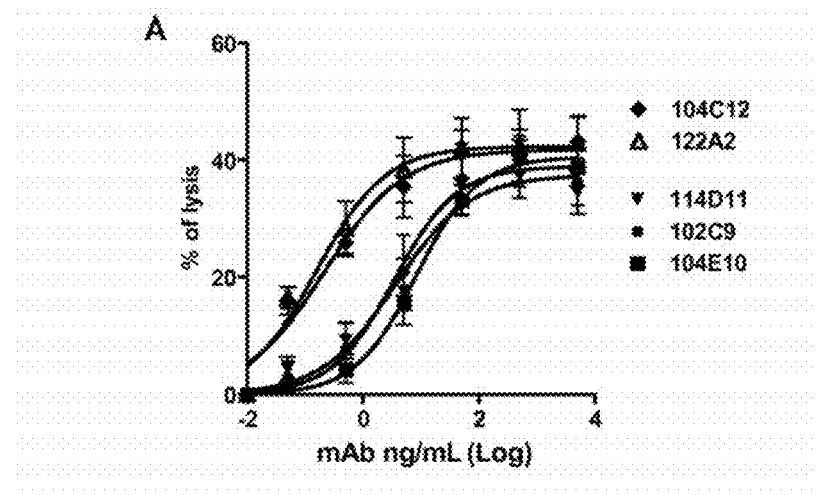
FIG. 4. ADCC activities induced by the chimeric antibodies of the invention and humanized antibody BIIB059 with respect to Fcγ chain-CD303 Jurkat cells (A) or CAL-1 cells (B). (A) The percentage of lysis by ADCC (% lysis, as defined in Example 2) of Fcγ chain-CD303 Jurkat target cells induced by the chimeric antibodies according to the invention is represented as a function of antibody concentration (ng/mL, logarithmic scale). (B) The percentage of lysis by ADCC (% lysis, as defined in Example 2) of CAL-1 target cells induced by the chimeric antibodies according to the invention, 122A2 and 102E9, and by humanized antibody BIIB059 is represented as a function of antibody concentration (ng/mL, logarithmic scale).

The results of the tests for ADCC of the five chimeric antibodies according to the invention on Fcγ chain-CD303 Jurkat target cells are presented in FIG. 4A and in Table 26 below.

TABLE 26

ADCC induced by the antibodies according to the invention on Fcγ chain-CD303 Jurkat target cells.

|  | 104C12 | 122A2 | 114D11 | 102E9 | 104E10 |
|---|---|---|---|---|---|
| Emax (% lysis) | 41.81 | 42.35 | 37.44 | 38.92 | 40.54 |
| EC50 (ng/mL) | 0.2143 | 0.1592 | 3.612 | 3.424 | 8.280 |

Emax: maximum lysis obtained with this antibody, expressed as a percentage of lysis.
EC50 (ng/mL): concentration of antibody in ng/mL to obtain 50% of the maximum lysis obtained for this antibody.

These results show that the five anti-CD303 chimeric antibodies induce lysis of Jurkat-CD303 cells (Emax about 40%). The EC50 values for 104C12 (EC50: 0.21 ng/mL), 122A2 (EC50: 0.16 ng/mL), 114D11 (EC50: 3.6 ng/mL), 102E9 (EC50: 3.4 ng/mL) and 104E10 (EC50: 8.3 ng/mL) suggest that the antibodies having high affinity are more effective with regard to ADCC than the antibodies having lower affinity.

Figure 4B:
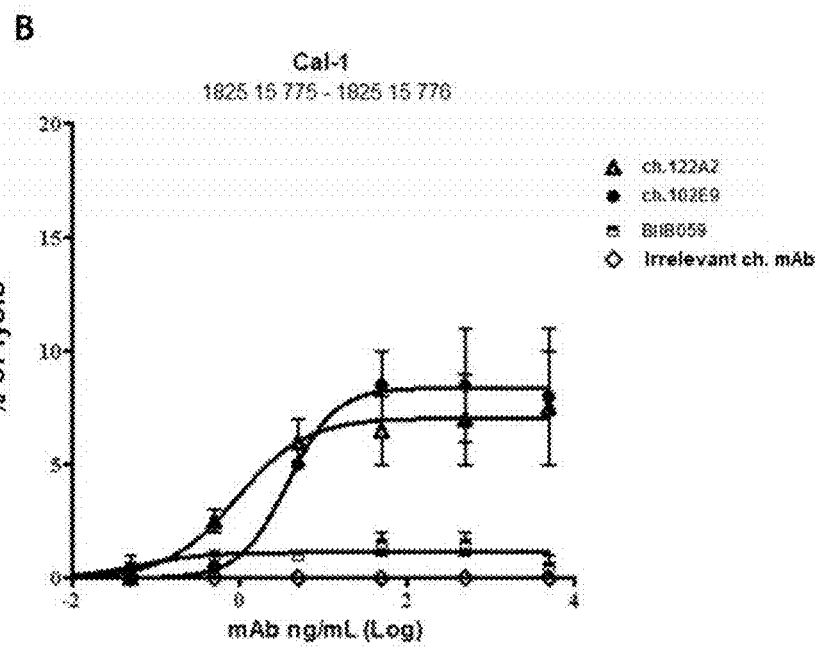

The results of the tests for ADCC of an irrelevant antibody (anti-factor VIII inhibitor antibodies, Anti Id FVIII), of the two chimeric antibodies according to the invention, 122A2 and 102E9, and of humanized antibody B1113059 on CAL-1 target cells are presented in FIG. 4B and in Table 27 below.

TABLE 27

ADCC induced by the antibodies according to the invention on Fcγ chain-CD303 Jurkat target cells.

|  | Anti Id FVIII | 122A2 | 102E9 | BIIB059 |
|---|---|---|---|---|
| Emax (% lysis) | nd | 7.04 | 8.38 | 1.12 |
| EC50 (ng/mL) | nd | 0.93 | 3.80 | nd |

Emax: maximum lysis obtained with this antibody, expressed as a percentage of lysis.
EC50 (ng/mL): concentration of antibody in ng/mL to obtain 50% of the maximum lysis obtained for this antibody.
nd: not detectable.

These results show that, unlike humanized antibody 6116059, the two chimeric antibodies according to the invention, 122A2 and 102E9, are capable of inducing lysis of CAL-1 cells very weakly expressing the CD303 antigen. Moreover, the stronger ADCC response of the chimeric antibody according to the invention 122A2 compared to the chimeric antibody according to the invention 102E9 also suggests than the antibodies having high affinity are more effective with regard to ADCC than the antibodies having lower affinity.

Inhibition of IFN-α Secretion

Figure 5:
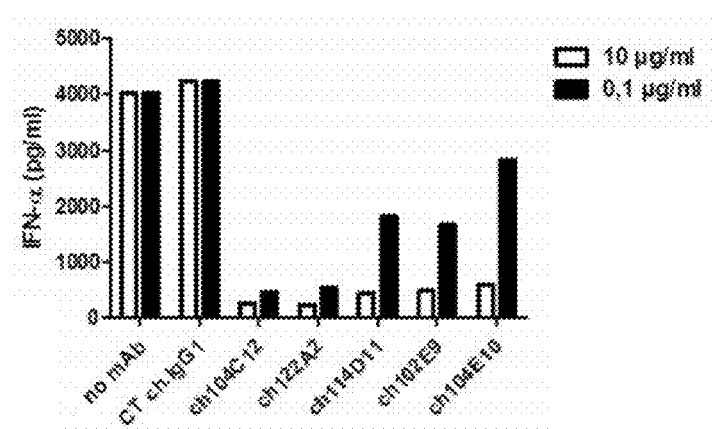
FIG. 5. Inhibition induced by the antibodies of the invention of IFN-α secretion by pDCs. Amount of IFN-α (in pg/mL) secreted by CpG-activated purified pDCs, in the presence of the chimeric antibodies of the invention at 10 and 0.1 μg/mL, and of an irrelevant control chimeric antibody.

The results of the tests for inhibition of IFN-α secretion by activated pDCs are presented in FIG. 5.

These results show that the five anti-CD303 chimeric antibodies induce inhibition of IFN-α secreted by CpG-activated pDCs and this at both concentrations tested (10 and 0.1 µg/mL). At the concentration of 0.1 µg/mL, the IFN-α assays show an advantage for antibodies 104C12 and 122A2 compared to the other three antibodies (114D11, 102E9, 104E10).

Inhibition of TNF-α Secretion

Figure 6:
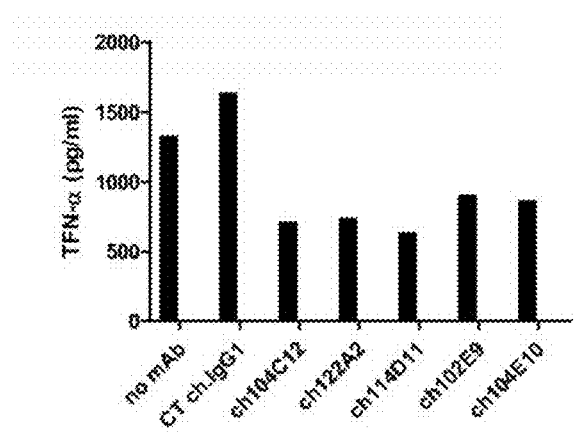
FIG. 6. Inhibition induced by the antibodies of the invention of TNF-α secretion by CpG-activated purified pDCs, in the presence of the chimeric antibodies (10 μg/mL) of the invention and of an irrelevant control chimeric antibody.

The results of the tests for inhibition of TNF-α secretion by activated pDCs are presented in FIG. 6.

These results show that the five anti-CD303 chimeric antibodies at 10 µg/mL induce inhibition of TNF-α secreted by CpG-activated pDCs.

Complement-Dependent Cytotoxicity (CDC) Activity

Figure 7:
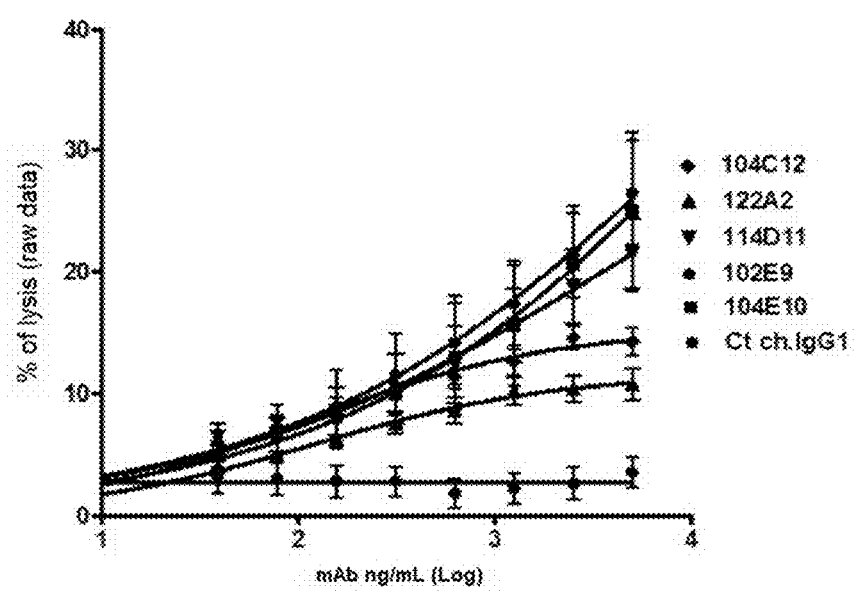
FIG. 7. CDC activities induced by the antibodies of the invention with respect to Fcγ chain-CD303 Jurkat cells. The percentage of lysis by CDC (% lysis, as defined in Example 2) of Fcγ chain-CD303 Jurkat target cells induced by the chimeric antibodies according to the invention is represented as a function of antibody concentration (ng/mL, logarithmic scale).

The results of the CDC tests are presented in FIG. 7, and show that the five chimeric antibodies indeed have CDC activity.

Example 3. Preparation and Characterization of Humanized Antibodies Derived from Chimeric Antibodies 122A2 and 102E9

Materials and Methods
Definition of Humanized Sequences

A work of humanization in silico, making use of the IMGT.org database and modeling, was undertaken to define various sequences of the variable portions of the heavy and light chains containing "human amino acids" instead of their murine homologues.

For each VH or VL domain, the human gene encoding a VH or VL domain having the amino acid sequence closest to that of the murine sequence of the original chimeric antibody was determined. The closest human VH and VL genes determined for chimeric antibodies 122A2 and 102E9 are mentioned in Table 28 below:

TABLE 28

The human VH and VL genes closest to the murine sequences of the original chimeric antibody (IMGT nomenclature).

|  | VH | VL |
| --- | --- | --- |
| 122A2 | IGHV1-2*02 | IGKV1-33*01 |
| 102E9 | IGHV7-4-1*02 | IGKV1-9*01 |

For each VH and VL domain, based on an alignment between the murine amino acid sequence of the original chimeric antibody and the amino acid sequence of the closest human gene, the different mutation positions between the two amino acid sequences (murine/human) were determined, and several murine sequences incorporating a variable number of mutations replacing a murine amino acid with a human amino acid were generated.

Thus, for each of antibodies 122A2 and 102E9, three versions of each heavy chain variable portion (Hha, Hhb and Hhc) and light chain variable portion (Kha, Khb and Khc) were determined. A fourth version of the light chain variable portion (Khd) is added, concerning antibody 122A2. These various sequences comprise variable numbers of mutations relative to the VH and VL regions of the original chimeric antibody, as described in Table 29 below:

TABLE 29

Mutations of the amino acid sequences of the VH and VL regions of the humanized antibodies derived from chimeric antibodies 122A2 and 102E9, compared to the VH and VL regions of the original chimeric antibody.

|  |  | Mutations* | Number of mutations relative to the chimeric antibody |
| --- | --- | --- | --- |
| Humanized antibodies derived from chimeric antibody 122A2 |
| 122A2 VH humanized | Hha** | L12V/R14K/V17A/S45A/A76V/T85S/A92S/E97D/S99T/I101V/S123L | 11 |
|  | Hhb | L12V/R14K/V17A/K43R/S45A/A76V/K82T/T85S/A92S/T95R/E97D/S99T/I101V/S123L | 14 |
|  | Hhc | L12V/R14K/V17A/K43R/S45A/H46P/A47G/K48Q/S49G/A76V/T85S/A92S/E97D/S99T/I101V/S123L | 16 |
| 122A2 VL humanized | Kha** | T7S/S22T/R24Q/S69T/F103Y | 5 |
|  | Khb | T7S/T8P/L15V/S22T/R24Q/S69T/F103Y | 7 |
|  | Khc | T7S/S22T/R24Q/R66N/S69T/D95Q/F103Y | 7 |
|  | Khd | T7S/T8P/L15V/S22T/R24Q/R66N/S69T/D95Q/F103Y | 9 |
| Humanized antibodies derived from chimeric antibody 102E9 |
| 102E9 VH humanized | Hha** | D11E/T18S/K48Q/A77V/E81D/S82T/A84V/F88Y/N93S/F103Y | 10 |
|  | Hhb | D11E/T18S/K43R/K48Q/D69Q/A77V/E81D/S82T/A84V/F88Y/N93S/F103Y | 12 |
|  | Hhc | P9S/D11E/T18S/K43R/K48Q/D69Q/A77V/E81D/S82T/A84V/F88Y/N93S/F103Y | 13 |
| 102E9 VL humanized | Kha | V3Q/A9S/I10F/M11L/K18R/T48K/S49A/A74S/S86E/S88T/R93S/A99F | 12 |
|  | Khb** | V3Q/A9S/I10F/M11L/K18R/S49A/A74S/S88T/A99F | 9 |
|  | Khc | V3Q/A9S/I10F/M11L/E17D/K18R/T48K/S49A/A74S/S86E/S88T/R93S/E95Q/A99F | 14 |

For each VH or VL domain, the sequence with the minimum number of mutations relative to the VH and VL regions of the original chimeric antibody is indicated by **.
The additional mutations of the other sequences relative to the sequence indicated by ** are underlined.
**The position of the amino acid residues corresponds to IMGT unique numbering.

Preparation of the Expression Vectors

The various sequences were synthesized as linear double-stranded DNA, called "String", with codon optimization for *Rattus norvegicus*.

Figures 8A, 8B:
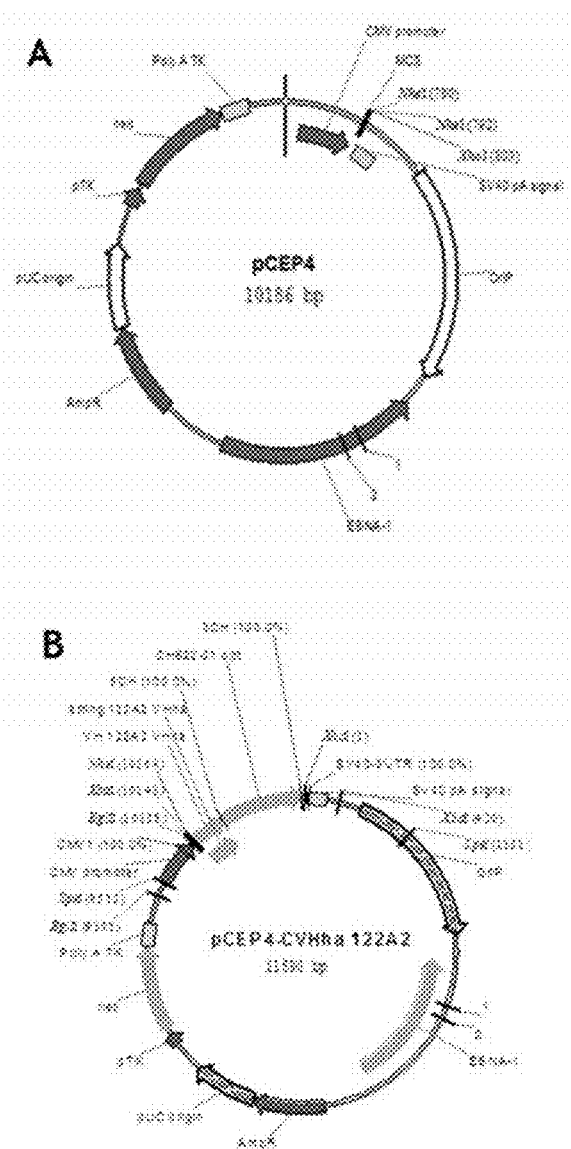
FIG. 8. Maps of the empty vector pCEP4 (A) and of the expression vectors for the heavy or light chains of humanized antibodies 122A2 (B to H) and 102E9 (I to N).
Figures 8C, 8D:
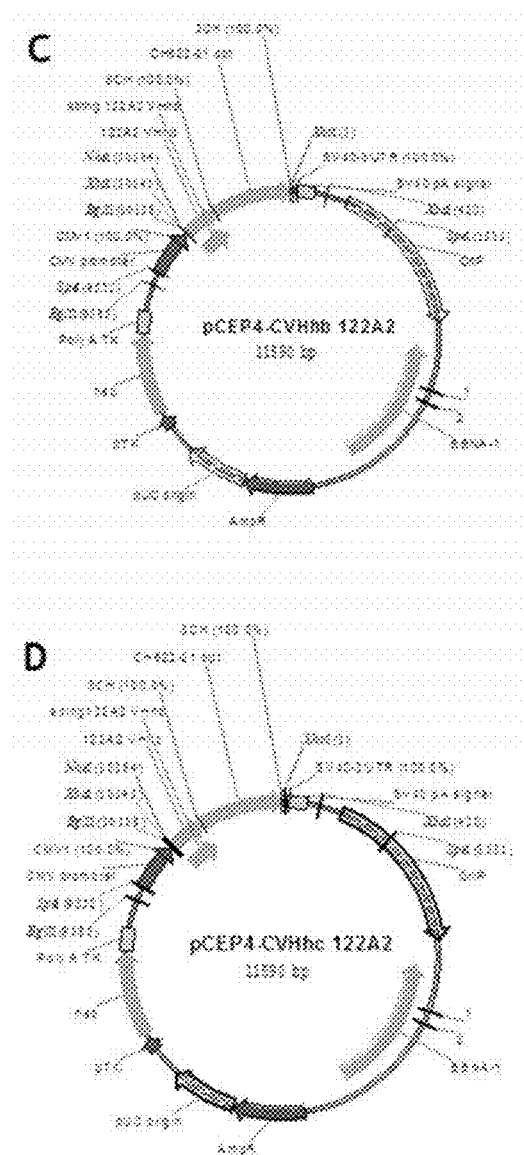
Figures 8E, 8F:
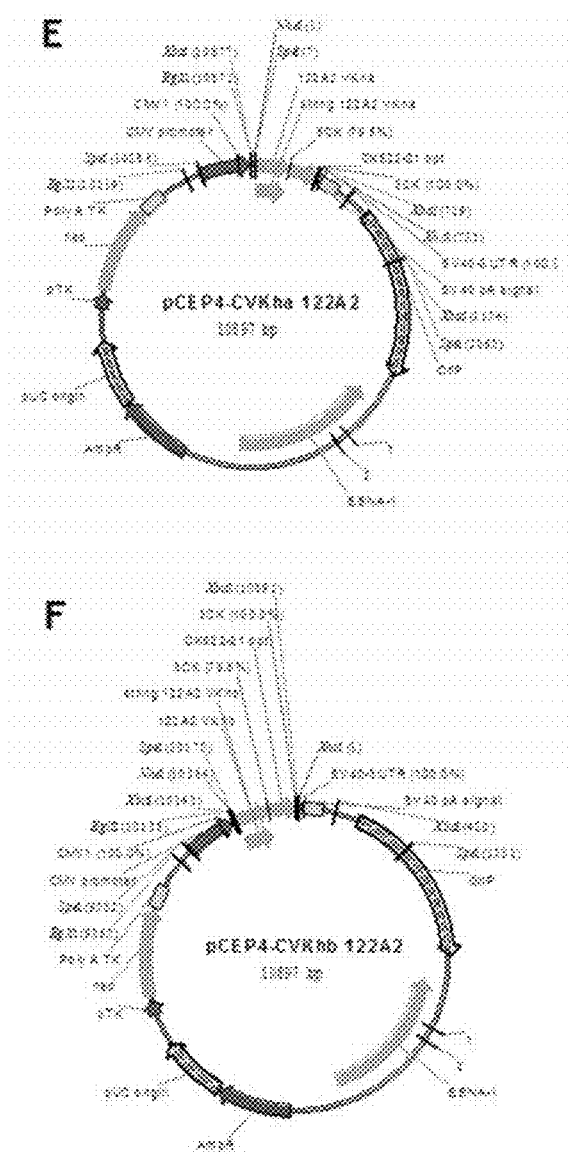
Figures 8G, 8H:
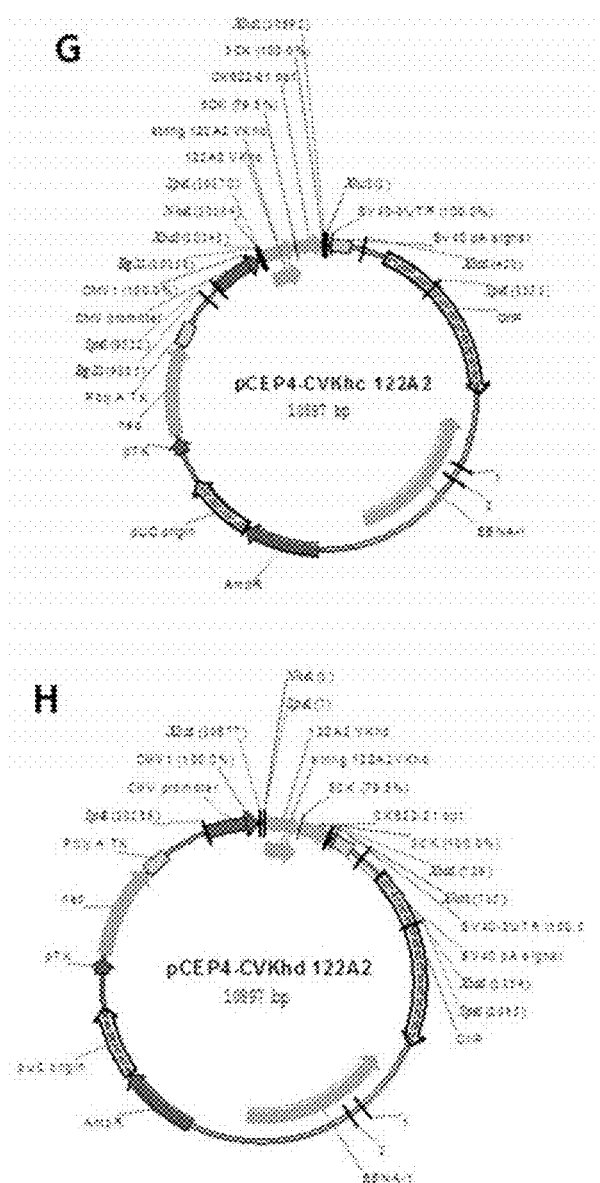
Figure 8I:
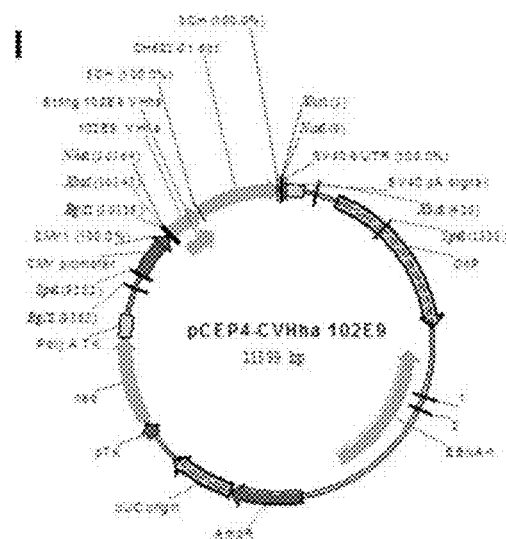
Figure 8J:
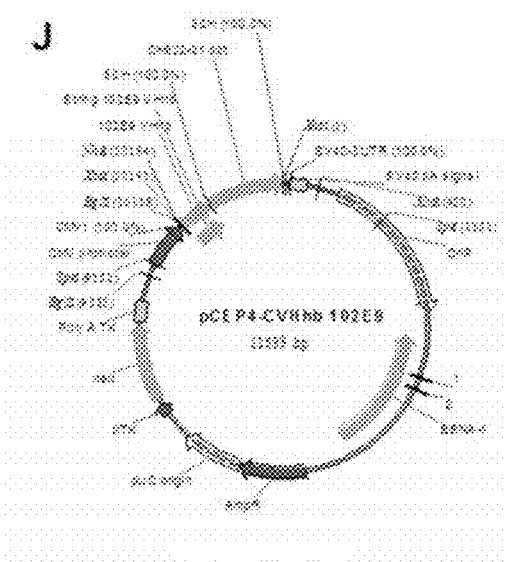
Figures 8K, 8L:
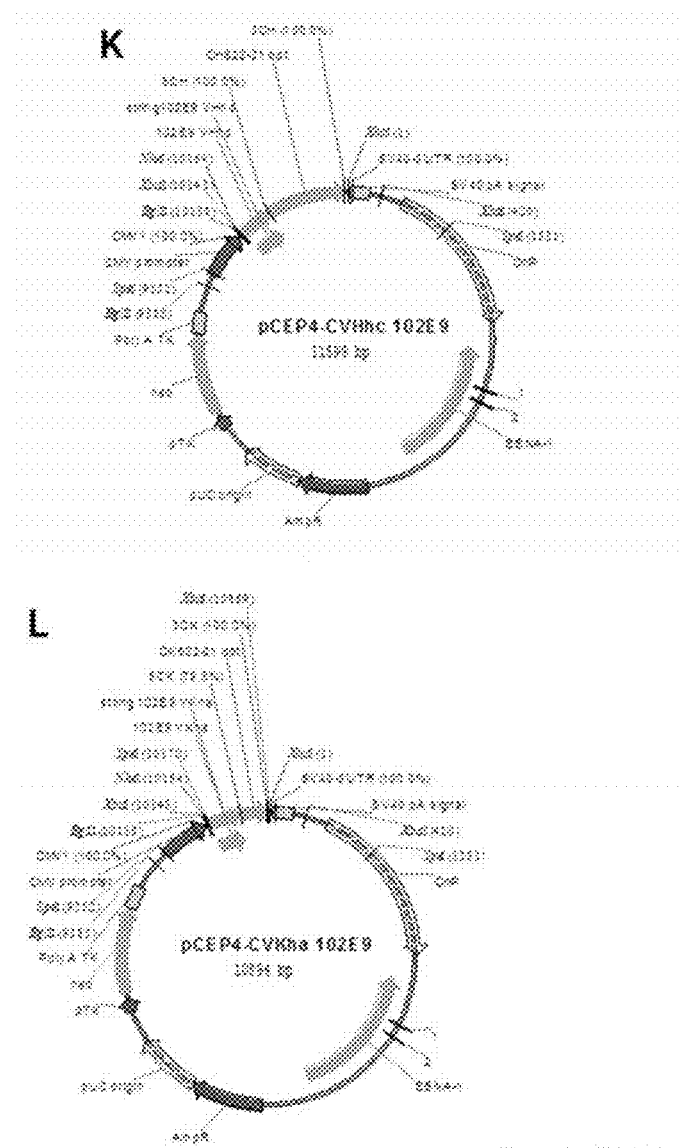
Figure 8M:
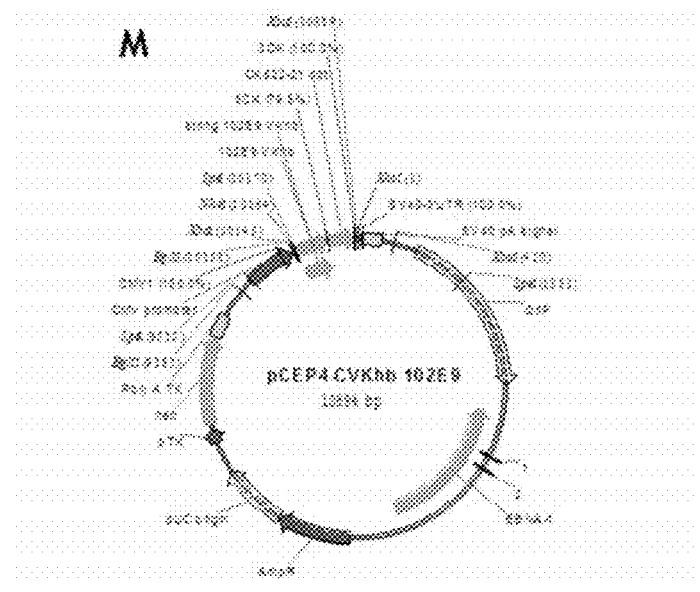
Figure 8N:
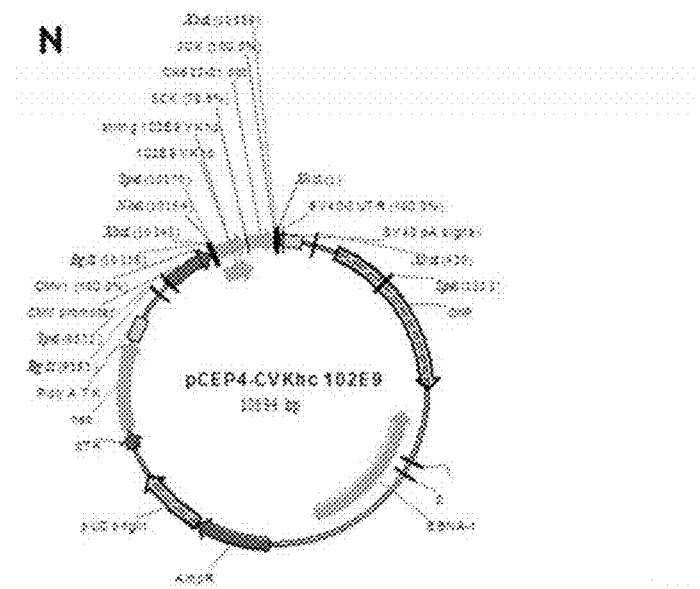

The construction of the expression vectors encoding the humanized anti-CD303 antibodies is carried out by homologous recombination, by means of the In-Fusion® HD Cloning Kit (Clontech® Laboratories). The expression vector selected for each Ig heavy and light chain is the commercial vector pCEP4 (Invitrogen). It has the advantage of being highly productive when used in combination with the human cell line FreeStyle HEK-293, a line used to produce sufficient amounts of antibody quickly in order to carry out certain tests. pCEP4 is monocistronic, 10,186 bp in size and has all the elements necessary for expressing the genes of interest, i.e., an ampicillin-resistance gene, an origin of replication (pUC origin), a CMV promoter and an SV40 poly A (see FIG. 8A). The sequences of interest are cloned between the NheI and XhoI restriction sites, and downstream of the promoter (see FIGS. 8B-8N). First, digestion by these enzymes is carried out in order to open the vector where desired. Purification using the NucleoSpin Plasmid Kit (Macherey-Nagel) is then necessary to purify the linearized vector, reduced to 10,163 bp. In parallel with the synthesis of the variable portions, the constant portions of the heavy and light chains were prepared by PCR amplification, using vector CHK622-21 as matrix, and containing the constant portions of the H and K chains optimized for *Rattus norvegicus*. This PCR was carried out using a high-fidelity DNA polymerase, Herculase II Fusion (Agilent Technologies) and primers defined so as to add, to the constant portions, restriction sites for cloning at their 3' ends, as well as 15 bp complementary to the vector to allow recombinational cloning. Once the PCR is carried out, a purification gel (1.25% low agarose) is run to confirm that the fragments of interest were indeed amplified and as a means to recover said fragments. The samples are caused to migrate through the purification gel under low voltage to provide good separation of the DNA fragments.

Once all the gene elements are prepared, they can be assembled by means of the In-Fusion® kit. Thus, the mixture, i.e., the linearized vector (0.5 µL), the "string" (1 µL) at an initial concentration of 50 ng/µL, and the heavy or light chain constant portion (1 µL) brought up to 10 µL with sterile water, is added into the kit's tube containing the lyophilized product notably consisting of the high-fidelity PCR enzyme CloneAmp™ HiFi. The mixture is then incubated for 15 minutes at 37° C., then 15 minutes at 50° C. In parallel, ligation with only the linearized vector, without the variable and constant portions, is carried out and will be used as the negative control for the experiment.

The vectors were then cloned into highly competent *E. coli* NEB 5-alpha bacteria, and the sequences of the various clones of each vector were confirmed by sequencing. When the clone is declared to match in sequence, a bacterial culture (300 mL) of the selected clone is prepared in order to purify the vector of interest contained therein, using the NucleoBond Xtra EF kit (Macherey-Nagel). The plasmids obtained are sterile and in sufficient amounts to carry out cotransfections in the production line.

Production of the Antibodies in FreeStyle HEK-293 Cells

The antibodies are produced by transient cotransfection from the FreeStyle human embryonic kidney (HEK)-293 cell line. This last is an immortalized cell line that has the capacity to proliferate in suspension and in the absence of serum. This HEK line, cultured in Freestyle F17 Expression Medium (Life Technologies), supplemented with 8 mM glutamine, also allows greater and faster productivity of recombinant proteins.

During the cotransfections, the controls used to validate the experiments are the growth control, which corresponds to an HEK cell culture not having undergone transfection, and a line that has been transfected with a vector, pMAX, encoding a fluorescent protein, GFP, which is used after 24 hours to determine the transfection rate. The buffer used to dilute the DNA, the transfection agent and the cells is OptiMEM® (Life Technologies). Polyethylenimine (PEI) is the transfection agent (TA), which will make it possible to introduce the vectors into the cells. A 1:2 ratio of DNA to TA and a 1:3 ratio of vector comprising the H chain to vector comprising the K chain are observed. After contacting the DNA/TA complex with the cells, the latter are then cultured with shaking at 37° C., with 8% $CO_2$.

At the conclusion of 7 days of production post-cotransfection, the cell cultures are centrifuged for 15 minutes at 3,000 g. The clarified supernatant, containing the antibodies produced, is collected and assayed using a commercial kit, FastELISA (RD-Biotech), in order to precisely estimate the amount of antibody of each supernatant for carrying out thereafter affinity studies of the humanized antibodies with respect to the CD303 protein.

Production of Certain Humanized Derivatives of Chimeric Antibody 122A2 by YB2/0 Clones Stably Transfected with an Expression Vector YB2/0 clones were stably transfected with an expression vector comprising nucleic sequences encoding humanized antibodies 122A2H5, 122A2H7, 122A2H9 and 122A2H10 derived from chimeric antibody 122A2. The antibodies were then produced and their amount in the supernatant was assayed.

From the monocistronic vectors used for transient transfection in the HEK line, the light chains (122A2H5: pCEP4_Kha_122 A2; 122A2H9: pCEP4_Khb_122 A2; 122A2H10: pCEP4_Khb_122 A2; 122A2H7: pCEP4_Kha_122 A2) were introduced by SpeI-XbaI digestion into the HKgenEFss vector to obtain an intermediate vector. Then, on these intermediate vectors, NheI-AscI digestion was carried out to introduce the heavy chain (122A2H5: pCEP4_Hha_122 A2; 122A2H9: pCEP4_Hha_122 A2; 122A2H10: pCEP4_Hhb_122 A2; 122A2H7: pCEP4_Hhc_122 A2).

Characterization of the Antigen-Binding of the Antibodies Produced, by ELISA

The study of the binding capacity of the various antibodies produced in FreeStyle HEK-293 cells is carried out by enzyme-linked immunosorbent assay (ELISA).

This technique, which uses a colorimetric approach, makes it possible to detect and visualize antigen-antibody interactions. The principle of ELISA is, first, to coat each well of a MaxiSorp plate with 10 ng of the antigen, in this case the CD303 ectodomain. The latter was purchased from the supplier Mybiosource. Second, the various antibodies produced, contained in the supernatant, are all diluted to the same concentration, and contacted with the antigen to allow them to bind. A third step consists in adding the secondary antibodies, HRP-conjugated anti-human antibody, necessary for amplified detection of the antigen-binding of the anti-CD303 antibodies. Lastly, detection is carried out using a solution containing the substrate for the enzyme (3,3',5,5'-tetramethylbenzidine, or TMB). The appearance of coloring of the substrate indicates the formation of the antigen-antibody complex. The intensity of this coloring is proportional to the amount of enzyme present and thus to the amount of antibody tested bound to the antigen. The reaction is stopped by adding $H_2SO_4$ (acid). These colors are read using a spectrophotometer at a wavelength of 450 nm.

Characterization of the Antigen-Binding of the Antibodies Produced, by Flow Cytometry With the aim of confirming the results obtained by ELISA, the various antibodies produced in FreeStyle HEK-293 cells are evaluated by flow cytometry. Flow cytometry makes it possible to confirm that, in a cellular context, the recombinant antibody is capable of binding to its antigen, and thus to confirm the results obtained by ELISA.

The line used to carry out this technique, CAL-1, is a leukemic cell line of plasmacytoid dendritic cells obtained from a BPDCN patient. The antibodies produced were tested in supernatant, but also in forms purified by affinity chromatography with protein A-sepharose (not elaborated upon herein).

For cell staining, the cells and the antibodies are prediluted with PBS/1% FCS. In a 100 μL reaction volume, $1·10^5$ cells are incubated at 4° C. for 30 minutes with the anti-CD303 antibodies to be tested, at two concentrations: 0.1 μg/mL or 1 μg/mL. This incubation is followed with several washings. The cell/antibody complexes thus formed are then contacted for 30 minutes at 4° C. with the secondary antibody diluted 1:50, an anti-human IgG Fc F(ab')$_2$ coupled to a fluorochrome, phycoerythrin. The cells are finally washed and studied by flow cytometry (FC500, Beckman Coulter), by measuring notably the mean fluorescence intensity (MFI). Various negative controls are used to eliminate possible nonspecific binding, such as: the cells alone or directly in contact with the secondary antibody, or replacing the antibody tested with an irrelevant chimeric antibody (factor VIII anti-idiotype). Finally, other controls, such as the use of the supernatant (mock), make it possible to show that the latter does not influence the affinity of the antibodies to the membrane antigen.

Inhibition of IFN-α Secretion
Preparation of the Cells

Peripheral blood mononuclear cells (PBMCs) are isolated from peripheral blood of healthy donors by Ficoll density gradient. $10^7$ cells/well (200 μL) are transferred to a 24-well flat-bottom culture plate, in the presence of 1 μM CpG ODN 2216-1 (Invivogen) and 10 ng/mL IL-3 (product no.: 130-093-909, Miltenyi Biotec). The anti-CD303 or irrelevant antibodies were added at various concentrations (0 to 1 μg/mL) in RPMI 10% FCS medium. The plate was then incubated overnight at 37° C. with 7% $CO_2$.

IFN-α Assay

The culture supernatants of each well are collected and assayed by ELISA by using the Human IFN-α Module Set kit (product no.: BMS216MST, eBioscience).

Induction of IL-2 Secretion by Jurkat-CD16 Cells

This test evaluates the capacity of the anti-CD303 antibodies to bind to CD16 (Fcγ receptor III) expressed on CD16 Jurkat cells and to induce IL-2 secretion.

This test consists in contacting, in a 96-well plate: anti-CD303 antibodies, target cells expressing CD303, CD16 Jurkat cells and phorbol myristate acetate PMA).

After incubating at 37° C. overnight, the plates are centrifuged and the amount of IL-2 secreted is assayed in the supernatant.

Results
Cotransfection of the Vectors Produced in HEK-293F Cells

From vectors expressing the humanized heavy and light chain sequences, various heavy (H) chain/light (L or K) chain combinations were produced by transient cotransfection in HEK-293F cells, in order to produce various representative versions of the two candidate antibodies. In this manner, the following were produced (see Table 30 below):
1. hybrid antibodies (one of the two Ig chains is humanized, the other is chimeric), and
2. humanized antibodies.

TABLE 30

Names of the hybrid or humanized antibodies derived from chimeric antibodies 122A2 and 102E9, as a function of the humanized heavy and light chains used.

Derivatives of chimeric antibody 122A2

|  | 122A2-H | 122A2-Hha | 122A2-Hhb | 122A2-Hhc |
|---|---|---|---|---|
| 122A2-K | 122A2 (chimeric) | 122A2H1 (hybrid) | 122A2H2 (hybrid) | 122A2H3 (hybrid) |
| 122A2-Kha | 122A2H4 (hybrid) | 122A2H5 (humanized) | 122A2H6 (humanized) | 122A2H7 (humanized) |
| 122A2-Khb | 122A2H8 (hybrid) | 122A2H9 (humanized) | 122A2H10 (humanized) | 122A2H11 (humanized) |
| 122A2-Khc | 122A2H12 (hybrid) | 122A2H13 (humanized) | 122A2H14 (humanized) | 122A2H15 (humanized) |
| 122A2-Khd | 122A2H16 (hybrid) | 122A2H17 (humanized) | 122A2H18 (humanized) | 122A2H19 (humanized) |

Derivatives of chimeric antibody 102E9

|  | 102E9-H | 102E9-Hha | 102E9-Hhb | 102E9-Hhc |
|---|---|---|---|---|
| 102E9-K | 102E9 (chimeric) | 102E9H1 (hybrid) | 102E9H2 (hybrid) | 102E9H3 (hybrid) |
| 102E9-Kha | 102E9H4 (hybrid) | 102E9H5 (humanized) | 102E9H6 (humanized) | 102E9H7 (humanized) |
| 102E9-Khb | 102E9H8 (hybrid) | 102E9H9 (humanized) | 102E9H10 (humanized) | 102E9H11 (humanized) |
| 102E9-Khc | 102E9H12 (hybrid) | 102E9H13 (humanized) | 102E9H14 (humanized) | 102E9H15 (humanized) |

During the various transient cotransfections carried out to produce the set of 36 molecules, transfection efficiency was determined on day 1 using the vector pMAX.

At the conclusion of production on day 7, the supernatants, containing the proteins produced, are collected, centrifuged, filtered and finally assayed to measure the titer in IgG produced (see Tables 31 and 32 below). The concentrations thus obtained vary as a function of the type of H chain and K chain, i.e., chimeric or humanized, possessed by the various versions of the antibodies produced.

TABLE 31

Concentrations in μg/mL on day 7 of the various supernatants containing the antibodies produced (chimeric antibody 122A2 and hybrid or humanized derivatives thereof), determined using the FastELISA kit.

| Antibody | Heavy chain | Light chain | Concentration on day 7 (μg/mL) |
|---|---|---|---|
| Original chimeric antibody ||||
| 122A2 | H | K | 0.75 |
| Hybrid antibodies ||||
| 122A2H1 | Hha | K | 0.13 |
| 122A2H2 | Hhb | K | 0.42 |
| 122A2H3 | Hhc | K | 0.67 |
| 122A2H4 | H | Kha | 1.18 |
| 122A2H8 | H | Khb | 1.17 |
| 122A2H12 | H | Khc | 1.41 |
| 122A2H16 | H | Khd | 1.33 |
| Humanized antibodies ||||
| 122A2H5 | Hha | Kha | 5.37 |
| 122A2H9 | Hha | Khb | 4.41 |
| 122A2H13 | Hha | Khc | 6.40 |
| 122A2H17 | Hha | Khd | 7.75 |
| 122A2H6 | Hhb | Kha | 43.57 |
| 122A2H10 | Hhb | Khb | 69.28 |
| 122A2H14 | Hhb | Khc | 55.20 |
| 122A2H18 | Hhb | Khd | 69.40 |
| 122A2H7 | Hhc | Kha | 50.80 |
| 122A2H11 | Hhc | Khb | 44.76 |
| 122A2H15 | Hhc | Khc | 31.96 |
| 122A2H19 | Hhc | Khd | 19.15 |

TABLE 32

Concentrations in µg/mL on day 7 of the various supernatants containing the antibodies produced (chimeric antibody 102E9 and hybrid or humanized derivatives thereof), determined using the FastELISA kit.

| Antibody | Heavy chain | Light chain | Concentration on day 7 (µg/mL) |
|---|---|---|---|
| Original chimeric antibody | | | |
| 102E9 | H | K | 3.4 |
| Hybrid antibodies | | | |
| 102E9H1 | Hha | K | 6.8 |
| 102E9H2 | Hhb | K | 5.3 |
| 102E9H3 | Hhc | K | 2.2 |
| 102E9H4 | H | Kha | 1.8 |
| 102E9H8 | H | Khb | 1.4 |
| 102E9H12 | H | Khc | 1.5 |
| Humanized antibodies | | | |
| 102E9H5 | Hha | Kha | 22.9 |
| 102E9H9 | Hha | Khb | 11.6 |
| 102E9H13 | Hha | Khc | 18.3 |
| 102E9H6 | Hhb | Kha | 15.3 |
| 102E9H10 | Hhb | Khb | 9.9 |
| 102E9H14 | Hhb | Khc | 17.2 |
| 102E9H7 | Hhc | Kha | 7.7 |
| 102E9H11 | Hhc | Khb | 4.9 |
| 102E9H15 | Hhc | Khc | 9.9 |

It can be noted that the antibody concentration is dependent on the combinations produced but also on the type of H and/or K chain (humanized or chimeric). In this context, the productivity of chimeric antibodies 122A2 and 102E9, as well as that of most of the hybrids (combination of a chimeric H or K chain and a humanized H or K chain, as indicated above), is much lower than the rest of the molecules. This observation is related to expression of the chimeric H and K chains, which is unfavorable to satisfactory cellular expression.

What differentiates the chimeric antibodies from the humanized antibodies are the amino acids that have been mutated; the variations in productivity are uniquely dependent on a few amino acids.

Thus, for the antibodies derived from 102E9, the hybrid antibodies having the chimeric heavy or light chain and the humanized antibodies with the Hhc heavy chain (102E9H7, 102E9H11 and 102E9H15) all have lower productivity.

In the case of the antibodies derived from 122A2, it is the chimeric K and humanized H Hha chains that lead to lower productivity. Chimeric antibody 122A2 is found to have the lowest productivity compared to certain of its hybrid and humanized derivatives. Fortuitously, humanization made it possible to increase the volume titer by up to a factor of 100, in the case of 122A2H10 (Hhb, Khb).

Lastly, it is noted that humanized antibodies 122A2 are produced better overall than humanized antibodies 102E9. That confirms that expression of antibodies of the same isotype is highly dependent on their primary sequence and chiefly on their variable portions.

Characterization of the Antigen-Binding of the Antibodies Produced, by ELISA

ELISAs were carried out from the culture supernatants collected after production. First, they are all diluted to the same concentration, so that all the samples are under the same conditions. Furthermore, the initial dilutions are made using centrifuged, filtered supernatant from the cell cultures used as growth controls during the transfections. These cultures do not express an antibody, and are thus referred to as "mock" cultures. The samples are then diluted to half, on MaxiSorp 96-well plates, using buffer containing PBS, 4% BSA and 0.05% Tween.

All the antibodies produced, whether derived from 122A2 or 102E9, give a color signal whose intensity is quantifiable when read by spectrophotometry. This may be interpreted as being the capacity of the various antibodies to bind specifically to the CD303 ectodomain. There are however differences in affinity for the antigen, which are expressed as differences in $OD_{450}$.

Thus, it was possible, for each antibody produced, to graphically represent $OD_{450}$ as a function of antibody concentration. The result is a biphasic curve with an exponential phase leading to a plateau. This graphical representation made it possible to classify the antibodies tested and the chimeric antibody from which they are derived as a function of their affinity for the CD303 antigen.

Figure 9A:
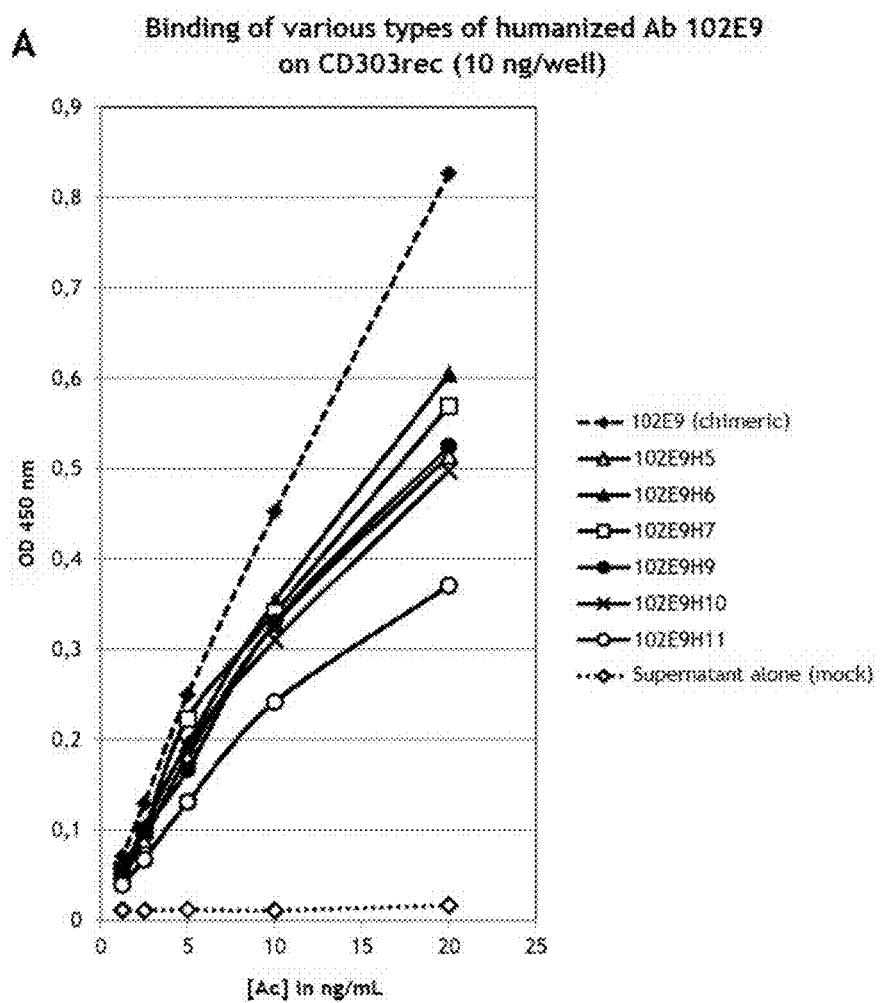
FIG. 9. Antigen-binding of humanized antibodies derived from antibody 102E9. OD at 450 nm as a function of the concentration of humanized antibodies derived from antibody 102E9 tested at 1.25, 2.5, 5, 10 and 20 ng/mL, accompanied by the controls: supernatant alone (mock) and chimeric antibody 102E9. (A) Humanized antibodies 102E9H5, 102E9H6, 102E9H7, 102E9H9, 102E9H10 and 102E9H11. (B) Humanized antibodies 102E9H13, 102E9H14, and 102E9H15.
Figure 9B:
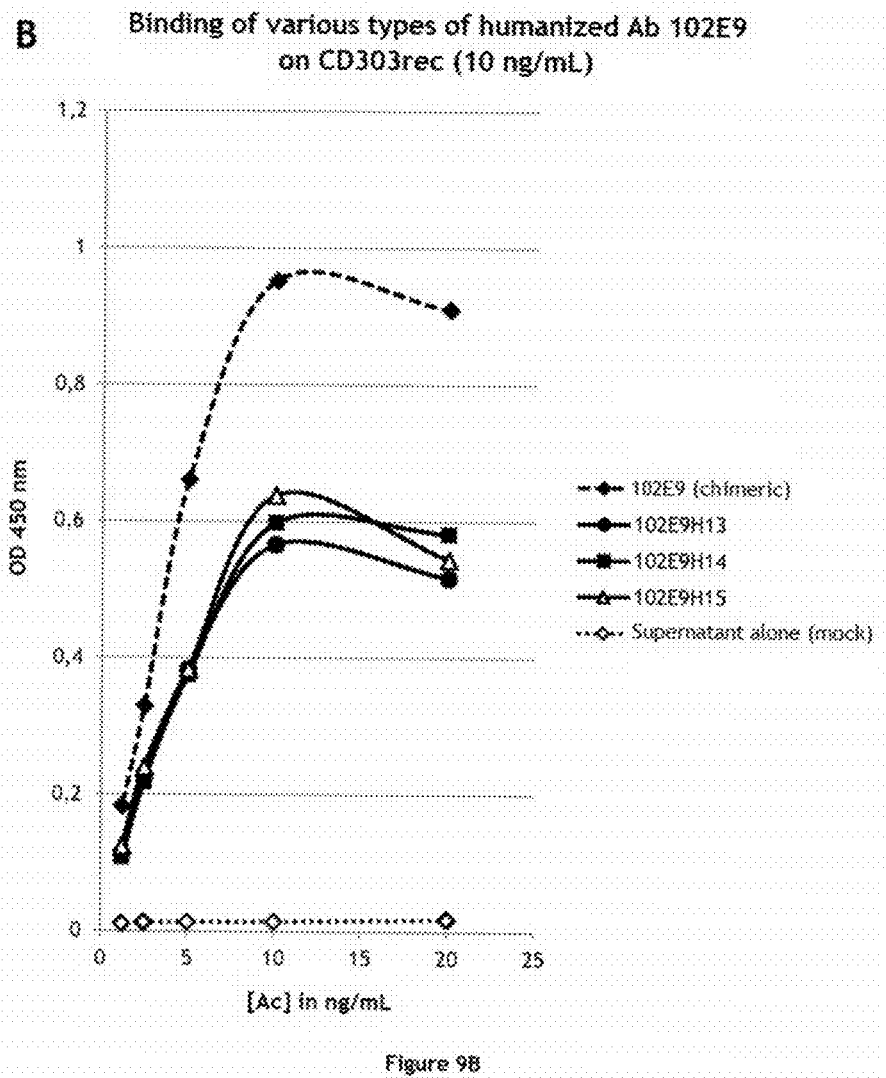
Figure 10:
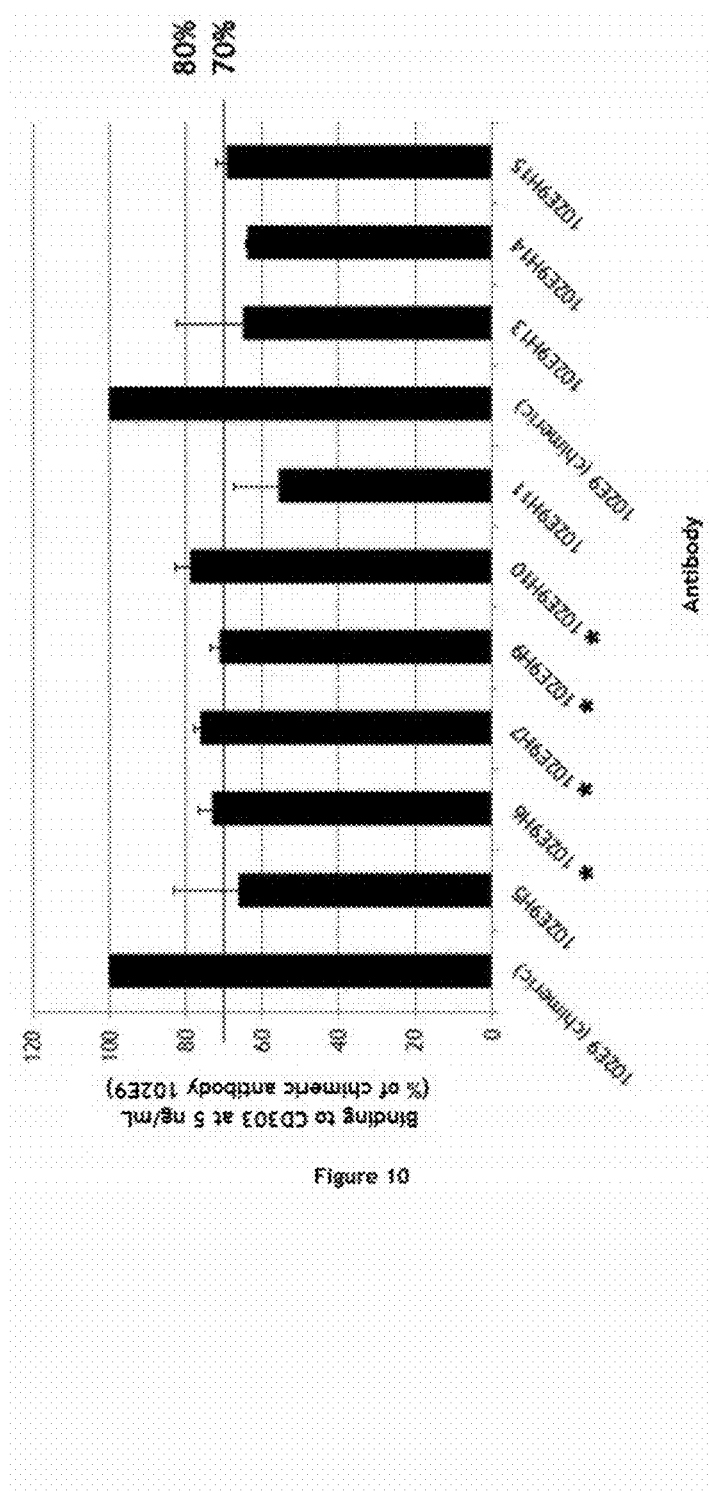
FIG. 10. Antigen-binding of humanized antibodies derived from antibody 102E9 at 5 ng/mL antibody. Comparison of the relative affinities of humanized antibodies derived from 102E9 for the CD303 ectodomain, the binding of the chimeric antibody being 100%. The antibodies exhibiting binding similar to that of the chimeric antibody (relative affinity of at least 70%) are indicated by*.

In the case of the antibodies derived from 102E9, the antibodies deposited in each well range from 1.25 ng/mL to 20 ng/mL. Saturation of the $OD_{450}$ signal appears as of a concentration of about 10 ng/mL antibody. FIG. 9 shows the results obtained for the various humanized antibodies. A concentration of 5 ng/mL is used to classify the humanized antibodies (FIG. 10).

None of the humanized antibodies binds to the CD303 antigen as well as the chimeric antibody. Nevertheless, all the humanized antibodies preserve a reasonable capacity to bind to the CD303 antigen. Humanized antibody 102E9H10 has the best CD303 antigen-binding capacity among all the humanized antibodies. It represents a loss of binding of only about 20% compared to the original chimeric antibody, 102E9 (FIG. 10). Three other humanized antibodies, 102E9H6, 102E9H7 and 102E9H9, also have a binding capacity similar to the reference chimeric antibody. They have a CD303 ectodomain-binding capacity of 73% (102E9H6), 76% (102E9H7) and 71% (102E9H9), respectively.

Figure 11A:
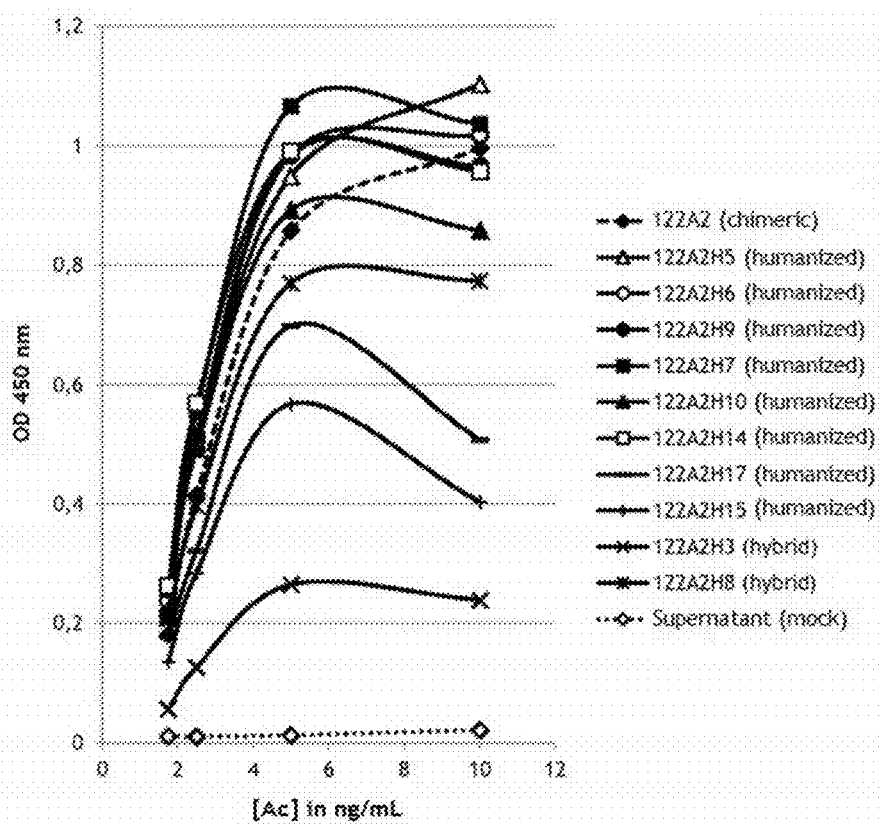
FIG. 11. Antigen-binding of humanized antibodies derived from antibody 122A2. OD at 450 nm as a function of the concentration of humanized antibodies derived from antibody 122A2 tested at 1.75, 2.5, 5, and 10 ng/mL, accompanied by the controls: supernatant alone (mock) and chimeric antibody 102E9. (A) Humanized antibodies 122A2H5, 122A2H6, 122A2H9, 122A2H7, 122A2H10, 122A2H14, 122A2H17, 122A2H15, and hybrid antibodies 122A2H3 and 122A2H8. (B) Humanized antibodies 122A2H5, 122A2H6, 122A2H9, 122A2H7, 122A2H10, 122A2H14, 122A2H17, 122A2H13, 122A2H18, and 122A2H11. (C) Humanized hybrid antibodies 122A2H15 and 122A2H19, and antibodies 122A2H4, 122A2H8, 122A2H12, 122A2H16, 122A2H1, 122A2H2 and 122A2H3.
Figure 11B:
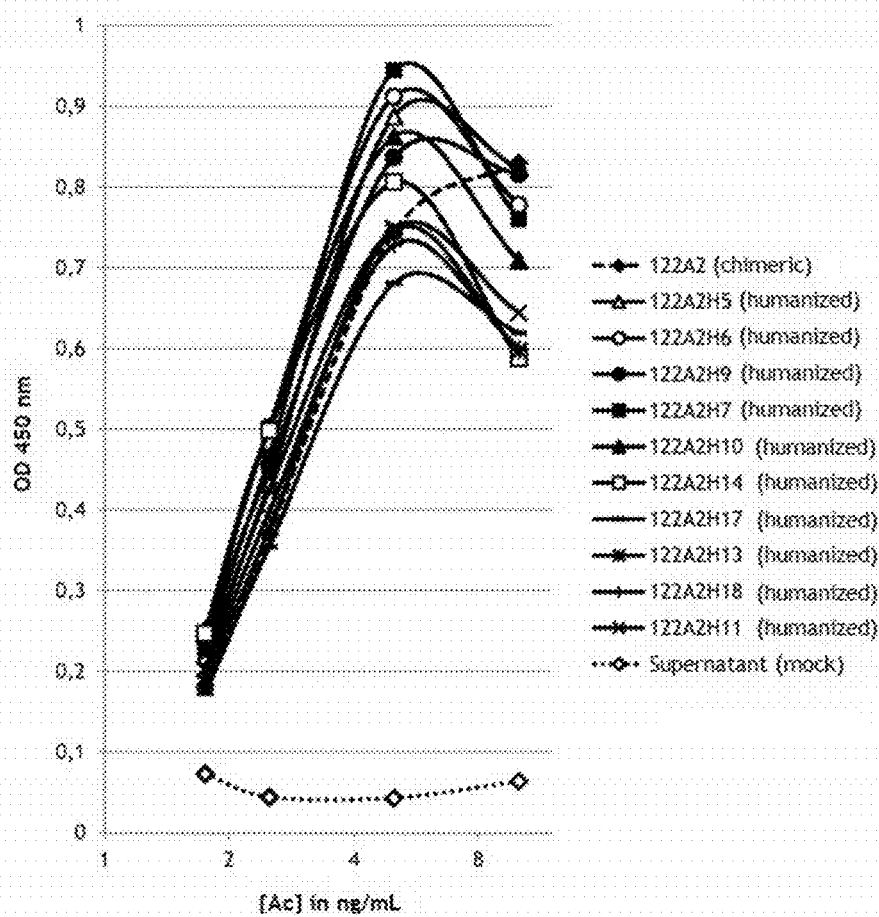
Figure 11C:
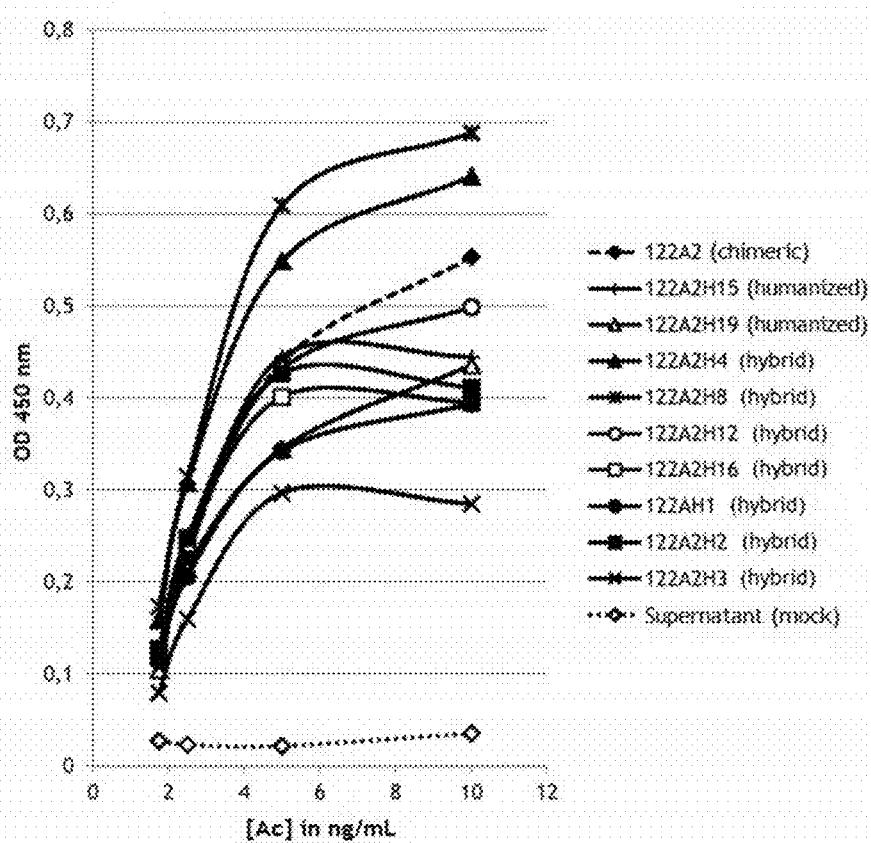
Figure 12:
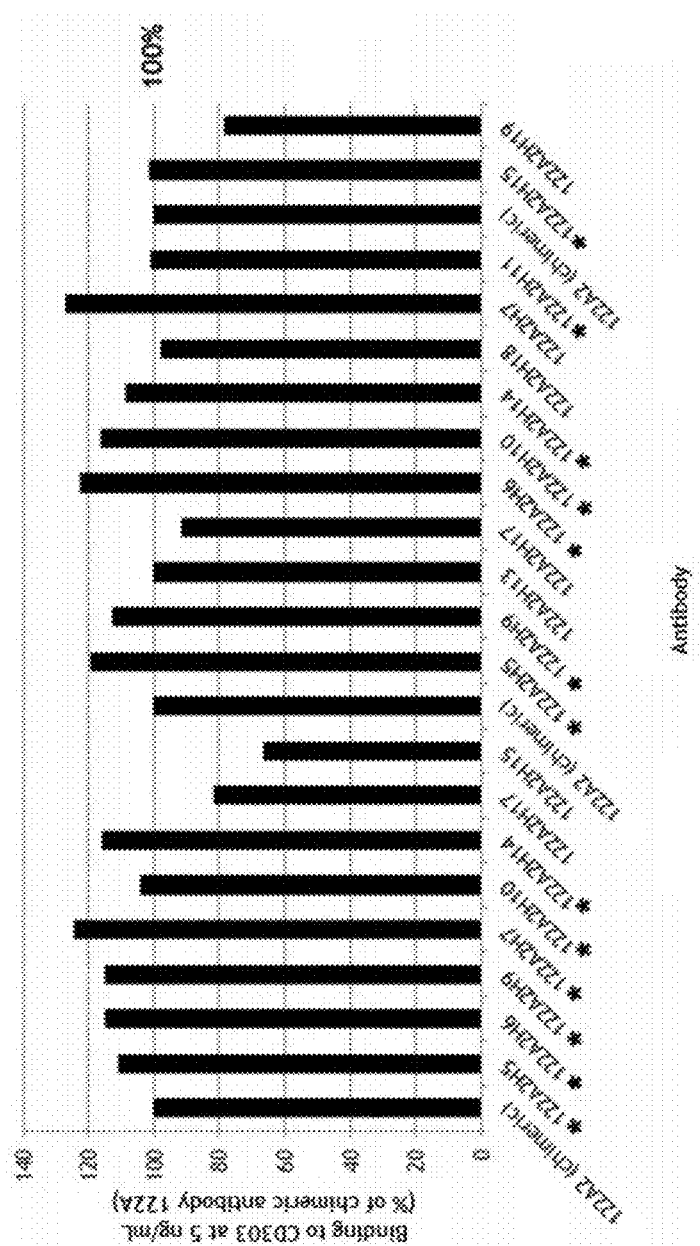
FIG. 12. Antigen-binding of humanized antibodies derived from antibody 102E9 at 5 ng/mL antibody. Comparison of the relative affinities of humanized antibodies derived from 102E9 for the CD303 ectodomain, the binding of the chimeric antibody being at 100%. The antibodies exhibiting better binding than that of the chimeric antibody (relative affinity>100%) are indicated by*.

In the case of the antibodies derived from 122A2, the antibody concentrations tested range from 1.75 to 10 ng/mL. The controls used are the same ones as before: the supernatant alone (mock) and the chimeric antibody, here 122A2. FIG. 11 shows the results obtained for the various humanized antibodies. A concentration of 5 ng/mL is used to classify the humanized antibodies (FIG. 12).

All the antibodies tested are capable of binding to the CD303 ectodomain. The "supernatant" negative control sample has an $OD_{450}$ near zero. There is thus no nonspecific binding due to the supernatant. Moreover, a dose-response effect is also observed for all the samples tested. Most of the curves representing the various humanized antibodies are similar in appearance to that of chimeric antibody 122A2.

Lastly, several humanized antibodies of 122A2 (122A2H5, 122A2H6, 122A2H7, 122A2H9, 122A2H10, 122A2H11, 122A2H14 and 122A2H15) appear to have a CD303 ectodomain-binding capacity at least equal to (122A2H11 and 122A2H15), and sometimes significantly higher than (122A2H5, 122A2H6, 122A2H7, 122A2H9, 122A2H10, and 122A2H14), that of the chimeric antibody.

Characterization by Flow Cytometry of the Antigen-Binding of the Antibodies Produced Antibody-binding was also studied by flow cytometry to confirm the results obtained by ELISA.

For antibody 102E9, humanized antibodies 102E9H10, 102E9H6, 102E9H7, 102E9H9 and chimeric antibody 102E9 were selected to be characterized by this technique.

For antibody 122A2, humanized antibodies 122A2H5, 122A2H6, 122A2H9, 122A2H7, 122A2H10, 122A2H14, 122A2H17, 122A2H15, hybrid antibodies 122A2H8, 122A2H3 and chimeric antibody 122A2 in supernatant were selected for the characterization. 122A2H8 represents the best hybrid antibody with affinity higher than that of the chimeric antibody, while 122A2H3 has much lower affinity than that of the parent antibody. The humanized antibodies selected count among those that have better affinity for the target protein compared to the original chimeric antibody.

In the case of antibody 102E9, there are few differences between the humanized and the chimeric antibodies (not illustrated here).

Figure 13:
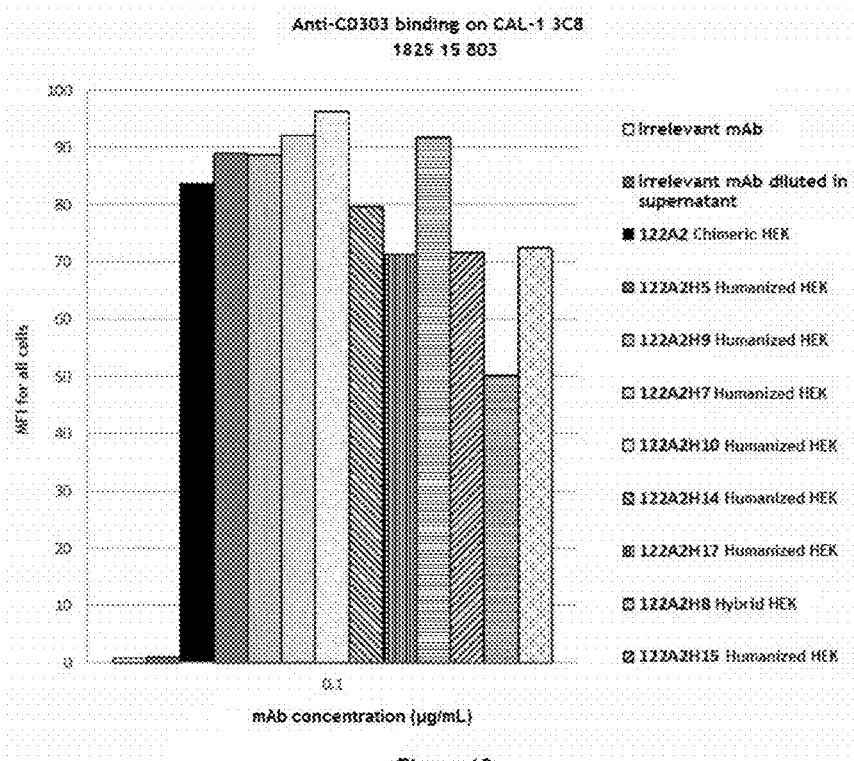
FIG. 13. CD303-binding on CAL-1 cells of various antibodies derived from 122A2 selected at a concentration of 0.1 µg/mL (in supernatant): observation of mean fluorescence intensity (MFI) by flow cytometry. Irrelevant mAb-supernatant: irrelevant mAb diluted in supernatant. hum: humanized antibody. hyb: hybrid antibody.

In the case of antibody 122A2, the results are presented in FIG. 13 (which represents the mean fluorescence for each antibody tested, at a concentration of 0.1 μg/mL), and show that certain humanized antibodies (tested in supernatant) show better affinity compared to chimeric antibody 122A2. That is the case notably of humanized antibodies 122A2H5, 122A2H9, 102E9H7, and 122A2H10. The other humanized antibodies previously identified by ELISA as having a binding capacity at least equal to that of the chimeric antibody and tested by flow cytometry (122A2H14 and 122A2H15) have in the cytometry test binding (MFI) that is slightly lower than that of the chimeric antibody, but that remains close to that of the chimeric antibody. Consequently, the results obtained by flow cytometry back up those previously obtained by ELISA.

The same antibodies were evaluated in purified form and they show the same results.

Inhibition of IFN-α Secretion

Figure 14:
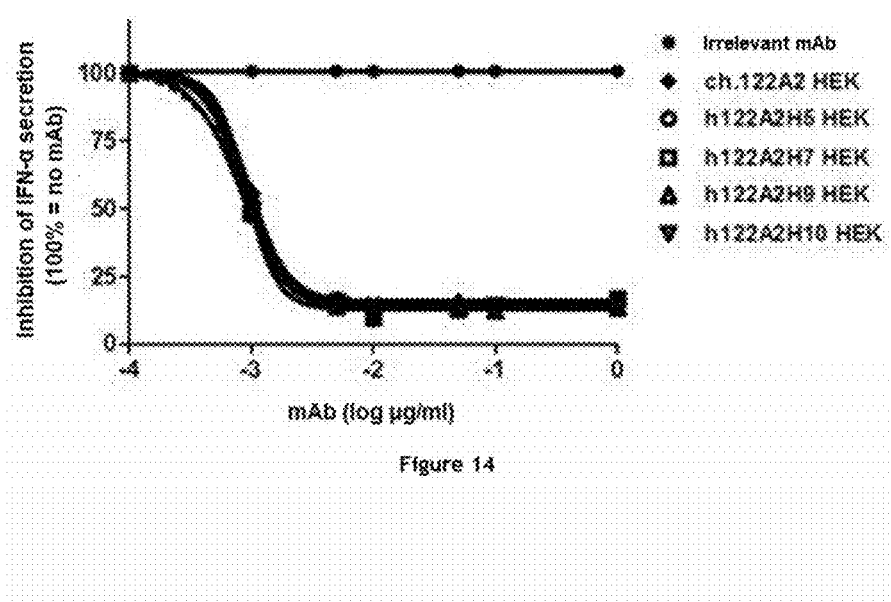
FIG. 14. Inhibition of IFN-α secretion by chimeric antibody 122A2 and humanized antibodies derived from 122A2.
Figures 15A, 15B:
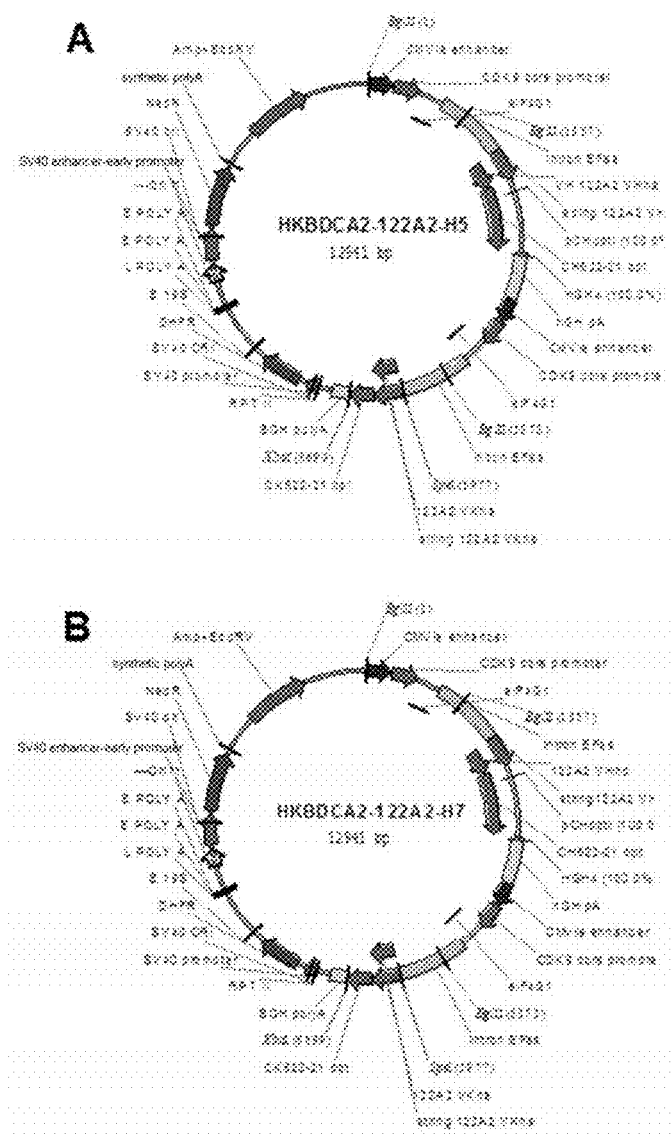
FIG. 15. Maps of the expression vectors for the heavy or light chains of humanized antibodies 122A2H5 (A), 122A2H7 (B), 122A2H9 (C) and 122A2H10 (D), for production in YB2/0 cells.
Figures 15C, 15D:
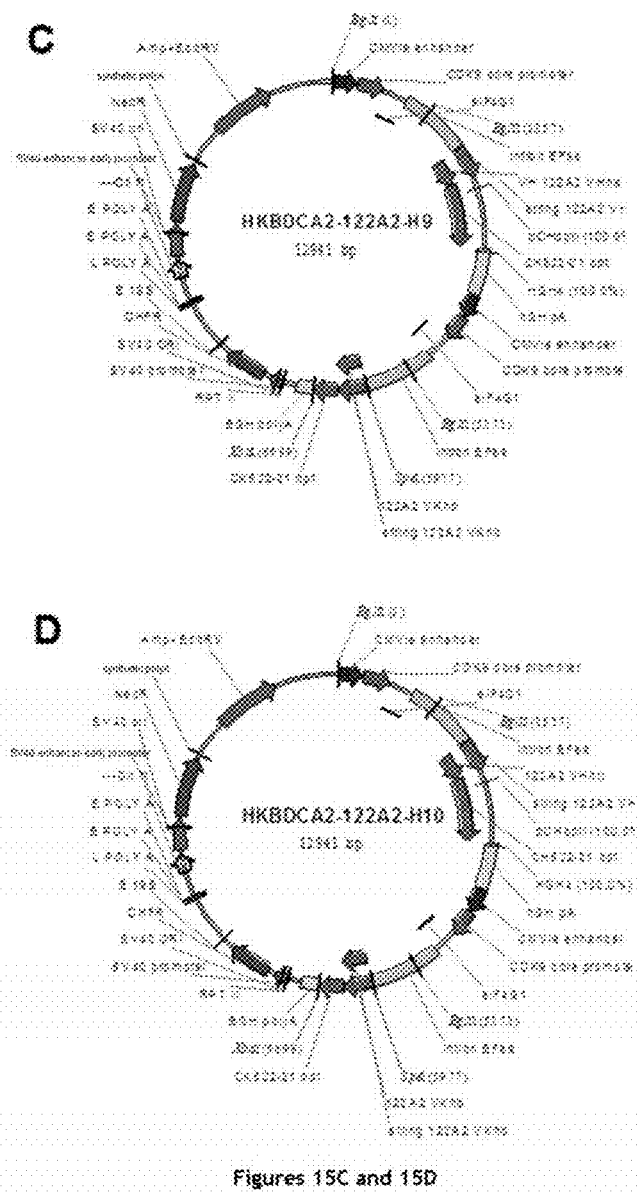

CpG motifs induce IFN-α secretion from pDCs contained in PBMCs. In this experiment (FIG. 14), inhibition of IFN-α secretion mediated by various anti-CD303 antibodies (chimeric 122A2 and four humanized antibodies 122A2) were compared.

The IC50 values (Table 33 below) were:
0.95 ng/mL for chimeric antibody ch.122A2,
0.81 ng/mL for humanized antibody h122A2H5,
0.86 ng/mL for humanized antibody h122A2H7,
0.91 ng/mL for humanized antibody h122A2H9, and
0.94 ng/mL for humanized antibody h122A2H10.

TABLE 33

50% inhibitory concentrations (IC50) for IFN-α secretion from pDCs contained in PBMCs.

|  | IC50 (ng/mL) |
|---|---|
| Irrelevant control mAb | n/a |
| ch.122A2 | 0.9589 |
| h122A2H5 | 0.8186 |
| h122A2H7 | 0.8647 |
| h122A2H9 | 0.9108 |
| h122A2H10 | 0.9472 | n/a: not applicable.

These results show that the four humanized monoclonal antibodies 122A2 tested are capable of inhibiting IFN-α secretion, with an IC50 lower than or equal to that of the chimeric antibody.

Production by YB2/0 Clones Stably Transfected with an Expression Vector for Humanized Antibodies Derived from Chimeric Antibody 122A2

Humanized antibodies 122A2H5, 122A2H7, 122A2H9 and 122A2H10, derived from chimeric antibody 122A2, appeared particularly advantageous in terms of productivity and antigen-binding. They were thus selected to produce YB2/0 clones stably transfected with an expression vector for these antibodies.

The maps of the HKgenEFss vectors expressing humanized antibodies 122A2H5, 122A2H7, 122A2H9 and 122A2H10 are presented in FIGS. 15A to 15D.

The supernatant assay data for the four clones thus obtained are presented in Table 34 below, and show that these four humanized antibodies can be produced with satisfactory productivity, with antibody 122A2H9 having the best productivity.

TABLE 34

Assay of the humanized antibody produced in the supernatant of stable YB2/0 clones expressing humanized antibodies 122A2H5, 122A2H7, 122A2H9 and 122A2H10, derived from chimeric antibody 122A2.

| Antibody | Supernatant assay (μg/mL) |
|---|---|
| 122A2H5 | 17.96 |
| 122A2H7 | 19.8 |
| 122A2H9 | 20.47 |
| 122A2H10 | 19.32 |

Induction of IL-2 Secretion by Jurkat-CD16 Cells

The capacity of humanized antibody 122A2H9, derived from chimeric antibody 122A2 and produced by stable YB2/0 clones, to bind CD16 and to induce IL-2 secretion by Jurkat-CD16 cells was tested and compared to that of chimeric antibody 122A2.

Figure 16:
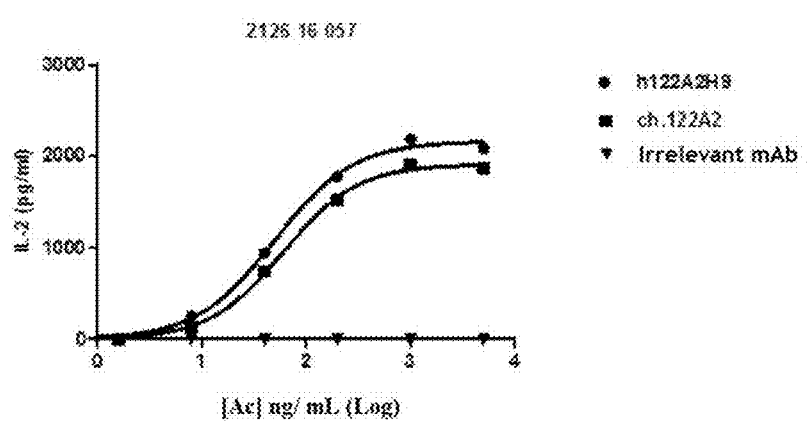
FIG. 16. Release of IL-2 by CD16 Jurkat cells activated by chimeric antibody 122A2, by humanized antibody 122A2H9, or by an irrelevant antibody.

An exemplary result obtained is presented in FIG. 16. In addition, the results of several experiments are presented in Table 35, expressed below in ng/mL (50%) in Table 1, this value representing the amount of antibody necessary to reach 50% of the plateau of the chimeric antibody. A lower value indicates better activity.

TABLE 35

Amount of antibody necessary to reach 50% of the plateau of the chimeric antibody, expressed either in ng/mL (upper portion of the table) or as a ratio between the two antibodies, the values for chimeric antibody ch122A2 being arbitrarily set to 1 so as to even out the variations between experiments.

|  | 2126 16 057 | 2126 16 059 | 2126 16 066 | Mean | SD |
|---|---|---|---|---|---|
|  | 50% (ng/mL) | | | | |
| ch122A2 | 60.57 | 124 | 60 | 92 | 45 |
| 122A2H9 | 40 | 97 | 44 | 60 | 31 |
|  | 50%, with ch122A2 = 1 | | | | |
| ch122A2 | 1 | 1 | 1 | 1 | 0.00 |
| 122A2H9 | 0.66 | 0.78 | 0.74 | 0.73 | 0.06 |

These results show that, despite an Fc fragment sequence identical to that of the chimeric antibody, humanized antibody 122A2H9 induces slightly higher IL-2 secretion by Jurkat-CD16 cells than that of the chimeric antibody.

Conclusions

In order to optimize the immunogenic tolerance of the antibodies, humanization was carried out on two of the five chimeric antibodies generated by the inventors, with the objective of preserving similar or not significantly different affinity for the CD303 antigen. To that end, several humanized heavy and light chains were tested in combination for each of the original antibodies, and transfected into HEK-293F cells.

Following the assay of the samples, it was noted that the antibody concentration is dependent on the original amino acid sequence (humanized antibodies derived from 122A2 are produced better than humanized antibodies derived from 102E9), on the combinations produced, and also on the type of H and/or K chain (humanized or chimeric). These data confirm that, overall, expression of antibodies of the same isotype is highly dependent on their primary sequence and chiefly on their variable portions. Moreover, numerous humanized antibodies, derived from one or the other of the original two chimeric antibodies, are produced better than the original chimeric antibodies.

The antibodies thus produced were characterized by ELISA. Insofar as the antibodies tested were similar to one another, it was difficult to identify the humanized antibodies having the same antigen-binding characteristics as the original chimeric antibodies. Where the antibodies were tested at several concentrations, the analyses were focused on the concentrations where a real difference in $OD_{450}$ between the various antibodies is observed. Thus, a concentration of 5 ng/mL made it possible to show that the best humanized antibody from 102E9, 102E9H10, has a CD303 ectodomain-binding capacity that is 80% of that of the chimeric antibody. In this manner, four humanized antibodies (102E9H10, 102E9H6, 102E9H7 and 102E9H9) were identified and selected to be confirmed by flow cytometry, as humanized antibodies of interest.

In the case of the humanized antibodies derived from 122A2, several antibodies are clearly identified as of the first ELISA as having a CD303 ectodomain-binding capacity at least equal to (122A2H11 and 122A2H15), indeed higher than (122A2H5, 122A2H6, 122A2H7, 122A2H9, 122A2H10, and 122A2H14), that of the chimeric antibody. These results obtained from the supernatants were supplemented by an orthogonal method using flow cytometry.

On the whole, the results presented above show that, for each chimeric antibody 122A2 and 102E9, it was possible to generate humanized antibodies (thus with reduced immunogenicity in humans), which can be produced with better productivity than the original chimeric antibody, and which have a CD303 antigen-binding capacity that is:

At least close to that of the chimeric antibody for the derivatives of chimeric antibody 102E9 (at least 80% for antibody 102E9H10, at least 70% for antibodies 102E9H6, 102E9H7 and 102E9H9).

At least equal to (122A2H11 and 122A2H15), indeed higher than (122A2H5, 122A2H6, 122A2H7, 122A2H9, 122A2H10, and 122A2H14), that of the chimeric antibody for the derivatives of chimeric antibody 122A2.

Moreover, humanized antibodies derived from 122A2 are capable of inhibiting IFN-α secretion as well as chimeric antibody 122A2.

For certain humanized antibodies derived from 122A2, stably transfected YB2/0 clones were able to be obtained, which produce the antibody with satisfactory productivity. These antibodies have a strong capacity to bind to CD16 and to induce IL-2 secretion by Jurkat-CD16 cells.

BIBLIOGRAPHIC REFERENCES

Almagro et al. Frontiers in Bioscience 13, 1619-1633, Jan. 1, 2008.
Brochet, X. et al. Nucl. Acids Res. 36, W503-508 (2008).
Cao W. J Clin Cell Immunol. 2014 Apr. 22; 5(2):212.
Cardarelli et al. Clin Cancer Res 2009 Apr. 28; 15:3376-3383.
Cardarelli et al. Cancer Immunol Immunother. 2010. 59. 257-265,
Cibelli et al., 1998 Science, 280:1256-1258.
Dall'Acqua et al. 2002, J Immunol.; 169:5171-80.
Dall'Acqua et al. 2006, J. Biol. Chem.; 281:23514-24. (a).
Dall'Acqua et al. J Immunol 2006; 177:1129-1138. (b).
Dzionek A., et al. (2001) J. Exp. Med. 194, 1823-1834.
Edelman, G. M. et al., Proc. Natl. Acad. USA, 63, 78-85 (1969).
Ehrenmann F., Kaas Q. and Lefranc M.-P. Nucleic Acids Res., 38, D301-307 (2010).
Ehrenmann, F., Lefranc, M.-P. Cold Spring Harbor Protoc., 6, 737-749 (2011).
EP1176195A1.
Fisher R, et al. Vaccine 21 (2003) 820-825.
Forthal et al, J Immunol 2010; 185; 6876-6882.
Gordon et al., 1980 Proc Natl Acad Sci USA.; 77:7380-4.
Herbst R. et al. J Pharmacol Exp Ther. 2010 October; 335(1):213-22.
Hinton et al. 2004, J Biol Chem.; 279:6213-6.
Idusogie E E et al. J Immunol. 2001; 166:2571-5.
Imai-Nishiya et al, BMC Biotechnology 2007, 7:84.
Jones et al. Nature, 321:522-525, 1986.
Kabat et al., Sequences of Proteins of Immunological Interest, 5th Ed. Public Health Service, National Institutes of Health, Bethesda, Md. (1991).
Kanda Y et al, Journal of Biotechnology 130 (2007) 300-310.
Lazar, G. A., et al. Proc Natl Acad Sci USA. 103(11): 4005-10.
Lefranc, M.-P. et al. Dev. Comp. Immunol., 27, 55-77 (2003).
Ma J K, et al. Nat Rev Genet. 2003 October; 4(10):794-805.
Maeda T et al., Int J Hematol. 2005 February; 81(2):148-54.
Manipulating the Mouse Embryo, A Laboratory Manual, Second edition, Cold Spring Harbor Laboratory Press (1994).
Moore G L. Et al. mAbs 2:2, 181-189; March/April, 2010.
Mod K, et al. Biotechnol Bioeng. 2004 Dec. 30; 88(7):901-8.
Needleman et Wunsch. J. Mol. Biol. 48,443-453, 1970.
Olivier S. et al. MAbs. 2010 July-August; 2(4): 405-415.
Riechmann et al. Nature, 332: 323-327, 1988.
Ryan et al., 1997 Science; 278: 873-876.
Schillberg S, et al. Vaccine 23 (2005) 1764-1769.
Shields R L, et al. J Biol Chem. 2001 Mar. 2; 276(9):6591-604.
Shields R L, et al. J Biol Chem. 2002 Jul. 26; 277(30): 26733-40.
Shinkawa T, et al. J Biol Chem. 2003 Jan. 31; 278(5):3466-73.
Stoger E, et al. Molecular Breeding 9:149-158, 2002.
Suzuki et al. Clin Cancer Res 2007 Mar. 15; 13:1875-1882.
Umana et al. Nat Biotechnol. 1999 February; 17(2):176-80.
Urlaub et al., Cell 33[2], 405-412, 1983.
Verhoeyen et al. BioEssays, 8:74, 1988.
Verhoeyen et al. Science, 239:1534-1536, 1988.
WO00/42072.
WO00/26357.
WO01/365487.
WO01/77181.
WO01/26455.
WO02/060919.
WO2004/029207.
WO2004/063351.
WO2004/074455.
WO2004/050847.

WO2005/033281.
WO2007/048077.
WO2007/106078.
WO2008/028686.
WO2010/045193.
WO2010/106180.
WO2011/114063.
WO2012/041768.
WO2012/080642.
WO2012/175751.
WO2013/061010.
WO2013/117871.
WO2014/09339.
WO90/04036.
WO95/17085.
WO99/51642.
Wollenberg A. et al. J Invest Dermatol. 2002 November; 119(5):1096-102.
Yamane-Ohnuki N. et al. Biotechnol Bioeng. 2004 Sep. 5; 87(5):614-22.

The invention claimed is:

1. A monoclonal antibody directed against the ectodomain of human CD303 antigen (SEQ ID NO: 130), wherein:
   a) said antibody has heavy and light chains variable regions comprising the following amino acid sequences:
      i) antibody 122A2: heavy chain: SEQ ID NO: 43, light chain: SEQ ID NO: 48,
      ii) antibody 122A2H5: heavy chain: SEQ ID NO: 131, light chain: SEQ ID NO: 134,
      iii) antibody 122A2H6: heavy chain: SEQ ID NO: 132, light chain: SEQ ID NO: 134,
      iv) antibody 122A2H7: heavy chain: SEQ ID NO: 133, light chain: SEQ ID NO: 134,
      v) antibody 122A2H9: heavy chain: SEQ ID NO: 131, light chain: SEQ ID NO: 135,
      vi) antibody 122A2H10: heavy chain: SEQ ID NO: 132, light chain: SEQ ID NO: 135,
      vii) antibody 122A2H11: heavy chain: SEQ ID NO: 133, light chain: SEQ ID NO: 135,
      viii) antibody 122A2H14: heavy chain: SEQ ID NO: 132, light chain: SEQ ID NO: 136, or
      ix) antibody 122A2H15: heavy chain: SEQ ID NO: 133, light chain: SEQ ID NO: 136; and
   b) the light and heavy chain constant regions of the monoclonal antibody are constant regions from a non-murine species.

2. The monoclonal antibody according to claim 1, wherein the monoclonal antibody is a chimeric antibody.

3. The monoclonal antibody according to claim 2, wherein the monoclonal antibody is a chimeric antibody whose heavy and light chains constant region is of human origin.

4. The monoclonal antibody according to claim 3, wherein the monoclonal antibody has heavy and light chains comprising the following amino acid sequences:
   i) antibody 122A2: heavy chain: SEQ ID NO: 55 or SEQ ID NO: 145, light chain: SEQ ID NO: 60.

5. The monoclonal antibody according to claim 1, wherein the monoclonal antibody is a humanized antibody.

6. The monoclonal antibody according to claim 5, wherein the monoclonal antibody has heavy and light chains variable regions comprising the following amino acid sequences:
   i) antibody 122A2H5: heavy chain: SEQ ID NO: 131, light chain: SEQ ID NO: 134,
   ii) antibody 122A2H6: heavy chain: SEQ ID NO: 132, light chain: SEQ ID NO: 134,
   iii) antibody 122A2H7: heavy chain: SEQ ID NO: 133, light chain: SEQ ID NO: 134,
   iv) antibody 122A2H9: heavy chain: SEQ ID NO: 131, light chain: SEQ ID NO: 135,
   v) antibody 122A2H10: heavy chain: SEQ ID NO: 132, light chain: SEQ ID NO: 135, or
   vi) antibody 122A2H14: heavy chain: SEQ ID NO: 132, light chain: SEQ ID NO: 136.

7. The monoclonal antibody according to claim 6, wherein the monoclonal antibody has heavy and light chains comprising the following amino acid sequences:
   i) antibody 122A2H5: heavy chain: SEQ ID NO: 150, light chain: SEQ ID NO: 153,
   ii) antibody 122A2H6: heavy chain: SEQ ID NO: 151, light chain: SEQ ID NO: 153,
   iii) antibody 122A2H7: heavy chain: SEQ ID NO: 152, light chain: SEQ ID NO: 153,
   iv) antibody 122A2H9: heavy chain: SEQ ID NO: 150, light chain: SEQ ID NO: 154,
   v) antibody 122A2H10: heavy chain: SEQ ID NO: 151, light chain: SEQ ID NO: 154, or
   vi) antibody 122A2H14: heavy chain: SEQ ID NO: 151, light chain: SEQ ID NO: 155.

8. The monoclonal antibody according to claim 1, wherein the monoclonal antibody is of IgG isotype.

9. The monoclonal antibody according to claim 1, wherein the heavy chain and/or the light chain of the monoclonal antibody further comprise(s) a heterologous signal peptide of SEQ ID NO: 65.

10. The monoclonal antibody according to claim 1, wherein the monoclonal antibody is produced in a cell line selected from: SP2/0; YB2/0; IR983F; human myeloma Namalwa; PERC6; CHO cell lines, notably CHOK-1, CHO-Lec10, CHO-Lec1, CHO-Lec13, CHO Pro-5, CHO dhfr−, or the CHO cell line deleted for both alleles encoding the FUT8 gene and/or the GMD gene; Wil-2; Jurkat; Vero; Molt-4; COS-7; 293-HEK; BHK; K6H6; NSO; SP2/0-Ag 14, P3X63Ag8.653, duck embryonic cell line EB66® (Valneva); rat hepatoma cell lines H4-II-E (DSM ACC3129) and H4-II-Es (DSM ACC3130), NM-H9D8 (DSM ACC2806), NM-H9D8-E6 (DSM ACC 2807) and NM H9D8-E6Q12 (DSM ACC 2856).

11. The monoclonal antibody according to claim 1, having:
   a) fucose content less than or equal to 65%;
   b) oligomannose-type N-glycans content greater than or equal to 30%; or
   c) galactose content greater than or equal to 50%.

12. The monoclonal antibody according to claim 1, wherein:
   a) the Fc fragment has the following mutations or combinations of mutations in their Fc fragment:
      N315D/A330V/N361D/A378V/N434Y,
      P230S/N315D/M428L/N434Y,
      E294del/T307P/N434Y,
      T307A/N315D/A330V/E382V/N389T/N434Y,
      V259I/N315D/N434Y, or
      T256N/A378V/S383N/N434Y,
   wherein the numbering of Fc fragment amino acids is that of the EU index of Kabat; or
   b) the monoclonal antibody has a deletion of the amino acid at position 293 (Del293) or 294 (Del294) of the Fc fragment, where the numbering of Fc fragment amino acids is that of the EU index of Kabat.

13. A functional fragment of the monoclonal antibody according to claim 1, wherein the functional fragment is selected from the fragments Fv, ScFv, Fab, F(ab')2, Fab', scFv-Fc and diabodies.

14. A nucleic acid encoding the heavy and light chain of a monoclonal antibody according to claim 1.

15. The nucleic acid according to claim 14, comprising at least one of SEQ ID NOs: 86, 91, and 181 to 186.

16. A vector comprising a nucleic acid according to claim 14.

17. A host cell, transgenic non-human animal or transgenic plant comprising at least one nucleic acid according to claim 14 or a vector comprising the nucleic acid.

18. The host cell according to claim 17, selected from the following lines: SP2/0; YB2/0; IR983F; human myeloma Namalwa; PERC6; CHO cell lines, notably CHO-K-1, CHO-Lec10, CHO-Lec1, CHO-Lec13, CHO Pro-5, CHO dhfr-, or the CHO cell line deleted for both alleles encoding the FUT8 gene and/or the GMD gene; Wil-2; Jurkat; Vero; Molt-4; COS-7; 293-HEK; BHK; K6H6; NSO; SP2/0-Ag 14, P3X63Ag8.653, duck embryonic cell line EB66® (Valneva); rat hepatoma cell lines H4-II-E (DSM ACC3129) and H4-II-Es (DSM ACC3130), NM-H9D8 (DSM ACC2806), NM-H9D8-E6 (DSM ACC 2807) and NM H9D8-E6Q12 (DSM ACC 2856).

* * * * *

SEQUENCE LISTING

```
<160> NUMBER OF SEQ ID NOS: 240

<210> SEQ ID NO 1
<211> LENGTH: 8
<212> TYPE: PRT
<213> ORGANISM: artificial
<220> FEATURE:
<223> OTHER INFORMATION: CDR1-H-family 1

<400> SEQUENCE: 1

Gly Tyr Thr Phe Thr Asp Tyr Ser
1               5

<210> SEQ ID NO 2
<211> LENGTH: 8
<212> TYPE: PRT
<213> ORGANISM: artificial
<220> FEATURE:
<223> OTHER INFORMATION: CDR2-H-family 1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 2

Ile Ser Xaa Tyr Tyr Gly Asp Xaa
1               5

<210> SEQ ID NO 3
<211> LENGTH: 11
<212> TYPE: PRT
<213> ORGANISM: artificial
<220> FEATURE:
<223> OTHER INFORMATION: CDR3-H-family 1
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 3

Ala Arg Asn Xaa Xaa Xaa Tyr Xaa Xaa Xaa Tyr
1               5                   10

<210> SEQ ID NO 4
<211> LENGTH: 6
<212> TYPE: PRT
<213> ORGANISM: artificial
<220> FEATURE:
<223> OTHER INFORMATION: CDR1-L-family 1
<220> FEATURE:
<221> NAME/KEY: misc_feature
```

```
<222> LOCATION: (4)..(4)
<223> OTHER INFORMATION: Xaa can be any naturally occurring amino acid

<400> SEQUENCE: 4

Gln Asp Ile Xaa Asn Tyr
1               5

<210> SEQ ID NO 5
<211> LENGTH: 3
<212> TYPE: PRT
<213> ORGANISM: artificial
<220> FEATURE:
<223> OTHER INFORMATION: CDR2-L-family 1

<400> SEQUENCE: 5

Tyr Thr Ser
1

<210> SEQ ID NO 6
<211> LENGTH: 9
<212> TYPE: PRT
<213> ORGANISM: artificial
<220> FEATURE:
<223> OTHER INFORMATION: CDR3-L-family 1
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Gln Gln Gly Xaa Thr Leu Pro Trp Thr
1               5

<210> SEQ ID NO 7
<211> LENGTH: 8
<212> TYPE: PRT
<213> ORGANISM: artificial
<220> FEATURE:
<223> OTHER INFORMATION: CDR1-H-family 2
<220> FEATURE:
<221> NAME/KEY: misc_feature
<222> LOCATION: (7)..(7)
<223> OTHER INFORMATION: Xaa can be any naturally occurring amino acid

<400> SEQUENCE: 7

Gly Tyr Thr Phe Thr Asp Xaa Ser
1               5

<210> SEQ ID NO 8
<211> LENGTH: 8
<212> TYPE: PRT
<213> ORGANISM: artificial
<220> FEATURE:
<223> OTHER INFORMATION: CDR2-H-family 2
<220> FEATURE:
<221> NAME/KEY: misc_feature
<222> LOCATION: (7)..(7)
<223> OTHER INFORMATION: Xaa can be any naturally occurring amino acid

<400> SEQUENCE: 8

Ile Asn Thr Glu Thr Gly Xaa Pro
1               5

<210> SEQ ID NO 9
<211> LENGTH: 14
<212> TYPE: PRT
<213> ORGANISM: artificial
<220> FEATURE:
<223> OTHER INFORMATION: CDR3-H-family 2
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 9

Xaa Arg Asn Gly Tyr Tyr Val Gly Tyr Tyr Ala Xaa Asp Tyr
1               5                   10

<210> SEQ ID NO 10
<211> LENGTH: 5
<212> TYPE: PRT
<213> ORGANISM: artificial
<220> FEATURE:
<223> OTHER INFORMATION: CDR1-L-family 2
<220> FEATURE:
<221> NAME/KEY: misc_feature
<222> LOCATION: (4)..(4)
<223> OTHER INFORMATION: Xaa can be any naturally occurring amino acid

<400> SEQUENCE: 10

Ser Ser Val Xaa Tyr
1               5

<210> SEQ ID NO 11
<211> LENGTH: 3
<212> TYPE: PRT
<213> ORGANISM: artificial
<220> FEATURE:
<223> OTHER INFORMATION: CDR2-L-family 2

<400> SEQUENCE: 11

Ser Thr Ser
1

<210> SEQ ID NO 12
<211> LENGTH: 9
<212> TYPE: PRT
<213> ORGANISM: artificial
<220> FEATURE:
<223> OTHER INFORMATION: CDR3-L-family 2
<220> FEATURE:
<221> NAME/KEY: misc_feature
<222> LOCATION: (8)..(8)
<223> OTHER INFORMATION: Xaa can be any naturally occurring amino acid

<400> SEQUENCE: 12

Gln Gln Arg Arg Ser Tyr Pro Xaa Thr
1               5

<210> SEQ ID NO 13
<211> LENGTH: 8
<212> TYPE: PRT
<213> ORGANISM: artificial
<220> FEATURE:
<223> OTHER INFORMATION: CDR1-H-122A2

<400> SEQUENCE: 13

Gly Tyr Thr Phe Thr Asp Tyr Ser
1               5

<210> SEQ ID NO 14
<211> LENGTH: 8
<212> TYPE: PRT
<213> ORGANISM: artificial
```

```
<220> FEATURE:
<223> OTHER INFORMATION: CDR2-H-122A2

<400> SEQUENCE: 14

Ile Ser Thr Tyr Tyr Gly Asp Ser
1               5

<210> SEQ ID NO 15
<211> LENGTH: 11
<212> TYPE: PRT
<213> ORGANISM: artificial
<220> FEATURE:
<223> OTHER INFORMATION: CDR3-H-122A2

<400> SEQUENCE: 15

Ala Arg Asn Gly Asn Phe Tyr Val Met Asp Tyr
1               5                   10

<210> SEQ ID NO 16
<211> LENGTH: 6
<212> TYPE: PRT
<213> ORGANISM: artificial
<220> FEATURE:
<223> OTHER INFORMATION: CDR1-L-122A2

<400> SEQUENCE: 16

Gln Asp Ile Ser Asn Tyr
1               5

<210> SEQ ID NO 17
<211> LENGTH: 3
<212> TYPE: PRT
<213> ORGANISM: artificial
<220> FEATURE:
<223> OTHER INFORMATION: CDR2-L-122A2

<400> SEQUENCE: 17

Tyr Thr Ser
1

<210> SEQ ID NO 18
<211> LENGTH: 9
<212> TYPE: PRT
<213> ORGANISM: artificial
<220> FEATURE:
<223> OTHER INFORMATION: CDR3-L-122A2

<400> SEQUENCE: 18

Gln Gln Gly Asn Thr Leu Pro Trp Thr
1               5

<210> SEQ ID NO 19
<211> LENGTH: 8
<212> TYPE: PRT
<213> ORGANISM: artificial
<220> FEATURE:
<223> OTHER INFORMATION: CDR1-H-102E9

<400> SEQUENCE: 19

Gly Tyr Thr Phe Thr Asp Tyr Ser
1               5

<210> SEQ ID NO 20
<211> LENGTH: 8
<212> TYPE: PRT
<213> ORGANISM: artificial
<220> FEATURE:
```

<223> OTHER INFORMATION: CDR2-H-102E9

<400> SEQUENCE: 20

Ile Asn Thr Glu Thr Gly Glu Pro
1               5

<210> SEQ ID NO 21
<211> LENGTH: 14
<212> TYPE: PRT
<213> ORGANISM: artificial
<220> FEATURE:
<223> OTHER INFORMATION: CDR3-H-102E9

<400> SEQUENCE: 21

Thr Arg Asn Gly Tyr Tyr Val Gly Tyr Tyr Ala Met Asp Tyr
1               5                   10

<210> SEQ ID NO 22
<211> LENGTH: 5
<212> TYPE: PRT
<213> ORGANISM: artificial
<220> FEATURE:
<223> OTHER INFORMATION: CDR1-L-102E9

<400> SEQUENCE: 22

Ser Ser Val Ile Tyr
1               5

<210> SEQ ID NO 23
<211> LENGTH: 3
<212> TYPE: PRT
<213> ORGANISM: artificial
<220> FEATURE:
<223> OTHER INFORMATION: CDR2-L-102E9

<400> SEQUENCE: 23

Ser Thr Ser
1

<210> SEQ ID NO 24
<211> LENGTH: 9
<212> TYPE: PRT
<213> ORGANISM: artificial
<220> FEATURE:
<223> OTHER INFORMATION: CDR3-L-102E9

<400> SEQUENCE: 24

Gln Gln Arg Arg Ser Tyr Pro Phe Thr
1               5

<210> SEQ ID NO 25
<211> LENGTH: 8
<212> TYPE: PRT
<213> ORGANISM: artificial
<220> FEATURE:
<223> OTHER INFORMATION: CDR1-H-104C12

<400> SEQUENCE: 25

Gly Tyr Thr Phe Thr Asp Tyr Ser
1               5

<210> SEQ ID NO 26
<211> LENGTH: 8
<212> TYPE: PRT
<213> ORGANISM: artificial
<220> FEATURE:
<223> OTHER INFORMATION: CDR2-H-104C12

```
<400> SEQUENCE: 26

Ile Ser Pro Tyr Tyr Gly Asp Thr
1               5

<210> SEQ ID NO 27
<211> LENGTH: 11
<212> TYPE: PRT
<213> ORGANISM: artificial
<220> FEATURE:
<223> OTHER INFORMATION: CDR3-H-104C12

<400> SEQUENCE: 27

Ala Arg Asn Asp Asp Tyr Tyr Arg Phe Ala Tyr
1               5                   10

<210> SEQ ID NO 28
<211> LENGTH: 6
<212> TYPE: PRT
<213> ORGANISM: artificial
<220> FEATURE:
<223> OTHER INFORMATION: CDR1-L-104C12

<400> SEQUENCE: 28

Gln Asp Ile Asn Asn Tyr
1               5

<210> SEQ ID NO 29
<211> LENGTH: 3
<212> TYPE: PRT
<213> ORGANISM: artificial
<220> FEATURE:
<223> OTHER INFORMATION: CDR2-L-104C12

<400> SEQUENCE: 29

Tyr Thr Ser
1

<210> SEQ ID NO 30
<211> LENGTH: 9
<212> TYPE: PRT
<213> ORGANISM: artificial
<220> FEATURE:
<223> OTHER INFORMATION: CDR3-L-104C12

<400> SEQUENCE: 30

Gln Gln Gly Lys Thr Leu Pro Trp Thr
1               5

<210> SEQ ID NO 31
<211> LENGTH: 8
<212> TYPE: PRT
<213> ORGANISM: artificial
<220> FEATURE:
<223> OTHER INFORMATION: CDR1-H-114D11

<400> SEQUENCE: 31

Gly Tyr Thr Phe Thr Asp Ser Ser
1               5

<210> SEQ ID NO 32
<211> LENGTH: 8
<212> TYPE: PRT
<213> ORGANISM: artificial
<220> FEATURE:
<223> OTHER INFORMATION: CDR2-H-114D11
```

```
<400> SEQUENCE: 32

Ile Asn Thr Glu Thr Gly Gly Pro
1               5

<210> SEQ ID NO 33
<211> LENGTH: 14
<212> TYPE: PRT
<213> ORGANISM: artificial
<220> FEATURE:
<223> OTHER INFORMATION: CDR3-H-114D11

<400> SEQUENCE: 33

Ala Arg Asn Gly Tyr Tyr Val Gly Tyr Tyr Ala Leu Asp Tyr
1               5                   10

<210> SEQ ID NO 34
<211> LENGTH: 5
<212> TYPE: PRT
<213> ORGANISM: artificial
<220> FEATURE:
<223> OTHER INFORMATION: CDR1-L-114D11

<400> SEQUENCE: 34

Ser Ser Val Phe Tyr
1               5

<210> SEQ ID NO 35
<211> LENGTH: 3
<212> TYPE: PRT
<213> ORGANISM: artificial
<220> FEATURE:
<223> OTHER INFORMATION: CDR2-L-114D11

<400> SEQUENCE: 35

Ser Thr Ser
1

<210> SEQ ID NO 36
<211> LENGTH: 9
<212> TYPE: PRT
<213> ORGANISM: artificial
<220> FEATURE:
<223> OTHER INFORMATION: CDR3-L-114D11

<400> SEQUENCE: 36

Gln Gln Arg Arg Ser Tyr Pro Tyr Thr
1               5

<210> SEQ ID NO 37
<211> LENGTH: 8
<212> TYPE: PRT
<213> ORGANISM: artificial
<220> FEATURE:
<223> OTHER INFORMATION: CDR1-H-104E10

<400> SEQUENCE: 37

Gly Tyr Thr Phe Thr Asp Tyr Ser
1               5

<210> SEQ ID NO 38
<211> LENGTH: 8
<212> TYPE: PRT
<213> ORGANISM: artificial
<220> FEATURE:
<223> OTHER INFORMATION: CDR2-H-104E10

<400> SEQUENCE: 38
```

```
Ile Asn Thr Glu Thr Gly Glu Pro
1               5
```

<210> SEQ ID NO 39
<211> LENGTH: 14
<212> TYPE: PRT
<213> ORGANISM: artificial
<220> FEATURE:
<223> OTHER INFORMATION: CDR3-H-104E10

<400> SEQUENCE: 39

```
Ala Arg Asn Gly Tyr Tyr Val Gly Tyr Tyr Ala Met Asp Tyr
1               5                   10
```

<210> SEQ ID NO 40
<211> LENGTH: 5
<212> TYPE: PRT
<213> ORGANISM: artificial
<220> FEATURE:
<223> OTHER INFORMATION: CDR1-L-104E10

<400> SEQUENCE: 40

```
Ser Ser Val Ile Tyr
1               5
```

<210> SEQ ID NO 41
<211> LENGTH: 3
<212> TYPE: PRT
<213> ORGANISM: artificial
<220> FEATURE:
<223> OTHER INFORMATION: CDR2-L-104E10

<400> SEQUENCE: 41

```
Ser Thr Ser
1
```

<210> SEQ ID NO 42
<211> LENGTH: 9
<212> TYPE: PRT
<213> ORGANISM: artificial
<220> FEATURE:
<223> OTHER INFORMATION: CDR3-L-104E10

<400> SEQUENCE: 42

```
Gln Gln Arg Arg Ser Tyr Pro Tyr Thr
1               5
```

<210> SEQ ID NO 43
<211> LENGTH: 118
<212> TYPE: PRT
<213> ORGANISM: artificial
<220> FEATURE:
<223> OTHER INFORMATION: VH-122A2

<400> SEQUENCE: 43

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Thr Tyr Tyr Gly Asp Ser Asn Tyr Asn Gln Lys Phe
    50                  55                  60

Lys Gly Lys Ala Thr Met Thr Val Asp Lys Ser Ser Thr Thr Ala Tyr
```

```
                65                  70                  75                  80
Met Glu Leu Ala Arg Leu Thr Ser Glu Asp Ser Ala Ile Tyr Tyr Cys
                85                  90                  95

Ala Arg Asn Gly Asn Phe Tyr Val Met Asp Tyr Trp Gly Gln Gly Thr
            100                 105                 110

Ser Val Thr Val Ser Ser
        115

<210> SEQ ID NO 44
<211> LENGTH: 121
<212> TYPE: PRT
<213> ORGANISM: artificial
<220> FEATURE:
<223> OTHER INFORMATION: VH-102E9

<400> SEQUENCE: 44

Gln Ile His Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Ser Ser Ala Ser Thr Ala Phe
65                  70                  75                  80

Leu Gln Ile Asn Asn Leu Lys Asn Glu Asp Thr Ser Thr Tyr Phe Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ser
        115                 120

<210> SEQ ID NO 45
<211> LENGTH: 118
<212> TYPE: PRT
<213> ORGANISM: artificial
<220> FEATURE:
<223> OTHER INFORMATION: VH-104C12

<400> SEQUENCE: 45

Gln Val Gln Leu Gln Gln Ser Gly Ala Glu Leu Val Gly Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Pro Tyr Tyr Gly Asp Thr Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Ser Leu Thr Ser Glu Asp Ser Ala Ile Tyr Phe Cys
                85                  90                  95

Ala Arg Asn Asp Asp Tyr Tyr Arg Phe Ala Tyr Trp Gly Gln Gly Thr
            100                 105                 110

Leu Val Thr Val Ser Ala
        115
```

<210> SEQ ID NO 46
<211> LENGTH: 121
<212> TYPE: PRT
<213> ORGANISM: artificial
<220> FEATURE:
<223> OTHER INFORMATION: VH-114D11

<400> SEQUENCE: 46

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Ser
            20                  25                  30

Ser Met His Trp Val Gln Gln Ala Pro Asn Lys Gly Leu Lys Trp Met
        35                  40                  45

Gly Trp Ile Asn Thr Glu Thr Gly Gly Pro Thr Tyr Ala Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Arg Asn Gly Tyr Tyr Val Gly Tyr Tyr Ala Leu Asp Tyr Trp Gly
            100                 105                 110

Gln Gly Thr Ser Val Thr Val Ser Ser
        115                 120

<210> SEQ ID NO 47
<211> LENGTH: 121
<212> TYPE: PRT
<213> ORGANISM: artificial
<220> FEATURE:
<223> OTHER INFORMATION: VH-104E10

<400> SEQUENCE: 47

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Phe Lys Asn Glu Asp Thr Ala Thr Tyr Phe Cys
                85                  90                  95

Ala Arg Asn Gly Tyr Tyr Val Gly Tyr Tyr Ala Met Asp Tyr Trp Gly
            100                 105                 110

Gln Gly Thr Ser Val Thr Val Ser Ser
        115                 120

<210> SEQ ID NO 48
<211> LENGTH: 107
<212> TYPE: PRT
<213> ORGANISM: artificial
<220> FEATURE:
<223> OTHER INFORMATION: VL-122A2

<400> SEQUENCE: 48

Asp Ile Gln Met Thr Gln Thr Thr Ser Ser Leu Ser Ala Ser Leu Gly

```
                1               5                  10                  15
            Asp Arg Val Thr Ile Ser Cys Arg Ala Ser Gln Asp Ile Ser Asn Tyr
                            20                  25                  30

Leu Asn Trp Tyr Gln Gln Lys Pro Asp Gly Thr Val Lys Leu Leu Ile
                        35                  40                  45

Tyr Tyr Thr Ser Arg Leu His Ser Gly Val Pro Ser Arg Phe Ser Gly
                    50                  55                  60

Ser Gly Ser Gly Thr Asp Tyr Ser Leu Thr Ile Ser Asn Leu Asp Gln
            65                  70                  75                  80

Glu Asp Ile Ala Thr Tyr Phe Cys Gln Gln Gly Asn Thr Leu Pro Trp
                            85                  90                  95

Thr Phe Gly Gly Gly Thr Lys Leu Glu Ile Lys
                        100                 105

<210> SEQ ID NO 49
<211> LENGTH: 106
<212> TYPE: PRT
<213> ORGANISM: artificial
<220> FEATURE:
<223> OTHER INFORMATION: VL-102E9

<400> SEQUENCE: 49

Gln Ile Val Leu Thr Gln Ser Pro Ala Ile Met Ser Ala Ser Pro Gly
            1               5                   10                  15

Glu Lys Val Thr Ile Thr Cys Ser Ala Ser Ser Ser Val Ile Tyr Ile
                            20                  25                  30

His Trp Phe Gln Gln Lys Pro Gly Thr Ser Pro Lys Leu Trp Ile Tyr
                        35                  40                  45

Ser Thr Ser Tyr Leu Ala Ser Gly Val Pro Ala Arg Phe Ser Gly Ser
                    50                  55                  60

Gly Ser Gly Thr Ser Tyr Ser Leu Thr Ile Ser Arg Met Glu Ala Glu
            65                  70                  75                  80

Asp Ala Ala Thr Tyr Tyr Cys Gln Gln Arg Arg Ser Tyr Pro Phe Thr
                            85                  90                  95

Phe Gly Gly Gly Thr Lys Leu Glu Ile Lys
                        100                 105

<210> SEQ ID NO 50
<211> LENGTH: 107
<212> TYPE: PRT
<213> ORGANISM: artificial
<220> FEATURE:
<223> OTHER INFORMATION: VL-104C12

<400> SEQUENCE: 50

Asp Leu Gln Met Thr Gln Thr Pro Ser Ser Leu Ser Ala Ser Leu Gly
            1               5                   10                  15

Asp Arg Val Thr Ile Ser Cys Arg Ala Ser Gln Asp Ile Asn Asn Tyr
                            20                  25                  30

Leu Ser Trp Tyr Gln Glu Lys Pro Asp Gly Thr Phe Lys Leu Leu Ile
                        35                  40                  45

Tyr Tyr Thr Ser Arg Leu His Ser Gly Val Pro Ser Arg Phe Ser Gly
                    50                  55                  60

Ser Gly Ser Gly Thr Asp Tyr Ser Leu Thr Val Arg Asn Leu Glu Gln
            65                  70                  75                  80

Glu Asp Ile Gly Thr Tyr Phe Cys Gln Gln Gly Lys Thr Leu Pro Trp
                            85                  90                  95
```

Thr Phe Gly Gly Gly Thr Lys Leu Glu Ile Arg
            100                 105

<210> SEQ ID NO 51
<211> LENGTH: 106
<212> TYPE: PRT
<213> ORGANISM: artificial
<220> FEATURE:
<223> OTHER INFORMATION: VL-114D11

<400> SEQUENCE: 51

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Phe Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Ser Tyr Pro Tyr Thr
                85                  90                  95

Phe Gly Gly Gly Thr Lys Leu Glu Ile Lys
            100                 105

<210> SEQ ID NO 52
<211> LENGTH: 106
<212> TYPE: PRT
<213> ORGANISM: artificial
<220> FEATURE:
<223> OTHER INFORMATION: VL-104E10

<400> SEQUENCE: 52

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ile Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Ser Tyr Pro Tyr Thr
                85                  90                  95

Phe Gly Gly Gly Thr Lys Leu Glu Ile Lys
            100                 105

<210> SEQ ID NO 53
<211> LENGTH: 329
<212> TYPE: PRT
<213> ORGANISM: artificial
<220> FEATURE:
<223> OTHER INFORMATION: CH

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 54
<211> LENGTH: 107
<212> TYPE: PRT
<213> ORGANISM: artificial
<220> FEATURE:
<223> OTHER INFORMATION: CL

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
                    50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                     85                  90                  95

Pro Val Thr Lys Ser Phe Asn Arg Gly Glu Cys
                100                 105

<210> SEQ ID NO 55
<211> LENGTH: 447
<212> TYPE: PRT
<213> ORGANISM: artificial
<220> FEATURE:
<223> OTHER INFORMATION: VH-CH-122A2

<400> SEQUENCE: 55

Gln Val Gln Leu Gln Gln Ser Gly Ala Glu Leu Val Arg Pro Gly Val
  1               5                  10                  15

Ser Val Lys Ile Ser Cys Lys Gly Ser Gly Tyr Thr Phe Thr Asp Tyr
                 20                  25                  30

Ser Met His Trp Val Lys Gln Ser His Ala Lys Ser Leu Glu Trp Ile
             35                  40                  45

Gly Val Ile Ser Thr Tyr Tyr Gly Asp Ser Asn Tyr Asn Gln Lys Phe
         50                  55                  60

Lys Gly Lys Ala Thr Met Thr Val Asp Lys Ser Ser Thr Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Asn Gly Asn Phe Tyr Val Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
                305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 56
<211> LENGTH: 450
<212> TYPE: PRT
<213> ORGANISM: artificial
<220> FEATURE:
<223> OTHER INFORMATION: VH-CH-102E9

<400> SEQUENCE: 56

Gln Ile His Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
                35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Ser Ser Ala Ser Thr Ala Phe
65                  70                  75                  80

Leu Gln Ile Asn Asn Leu Lys Asn Glu Asp Thr Ser Thr Tyr Phe Cys
                85                  90                  95

Thr Arg Asn Gly Tyr Tyr Val Gly Tyr Tyr Ala Met Asp Tyr Trp Gly
                100                 105                 110

Gln Gly Thr Ser Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Lys Thr His Thr Cys Pro Pro Cys Pro Ala Pro Glu Leu Leu Gly
```

```
                 225                 230                 235                 240
Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 57
<211> LENGTH: 447
<212> TYPE: PRT
<213> ORGANISM: artificial
<220> FEATURE:
<223> OTHER INFORMATION: VH-CH-104C12

<400> SEQUENCE: 57

Gln Val Gln Leu Gln Gln Ser Gly Ala Glu Leu Val Gly Pro Gly Val
1               5                   10                  15

Ser Val Lys Ile Ser Cys Lys Gly Ser Gly Tyr Thr Phe Thr Asp Tyr
                20                  25                  30

Ser Met His Trp Val Lys Gln Ser His Ala Lys Ser Leu Glu Trp Ile
            35                  40                  45

Gly Val Ile Ser Pro Tyr Tyr Gly Asp Thr Asn Tyr Asn Gln Lys Phe
        50                  55                  60

Lys Gly Lys Ala Thr Met Thr Val Asp Lys Ser Ser Ser Thr Ala Tyr
65                  70                  75                  80

Met Glu Leu Ala Ser Leu Thr Ser Glu Asp Ser Ala Ile Tyr Phe Cys
                85                  90                  95

Ala Arg Asn Asp Asp Tyr Tyr Arg Phe Ala Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
```

```
                    130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 58
<211> LENGTH: 450
<212> TYPE: PRT
<213> ORGANISM: artificial
<220> FEATURE:
<223> OTHER INFORMATION: VH-CH-114D11

<400> SEQUENCE: 58

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Ser
                20                  25                  30

Ser Met His Trp Val Gln Gln Ala Pro Asn Lys Gly Leu Lys Trp Met
            35                  40                  45

Gly Trp Ile Asn Thr Glu Thr Gly Gly Pro Thr Tyr Ala Asp Asp Phe
```

```
                50                  55                  60
Lys Gly Arg Phe Ala Phe Ser Leu Glu Thr Ser Ala Arg Thr Ala Tyr
 65                  70                  75                  80

Leu Gln Ile Asn Asn Leu Lys Asn Glu Asp Thr Ala Thr Tyr Phe Cys
                     85                  90                  95

Ala Arg Asn Gly Tyr Tyr Val Gly Tyr Ala Leu Asp Tyr Trp Gly
                100                 105                 110

Gln Gly Thr Ser Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 59
```

```
<211> LENGTH: 450
<212> TYPE: PRT
<213> ORGANISM: artificial
<220> FEATURE:
<223> OTHER INFORMATION: VH-CH-104E10

<400> SEQUENCE: 59

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Phe Lys Asn Glu Asp Thr Ala Thr Tyr Phe Cys
                85                  90                  95

Ala Arg Asn Gly Tyr Tyr Val Gly Tyr Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly
    450

<210> SEQ ID NO 60
<211> LENGTH: 214
<212> TYPE: PRT
<213> ORGANISM: artificial
<220> FEATURE:
<223> OTHER INFORMATION: VL-CL-122A2

<400> SEQUENCE: 60

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 213
<212> TYPE: PRT
<213> ORGANISM: artificial
<220> FEATURE:
<223> OTHER INFORMATION: VL-CL-102E9

<400> SEQUENCE: 61

Gln Ile Val Leu Thr Gln Ser Pro Ala Ile Met Ser Ala Ser Pro Gly
```

```
  1               5                  10                 15
Glu Lys Val Thr Ile Thr Cys Ser Ala Ser Ser Ser Val Ile Tyr Ile
                 20                 25                 30

His Trp Phe Gln Gln Lys Pro Gly Thr Ser Pro Lys Leu Trp Ile Tyr
                 35                 40                 45

Ser Thr Ser Tyr Leu Ala Ser Gly Val Pro Ala Arg Phe Ser Gly Ser
 50                  55                 60

Gly Ser Gly Thr Ser Tyr Ser Leu Thr Ile Ser Arg Met Glu Ala Glu
 65                  70                 75                 80

Asp Ala Ala Thr Tyr Tyr Cys Gln Gln Arg Arg Ser Tyr Pro Phe Thr
                 85                 90                 95

Phe Gly Gly Gly Thr Lys Leu Glu Ile Lys Arg Thr Val Ala Ala Pro
                100                105                110

Ser Val Phe Ile Phe Pro Pro Ser Asp Glu Gln Leu Lys Ser Gly Thr
                115                120                125

Ala Ser Val Val Cys Leu Leu Asn Asn Phe Tyr Pro Arg Glu Ala Lys
                130                135                140

Val Gln Trp Lys Val Asp Asn Ala Leu Gln Ser Gly Asn Ser Gln Glu
145                 150                155                160

Ser Val Thr Glu Gln Asp Ser Lys Asp Ser Thr Tyr Ser Leu Ser Ser
                165                170                175

Thr Leu Thr Leu Ser Lys Ala Asp Tyr Glu Lys His Lys Val Tyr Ala
                180                185                190

Cys Glu Val Thr His Gln Gly Leu Ser Ser Pro Val Thr Lys Ser Phe
                195                200                205

Asn Arg Gly Glu Cys
210

<210> SEQ ID NO 62
<211> LENGTH: 214
<212> TYPE: PRT
<213> ORGANISM: artificial
<220> FEATURE:
<223> OTHER INFORMATION: VL-CL-104C12

<400> SEQUENCE: 62

Asp Leu Gln Met Thr Gln Thr Pro Ser Ser Leu Ser Ala Ser Leu Gly
 1               5                  10                 15

Asp Arg Val Thr Ile Ser Cys Arg Ala Ser Gln Asp Ile Asn Asn Tyr
                 20                 25                 30

Leu Ser Trp Tyr Gln Glu Lys Pro Asp Gly Thr Phe Lys Leu Leu Ile
                 35                 40                 45

Tyr Tyr Thr Ser Arg Leu His Ser Gly Val Pro Ser Arg Phe Ser Gly
 50                  55                 60

Ser Gly Ser Gly Thr Asp Tyr Ser Leu Thr Val Arg Asn Leu Glu Gln
 65                  70                 75                 80

Glu Asp Ile Gly Thr Tyr Phe Cys Gln Gln Gly Lys Thr Leu Pro Trp
                 85                 90                 95

Thr Phe Gly Gly Gly Thr Lys Leu Glu Ile Arg Arg Thr Val Ala Ala
                100                105                110

Pro Ser Val Phe Ile Phe Pro Pro Ser Asp Glu Gln Leu Lys Ser Gly
                115                120                125

Thr Ala Ser Val Val Cys Leu Leu Asn Asn Phe Tyr Pro Arg Glu Ala
                130                135                140

Lys Val Gln Trp Lys Val Asp Asn Ala Leu Gln Ser Gly Asn Ser Gln
```

```
                   145                 150                 155                 160
Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                210
```

<210> SEQ ID NO 63
<211> LENGTH: 213
<212> TYPE: PRT
<213> ORGANISM: artificial
<220> FEATURE:
<223> OTHER INFORMATION: VL-CL-114D11

<400> SEQUENCE: 63

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Phe Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Ser Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
            210
```

<210> SEQ ID NO 64
<211> LENGTH: 213
<212> TYPE: PRT
<213> ORGANISM: artificial
<220> FEATURE:
<223> OTHER INFORMATION: VL-CL-104E10

<400> SEQUENCE: 64

```
Gln Ile Val Leu Thr Gln Ser Pro Ala Ile Met Ser Ala Ser Pro Gly
1               5                   10                  15
```

```
Glu Lys Val Thr Met Thr Cys Ser Ala Ser Ser Ser Val Ile Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Ser Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 65
<211> LENGTH: 18
<212> TYPE: PRT
<213> ORGANISM: artificial
<220> FEATURE:
<223> OTHER INFORMATION: MB7 signal peptide

<400> SEQUENCE: 65

Met Arg Trp Ser Trp Ile Phe Leu Leu Leu Ser Ile Thr Ser Ala
1               5                   10                  15

Asn Ala

<210> SEQ ID NO 66
<211> LENGTH: 136
<212> TYPE: PRT
<213> ORGANISM: artificial
<220> FEATURE:
<223> OTHER INFORMATION: MB7-VH-122A2

<400> SEQUENCE: 66

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Leu Val Arg Pro
                20                  25                  30

Gly Val Ser Val Lys Ile Ser Cys Lys Gly Ser Gly Tyr Thr Phe Thr
            35                  40                  45

Asp Tyr Ser Met His Trp Val Lys Gln Ser His Ala Lys Ser Leu Glu
50                  55                  60

Trp Ile Gly Val Ile Ser Thr Tyr Tyr Gly Asp Ser Asn Tyr Asn Gln
65                  70                  75                  80
```

```
Lys Phe Lys Gly Lys Ala Thr Met Thr Val Asp Lys Ser Ser Thr Thr
                85                  90                  95

Ala Tyr Met Glu Leu Ala Arg Leu Thr Ser Glu Asp Ser Ala Ile Tyr
            100                 105                 110

Tyr Cys Ala Arg Asn Gly Asn Phe Tyr Val Met Asp Tyr Trp Gly Gln
        115                 120                 125

Gly Thr Ser Val Thr Val Ser Ser
    130                 135

<210> SEQ ID NO 67
<211> LENGTH: 139
<212> TYPE: PRT
<213> ORGANISM: artificial
<220> FEATURE:
<223> OTHER INFORMATION: MB7-VH-102E9

<400> SEQUENCE: 67

Met Arg Trp Ser Trp Ile Phe Leu Leu Leu Ser Ile Thr Ser Ala
1               5                   10                  15

Asn Ala Gln Ile His Leu Val Gln Ser Gly Pro Asp Leu Lys Lys Pro
            20                  25                  30

Gly Glu Thr Val Lys Ile Ser Cys Lys Ala Ser Gly Tyr Thr Phe Thr
        35                  40                  45

Asp Tyr Ser Met His Trp Val Lys Gln Ala Pro Gly Lys Gly Leu Lys
    50                  55                  60

Trp Met Gly Trp Ile Asn Thr Glu Thr Gly Glu Pro Thr Tyr Ala Asp
65                  70                  75                  80

Asp Phe Lys Gly Arg Phe Ala Phe Ser Leu Glu Ser Ser Ala Ser Thr
                85                  90                  95

Ala Phe Leu Gln Ile Asn Asn Leu Lys Asn Glu Asp Thr Ser Thr Tyr
            100                 105                 110

Phe Cys Thr Arg Asn Gly Tyr Tyr Val Gly Tyr Tyr Ala Met Asp Tyr
        115                 120                 125

Trp Gly Gln Gly Thr Ser Val Thr Val Ser Ser
    130                 135

<210> SEQ ID NO 68
<211> LENGTH: 136
<212> TYPE: PRT
<213> ORGANISM: artificial
<220> FEATURE:
<223> OTHER INFORMATION: MB7-VH-104C12

<400> SEQUENCE: 68

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Leu Val Gly Pro
            20                  25                  30

Gly Val Ser Val Lys Ile Ser Cys Lys Gly Ser Gly Tyr Thr Phe Thr
        35                  40                  45

Asp Tyr Ser Met His Trp Val Lys Gln Ser His Ala Lys Ser Leu Glu
    50                  55                  60

Trp Ile Gly Val Ile Ser Pro Tyr Tyr Gly Asp Thr Asn Tyr Asn Gln
65                  70                  75                  80

Lys Phe Lys Gly Lys Ala Thr Met Thr Val Asp Lys Ser Ser Thr Thr
                85                  90                  95

Ala Tyr Met Glu Leu Ala Ser Leu Thr Ser Glu Asp Ser Ala Ile Tyr
            100                 105                 110
```

Phe Cys Ala Arg Asn Asp Asp Tyr Tyr Arg Phe Ala Tyr Trp Gly Gln
            115                 120                 125

Gly Thr Leu Val Thr Val Ser Ala
        130                 135

<210> SEQ ID NO 69
<211> LENGTH: 139
<212> TYPE: PRT
<213> ORGANISM: artificial
<220> FEATURE:
<223> OTHER INFORMATION: MB7-VH-114D11

<400> SEQUENCE: 69

Met Arg Trp Ser Trp Ile Phe Leu Leu Leu Ser Ile Thr Ser Ala
1               5                   10                  15

Asn Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asp Ser Ser Met His Trp Val Gln Gln Ala Pro Asn Lys Gly Leu Lys
    50                  55                  60

Trp Met Gly Trp Ile Asn Thr Glu Thr Gly Gly Pro Thr Tyr Ala Asp
65                  70                  75                  80

Asp Phe Lys Gly Arg Phe Ala Phe Ser Leu Glu Thr Ser Ala Arg Thr
                85                  90                  95

Ala Tyr Leu Gln Ile Asn Asn Leu Lys Asn Glu Asp Thr Ala Thr Tyr
            100                 105                 110

Phe Cys Ala Arg Asn Gly Tyr Tyr Val Gly Tyr Tyr Ala Leu Asp Tyr
        115                 120                 125

Trp Gly Gln Gly Thr Ser Val Thr Val Ser Ser
    130                 135

<210> SEQ ID NO 70
<211> LENGTH: 139
<212> TYPE: PRT
<213> ORGANISM: artificial
<220> FEATURE:
<223> OTHER INFORMATION: MB7-VH-104E10

<400> SEQUENCE: 70

Met Arg Trp Ser Trp Ile Phe Leu Leu Leu Ser Ile Thr Ser Ala
1               5                   10                  15

Asn Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asp Tyr Ser Met His Trp Val Lys Gln Ala Pro Gly Lys Gly Leu Lys
    50                  55                  60

Trp Met Gly Trp Ile Asn Thr Glu Thr Gly Glu Pro Thr Tyr Ala Asp
65                  70                  75                  80

Asp Phe Lys Gly Arg Phe Ala Phe Ser Leu Glu Thr Ser Ala Thr Thr
                85                  90                  95

Ala Tyr Leu Gln Ile Asn Asn Phe Lys Asn Glu Asp Thr Ala Thr Tyr
            100                 105                 110

Phe Cys Ala Arg Asn Gly Tyr Tyr Val Gly Tyr Tyr Ala Met Asp Tyr
        115                 120                 125

Trp Gly Gln Gly Thr Ser Val Thr Val Ser Ser

<210> SEQ ID NO 71
<211> LENGTH: 125
<212> TYPE: PRT
<213> ORGANISM: artificial
<220> FEATURE:
<223> OTHER INFORMATION: MB7-VL-122A2

<400> SEQUENCE: 71

Met Arg Trp Ser Trp Ile Phe Leu Leu Leu Ser Ile Thr Ser Ala
1               5                   10                  15

Asn Ala Asp Ile Gln Met Thr Gln Thr Thr Ser Ser Leu Ser Ala Ser
            20                  25                  30

Leu Gly Asp Arg Val Thr Ile Ser Cys Arg Ala Ser Gln Asp Ile Ser
        35                  40                  45

Asn Tyr Leu Asn Trp Tyr Gln Gln Lys Pro Asp Gly Thr Val Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Asp Gln Glu Asp Ile Ala Thr Tyr Phe Cys Gln Gln Gly Asn Thr Leu
            100                 105                 110

Pro Trp Thr Phe Gly Gly Gly Thr Lys Leu Glu Ile Lys
        115                 120                 125

<210> SEQ ID NO 72
<211> LENGTH: 124
<212> TYPE: PRT
<213> ORGANISM: artificial
<220> FEATURE:
<223> OTHER INFORMATION: MB7-VL-102E9

<400> SEQUENCE: 72

Met Arg Trp Ser Trp Ile Phe Leu Leu Leu Ser Ile Thr Ser Ala
1               5                   10                  15

Asn Ala Gln Ile Val Leu Thr Gln Ser Pro Ala Ile Met Ser Ala Ser
            20                  25                  30

Pro Gly Glu Lys Val Thr Ile Thr Cys Ser Ala Ser Ser Ser Val Ile
        35                  40                  45

Tyr Ile His Trp Phe Gln Gln Lys Pro Gly Thr Ser Pro Lys Leu Trp
    50                  55                  60

Ile Tyr Ser Thr Ser Tyr Leu Ala Ser Gly Val Pro Ala Arg Phe Ser
65                  70                  75                  80

Gly Ser Gly Ser Gly Thr Ser Tyr Ser Leu Thr Ile Ser Arg Met Glu
                85                  90                  95

Ala Glu Asp Ala Ala Thr Tyr Tyr Cys Gln Gln Arg Arg Ser Tyr Pro
            100                 105                 110

Phe Thr Phe Gly Gly Gly Thr Lys Leu Glu Ile Lys
        115                 120

<210> SEQ ID NO 73
<211> LENGTH: 125
<212> TYPE: PRT
<213> ORGANISM: artificial
<220> FEATURE:
<223> OTHER INFORMATION: MB7-VL-104C12

<400> SEQUENCE: 73

```
Met Arg Trp Ser Trp Ile Phe Leu Leu Leu Ser Ile Thr Ser Ala
1               5                   10                  15

Asn Ala Asp Leu Gln Met Thr Gln Thr Pro Ser Ser Leu Ser Ala Ser
            20                  25                  30

Leu Gly Asp Arg Val Thr Ile Ser Cys Arg Ala Ser Gln Asp Ile Asn
        35                  40                  45

Asn Tyr Leu Ser Trp Tyr Gln Glu Lys Pro Asp Gly Thr Phe Lys Leu
    50                  55                  60

Leu Ile Tyr Tyr Thr Ser Arg Leu His Ser Gly Val Pro Ser Arg Phe
65              70                  75                  80

Ser Gly Ser Gly Ser Gly Thr Asp Tyr Ser Leu Thr Val Arg Asn Leu
            85                  90                  95

Glu Gln Glu Asp Ile Gly Thr Tyr Phe Cys Gln Gln Gly Lys Thr Leu
            100                 105                 110

Pro Trp Thr Phe Gly Gly Gly Thr Lys Leu Glu Ile Arg
        115                 120                 125

<210> SEQ ID NO 74
<211> LENGTH: 124
<212> TYPE: PRT
<213> ORGANISM: artificial
<220> FEATURE:
<223> OTHER INFORMATION: MB7-VL-114D11

<400> SEQUENCE: 74

Met Arg Trp Ser Trp Ile Phe Leu Leu Leu Ser Ile Thr Ser Ala
1               5                   10                  15

Asn Ala Gln Ile Val Leu Thr Gln Ser Pro Ala Ile Met Ser Ala Ser
            20                  25                  30

Pro Gly Glu Lys Val Thr Ile Thr Cys Ser Ala Ser Ser Ser Val Phe
        35                  40                  45

Tyr Met His Trp Phe Gln Gln Lys Pro Gly Thr Ser Pro Lys Leu Trp
    50                  55                  60

Ile Tyr Ser Thr Ser Asn Leu Ala Ser Gly Val Pro Ala Arg Phe Ser
65              70                  75                  80

Gly Ser Gly Ser Gly Thr Ser Tyr Ser Leu Thr Ile Ser Arg Met Glu
            85                  90                  95

Ala Glu Asp Ala Ala Thr Tyr Tyr Cys Gln Gln Arg Arg Ser Tyr Pro
            100                 105                 110

Tyr Thr Phe Gly Gly Gly Thr Lys Leu Glu Ile Lys
        115                 120

<210> SEQ ID NO 75
<211> LENGTH: 124
<212> TYPE: PRT
<213> ORGANISM: artificial
<220> FEATURE:
<223> OTHER INFORMATION: MB7-VL-104E10

<400> SEQUENCE: 75

Met Arg Trp Ser Trp Ile Phe Leu Leu Leu Ser Ile Thr Ser Ala
1               5                   10                  15

Asn Ala Gln Ile Val Leu Thr Gln Ser Pro Ala Ile Met Ser Ala Ser
            20                  25                  30

Pro Gly Glu Lys Val Thr Met Thr Cys Ser Ala Ser Ser Ser Val Ile
        35                  40                  45

Tyr Met His Trp Phe Gln Gln Lys Pro Gly Thr Ser Pro Lys Leu Trp
```

```
                50              55              60
Ile Tyr Ser Thr Ser Asn Leu Ala Ser Gly Val Pro Ala Arg Phe Ser
65                  70                  75                  80

Gly Ser Gly Ser Gly Thr Ser Tyr Ser Leu Thr Ile Ser Arg Met Glu
                    85                  90                  95

Ala Glu Asp Ala Ala Thr Tyr Tyr Cys Gln Gln Arg Arg Ser Tyr Pro
                100                 105                 110

Tyr Thr Phe Gly Gly Gly Thr Lys Leu Glu Ile Lys
            115                 120

<210> SEQ ID NO 76
<211> LENGTH: 465
<212> TYPE: PRT
<213> ORGANISM: artificial
<220> FEATURE:
<223> OTHER INFORMATION: MB7-VH-CH-122A2

<400> SEQUENCE: 76

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Leu Val Arg Pro
                20                  25                  30

Gly Val Ser Val Lys Ile Ser Cys Lys Gly Ser Gly Tyr Thr Phe Thr
                35                  40                  45

Asp Tyr Ser Met His Trp Val Lys Gln Ser His Ala Lys Ser Leu Glu
            50                  55                  60

Trp Ile Gly Val Ile Ser Thr Tyr Tyr Gly Asp Ser Asn Tyr Asn Gln
65                  70                  75                  80

Lys Phe Lys Gly Lys Ala Thr Met Thr Val Asp Lys Ser Ser Thr Thr
                85                  90                  95

Ala Tyr Met Glu Leu Ala Arg Leu Thr Ser Glu Asp Ser Ala Ile Tyr
                100                 105                 110

Tyr Cys Ala Arg Asn Gly Asn Phe Tyr Val Met Asp Tyr Trp Gly Gln
            115                 120                 125

Gly Thr Ser Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
```

```
            290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
                355                 360                 365
Thr Leu Pro Pro Ser Arg Asp Glu Leu Thr Lys Asn Gln Val Ser Leu
                370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
                435                 440                 445
Glu Ala Leu His Asn His Tyr Thr Gln Lys Ser Leu Ser Leu Ser Pro
                450                 455                 460
Gly
465

<210> SEQ ID NO 77
<211> LENGTH: 468
<212> TYPE: PRT
<213> ORGANISM: artificial
<220> FEATURE:
<223> OTHER INFORMATION: MB7-VH-CH-102E9

<400> SEQUENCE: 77

Met Arg Trp Ser Trp Ile Phe Leu Leu Leu Leu Ser Ile Thr Ser Ala
1               5                   10                  15
Asn Ala Gln Ile His Leu Val Gln Ser Gly Pro Asp Leu Lys Lys Pro
                20                  25                  30
Gly Glu Thr Val Lys Ile Ser Cys Lys Ala Ser Gly Tyr Thr Phe Thr
                35                  40                  45
Asp Tyr Ser Met His Trp Val Lys Gln Ala Pro Gly Lys Gly Leu Lys
            50                  55                  60
Trp Met Gly Trp Ile Asn Thr Glu Thr Gly Glu Pro Thr Tyr Ala Asp
65                  70                  75                  80
Asp Phe Lys Gly Arg Phe Ala Phe Ser Leu Glu Ser Ser Ala Ser Thr
                85                  90                  95
Ala Phe Leu Gln Ile Asn Asn Leu Lys Asn Glu Asp Thr Ser Thr Tyr
                100                 105                 110
Phe Cys Thr Arg Asn Gly Tyr Tyr Val Gly Tyr Ala Met Asp Tyr
                115                 120                 125
Trp Gly Gln Gly Thr Ser Val Thr Val Ser Ser Ala Ser Thr Lys Gly
130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
```

```
            180                 185                 190
Pro Ala Val Leu Gln Ser Ser Gly Leu Tyr Ser Leu Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                    325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly
465

<210> SEQ ID NO 78
<211> LENGTH: 465
<212> TYPE: PRT
<213> ORGANISM: artificial
<220> FEATURE:
<223> OTHER INFORMATION: MB7-VH-CH-104C12

<400> SEQUENCE: 78

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Leu Val Gly Pro
                20                  25                  30

Gly Val Ser Val Lys Ile Ser Cys Lys Gly Ser Gly Tyr Thr Phe Thr
            35                  40                  45

Asp Tyr Ser Met His Trp Val Lys Gln Ser His Ala Lys Ser Leu Glu
        50                  55                  60

Trp Ile Gly Val Ile Ser Pro Tyr Tyr Gly Asp Thr Asn Tyr Asn Gln
```

```
              65                  70                  75                  80
Lys Phe Lys Gly Lys Ala Thr Met Thr Val Asp Lys Ser Ser Thr
                    85                  90                  95

Ala Tyr Met Glu Leu Ala Ser Leu Thr Ser Glu Asp Ser Ala Ile Tyr
                100                 105                 110

Phe Cys Ala Arg Asn Asp Asp Tyr Tyr Arg Phe Ala Tyr Trp Gly Gln
                115                 120                 125

Gly Thr Leu Val Thr Val Ser Ala Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
                275                 280                 285

Asp Pro Glu Val Lys Phe Asn Trp Tyr Val Asp Gly Val Glu Val His
                290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Asp Glu Leu Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
                450                 455                 460

Gly
465

<210> SEQ ID NO 79
```

```
<211> LENGTH: 468
<212> TYPE: PRT
<213> ORGANISM: artificial
<220> FEATURE:
<223> OTHER INFORMATION: MB7-VH-CH-114D11

<400> SEQUENCE: 79

Met Arg Trp Ser Trp Ile Phe Leu Leu Leu Ser Ile Thr Ser Ala
1               5                   10                  15

Asn Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asp Ser Ser Met His Trp Val Gln Gln Ala Pro Asn Lys Gly Leu Lys
    50                  55                  60

Trp Met Gly Trp Ile Asn Thr Glu Thr Gly Gly Pro Thr Tyr Ala Asp
65                  70                  75                  80

Asp Phe Lys Gly Arg Phe Ala Phe Ser Leu Glu Thr Ser Ala Arg Thr
                85                  90                  95

Ala Tyr Leu Gln Ile Asn Asn Leu Lys Asn Glu Asp Thr Ala Thr Tyr
            100                 105                 110

Phe Cys Ala Arg Asn Gly Tyr Tyr Val Gly Tyr Tyr Ala Leu Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380
```

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 80
<211> LENGTH: 468
<212> TYPE: PRT
<213> ORGANISM: artificial
<220> FEATURE:
<223> OTHER INFORMATION: MB7-VH-CH-104E10

<400> SEQUENCE: 80

Met Arg Trp Ser Trp Ile Phe Leu Leu Leu Ser Ile Thr Ser Ala
1               5                   10                  15

Asn Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asp Tyr Ser Met His Trp Val Lys Gln Ala Pro Gly Lys Gly Leu Lys
    50                  55                  60

Trp Met Gly Trp Ile Asn Thr Glu Thr Gly Glu Pro Thr Tyr Ala Asp
65                  70                  75                  80

Asp Phe Lys Gly Arg Phe Ala Phe Ser Leu Glu Thr Ser Ala Thr Thr
                85                  90                  95

Ala Tyr Leu Gln Ile Asn Asn Phe Lys Asn Glu Asp Thr Ala Thr Tyr
            100                 105                 110

Phe Cys Ala Arg Asn Gly Tyr Tyr Val Gly Tyr Tyr Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270
```

```
Leu Met Ile Ser Arg Thr Pro Glu Val Thr Cys Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 81
<211> LENGTH: 232
<212> TYPE: PRT
<213> ORGANISM: artificial
<220> FEATURE:
<223> OTHER INFORMATION: MB7-VL-CL-122A2

<400> SEQUENCE: 81

Met Arg Trp Ser Trp Ile Phe Leu Leu Leu Ser Ile Thr Ser Ala
1               5                   10                  15

Asn Ala Asp Ile Gln Met Thr Gln Thr Thr Ser Ser Leu Ser Ala Ser
            20                  25                  30

Leu Gly Asp Arg Val Thr Ile Ser Cys Arg Ala Ser Gln Asp Ile Ser
        35                  40                  45

Asn Tyr Leu Asn Trp Tyr Gln Gln Lys Pro Asp Gly Thr Val Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Asp Gln Glu Asp Ile Ala Thr Tyr Phe Cys Gln Gln Gly Asn Thr Leu
            100                 105                 110

Pro Trp Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160
```

-continued

Glu Ala Lys Val Gln Trp Lys Val Asp Asn Ala Leu Gln Ser Gly Asn
            165                 170                 175

Ser Gln Glu Ser Val Thr Glu Gln Asp Ser Lys Asp Ser Thr Tyr Ser
        180                 185                 190

Leu Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 82
<211> LENGTH: 231
<212> TYPE: PRT
<213> ORGANISM: artificial
<220> FEATURE:
<223> OTHER INFORMATION: MB7-VL-CL-102E9

<400> SEQUENCE: 82

Met Arg Trp Ser Trp Ile Phe Leu Leu Leu Leu Ser Ile Thr Ser Ala
1               5                   10                  15

Asn Ala Gln Ile Val Leu Thr Gln Ser Pro Ala Ile Met Ser Ala Ser
            20                  25                  30

Pro Gly Glu Lys Val Thr Ile Thr Cys Ser Ala Ser Ser Val Ile
        35                  40                  45

Tyr Ile His Trp Phe Gln Gln Lys Pro Gly Thr Ser Pro Lys Leu Trp
    50                  55                  60

Ile Tyr Ser Thr Ser Tyr Leu Ala Ser Gly Val Pro Ala Arg Phe Ser
65                  70                  75                  80

Gly Ser Gly Ser Gly Thr Ser Tyr Ser Leu Thr Ile Ser Arg Met Glu
                85                  90                  95

Ala Glu Asp Ala Ala Thr Tyr Tyr Cys Gln Gln Arg Ser Ser Tyr Pro
            100                 105                 110

Phe Thr Phe Gly Gly Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 83
<211> LENGTH: 232
<212> TYPE: PRT
<213> ORGANISM: artificial
<220> FEATURE:
<223> OTHER INFORMATION: MB7-VL-CL-104C12

```
<400> SEQUENCE: 83

Met Arg Trp Ser Trp Ile Phe Leu Leu Leu Ser Ile Thr Ser Ala
1               5                   10                  15

Asn Ala Asp Leu Gln Met Thr Gln Thr Pro Ser Ser Leu Ser Ala Ser
                20                  25                  30

Leu Gly Asp Arg Val Thr Ile Ser Cys Arg Ala Ser Gln Asp Ile Asn
            35                  40                  45

Asn Tyr Leu Ser Trp Tyr Gln Glu Lys Pro Asp Gly Thr Phe Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Ser Leu Thr Val Arg Asn Leu
                85                  90                  95

Glu Gln Glu Asp Ile Gly Thr Tyr Phe Cys Gln Gln Gly Lys Thr Leu
            100                 105                 110

Pro Trp Thr Phe Gly Gly Gly Thr Lys Leu Glu Ile Arg Arg Thr Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 84
<211> LENGTH: 231
<212> TYPE: PRT
<213> ORGANISM: artificial
<220> FEATURE:
<223> OTHER INFORMATION: MB7-VL-CL-114D11

<400> SEQUENCE: 84

Met Arg Trp Ser Trp Ile Phe Leu Leu Leu Ser Ile Thr Ser Ala
1               5                   10                  15

Asn Ala Gln Ile Val Leu Thr Gln Ser Pro Ala Ile Met Ser Ala Ser
                20                  25                  30

Pro Gly Glu Lys Val Thr Ile Thr Cys Ser Ala Ser Ser Ser Val Phe
            35                  40                  45

Tyr Met His Trp Phe Gln Gln Lys Pro Gly Thr Ser Pro Lys Leu Trp
    50                  55                  60

Ile Tyr Ser Thr Ser Asn Leu Ala Ser Gly Val Pro Ala Arg Phe Ser
65                  70                  75                  80

Gly Ser Gly Ser Gly Thr Ser Tyr Ser Leu Thr Ile Ser Arg Met Glu
                85                  90                  95

Ala Glu Asp Ala Ala Thr Tyr Tyr Cys Gln Gln Arg Ser Ser Tyr Pro
            100                 105                 110

Tyr Thr Phe Gly Gly Gly Thr Lys Leu Glu Ile Lys Arg Thr Val Ala
```

```
                 115                 120                 125
Ala Pro Ser Val Phe Ile Phe Pro Pro Ser Asp Glu Gln Leu Lys Ser
            130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
                195                 200                 205

Tyr Ala Cys Glu Val Thr His Gln Gly Leu Ser Ser Pro Val Thr Lys
            210                 215                 220

Ser Phe Asn Arg Gly Glu Cys
225                 230

<210> SEQ ID NO 85
<211> LENGTH: 231
<212> TYPE: PRT
<213> ORGANISM: artificial
<220> FEATURE:
<223> OTHER INFORMATION: MB7-VL-CL-104E10

<400> SEQUENCE: 85

Met Arg Trp Ser Trp Ile Phe Leu Leu Leu Ser Ile Thr Ser Ala
1               5                   10                  15

Asn Ala Gln Ile Val Leu Thr Gln Ser Pro Ala Ile Met Ser Ala Ser
                20                  25                  30

Pro Gly Glu Lys Val Thr Met Thr Cys Ser Ala Ser Ser Ser Val Ile
            35                  40                  45

Tyr Met His Trp Phe Gln Gln Lys Pro Gly Thr Ser Pro Lys Leu Trp
        50                  55                  60

Ile Tyr Ser Thr Ser Asn Leu Ala Ser Gly Val Pro Ala Arg Phe Ser
65                  70                  75                  80

Gly Ser Gly Ser Gly Thr Ser Tyr Ser Leu Thr Ile Ser Arg Met Glu
                85                  90                  95

Ala Glu Asp Ala Ala Thr Tyr Tyr Cys Gln Gln Arg Arg Ser Tyr Pro
            100                 105                 110

Tyr Thr Phe Gly Gly Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
            130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
                195                 200                 205

Tyr Ala Cys Glu Val Thr His Gln Gly Leu Ser Ser Pro Val Thr Lys
            210                 215                 220

Ser Phe Asn Arg Gly Glu Cys
225                 230
```

<210> SEQ ID NO 86
<211> LENGTH: 354
<212> TYPE: DNA
<213> ORGANISM: artificial
<220> FEATURE:
<223> OTHER INFORMATION: VH-122A2

<400> SEQUENCE: 86

```
caggtccagc tgcagcagtc tggggctgag ctggtgaggc ctggggtctc agtgaagatt      60
tcctgcaagg gttctggcta cacattcact gattattcta tgcactgggt gaagcagagt     120
catgcaaaga gtctagagtg gattggagtt attagtactt actatggtga ttctaactat     180
aaccagaagt tcaagggcaa ggccacaatg actgtagaca atcctccaca cacagcctat     240
atggaacttg ccagactgac atctgaggat tctgccatct attactgtgc aagaaatggt     300
aatttctatg ttatggacta ctggggtcaa ggaacctcag tcaccgtctc ctca           354
```

<210> SEQ ID NO 87
<211> LENGTH: 363
<212> TYPE: DNA
<213> ORGANISM: artificial
<220> FEATURE:
<223> OTHER INFORMATION: VH-102E9

<400> SEQUENCE: 87

```
cagatccatt tggtgcagtc tggacctgac ctgaagaagc tggagagaca agtcaagatc      60
tcctgcaagg cttctggtta taccttcaca gactattcaa tgcactgggt gaagcaggct     120
ccaggaaagg gtttaaagtg gatgggctgg ataaacactg agactggtga accaacatat     180
gcagatgact tcaagggacg gtttgccttc tctttggaaa gttctgccag cactgccttt     240
ttgcagatca acaacctcaa aaatgaggac acgtctacat atttctgtac tagaaatggt     300
tactacgtgg gttactatgc tatggactac tggggtcaag gaacctcagt caccgtctcc     360
tca                                                                    363
```

<210> SEQ ID NO 88
<211> LENGTH: 353
<212> TYPE: DNA
<213> ORGANISM: artificial
<220> FEATURE:
<223> OTHER INFORMATION: VH-104C12

<400> SEQUENCE: 88

```
caggtccagc tgcagcagtc tggggctgag ctggtggggc ctggggtctc agtgaagatt      60
tcctgcaagg gttctggcta cacattcact gattattcta tgcactgggt aaagcagagt     120
catgcaaaga gtctagagtg gattggagtt attagtcctt actatggtga tactaactac     180
aaccagaagt tcaagggcaa ggccacaatg actgtagaca atcctccagc acagcctat      240 atggaacttg ccagtctgac atctgaggat tctgccatct atttctgtgc aagaaatgat     300
gattactaca ggtttgctta ctggggccaa gggactctgg tcactgtctc tgc            353
```

<210> SEQ ID NO 89
<211> LENGTH: 363
<212> TYPE: DNA
<213> ORGANISM: artificial
<220> FEATURE:
<223> OTHER INFORMATION: VH-114D11

<400> SEQUENCE: 89

```
cagatccagt tggtgcagtc tggacctgag ctgaagaagc tggagagaca agtcaagatc      60
```

```
tcctgcaagg cttctggtta taccttcaca gactcttcaa tgcactgggt gcagcaggct    120
ccaaacaagg gtttaaagtg gatgggctgg ataaacactg agactggtgg gccaacgtat    180
gcagatgatt tcaagggacg gtttgccttc tctttggaaa cctctgccag aactgcctat    240
ttgcagatca acaacctcaa aaatgaggac acggctacat atttctgtgc tagaaatgga    300
tactacgtgg ggtactatgc tctggactac tggggtcaag gaacctcagt caccgtctcc    360
tca                                                                  363
```

```
<210> SEQ ID NO 90
<211> LENGTH: 363
<212> TYPE: DNA
<213> ORGANISM: artificial
<220> FEATURE:
<223> OTHER INFORMATION: VH-104E10

<400> SEQUENCE: 90
cagatccagt tggtgcagtc tggacctgag ctgaagaagc ctggagagac agtcaagatc     60
tcctgcaagg cttctggtta taccttcaca gactattcaa tgcactgggt gaagcaggct    120
ccaggaaagg gtttaaagtg gatgggctgg ataaacactg agactggtga gccaacatat    180
gcagatgact tcaagggacg gtttgccttc tctttggaaa cctctgccac cactgcctat    240
ttgcagatca acaacttcaa aaatgaggac acggctacat atttctgtgc tagaaatggt    300
tactacgtgg atattatgc tatggactac tggggtcaag gaacctcagt caccgtctcc    360
tca                                                                  363
```

```
<210> SEQ ID NO 91
<211> LENGTH: 321
<212> TYPE: DNA
<213> ORGANISM: artificial
<220> FEATURE:
<223> OTHER INFORMATION: VL-122A2

<400> SEQUENCE: 91
gatatccaga tgacacagac tacatcctcc ctgtctgcct ctctgggaga cagagtcacc     60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctgaccaa     240 gaagatattg ccacttactt tgccaacag gtaatacgc ttccttggac gttcggtgga     300
ggcaccaagc tggaaatcaa a                                              321
```

```
<210> SEQ ID NO 92
<211> LENGTH: 318
<212> TYPE: DNA
<213> ORGANISM: artificial
<220> FEATURE:
<223> OTHER INFORMATION: VL-102E9

<400> SEQUENCE: 92
caaattgttc tcacccagtc tccagcaatc atgtctgcat ctccagggga aaggtcacc     60 ataacctgca gtgccagctc aagtgtaatt tacattcact ggttccagca gaagccaggc    120
acttctccca aactctggat ttatagcaca tcctacctgg cttctggagt ccctgctcgc    180
ttcagtggca gtggatctgg gacctcttac tctctcacaa tcagccgaat ggaggctgaa    240
gatgctgcca cttattactg ccagcagagg agaagttacc cgttcacgtt cggagggggg    300
accaagctgg aaataaaa                                                  318
```

<210> SEQ ID NO 93
<211> LENGTH: 320
<212> TYPE: DNA
<213> ORGANISM: artificial
<220> FEATURE:
<223> OTHER INFORMATION: VL-104C12

<400> SEQUENCE: 93

| | | | | | |
|---|---|---|---|---|---|
| gatctccaga | tgacacagac | tccatcctcc | ctgtctgcct | ctctgggaga | cagagtcacc | 60 |
| atcagttgca | gggcaagtca | ggacattaac | aattatttaa | gctggtatca | ggagaaacca | 120 |
| gatggaactt | ttaaactcct | gatctactac | acatcaagat | acactcagg | agtcccatca | 180 |
| aggttcagtg | gcagtgggtc | tggaacagat | tattctctca | ccgttcgcaa | cctggaacag | 240 |
| gaagatattg | cacttacttt | tgccaacag | gtaaaacgc | ttccgtggac | gttcggtgga | 300 |
| ggcaccaagc | tggaaatcag | | | | | 320 |

<210> SEQ ID NO 94
<211> LENGTH: 318
<212> TYPE: DNA
<213> ORGANISM: artificial
<220> FEATURE:
<223> OTHER INFORMATION: VL-114D11

<400> SEQUENCE: 94

| | | | | | |
|---|---|---|---|---|---|
| caaattgttc | tcacccagtc | tccagcaatc | atgtctgcat | ctccagggga | gaaggtcacc | 60 |
| ataacctgca | gtgccagctc | aagtgtattt | tacatgcact | ggttccagca | gaagccaggc | 120 |
| acttctccca | aactctggat | ttatagcaca | tccaacctgg | cttctggagt | ccctgctcgc | 180 |
| ttcagtggca | gtggatctgg | gacctcttac | tctctcacaa | tcagccgaat | ggaggctgaa | 240 |
| gatgctgcca | cttattactg | ccagcaaagg | agaagttacc | cgtacacgtt | cggaggggggg | 300 |
| accaagctgg | aaataaaa | | | | | 318 |

<210> SEQ ID NO 95
<211> LENGTH: 318
<212> TYPE: DNA
<213> ORGANISM: artificial
<220> FEATURE:
<223> OTHER INFORMATION: VL-104E10

<400> SEQUENCE: 95

| | | | | | |
|---|---|---|---|---|---|
| caaattgttc | tcacccagtc | tccagcaatc | atgtctgcat | ctccagggga | gaaggtcacc | 60 |
| atgacctgca | gtgccagttc | aagtgtaatt | tacatgcact | ggttccagca | gaagccaggc | 120 |
| acttctccca | aactctggat | ttatagcaca | tccaacctgg | cttctggagt | ccctgctcgc | 180 |
| ttcagtggca | gtggatctgg | gacatcttac | tctctcacaa | tcagccgaat | ggaggctgaa | 240 |
| gatgctgcca | cttattactg | ccagcaaagg | agaagttacc | cgtacacgtt | cggaggggggg | 300 |
| accaagctgg | aaataaaa | | | | | 318 |

<210> SEQ ID NO 96
<211> LENGTH: 990
<212> TYPE: DNA
<213> ORGANISM: artificial
<220> FEATURE:
<223> OTHER INFORMATION: CH

<400> SEQUENCE: 96

| | | | | | |
|---|---|---|---|---|---|
| gcctccacca | agggcccatc | cgtgttcccc | ctggccccat | ccagcaagtc | tacctccgga | 60 |

| | |
|---|---|
| ggcacagccg ccctgggctg tctggtgaag gactacttcc ccgagccagt gaccgtgtcc | 120 |
| tggaactccg gagccctgac atccggcgtg cacaccttcc ccgccgtgct gcagtccagc | 180 |
| ggcctgtact ctctgtcttc cgtggtgacc gtgccatcca gctccctggg aacccagaca | 240 |
| tacatctgca acgtgaacca caagcctagc aacaccaagg tggacaagaa ggtggagcct | 300 |
| aagagctgtg acaagacaca cacatgccct ccttgtccag cccctgagct gctgggcggc | 360 |
| ccctccgtgt tcctgttccc ccccaagcct aaggatacccc tgatgatcag cagaaccccc | 420 |
| gaggtgacct gcgtggtggt ggacgtgtcc cacgaggatc ccgaggtgaa gttcaactgg | 480 |
| tacgtggacg gcgtggaggt gcacaacgct aagaccaagc ccagagagga gcagtacaac | 540 |
| agcacataca gagtggtgtc tgtgctgacc gtgctgcacc aggactggct gaacgggaag | 600 |
| gagtacaagt gcaaggtgtc caacaaggcc ctgcctgccc ctatcgagaa gaccatctct | 660 |
| aaggctaagg gcagccccg ggagccacag gtgtacaccc tgccacccag ccgcgacgag | 720 |
| ctgaccaaga accaggtgtc cctgacatgc ctggtgaagg gattctaccc cagcgacatc | 780 |
| gccgtggagt gggagagcaa cggccagccc gagaacaact acaagacaac ccctcccgtg | 840 |
| ctggacagcg atggatcctt cttcctgtac tccaagctga ccgtggacaa gagcaggtgg | 900 |
| cagcagggaa acgtgttctc ttgttccgtg atgcacgagg ctctgcacaa ccactacacc | 960 |
| cagaagtccc tgagcctgtc tccaggcaag | 990 |

<210> SEQ ID NO 97
<211> LENGTH: 321
<212> TYPE: DNA
<213> ORGANISM: artificial
<220> FEATURE:
<223> OTHER INFORMATION: CL

<400> SEQUENCE: 97

| | |
|---|---|
| cgaactgtgg ctgcaccaag tgtcttcatc tttcctccga gtgatgagca gctgaagagc | 60 |
| gggacagctt ctgtggtgtg tctgctgaat aacttctacc caagagaagc aaaggtccag | 120 |
| tggaaggtgg acaacgccct gcagtctggc aactcacagg agtctgtcac tgagcaggat | 180 |
| tccaaggaca gcacttacag cctgtccagc accctcactc tgtccaaagc cgactacgaa | 240 |
| aagcataagg tgtatgcttg tgaggtgacc caccagggac tgagcagccc tgtgacgaag | 300 |
| tccttcaacc ggggcgagtg c | 321 |

<210> SEQ ID NO 98
<211> LENGTH: 1344
<212> TYPE: DNA
<213> ORGANISM: artificial
<220> FEATURE:
<223> OTHER INFORMATION: VH-CH-122A2

<400> SEQUENCE: 98

| | |
|---|---|
| caggtccagc tgcagcagtc tggggctgag ctggtgaggc ctggggtctc agtgaagatt | 60 |
| tcctgcaagg gttctggcta cacattcact gattattcta tgcactgggt gaagcagagt | 120 |
| catgcaaaga gtctagagtg gattggagtt attagtactt actatggtga ttctaactat | 180 |
| aaccagaagt tcaagggcaa ggccacaatg actgtagaca aatcctccac cacagcctat | 240 |
| atggaacttg ccagactgac atctgaggat tctgccatct attactgtgc aagaaatggt | 300 |
| aatttctatg ttatggacta ctggggtcaa ggaacctcag tcaccgtctc ctcagcctcc | 360 |
| accaagggcc catccgtgtt ccccctggcc ccatccagca gtctacctc cggaggcaca | 420 |
| gccgccctgg gctgtctggt gaaggactac ttccccgagc cagtgaccgt gtcctggaac | 480 |

| | |
|---|---:|
| tccggagccc tgacatccgg cgtgcacacc ttccccgccg tgctgcagtc cagcggcctg | 540 |
| tactctctgt cttccgtggt gaccgtgcca tccagctccc tgggaaccca gacatacatc | 600 |
| tgcaacgtga accacaagcc tagcaacacc aaggtggaca gaaggtgga gcctaagagc | 660 |
| tgtgacaaga cacacacatg ccctccttgt ccagcccctg agctgctggg cggcccctcc | 720 |
| gtgttcctgt tccccccaa gcctaaggat accctgatga tcagcagaac cccgaggtg | 780 |
| acctgcgtgt ggtggacgt gtcccacgag gatcccgagg tgaagttcaa ctggtacgtg | 840 |
| gacggcgtgg aggtgcacaa cgctaagacc aagcccagag aggagcagta caacagcaca | 900 |
| tacagagtgg tgtctgtgct gaccgtgctg caccaggact ggctgaacgg aaggagtac | 960 |
| aagtgcaagg tgtccaacaa ggccctgcct gcccctatcg agaagaccat ctctaaggct | 1020 |
| aaggggcagc cccgggagcc acaggtgtac accctgccac ccagccgcga cgagctgacc | 1080 |
| aagaaccagg tgtccctgac atgcctggtg aagggattct accccagcga catcgccgtg | 1140 |
| gagtgggaga gcaacggcca gcccgagaac aactacaaga caacccctcc cgtgctggac | 1200 |
| agcgatggat ccttcttcct gtactccaag ctgaccgtgg acaagagcag gtggcagcag | 1260 |
| ggaaacgtgt tctcttgttc cgtgatgcac gaggctctgc acaaccacta cacccagaag | 1320 |
| tccctgagcc tgtctccagg caag | 1344 |

<210> SEQ ID NO 99
<211> LENGTH: 1353
<212> TYPE: DNA
<213> ORGANISM: artificial
<220> FEATURE:
<223> OTHER INFORMATION: VH-CH-102E9

<400> SEQUENCE: 99

| | |
|---|---:|
| cagatccatt tggtgcagtc tggacctgac ctgaagaagc ctggagagac agtcaagatc | 60 |
| tcctgcaagg cttctggtta taccttcaca gactattcaa tgcactgggt gaagcaggct | 120 |
| ccaggaaagg gtttaaagtg gatgggctgg ataaacactg agactggtga accaacatat | 180 |
| gcagatgact tcaagggacg gtttgccttc tctttggaaa gttctgccag cactgccttt | 240 |
| ttgcagatca acaacctcaa aaatgaggac acgtctacat atttctgtac tagaaatggt | 300 |
| tactacgtgg ttactatgc tatggactac tggggtcaag gaacctcagt caccgtctcc | 360 |
| tcagcctcca ccaagggccc atccgtgttc cccctggccc catccagcaa gtctacctcc | 420 |
| ggaggcacag ccgccctggg ctgtctggtg aaggactact ccccgagcc agtgaccgtg | 480 |
| tcctggaact ccggagccct gacatccggc gtgcacacct tccccgccgt gctgcagtcc | 540 |
| agcggcctgt actctctgtc ttccgtggtg accgtgccat ccagctccct gggaacccag | 600 |
| acatacatct gcaacgtgaa ccacaagcct agcaacacca aggtggacaa gaaggtggag | 660 |
| cctaagagct gtgacaagac acacacatgc cctccttgtc cagcccctga gctgctgggc | 720 |
| ggcccctccg tgttcctgtt cccccccaag cctaaggata ccctgatgat cagcagaacc | 780 |
| cccgaggtga cctgcgtggt ggtggacgtg tcccacgagg atcccgaggt gaagttcaac | 840 |
| tggtacgtgg acggcgtgga ggtgcacaac gctaagacca gcccagaga ggagcagtac | 900 |
| aacagcacat acagagtggt gtctgtgctg accgtgctgc accaggactg gctgaacggg | 960 |
| aaggagtaca agtgcaaggt gtccaacaag gccctgcctg cccctatcga gaagaccatc | 1020 |
| tctaaggcta aggggcagcc ccgggagcca caggtgtaca ccctgccacc cagccgcgac | 1080 |
| gagctgacca agaaccaggt gtccctgaca tgcctggtga agggattcta ccccagcgac | 1140 |

| | |
|---|---|
| atcgccgtgg agtgggagag caacggccag cccgagaaca actacaagac aaccccctccc | 1200 |
| gtgctggaca gcgatggatc cttcttcctg tactccaagc tgaccgtgga caagagcagg | 1260 |
| tggcagcagg gaaacgtgtt ctcttgttcc gtgatgcacg aggctctgca caaccactac | 1320 |
| acccagaagt ccctgagcct gtctccaggc aag | 1353 |

<210> SEQ ID NO 100
<211> LENGTH: 1343
<212> TYPE: DNA
<213> ORGANISM: artificial
<220> FEATURE:
<223> OTHER INFORMATION: VH-CH-104C12

<400> SEQUENCE: 100

| | |
|---|---|
| caggtccagc tgcagcagtc tggggctgag ctggtggggc ctggggtctc agtgaagatt | 60 |
| tcctgcaagg gttctggcta cacattcact gattattcta tgcactgggt aaagcagagt | 120 |
| catgcaaaga gtctagagtg gattggagtt attagtcctt actatggtga tactaactac | 180 |
| aaccagaagt tcaagggcaa ggccacaatg actgtagaca atcctccag cacagcctat | 240 |
| atggaacttg ccagtctgac atctgaggat tctgccatct atttctgtgc aagaaatgat | 300 |
| gattactaca ggtttgctta ctggggccaa gggactctgg tcactgtctc tgcgcctcca | 360 |
| ccaagggccc atccgtgttc cccctggccc catccagcaa gtctacctcc ggaggcacag | 420 |
| ccgccctggg ctgtctggtg aaggactact ccccgagcc agtgaccgtg tcctggaact | 480 |
| ccggagccct gacatccggc gtgcacacct tccccgccgt gctgcagtcc agcggcctgt | 540 |
| actctctgtc ttccgtggtg accgtgccat ccagctccct gggaacccag acatacatct | 600 |
| gcaacgtgaa ccacaagcct agcaacacca aggtggacaa gaaggtggag cctaagagct | 660 |
| gtgacaagac acacacatgc cctccttgtc cagcccctga gctgctgggc ggcccctccg | 720 |
| tgttcctgtt cccccccaag cctaaggata ccctgatgat cagcagaacc cccgaggtga | 780 |
| cctgcgtggt ggtggacgtg tcccacgagg atcccgaggt gaagttcaac tggtacgtgg | 840 |
| acggcgtgga ggtgcacaac gctaagacca gcccagaga ggagcagtac aacagcacat | 900 |
| acagagtggt gtctgtgctg accgtgctgc accaggactg gctgaacggg aaggagtaca | 960 |
| agtgcaaggt gtccaacaag gccctgcctg cccctatcga aagaccatc tctaaggcta | 1020 |
| aggggcagcc ccgggagcca caggtgtaca ccctgccacc cagccgcgac gagctgacca | 1080 |
| agaaccaggt gtccctgaca tgcctggtga agggattcta ccccagcgac atcgccgtgg | 1140 |
| agtgggagag caacggccag cccgagaaca actacaagac aaccccctccc gtgctggaca | 1200 |
| gcgatggatc cttcttcctg tactccaagc tgaccgtgga caagagcagg tggcagcagg | 1260 |
| gaaacgtgtt ctcttgttcc gtgatgcacg aggctctgca caaccactac acccagaagt | 1320 |
| ccctgagcct gtctccaggc aag | 1343 |

<210> SEQ ID NO 101
<211> LENGTH: 1353
<212> TYPE: DNA
<213> ORGANISM: artificial
<220> FEATURE:
<223> OTHER INFORMATION: VH-CH-114D11

<400> SEQUENCE: 101

| | |
|---|---|
| cagatccagt tggtgcagtc tggacctgag ctgaagaagc ctggagagac agtcaagatc | 60 |
| tcctgcaagg cttctggtta taccttcaca gactcttcaa tgcactgggt gcagcaggct | 120 |
| ccaaacaagg gtttaaagtg gatgggctgg ataaacactg agactggtgg gccaacgtat | 180 |

```
gcagatgatt tcaagggacg gtttgccttc tctttggaaa cctctgccag aactgcctat    240
ttgcagatca acaacctcaa aaatgaggac acggctacat atttctgtgc tagaaatgga    300
tactacgtgg ggtactatgc tctggactac tggggtcaag gaacctcagt caccgtctcc    360
tcagcctcca ccaagggccc atccgtgttc ccctggccc catccagcaa gtctacctcc     420
ggaggcacag ccgccctggg ctgtctggtg aaggactact ccccgagcc agtgaccgtg     480 tcctggaact ccggagccct gacatccggc gtgcacacct ccccgccgt gctgcagtcc     540 agcggcctgt actctctgtc ttccgtggtg accgtgccat ccagctccct gggaacccag    600
acatacatct gcaacgtgaa ccacaagcct agcaacacca aggtggacaa gaaggtggag    660
cctaagagct gtgacaagac acacacatgc cctccttgtc agcccctga gctgctgggc     720 ggcccctccg tgttcctgtt ccccccaag cctaaggata ccctgatgat cagcagaacc     780
cccgaggtga cctgcgtggt ggtggacgtg tcccacgagg atcccgaggt gaagttcaac    840
tggtacgtgg acggcgtgga ggtgcacaac gctaagacca gcccagaga ggagcagtac     900 aacagcacat acagagtggt gtctgtgctg accgtgctgc accaggactg gctgaacggg    960
aaggagtaca gtgcaaggt gtccaacaag gccctgcctg ccctatcga gaagaccatc     1020 tctaaggcta aggggcagcc ccgggagcca caggtgtaca ccctgccacc cagccgcgac   1080
gagctgacca gaaccaggt gtccctgaca tgcctggtga agggattcta ccccagcgac   1140
atcgccgtgg agtgggagag caacggccag cccgagaaca actacaagac aaccctccc    1200 gtgctggaca gcgatggatc cttcttcctg tactccaagc tgaccgtgga caagagcagg    1260
tggcagcagg gaaacgtgtt ctcttgttcc gtgatgcacg aggctctgca caaccactac    1320
acccagaagt ccctgagcct gtctccaggc aag                                 1353

<210> SEQ ID NO 102
<211> LENGTH: 1353
<212> TYPE: DNA
<213> ORGANISM: artificial
<220> FEATURE:
<223> OTHER INFORMATION: VH-CH-104E10

<400> SEQUENCE: 102
cagatccagt tggtgcagtc tggacctgag ctgaagaagc ctggagagac agtcaagatc     60
tcctgcaagg cttctggtta taccttcaca gactattcaa tgcactgggt gaagcaggct    120
ccaggaaagg gtttaaagtg gatgggctgg ataaacactg agactggtga gccaacatat    180
gcagatgact tcaagggacg gtttgccttc tctttggaaa cctctgccac cactgcctat    240
ttgcagatca acaacttcaa aaatgaggac acggctacat atttctgtgc tagaaatggt    300
tactacgtgg atattatgc tatggactac tggggtcaag gaacctcagt caccgtctcc     360
tcagcctcca ccaagggccc atccgtgttc ccctggccc catccagcaa gtctacctcc     420
ggaggcacag ccgccctggg ctgtctggtg aaggactact ccccgagcc agtgaccgtg     480 tcctggaact ccggagccct gacatccggc gtgcacacct ccccgccgt gctgcagtcc     540 agcggcctgt actctctgtc ttccgtggtg accgtgccat ccagctccct gggaacccag    600
acatacatct gcaacgtgaa ccacaagcct agcaacacca aggtggacaa gaaggtggag    660
cctaagagct gtgacaagac acacacatgc cctccttgtc agcccctga gctgctgggc     720 ggcccctccg tgttcctgtt ccccccaag cctaaggata ccctgatgat cagcagaacc     780
cccgaggtga cctgcgtggt ggtggacgtg tcccacgagg atcccgaggt gaagttcaac    840
```

| | |
|---|---|
| tggtacgtgg acggcgtgga ggtgcacaac gctaagacca agcccagaga ggagcagtac | 900 |
| aacagcacat acagagtggt gtctgtgctg accgtgctgc accaggactg gctgaacggg | 960 |
| aaggagtaca agtgcaaggt gtccaacaag gccctgcctg cccctatcga aagaccatc | 1020 |
| tctaaggcta aggggcagcc ccgggagcca caggtgtaca ccctgccacc cagccgcgac | 1080 |
| gagctgacca agaaccaggt gtccctgaca tgcctggtga agggattcta ccccagcgac | 1140 |
| atcgccgtgg agtgggagag caacggccag cccgagaaca actacaagac aacccctccc | 1200 |
| gtgctggaca gcgatggatc cttcttcctg tactccaagc tgaccgtgga caagagcagg | 1260 |
| tggcagcagg gaaacgtgtt ctcttgttcc gtgatgcacg aggctctgca caaccactac | 1320 |
| acccagaagt ccctgagcct gtctccaggc aag | 1353 |

<210> SEQ ID NO 103
<211> LENGTH: 642
<212> TYPE: DNA
<213> ORGANISM: artificial
<220> FEATURE:
<223> OTHER INFORMATION: VL-CL-122A2

<400> SEQUENCE: 103

| | |
|---|---|
| gatatccaga tgacacagac tacatcctcc ctgtctgcct ctctgggaga cagagtcacc | 60 |
| atcagttgca gggcaagtca ggacattagc aattatttaa actggtatca gcagaaacca | 120 |
| gatggaactg ttaaactcct gatctactac acatcaagat acactcagg agtcccatca | 180 |
| aggttcagtg gcagtgggtc tggaacagat tattctctca ccattagcaa cctggaccaa | 240 |
| gaagatattg ccacttactt ttgccaacag ggtaatacgc ttccttggac gttcggtgga | 300 |
| ggcaccaagc tggaaatcaa acgaactgtg gctgcaccaa gtgtcttcat ctttcctccg | 360 |
| agtgatgagc agctgaagag cggacagct tctgtggtgt gtctgctgaa taacttctac | 420 |
| ccaagagaag caaaggtcca gtggaaggtg acaacgccc tgcagtctgg caactcacag | 480 |
| gagtctgtca ctgagcagga ttccaaggac agcacttaca gcctgtccag cacccctcact | 540 |
| ctgtccaaag ccgactacga aaagcataag gtgtatgctt gtgaggtgac ccaccaggga | 600 |
| ctgagcagcc ctgtgacgaa gtccttcaac cggggcgagt gc | 642 |

<210> SEQ ID NO 104
<211> LENGTH: 639
<212> TYPE: DNA
<213> ORGANISM: artificial
<220> FEATURE:
<223> OTHER INFORMATION: VL-CL-102E9

<400> SEQUENCE: 104

| | |
|---|---|
| caaattgttc tcacccagtc tccagcaatc atgtctgcat ctccagggga gaaggtcacc | 60 |
| ataacctgca gtgccagctc aagtgtaatt tacattcact ggttccagca gaagccaggc | 120 |
| acttctccca aactctggat ttatagcaca tcctacctgg cttctggagt ccctgctcgc | 180 |
| ttcagtggca gtggatctgg gacctcttac tctctcacaa tcagccgaat ggaggctgaa | 240 |
| gatgctgcca cttattactg ccagcagagg agaagttacc cgttcacgtt cggagggggg | 300 |
| accaagctgg aaataaaacg aactgtggct gcaccaagtg tcttcatctt tcctccgagt | 360 |
| gatgagcagc tgaagagcgg acagcttct gtggtgtgtc tgctgaataa cttctaccca | 420 |
| agagaagcaa aggtccagtg gaaggtggac aacgccctgc agtctggcaa ctcacaggag | 480 |
| tctgtcactg agcaggattc caaggacagc acttacagcc tgtccagcac cctcactctg | 540 |
| tccaaagccg actacgaaaa gcataaggtg tatgcttgtg aggtgaccca ccaggactg | 600 |

```
agcagccctg tgacgaagtc cttcaaccgg ggcgagtgc                             639
```

<210> SEQ ID NO 105
<211> LENGTH: 641
<212> TYPE: DNA
<213> ORGANISM: artificial
<220> FEATURE:
<223> OTHER INFORMATION: VL-CL-104C12

<400> SEQUENCE: 105

```
gatctccaga tgacacagac tccatcctcc ctgtctgcct ctctgggaga cagagtcacc        60
atcagttgca gggcaagtca ggacattaac aattatttaa gctggtatca ggagaaacca       120
gatggaactt ttaaactcct gatctactac acatcaagat tacactcagg agtcccatca       180
aggttcagtg gcagtgggtc tggaacagat tattctctca ccgttcgcaa cctgaacag        240
gaagatattg gcacttactt ttgccaacag ggtaaaacgc ttccgtggac gttcggtgga       300
ggcaccaagc tggaaatcag cgaactgtgg ctgcaccaag tgtcttcatc tttcctccga       360
gtgatgagca gctgaagagc gggacagctt ctgtggtgtg tctgctgaat aacttctacc       420
caagagaagc aaaggtccag tggaaggtgg acaacgccct gcagtctggc aactcacagg       480
agtctgtcac tgagcaggat ccaaggaca gcacttacag cctgtccagc accctcactc        540
tgtccaaagc cgactacgaa aagcataagg tgtatgcttg tgaggtgacc caccagggac       600
tgagcagccc tgtgacgaag tccttcaacc ggggcgagtg c                          641
```

<210> SEQ ID NO 106
<211> LENGTH: 639
<212> TYPE: DNA
<213> ORGANISM: artificial
<220> FEATURE:
<223> OTHER INFORMATION: VL-CL-114D11

<400> SEQUENCE: 106

```
caaattgttc tcacccagtc tccagcaatc atgtctgcat ctccagggga aaggtcacc        60
ataacctgca gtgccagctc aagtgtattt tacatgcact ggttccagca gaagccaggc       120
acttctccca aactctggat ttatagcaca tccaacctgg cttctggagt ccctgctcgc       180
ttcagtggca gtggatctgg gacctcttac tctctcacaa tcagccgaat ggaggctgaa       240
gatgctgcca cttattactg ccagcaaagg agaagttacc cgtacacgtt cggaggggg        300
accaagctgg aaataaaacg aactgtggct gcaccaagtg tcttcatctt cctccgagt        360
gatgagcagc tgaagagcgg acagcttct gtggtgtgtc tgctgaataa cttctaccca        420
agagaagcaa aggtccagtg gaaggtggac aacgccctgc agtctggcaa ctcacaggag       480
tctgtcactg agcaggattc caaggacagc acttacagcc tgtccagcac cctcactctg       540
tccaaagccg actacgaaaa gcataaggtg tatgcttgtg aggtgaccca ccagggactg       600
agcagccctg tgacgaagtc cttcaaccgg ggcgagtgc                              639
```

<210> SEQ ID NO 107
<211> LENGTH: 639
<212> TYPE: DNA
<213> ORGANISM: artificial
<220> FEATURE:
<223> OTHER INFORMATION: VL-CL-104E10

<400> SEQUENCE: 107

```
caaattgttc tcacccagtc tccagcaatc atgtctgcat ctccagggga aaggtcacc        60
```

| | |
|---|---|
| atgacctgca gtgccagttc aagtgtaatt tacatgcact ggttccagca gaagccaggc | 120 |
| acttctccca aactctggat ttatagcaca tccaacctgg cttctggagt ccctgctcgc | 180 |
| ttcagtggca gtggatctgg gacatcttac tctctcacaa tcagccgaat ggaggctgaa | 240 |
| gatgctgcca cttattactg ccagcaaagg agaagttacc cgtacacgtt cggaggggg | 300 |
| accaagctgg aaataaaacg aactgtggct gcaccaagtg tcttcatctt cctccgagt | 360 |
| gatgagcagc tgaagagcgg acagcttct gtggtgtgtc tgctgaataa cttctaccca | 420 |
| agagaagcaa aggtccagtg gaaggtggac aacgccctgc agtctggcaa ctcacaggag | 480 |
| tctgtcactg agcaggattc caaggacagc acttacagcc tgtccagcac cctcactctg | 540 |
| tccaaagccg actacgaaaa gcataaggtg tatgcttgtg aggtgaccca ccagggactg | 600 |
| agcagccctg tgacgaagtc cttcaaccgg ggcgagtgc | 639 |

<210> SEQ ID NO 108
<211> LENGTH: 54
<212> TYPE: DNA
<213> ORGANISM: artificial
<220> FEATURE:
<223> OTHER INFORMATION: MB7 signal peptide

<400> SEQUENCE: 108

| | |
|---|---|
| atgaggtggt cctggatctt cctgctgctg ctgagcatca ccagcgccaa cgcc | 54 |

<210> SEQ ID NO 109
<211> LENGTH: 408
<212> TYPE: DNA
<213> ORGANISM: artificial
<220> FEATURE:
<223> OTHER INFORMATION: MB7-VH-122A2

<400> SEQUENCE: 109

| | |
|---|---|
| atgaggtggt cctggatctt cctgctgctg ctgagcatca ccagcgccaa cgcccaggtc | 60 |
| cagctgcagc agtctggggc tgagctggtg aggcctgggg tctcagtgaa gatttcctgc | 120 |
| aagggttctg gctacacatt cactgattat tctatgcact gggtgaagca gagtcatgca | 180 |
| aagagtctag agtggattgg agttattagt acttactatg gtgattctaa ctataaccag | 240 |
| aagttcaagg gcaaggccac aatgactgta gacaaatcct ccaccacagc ctatatggaa | 300 |
| cttgccagac tgacatctga ggattctgcc atctattact gtgcaagaaa tggtaatttc | 360 |
| tatgttatgg actactgggg tcaaggaacc tcagtcaccg tctcctca | 408 |

<210> SEQ ID NO 110
<211> LENGTH: 417
<212> TYPE: DNA
<213> ORGANISM: artificial
<220> FEATURE:
<223> OTHER INFORMATION: MB7-VH-102E9

<400> SEQUENCE: 110

| | |
|---|---|
| atgaggtggt cctggatctt cctgctgctg ctgagcatca ccagcgccaa cgcccagatc | 60 |
| catttggtgc agtctggacc tgacctgaag aagcctggag agacagtcaa gatctcctgc | 120 |
| aaggcttctg gttataccct cacagactat tcaatgcact gggtgaagca ggctccagga | 180 |
| aagggtttaa agtggatggg ctggataaac actgagactg gtgaaccaac atatgcagat | 240 |
| gacttcaagg gacggtttgc cttctctttg gaaagtctg ccagcactgc cttttttgcag | 300 |
| atcaacaacc tcaaaaatga ggacacgtct acatatttct gtactagaaa tggttactac | 360 |
| gtgggttact atgctatgga ctactggggt caaggaacct cagtcaccgt ctcctca | 417 |

<210> SEQ ID NO 111
<211> LENGTH: 407
<212> TYPE: DNA
<213> ORGANISM: artificial
<220> FEATURE:
<223> OTHER INFORMATION: MB7-VH-104C12

<400> SEQUENCE: 111

| | | | | | |
|---|---|---|---|---|---|
| atgaggtggt | cctggatctt | cctgctgctg | ctgagcatca | ccagcgccaa | cgcccaggtc | 60 |
| cagctgcagc | agtctggggc | tgagctggtg | gggcctgggg | tctcagtgaa | gatttcctgc | 120 |
| aagggttctg | gctacacatt | cactgattat | tctatgcact | gggtaaagca | gagtcatgca | 180 |
| aagagtctag | agtggattgg | agttattagt | ccttactatg | gtgatactaa | ctacaaccag | 240 |
| aagttcaagg | gcaaggccac | aatgactgta | gacaaatcct | ccagcacagc | ctatatggaa | 300 |
| cttgccagtc | tgacatctga | ggattctgcc | atctatttct | gtgcaagaaa | tgatgattac | 360 |
| tacaggtttg | cttactgggg | ccaagggact | ctggtcactg | tctctgc | | 407 |

<210> SEQ ID NO 112
<211> LENGTH: 417
<212> TYPE: DNA
<213> ORGANISM: artificial
<220> FEATURE:
<223> OTHER INFORMATION: MB7-VH-114D11

<400> SEQUENCE: 112

| | | | | | |
|---|---|---|---|---|---|
| atgaggtggt | cctggatctt | cctgctgctg | ctgagcatca | ccagcgccaa | cgcccagatc | 60 |
| cagttggtgc | agtctggacc | tgagctgaag | aagcctggag | agacagtcaa | gatctcctgc | 120 |
| aaggcttctg | gttatacctt | cacagactct | tcaatgcact | gggtgcagca | ggctccaaac | 180 |
| aagggtttaa | agtggatggg | ctggataaac | actgagactg | gtgggccaac | gtatgcagat | 240 |
| gatttcaagg | gacggtttgc | cttctctttg | gaaacctctg | ccagaactgc | ctatttgcag | 300 |
| atcaacaacc | tcaaaaatga | ggacacggct | acatatttct | gtgctagaaa | tggatactac | 360 |
| gtggggtact | atgctctgga | ctactgggt | caaggaacct | cagtcaccgt | ctcctca | 417 |

<210> SEQ ID NO 113
<211> LENGTH: 417
<212> TYPE: DNA
<213> ORGANISM: artificial
<220> FEATURE:
<223> OTHER INFORMATION: MB7-VH-104E10

<400> SEQUENCE: 113

| | | | | | |
|---|---|---|---|---|---|
| atgaggtggt | cctggatctt | cctgctgctg | ctgagcatca | ccagcgccaa | cgcccagatc | 60 |
| cagttggtgc | agtctggacc | tgagctgaag | aagcctggag | agacagtcaa | gatctcctgc | 120 |
| aaggcttctg | gttatacctt | cacagactat | tcaatgcact | gggtgaagca | ggctccagga | 180 |
| aagggtttaa | agtggatggg | ctggataaac | actgagactg | gtgagccaac | atatgcagat | 240 |
| gacttcaagg | gacggtttgc | cttctctttg | gaaacctctg | ccaccactgc | ctatttgcag | 300 |
| atcaacaact | tcaaaaatga | ggacacggct | acatatttct | gtgctagaaa | tggttactac | 360 |
| gtgggatatt | atgctatgga | ctactgggt | caaggaacct | cagtcaccgt | ctcctca | 417 |

<210> SEQ ID NO 114
<211> LENGTH: 375
<212> TYPE: DNA
<213> ORGANISM: artificial
<220> FEATURE:

<223> OTHER INFORMATION: MB7-VL-122A2

<400> SEQUENCE: 114

| | |
|---|---|
| atgaggtggt cctggatctt cctgctgctg ctgagcatca ccagcgccaa cgccgatatc | 60 |
| cagatgacac agactacatc ctccctgtct gcctctctgg agacagagt caccatcagt | 120 |
| tgcagggcaa gtcaggacat tagcaattat ttaaactggt atcagcagaa accagatgga | 180 |
| actgttaaac tcctgatcta ctacacatca agattacact caggagtccc atcaaggttc | 240 |
| agtggcagtg ggtctggaac agattattct ctcaccatta gcaacctgga ccaagaagat | 300 |
| attgccactt acttttgcca acagggtaat acgcttcctt ggacgttcgg tggaggcacc | 360 |
| aagctggaaa tcaaa | 375 |

<210> SEQ ID NO 115
<211> LENGTH: 372
<212> TYPE: DNA
<213> ORGANISM: artificial
<220> FEATURE:
<223> OTHER INFORMATION: MB7-VL-102E9

<400> SEQUENCE: 115

| | |
|---|---|
| atgaggtggt cctggatctt cctgctgctg ctgagcatca ccagcgccaa cgcccaaatt | 60 |
| gttctcaccc agtctccagc aatcatgtct gcatctccag gggagaaggt caccataacc | 120 |
| tgcagtgcca gctcaagtgt aatttacatt cactggttcc agcagaagcc aggcacttct | 180 |
| cccaaactct ggatttatag cacatcctac ctggcttctg gagtccctgc tcgcttcagt | 240 |
| ggcagtggat ctgggacctc ttactctctc acaatcagcc gaatggaggc tgaagatgct | 300 |
| gccacttatt actgccagca gaggagaagt acccgttca cgttcggagg ggggaccaag | 360 |
| ctggaaataa aa | 372 |

<210> SEQ ID NO 116
<211> LENGTH: 374
<212> TYPE: DNA
<213> ORGANISM: artificial
<220> FEATURE:
<223> OTHER INFORMATION: MB7-VL-104C12

<400> SEQUENCE: 116

| | |
|---|---|
| atgaggtggt cctggatctt cctgctgctg ctgagcatca ccagcgccaa cgccgatctc | 60 |
| cagatgacac agactccatc ctccctgtct gcctctctgg agacagagt caccatcagt | 120 |
| tgcagggcaa gtcaggacat taacaattat ttaagctggt atcaggagaa accagatgga | 180 |
| acttttaaac tcctgatcta ctacacatca agattacact caggagtccc atcaaggttc | 240 |
| agtggcagtg ggtctggaac agattattct ctcaccgttc gcaacctgga acaggaagat | 300 |
| attggcactt acttttgcca acagggtaaa acgcttccgt ggacgttcgg tggaggcacc | 360 |
| aagctggaaa tcag | 374 |

<210> SEQ ID NO 117
<211> LENGTH: 372
<212> TYPE: DNA
<213> ORGANISM: artificial
<220> FEATURE:
<223> OTHER INFORMATION: MB7-VL-114D11

<400> SEQUENCE: 117

| | |
|---|---|
| atgaggtggt cctggatctt cctgctgctg ctgagcatca ccagcgccaa cgcccaaatt | 60 |
| gttctcaccc agtctccagc aatcatgtct gcatctccag gggagaaggt caccataacc | 120 |

```
tgcagtgcca gctcaagtgt attttacatg cactggttcc agcagaagcc aggcacttct      180
cccaaactct ggatttatag cacatccaac ctggcttctg gagtccctgc tcgcttcagt      240
ggcagtggat ctgggacctc ttactctctc acaatcagcc gaatggaggc tgaagatgct      300
gccacttatt actgccagca aaggagaagt acccgtaca cgttcggagg ggggaccaag       360
ctggaaataa aa                                                          372
```

<210> SEQ ID NO 118
<211> LENGTH: 372
<212> TYPE: DNA
<213> ORGANISM: artificial
<220> FEATURE:
<223> OTHER INFORMATION: MB7-VL-104E10

<400> SEQUENCE: 118

```
atgaggtggt cctggatctt cctgctgctg ctgagcatca ccagcgccaa cgcccaaatt      60
gttctcaccc agtctccagc aatcatgtct gcatctccag gggagaaggt caccatgacc      120
tgcagtgcca gttcaagtgt aatttacatg cactggttcc agcagaagcc aggcacttct     180
cccaaactct ggatttatag cacatccaac ctggcttctg gagtccctgc tcgcttcagt      240
ggcagtggat ctgggacatc ttactctctc acaatcagcc gaatggaggc tgaagatgct      300
gccacttatt actgccagca aaggagaagt acccgtaca cgttcggagg ggggaccaag       360
ctggaaataa aa                                                          372
```

<210> SEQ ID NO 119
<211> LENGTH: 1398
<212> TYPE: DNA
<213> ORGANISM: artificial
<220> FEATURE:
<223> OTHER INFORMATION: MB7-VH-CH-122A2

<400> SEQUENCE: 119

```
atgaggtggt cctggatctt cctgctgctg ctgagcatca ccagcgccaa cgcccaggtc      60
cagctgcagc agtctggggc tgagctggtg aggcctgggg tctcagtgaa gatttcctgc      120
aagggttctg gctacacatt cactgattat tctatgcact gggtgaagca gagtcatgca      180
aagagtctag agtggattgg agttattagt acttactatg gtgattctaa ctataaccag      240
aagttcaagg gcaaggccac aatgactgta gacaaatcct ccaccacagc ctatatggaa      300
cttgccagac tgacatctga ggattctgcc atctattact gtgcaagaaa tggtaatttc      360
tatgttatgg actactgggg tcaaggaacc tcagtcaccg tctcctcagc ctccaccaag      420
ggcccatccg tgttccccct ggccccatcc agcaagtcta cctccggagg cacagccgcc      480
ctgggctgtc tggtgaagga ctacttcccc gagccagtga ccgtgtcctg aactccgga      540 gccctgacat ccggcgtgca caccttcccc gccgtgctgc agtccagcgg cctgtactct      600
ctgtcttccg tggtgaccgt gccatccagc tccctgggaa cccagacata catctgcaac      660
gtgaaccaca agcctagcaa caccaaggtg gacaagaagg tggagcctaa agctgtgac      720 aagacacaca catgcccctcc ttgtccagcc cctgagctgc tgggcggcc ctccgtgttc      780 ctgttccccc ccaagcctaa ggatacccctg atgatcagca gaaccccga ggtgacctgc      840 gtggtggtgg acgtgtccca cgaggatccc gaggtgaagt tcaactggta cgtggacggc      900
gtggaggtgc acaacgctaa gaccaagccc agagaggagc agtacaacag cacatacaga      960
gtggtgtctg tgctgaccgt gctgcaccag gactggctga acgggaagga gtacaagtgc      1020
```

```
aaggtgtcca acaaggcect gcctgcccct atcgagaaga ccatctctaa ggctaagggg    1080
cagccccggg agccacaggt gtacaccctg ccacccagcc gcgacgagct gaccaagaac    1140
caggtgtccc tgacatgcct ggtgaaggga ttctacccca gcgacatcgc cgtggagtgg    1200
gagagcaacg gccagcccga gaacaactac aagacaaccc ctcccgtgct ggacagcgat    1260
ggatccttct tcctgtactc caagctgacc gtggacaaga gcaggtggca gcagggaaac    1320
gtgttctctt gttccgtgat gcacgaggct ctgcacaacc actacaccca gaagtccctg    1380
agcctgtctc caggcaag                                                  1398

<210> SEQ ID NO 120
<211> LENGTH: 1407
<212> TYPE: DNA
<213> ORGANISM: artificial
<220> FEATURE:
<223> OTHER INFORMATION: MB7-VH-CH-102E9

<400> SEQUENCE: 120
atgaggtggt cctggatctt cctgctgctg ctgagcatca ccagcgccaa cgcccagatc      60
catttggtgc agtctggacc tgacctgaag aagcctggag agacagtcaa gatctcctgc    120
aaggcttctg gttatacctt cacagactat tcaatgcact gggtgaagca ggctccagga    180
aagggtttaa agtggatggg ctggataaac actgagactg gtgaaccaac atatgcagat    240
gacttcaagg gacggtttgc cttctctttg gaaagttctg ccagcactgc cttttttgcag   300 atcaacaacc tcaaaaatga ggacacgtct acatatttct gtactagaaa tggttactac    360
gtgggttact atgctatgga ctactggggt caaggaacct cagtcaccgt ctcctcagcc    420
tccaccaagg gcccatccgt gttccccctg gccccatcca gcaagtctac ctccggaggc    480
acagccgccc tgggctgtct ggtgaaggac tacttccccg agccagtgac cgtgtcctgg    540
aactccggag ccctgacatc cggcgtgcac accttccccg ccgtgctgca gtccagcggc    600
ctgtactctc tgtcttccgt ggtgaccgtg ccatccagct ccctgggaac ccagacatac    660
atctgcaacg tgaaccacaa gcctagcaac accaaggtgg acaagaaggt ggagcctaag    720
agctgtgaca gacacacac atgccctcct tgtccagccc ctgagctgct gggcggcccc    780
tccgtgttcc tgttcccccc caagcctaag gatccctga tgatcagcag aacccccgag    840
gtgacctgcg tggtggtgga cgtgtcccac gaggatcccg aggtgaagtt caactggtac    900
gtggacggcg tggaggtgca caacgctaag accaagccca gagaggagca gtacaacagc    960
acatacagag tggtgtctgt gctgaccgtg ctgcaccagg actggctgaa cgggaaggag   1020
tacaagtgca aggtgtccaa caaggccctg cctgccccta tcgagaagac catctctaag   1080 gctaagggc agccccggga ccacaggtg tacaccctgc cacccagccg cgacgagctg    1140
accaagaacc aggtgtccct gacatgcctg gtgaagggat tctacccag cgacatcgcc    1200 gtggagtggg agagcaacgg ccagcccgag aacaactaca agacaacccc tcccgtgctg    1260
gacagcgatg gatccttctt cctgtactcc aagctgaccg tggacaagag caggtggcag    1320
cagggaaacg tgttctcttg ttccgtgatg cacgaggctc tgcacaacca ctacacccag    1380
aagtccctga gcctgtctcc aggcaag                                       1407

<210> SEQ ID NO 121
<211> LENGTH: 1397
<212> TYPE: DNA
<213> ORGANISM: artificial
<220> FEATURE:
<223> OTHER INFORMATION: MB7-VH-CH-104C12
```

<400> SEQUENCE: 121

```
atgaggtggt cctggatctt cctgctgctg ctgagcatca ccagcgccaa cgcccaggtc    60
cagctgcagc agtctggggc tgagctggtg gggcctgggg tctcagtgaa gatttcctgc   120
aagggttctg gctacacatt cactgattat tctatgcact gggtaaagca gagtcatgca   180
aagagtctag agtggattgg agttattagt ccttactatg gtgatactaa ctacaaccag   240
aagttcaagg gcaaggccac aatgactgta gacaaatcct ccagcacagc ctatatggaa   300
cttgccagtc tgacatctga ggattctgcc atctatttct gtgcaagaaa tgatgattac   360
tacaggtttg cttactgggg ccaagggact ctggtcactg tctctgcgcc tccaccaagg   420
gcccatccgt gttccccctg gccccatcca gcaagtctac ctccggaggc acagccgccc   480
tgggctgtct ggtgaaggac tacttccccg agccagtgac cgtgtcctgg aactccggag   540
ccctgacatc cggcgtgcac accttccccg ccgtgctgca gtccagcggc ctgtactctc   600
tgtcttccgt ggtgaccgtg ccatccagct ccctgggaac ccagacatac atctgcaacg   660
tgaaccacaa gcctagcaac accaaggtgg acaagaaggt ggagcctaag agctgtgaca   720
agacacacac atgccctcct gtccagccct gagctgct gggcggcccc tccgtgttcc   780
tgttccccc caagcctaag gatacctga tgatcagcag aaccccgag gtgacctgcg   840
tggtggtgga cgtgtcccac gaggatcccg aggtgaagtt caactggtac gtggacggcg   900
tggaggtgca caacgctaag accaagccca gagaggagca gtacaacagc catacagag   960
tggtgtctgt gctgaccgtg ctgcaccagg actggctgaa cgggaaggag tacaagtgca  1020
aggtgtccaa caaggccctg cctgccccta tcgagaagac catctctaag gctaaggggc  1080
agccccggga gccacaggtg tacaccctgc acccagccg cgacgagctg accaagaacc  1140
aggtgtccct gacatgcctg gtgaagggat tctaccccag cgacatcgcc gtggagtggg  1200
agagcaacgg ccagcccgag aacaactaca gacaaccccc tcccgtgctg gacagcgatg  1260
gatccttctt cctgtactcc aagctgaccg tggacaagag caggtggcag cagggaaacg  1320
tgttctcttg ttccgtgatg cacgaggctc tgcacaacca ctacacccag aagtccctga  1380
gcctgtctcc aggcaag                                                 1397
```

<210> SEQ ID NO 122
<211> LENGTH: 1407
<212> TYPE: DNA
<213> ORGANISM: artificial
<220> FEATURE:
<223> OTHER INFORMATION: MB7-VH-CH-114D11

<400> SEQUENCE: 122

```
atgaggtggt cctggatctt cctgctgctg ctgagcatca ccagcgccaa cgcccagatc    60
cagttggtgc agtctggacc tgagctgaag aagcctggag agacagtcaa gatctcctgc   120
aaggcttctg gttataccct cacagactct tcaatgcact gggtgcagca ggctccaaac   180
aagggtttaa agtggatggg ctggataaac actgagactg tgggccaac gtatgcagat   240
gatttcaagg gacggtttgc cttctctttg gaaacctctg ccagaactgc ctatttgcag   300
atcaacaacc tcaaaaatga ggacacggct acatatttct gtctagaaa tggatactac   360
gtggggtact atgctctgga ctactgggt caaggaacct cagtcaccgt ctcctcagcc   420
tccaccaagg gcccatccgt gttccccctg gccccatcca gcaagtctac ctccggaggc   480
acagccgccc tgggctgtct ggtgaaggac tacttccccg agccagtgac cgtgtcctgg   540
```

```
aactccggag ccctgacatc cggcgtgcac accttccccg ccgtgctgca gtccagcggc    600
ctgtactctc tgtcttccgt ggtgaccgtg ccatccagct ccctgggaac ccagacatac    660
atctgcaacg tgaaccacaa gcctagcaac accaaggtgg acaagaaggt ggagcctaag    720
agctgtgaca agacacacac atgccctcct tgtccagccc ctgagctgct gggcggcccc    780
tccgtgttcc tgttcccccc caagcctaag gataccctga tgatcagcag aacccccgag    840
gtgacctgcg tggtggtgga cgtgtcccac gaggatcccg aggtgaagtt caactggtac    900
gtggacggcg tggaggtgca aacgctaag accaagccca gagaggagca gtacaacagc    960
acatacagag tggtgtctgt gctgaccgtg ctgcaccagg actggctgaa cgggaaggag   1020
tacaagtgca aggtgtccaa caaggccctg cctgccccta tcgagaagac catctctaag   1080
gctaaggggc agccccggga gccacaggtg tacaccctgc cacccagccg cgacgagctg   1140
accaagaacc aggtgtccct gacatgcctg gtgaagggat tctaccccag cgacatcgcc   1200
gtggagtggg agagcaacgg ccagcccgag aacaactaca agacaacccc tcccgtgctg   1260
gacagcgatg gatccttctt cctgtactcc aagctgaccg tggacaagag caggtggcag   1320
cagggaaacg tgttctcttg ttccgtgatg cacgaggctc tgcacaacca ctacacccag   1380
aagtccctga gcctgtctcc aggcaag                                       1407

<210> SEQ ID NO 123
<211> LENGTH: 1407
<212> TYPE: DNA
<213> ORGANISM: artificial
<220> FEATURE:
<223> OTHER INFORMATION: MB7-VH-CH-104E10

<400> SEQUENCE: 123
atgaggtggt cctggatctt cctgctgctg ctgagcatca ccagcgccaa cgcccagatc     60
cagttggtgc agtctggacc tgagctgaag aagcctggag agacagtcaa gatctcctgc    120
aaggcttctg gttatacctt cacagactat tcaatgcact gggtgaagca ggctccagga    180
aagggtttaa agtggatggg ctggataaac actgagactg gtgagccaac atatgcagat    240
gacttcaagg gacggtttgc cttctctttg gaaacctctg ccaccactgc ctatttgcag    300
atcaacaact tcaaaaatga ggacacggct acatatttct gtgctagaaa tggttactac    360
gtgggatatt atgctatgga ctactggggt caaggaacct cagtcaccgt ctcctcagcc    420
tccaccaagg gcccatccgt gttccccctg gccccatcca gcaagtctac ctccggaggc    480
acagccgccc tgggctgtct ggtgaaggac tacttccccg agccagtgac cgtgtcctgg    540
aactccggag ccctgacatc cggcgtgcac accttccccg ccgtgctgca gtccagcggc    600
ctgtactctc tgtcttccgt ggtgaccgtg ccatccagct ccctgggaac ccagacatac    660
atctgcaacg tgaaccacaa gcctagcaac accaaggtgg acaagaaggt ggagcctaag    720
agctgtgaca agacacacac atgccctcct tgtccagccc ctgagctgct gggcggcccc    780
tccgtgttcc tgttcccccc caagcctaag gataccctga tgatcagcag aacccccgag    840
gtgacctgcg tggtggtgga cgtgtcccac gaggatcccg aggtgaagtt caactggtac    900
gtggacggcg tggaggtgca aacgctaag accaagccca gagaggagca gtacaacagc    960
acatacagag tggtgtctgt gctgaccgtg ctgcaccagg actggctgaa cgggaaggag   1020
tacaagtgca aggtgtccaa caaggccctg cctgccccta tcgagaagac catctctaag   1080
gctaaggggc agccccggga gccacaggtg tacaccctgc cacccagccg cgacgagctg   1140
accaagaacc aggtgtccct gacatgcctg gtgaagggat tctaccccag cgacatcgcc   1200
```

| | |
|---|---:|
| gtggagtgggg agagcaacgg ccagcccgag aacaactaca agacaacccc tcccgtgctg | 1260 |
| gacagcgatg gatccttctt cctgtactcc aagctgaccg tggacaagag caggtggcag | 1320 |
| cagggaaacg tgttctcttg ttccgtgatg cacgaggctc tgcacaacca ctacacccag | 1380 |
| aagtccctga gcctgtctcc aggcaag | 1407 |

<210> SEQ ID NO 124
<211> LENGTH: 696
<212> TYPE: DNA
<213> ORGANISM: artificial
<220> FEATURE:
<223> OTHER INFORMATION: MB7-VL-CL-122A2

<400> SEQUENCE: 124

| | |
|---|---:|
| atgaggtggt cctggatctt cctgctgctg ctgagcatca ccagcgccaa cgccgatatc | 60 |
| cagatgacac agactacatc ctccctgtct gcctctctgg agacagagt caccatcagt | 120 |
| tgcagggcaa gtcaggacat tagcaattat ttaaactggt atcagcagaa accagatgga | 180 |
| actgttaaac tcctgatcta ctacacatca agattacact caggagtccc atcaaggttc | 240 |
| agtggcagtg gtctggaac agattattct ctcaccatta gcaacctgga ccaagaagat | 300 |
| attgccactt acttttgcca acagggtaat acgcttcctt ggacgttcgg tggaggcacc | 360 |
| aagctggaaa tcaaacgaac tgtggctgca ccaagtgtct tcatctttcc tccgagtgat | 420 |
| gagcagctga gagcgggac agcttctgtg gtgtgtctgc tgaataactt ctacccaaga | 480 |
| gaagcaaagg tccagtggaa ggtggacaac gccctgcagt ctggcaactc acaggagtct | 540 |
| gtcactgagc aggattccaa ggacagcact tacagcctgt ccagcaccct cactctgtcc | 600 |
| aaagccgact acgaaaagca taaggtgtat gcttgtgagg tgacccacca gggactgagc | 660 |
| agccctgtga cgaagtcctt caaccggggc gagtgc | 696 |

<210> SEQ ID NO 125
<211> LENGTH: 693
<212> TYPE: DNA
<213> ORGANISM: artificial
<220> FEATURE:
<223> OTHER INFORMATION: MB7-VL-CL-102E9

<400> SEQUENCE: 125

| | |
|---|---:|
| atgaggtggt cctggatctt cctgctgctg ctgagcatca ccagcgccaa cgcccaaatt | 60 |
| gttctcaccc agtctccagc aatcatgtct gcatctccag gggagaaggt caccataacc | 120 |
| tgcagtgcca gctcaagtgt aatttacatt cactggttcc agcagaagcc aggcacttct | 180 |
| cccaaactct ggatttatag cacatcctac ctggcttctg gagtccctgc tcgcttcagt | 240 |
| ggcagtggat ctgggacctc ttactctctc acaatcagcc gaatggaggc tgaagatgct | 300 |
| gccacttatt actgccagca gaggagaagt tacccgttca cgttcggagg ggggaccaag | 360 |
| ctggaaataa aacgaactgt ggctgcacca agtgtcttca tctttcctcc gagtgatgag | 420 |
| cagctgaaga gcgggacagc ttctgtggtg tgtctgctga ataacttcta cccaagagaa | 480 |
| gcaaaggtcc agtggaaggt ggacaacgcc ctgcagtctg gcaactcaca ggagtctgtc | 540 |
| actgagcagg attccaagga cagcacttac agcctgtcca gcaccctcac tctgtccaaa | 600 |
| gccgactacg aaaagcataa ggtgtatgct tgtgaggtga cccaccaggg actgagcagc | 660 |
| cctgtgacga agtccttcaa ccggggcgag tgc | 693 |

<210> SEQ ID NO 126

<211> LENGTH: 695
<212> TYPE: DNA
<213> ORGANISM: artificial
<220> FEATURE:
<223> OTHER INFORMATION: MB7-VL-CL-104C12

<400> SEQUENCE: 126

```
atgaggtggt cctggatctt cctgctgctg ctgagcatca ccagcgccaa cgccgatctc      60
cagatgacac agactccatc ctccctgtct gcctctctgg agacagagt caccatcagt     120
tgcagggcaa gtcaggacat taacaattat ttaagctggt atcaggagaa accagatgga    180
acttttaaac tcctgatcta ctacacatca agattacact caggagtccc atcaaggttc    240
agtggcagtg ggtctggaac agattattct ctcaccgttc gcaacctgga acaggaagat    300
attggcactt acttttgcca acagggtaaa acgcttccgt ggacgttcgg tggaggcacc    360
aagctggaaa tcagcgaact gtggctgcac caagtgtctt catctttcct ccgagtgatg    420
agcagctgaa gagcgggaca gcttctgtgg tgtgtctgct gaataacttc tacccaagag    480
aagcaaaggt ccagtggaag gtggacaacg ccctgcagtc tggcaactca caggagtctg    540
tcactgagca ggattccaag acagcactt acagcctgtc cagcaccctc actctgtcca    600
aagccgacta cgaaaagcat aaggtgtatg cttgtgaggt gacccaccag ggactgagca    660
gccctgtgac gaagtccttc aaccggggcg agtgc                              695
```

<210> SEQ ID NO 127
<211> LENGTH: 693
<212> TYPE: DNA
<213> ORGANISM: artificial
<220> FEATURE:
<223> OTHER INFORMATION: MB7-VL-CL-114D11

<400> SEQUENCE: 127

```
atgaggtggt cctggatctt cctgctgctg ctgagcatca ccagcgccaa cgcccaaatt      60
gttctcaccc agtctccagc aatcatgtct gcatctccag gggagaaggt caccataacc    120
tgcagtgcca gctcaagtgt attttacatg cactggttcc agcagaagcc aggcacttct    180
cccaaactct ggatttatag cacatccaac ctggcttctg gagtccctgc tcgcttcagt    240
ggcagtggat ctgggacctc ttactctctc acaatcagcc gaatggaggc tgaagatgct    300
gccacttatt actgccagca aggagaagt tacccgtaca cgttcggagg ggggaccaag    360
ctggaaataa aacgaactgt ggctgcacca agtgtcttca tctttcctcc gagtgatgag    420
cagctgaaga gcgggacagc ttctgtggtg tgtctgctga ataacttcta cccaagagaa    480
gcaaaggtcc agtggaaggt ggacaacgcc ctgcagtctg gcaactcaca ggagtctgtc    540
actgagcagg attccaagga cagcacttac agcctgtcca gcaccctcac tctgtccaaa    600
gccgactacg aaaagcataa ggtgtatgct tgtgaggtga cccaccaggg actgagcagc    660
cctgtgacga agtccttcaa ccggggcgag tgc                                693
```

<210> SEQ ID NO 128
<211> LENGTH: 693
<212> TYPE: DNA
<213> ORGANISM: artificial
<220> FEATURE:
<223> OTHER INFORMATION: MB7-VL-CL-104E10

<400> SEQUENCE: 128

```
atgaggtggt cctggatctt cctgctgctg ctgagcatca ccagcgccaa cgcccaaatt      60
gttctcaccc agtctccagc aatcatgtct gcatctccag gggagaaggt caccatgacc    120
```

```
tgcagtgcca gttcaagtgt aatttacatg cactggttcc agcagaagcc aggcacttct      180
cccaaactct ggatttatag cacatccaac ctggcttctg gagtccctgc tcgcttcagt      240
ggcagtggat ctgggacatc ttactctctc acaatcagcc gaatggaggc tgaagatgct      300
gccacttatt actgccagca aggagaagt  tacccgtaca cgttcggagg ggggaccaag      360
ctggaaataa aacgaactgt ggctgcacca agtgtcttca tctttcctcc gagtgatgag      420
cagctgaaga gcgggacagc ttctgtggtg tgtctgctga ataacttcta cccaagagaa      480
gcaaaggtcc agtggaaggt ggacaacgcc ctgcagtctg gcaactcaca ggagtctgtc      540
actgagcagg attccaagga cagcacttac agcctgtcca gcaccctcac tctgtccaaa      600
gccgactacg aaaagcataa ggtgtatgct tgtgaggtga cccaccaggg actgagcagc      660
cctgtgacga gtccttcaa  ccggggcgag tgc                                   693

<210> SEQ ID NO 129
<211> LENGTH: 1313
<212> TYPE: DNA
<213> ORGANISM: Homo sapiens
<220> FEATURE:
<221> NAME/KEY: misc_feature
<223> OTHER INFORMATION: CD303 humain (AF293615.1)

<400> SEQUENCE: 129
cagtgattct cgtgcctcag cctcctgagt agccgaaatt acagacgtgt gccaccatgc       60
ttggctaatt ttttggattt ttagtagaga tggggtttca ctatgttggc caggctagtc      120
ttgaactcct ggcctgaagc aatccgccca cctcagcctc ccaaagtgct gagattatag      180
gcacgagcca ctacacctgg ccacaaaatt ctttaaagaa gccaatccca tcctccctca      240
agagccaagg ggccacctca ccctcttgtt acagcagatc ctgcctccca cagtcaccct      300
gctcccaagt gcaacctctg tctgaccctg catggtgtgc ggtgccctcc tgcctcaggc      360
cgcgaagaag gatctaaggg cttggcttgt ttgaaagaac cacaccccga agtaacatc       420 tttggagaaa gtgatacaag agcttctgca cccacctgat agaggaagtc caaagggtgt      480
gcgcacacac aatggtgcct gaagaagagc ctcaagaccg agagaaagga ctctggtggt      540
tccagttgaa ggtctggtcc atggcagtcg tatccatctt gctcctcagt gtctgtttca      600
ctgtgagttc tgtggtgcct cacaatttta tgtatagcaa aactgtcaag aggctgtcca      660
agttacgaga gtatcaacag tatcatccaa gcctgacctg cgtcatggaa ggaaaggaca      720
tagaagattg gagctgctgc ccaacccctt ggacttcatt tcagtctagt tgctacttta      780
tttctactgg gatgcaatct tggactaaga gtcaaaagaa ctgttctgtg atggggctg       840 atctggtggt gatcaacacc agggaagaac aggatttcat cattcagaat ctgaaaagaa      900
attcttctta ttttctgggg ctgtcagatc caggggtcg  gcgacattgg caatgggttg      960
accagacacc atacaatgaa aatgtcacat tctggcactc aggtgaaccc aataaccttg     1020
atgagcgttg tgcgataata aatttccgtt cttcagaaga atgggctgg  aatgacattc     1080 actgtcatgt acctcagaag tcaatttgca agatgaagaa gatctacata taaatgaaat     1140
attctccctg gaaatgtgtt tgggttggca tccaccgttg tagaaagcta aattgatttt     1200
ttaatttatg tgtaagtttt gtacaaggaa tgcccctaaa atgtttcagc aggctgtcac     1260
ctattacact tatgatataa tccaaaaaaa aaaaaaaaa  aaaaaaaaa  aaa            1313

<210> SEQ ID NO 130
<211> LENGTH: 213
```

<212> TYPE: PRT
<213> ORGANISM: Homo sapiens
<220> FEATURE:
<221> NAME/KEY: misc_feature
<223> OTHER INFORMATION: CD303 humain (AAL37036.1)

<400> SEQUENCE: 130

```
Met Val Pro Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
                20                  25                  30

Ser Val Cys Phe Thr Val Ser Ser Val Val Pro His Asn Phe Met Tyr
                35                  40                  45

Ser Lys Thr Val Lys Arg Leu Ser Lys Leu Arg Glu Tyr Gln Gln Tyr
            50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                    85                  90                  95

Ile Ser Thr Gly Met Gln Ser Trp Thr Lys Ser Gln Lys Asn Cys Ser
                100                 105                 110

Val Met Gly Ala Asp Leu Val Val Ile Asn Thr Arg Glu Glu Gln Asp
                115                 120                 125

Phe Ile Ile Gln Asn Leu Lys Arg Asn Ser Ser Tyr Phe Leu Gly Leu
            130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                    165                 170                 175

Asp Glu Arg Cys Ala Ile Ile Asn Phe Arg Ser Ser Glu Glu Trp Gly
                180                 185                 190

Trp Asn Asp Ile His Cys His Val Pro Gln Lys Ser Ile Cys Lys Met
            195                 200                 205

Lys Lys Ile Tyr Ile
        210
```

<210> SEQ ID NO 131
<211> LENGTH: 118
<212> TYPE: PRT
<213> ORGANISM: artificial
<220> FEATURE:
<223> OTHER INFORMATION: 122A2-VHha

<400> SEQUENCE: 131

```
Gln Val Gln Leu Gln Gln Ser Gly Ala Glu Val Val Lys Pro Gly Ala
1               5                   10                  15

Ser Val Lys Ile Ser Cys Lys Gly Ser Gly Tyr Thr Phe Thr Asp Tyr
                20                  25                  30

Ser Met His Trp Val Lys Gln Ala His Ala Lys Ser Leu Glu Trp Ile
            35                  40                  45

Gly Val Ile Ser Thr Tyr Tyr Gly Asp Ser Asn Tyr Asn Gln Lys Phe
        50                  55                  60

Lys Gly Lys Val Thr Met Thr Val Asp Lys Ser Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Asn Gly Asn Phe Tyr Val Met Asp Tyr Trp Gly Gln Gly Thr
```

Leu Val Thr Val Ser Ser
        115

<210> SEQ ID NO 132
<211> LENGTH: 118
<212> TYPE: PRT
<213> ORGANISM: artificial
<220> FEATURE:
<223> OTHER INFORMATION: 122A2-VHhb

<400> SEQUENCE: 132

Gln Val Gln Leu Gln Gln Ser Gly Ala Glu Val Val Lys Pro Gly Ala
1               5                   10                  15

Ser Val Lys Ile Ser Cys Lys Gly Ser Gly Tyr Thr Phe Thr Asp Tyr
            20                  25                  30

Ser Met His Trp Val Arg Gln Ala His Ala Lys Ser Leu Glu Trp Ile
        35                  40                  45

Gly Val Ile Ser Thr Tyr Tyr Gly Asp Ser Asn Tyr Asn Gln Lys Phe
    50                  55                  60

Lys Gly Lys Val Thr Met Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Gly Asn Phe Tyr Val Met Asp Tyr Trp Gly Gln Gly Thr
            100                 105                 110

Leu Val Thr Val Ser Ser
        115

<210> SEQ ID NO 133
<211> LENGTH: 118
<212> TYPE: PRT
<213> ORGANISM: artificial
<220> FEATURE:
<223> OTHER INFORMATION: 122A2-VHhc

<400> SEQUENCE: 133

Gln Val Gln Leu Gln Gln Ser Gly Ala Glu Val Val Lys Pro Gly Ala
1               5                   10                  15

Ser Val Lys Ile Ser Cys Lys Gly Ser Gly Tyr Thr Phe Thr Asp Tyr
            20                  25                  30

Ser Met His Trp Val Arg Gln Ala Pro Gly Gln Gly Leu Glu Trp Ile
        35                  40                  45

Gly Val Ile Ser Thr Tyr Tyr Gly Asp Ser Asn Tyr Asn Gln Lys Phe
    50                  55                  60

Lys Gly Lys Val Thr Met Thr Val Asp Lys Ser Ser Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Asn Gly Asn Phe Tyr Val Met Asp Tyr Trp Gly Gln Gly Thr
            100                 105                 110

Leu Val Thr Val Ser Ser
        115

<210> SEQ ID NO 134
<211> LENGTH: 107
<212> TYPE: PRT
<213> ORGANISM: artificial
<220> FEATURE:

<223> OTHER INFORMATION: 122A2-VKha

<400> SEQUENCE: 134

Asp Ile Gln Met Thr Gln Ser Thr Ser Ser Leu Ser Ala Ser Leu Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Thr Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys
            100                 105

<210> SEQ ID NO 135
<211> LENGTH: 107
<212> TYPE: PRT
<213> ORGANISM: artificial
<220> FEATURE:
<223> OTHER INFORMATION: 122A2-VKhb

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Thr Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys
            100                 105

<210> SEQ ID NO 136
<211> LENGTH: 107
<212> TYPE: PRT
<213> ORGANISM: artificial
<220> FEATURE:
<223> OTHER INFORMATION: 122A2-VKhc

<400> SEQUENCE: 136

Asp Ile Gln Met Thr Gln Ser Thr Ser Ser Leu Ser Ala Ser Leu Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Thr Gly Val Pro Ser Arg Phe Ser Gly
    50                  55                  60

Ser Gly Ser Gly Thr Asp Tyr Ser Leu Thr Ile Ser Asn Leu Gln Gln

-continued

```
                65                  70                  75                  80
Glu Asp Ile Ala Thr Tyr Tyr Cys Gln Gln Gly Asn Thr Leu Pro Trp
                        85                  90                  95

Thr Phe Gly Gly Gly Thr Lys Leu Glu Ile Lys
                100                 105

<210> SEQ ID NO 137
<211> LENGTH: 107
<212> TYPE: PRT
<213> ORGANISM: artificial
<220> FEATURE:
<223> OTHER INFORMATION: 122A2-VKhd

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Asn Leu His Thr Gly Val Pro Ser Arg Phe Ser Gly
50                  55                  60

Ser Gly Ser Gly Thr Asp Tyr Ser Leu Thr Ile Ser Asn Leu Gln Gln
65                  70                  75                  80

Glu Asp Ile Ala Thr Tyr Tyr Cys Gln Gln Gly Asn Thr Leu Pro Trp
                        85                  90                  95

Thr Phe Gly Gly Gly Thr Lys Leu Glu Ile Lys
                100                 105

<210> SEQ ID NO 138
<211> LENGTH: 121
<212> TYPE: PRT
<213> ORGANISM: artificial
<220> FEATURE:
<223> OTHER INFORMATION: 102E9-VHha

<400> SEQUENCE: 138

Gln Ile His Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ser Met His Trp Val Lys Gln Ala Pro Gly Gln Gly Leu Lys Trp Met
            35                  40                  45

Gly Trp Ile Asn Thr Glu Thr Gly Glu Pro Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                        85                  90                  95

Thr Arg Asn Gly Tyr Tyr Val Gly Tyr Tyr Ala Met Asp Tyr Trp Gly
                100                 105                 110

Gln Gly Thr Ser Val Thr Val Ser Ser
            115                 120

<210> SEQ ID NO 139
<211> LENGTH: 121
<212> TYPE: PRT
<213> ORGANISM: artificial
<220> FEATURE:
```

<223> OTHER INFORMATION: 102E9-VHhb

<400> SEQUENCE: 139

Gln Ile His Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Gln Asp Phe
    50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ser
        115                 120

<210> SEQ ID NO 140
<211> LENGTH: 121
<212> TYPE: PRT
<213> ORGANISM: artificial
<220> FEATURE:
<223> OTHER INFORMATION: 102E9-VHhc

<400> SEQUENCE: 140

Gln Ile His Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Gln Asp Phe
    50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ser
        115                 120

<210> SEQ ID NO 141
<211> LENGTH: 106
<212> TYPE: PRT
<213> ORGANISM: artificial
<220> FEATURE:
<223> OTHER INFORMATION: 102E9-VKha

<400> SEQUENCE: 141

Gln Ile Gln Leu Thr Gln Ser Pro Ser Phe Leu Ser Ala Ser Pro Gly
1               5                   10                  15

Glu Arg Val Thr Ile Thr Cys Ser Ala Ser Ser Ser Val Ile Tyr Ile
            20                  25                  30

His Trp Phe Gln Gln Lys Pro Gly Lys Ala Pro Lys Leu Trp Ile Tyr

```
                35                  40                  45
Ser Thr Ser Tyr Leu Ala Ser Gly Val Pro Ser Arg Phe Ser Gly Ser
         50                  55                  60

Gly Ser Gly Thr Glu Tyr Thr Leu Thr Ile Ser Ser Met Glu Ala Glu
 65                  70                  75                  80

Asp Phe Ala Thr Tyr Tyr Cys Gln Gln Arg Arg Ser Tyr Pro Phe Thr
                 85                  90                  95

Phe Gly Gly Gly Thr Lys Leu Glu Ile Lys
            100                 105

<210> SEQ ID NO 142
<211> LENGTH: 106
<212> TYPE: PRT
<213> ORGANISM: artificial
<220> FEATURE:
<223> OTHER INFORMATION: 102E9-VKhb

<400> SEQUENCE: 142

Gln Ile Gln Leu Thr Gln Ser Pro Ser Phe Leu Ser Ala Ser Pro Gly
 1               5                   10                  15

Glu Arg Val Thr Ile Thr Cys Ser Ala Ser Ser Ser Val Ile Tyr Ile
             20                  25                  30

His Trp Phe Gln Gln Lys Pro Gly Thr Ala Pro Lys Leu Trp Ile Tyr
         35                  40                  45

Ser Thr Ser Tyr Leu Ala Ser Gly Val Pro Ser Arg Phe Ser Gly Ser
         50                  55                  60

Gly Ser Gly Thr Ser Tyr Thr Leu Thr Ile Ser Arg Met Glu Ala Glu
 65                  70                  75                  80

Asp Phe Ala Thr Tyr Tyr Cys Gln Gln Arg Arg Ser Tyr Pro Phe Thr
                 85                  90                  95

Phe Gly Gly Gly Thr Lys Leu Glu Ile Lys
            100                 105

<210> SEQ ID NO 143
<211> LENGTH: 106
<212> TYPE: PRT
<213> ORGANISM: artificial
<220> FEATURE:
<223> OTHER INFORMATION: 102E9-VKhc

<400> SEQUENCE: 143

Gln Ile Gln Leu Thr Gln Ser Pro Ser Phe Leu Ser Ala Ser Pro Gly
 1               5                   10                  15

Asp Arg Val Thr Ile Thr Cys Ser Ala Ser Ser Ser Val Ile Tyr Ile
             20                  25                  30

His Trp Phe Gln Gln Lys Pro Gly Lys Ala Pro Lys Leu Trp Ile Tyr
         35                  40                  45

Ser Thr Ser Tyr Leu Ala Ser Gly Val Pro Ser Arg Phe Ser Gly Ser
         50                  55                  60

Gly Ser Gly Thr Glu Tyr Thr Leu Thr Ile Ser Ser Met Gln Ala Glu
 65                  70                  75                  80

Asp Phe Ala Thr Tyr Tyr Cys Gln Gln Arg Arg Ser Tyr Pro Phe Thr
                 85                  90                  95

Phe Gly Gly Gly Thr Lys Leu Glu Ile Lys
            100                 105

<210> SEQ ID NO 144
<211> LENGTH: 330
```

```
<212> TYPE: PRT
<213> ORGANISM: artificial
<220> FEATURE:
<223> OTHER INFORMATION: CH

<400> SEQUENCE: 144
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | | 210 | | | | | 215 | | | | | 220 | | | |
| Gln | Pro | Arg | Glu | Pro | Gln | Val | Tyr | Thr | Leu | Pro | Pro | Ser | Arg | Asp | Glu |
| 225 | | | | | 230 | | | | | 235 | | | | | 240 |
| Leu | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | | | 275 | | | | | 280 | | | | | 285 | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

```
<210> SEQ ID NO 145
<211> LENGTH: 448
<212> TYPE: PRT
<213> ORGANISM: artificial
<220> FEATURE:
<223> OTHER INFORMATION: VH-CH-122A2

<400> SEQUENCE: 145
```

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Thr Tyr Tyr Gly Asp Ser Asn Tyr Asn Gln Lys Phe
    50                  55                  60

Lys Gly Lys Ala Thr Met Thr Val Asp Lys Ser Ser Thr Thr Ala Tyr
65              70                  75                  80

Met Glu Leu Ala Arg Leu Thr Ser Glu Asp Ser Ala Ile Tyr Tyr Cys
                85                  90                  95

Ala Arg Asn Gly Asn Phe Tyr Val Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145             150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305             310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385             390                 395                 400

Ser Asp Gly Ser Phe Phe Leu Tyr Ser Lys Leu Thr Val Asp Lys Ser
                405                 410                 415
```

Arg Trp Gln Gln Gly Asn Val Phe Ser Cys Ser Val Met His Glu Ala
             420                 425                 430

Leu His Asn His Tyr Thr Gln Lys Ser Leu Ser Leu Ser Pro Gly Lys
             435                 440                 445

<210> SEQ ID NO 146
<211> LENGTH: 451
<212> TYPE: PRT
<213> ORGANISM: artificial
<220> FEATURE:
<223> OTHER INFORMATION: VH-CH-102E9

<400> SEQUENCE: 146

Gln Ile His Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Ser Ser Ala Ser Thr Ala Phe
65                  70                  75                  80

Leu Gln Ile Asn Asn Leu Lys Asn Glu Asp Thr Ser Thr Tyr Phe Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 147
<211> LENGTH: 448
<212> TYPE: PRT
<213> ORGANISM: artificial
<220> FEATURE:
<223> OTHER INFORMATION: VH-CH-104C12

<400> SEQUENCE: 147

Gln Val Gln Leu Gln Gln Ser Gly Ala Glu Leu Val Gly Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Pro Tyr Tyr Gly Asp Thr Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Ser Leu Thr Ser Glu Asp Ser Ala Ile Tyr Phe Cys
                85                  90                  95

Ala Arg Asn Asp Asp Tyr Tyr Arg Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 148
<211> LENGTH: 451
<212> TYPE: PRT
<213> ORGANISM: artificial
<220> FEATURE:
<223> OTHER INFORMATION: VH-CH-114D11

<400> SEQUENCE: 148

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Ser
            20                  25                  30

Ser Met His Trp Val Gln Gln Ala Pro Asn Lys Gly Leu Lys Trp Met
        35                  40                  45

Gly Trp Ile Asn Thr Glu Thr Gly Gly Pro Thr Tyr Ala Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Arg Asn Gly Tyr Tyr Val Gly Tyr Tyr Ala Leu Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

-continued

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 149
<211> LENGTH: 451
<212> TYPE: PRT
<213> ORGANISM: artificial
<220> FEATURE:
<223> OTHER INFORMATION: VH-CH-104E10

<400> SEQUENCE: 149

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60
```

```
Lys Gly Arg Phe Ala Phe Ser Leu Glu Thr Ser Ala Thr Thr Ala Tyr
 65                  70                  75                  80

Leu Gln Ile Asn Asn Phe Lys Asn Glu Asp Thr Ala Thr Tyr Phe Cys
             85                  90                  95

Ala Arg Asn Gly Tyr Tyr Val Gly Tyr Ala Met Asp Tyr Trp Gly
            100                 105                 110

Gln Gly Thr Ser Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 150
<211> LENGTH: 448
<212> TYPE: PRT
```

```
<213> ORGANISM: artificial
<220> FEATURE:
<223> OTHER INFORMATION: 122A2-VHha-CH

<400> SEQUENCE: 150

Gln Val Gln Leu Gln Gln Ser Gly Ala Glu Val Val Lys Pro Gly Ala
1               5                   10                  15

Ser Val Lys Ile Ser Cys Lys Gly Ser Gly Tyr Thr Phe Thr Asp Tyr
            20                  25                  30

Ser Met His Trp Val Lys Gln Ala His Ala Lys Ser Leu Glu Trp Ile
        35                  40                  45

Gly Val Ile Ser Thr Tyr Tyr Gly Asp Ser Asn Tyr Asn Gln Lys Phe
    50                  55                  60

Lys Gly Lys Val Thr Met Thr Val Asp Lys Ser Ser Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Asn Gly Asn Phe Tyr Val Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 151
<211> LENGTH: 448
<212> TYPE: PRT
<213> ORGANISM: artificial
<220> FEATURE:
<223> OTHER INFORMATION: 122A2-VHhb-CH

<400> SEQUENCE: 151

```
Gln Val Gln Leu Gln Gln Ser Gly Ala Glu Val Val Lys Pro Gly Ala
1               5                   10                  15

Ser Val Lys Ile Ser Cys Lys Gly Ser Gly Tyr Thr Phe Thr Asp Tyr
                20                  25                  30

Ser Met His Trp Val Arg Gln Ala His Ala Lys Ser Leu Glu Trp Ile
            35                  40                  45

Gly Val Ile Ser Thr Tyr Tyr Gly Asp Ser Asn Tyr Asn Gln Lys Phe
        50                  55                  60

Lys Gly Lys Val Thr Met Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Gly Asn Phe Tyr Val Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
            305                 310                 315                 320
        Lys Cys Lys Val Ser Asn Lys Ala Leu Pro Ala Pro Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Arg Asp Glu Leu Thr Lys Asn Gln Val Ser Leu Thr Cys
                        355                 360                 365

Leu Val Lys Gly Phe Tyr Pro Ser Asp Ile Ala Val Glu Trp Glu Ser
                        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                        405                 410                 415

Arg Trp Gln Gln Gly Asn Val Phe Ser Cys Ser Val Met His Glu Ala
                        420                 425                 430

Leu His Asn His Tyr Thr Gln Lys Ser Leu Ser Leu Ser Pro Gly Lys
                        435                 440                 445

<210> SEQ ID NO 152
<211> LENGTH: 448
<212> TYPE: PRT
<213> ORGANISM: artificial
<220> FEATURE:
<223> OTHER INFORMATION: 122A2-VHhc-CH

<400> SEQUENCE: 152

Gln Val Gln Leu Gln Gln Ser Gly Ala Glu Val Val Lys Pro Gly Ala
        1               5                   10                  15

Ser Val Lys Ile Ser Cys Lys Gly Ser Gly Tyr Thr Phe Thr Asp Tyr
                        20                  25                  30

Ser Met His Trp Val Arg Gln Ala Pro Gly Gln Gly Leu Glu Trp Ile
                        35                  40                  45

Gly Val Ile Ser Thr Tyr Tyr Gly Asp Ser Asn Tyr Asn Gln Lys Phe
                50                  55                  60

Lys Gly Lys Val Thr Met Thr Val Asp Lys Ser Ser Ser Thr Ala Tyr
        65                  70                  75                  80

Met Glu Leu Ser Arg Leu Thr Ser Asp Thr Ala Val Tyr Tyr Cys
                        85                  90                  95

Ala Arg Asn Gly Asn Phe Tyr Val Met Asp Tyr Trp Gly Gln Gly Thr
                        100                 105                 110

Leu Val Thr Val Ser Ser Ala Ser Thr Lys Gly Pro Ser Val Phe Pro
                        115                 120                 125

Leu Ala Pro Ser Ser Lys Ser Thr Ser Gly Gly Thr Ala Ala Leu Gly
                        130                 135                 140

Cys Leu Val Lys Asp Tyr Phe Pro Glu Pro Val Thr Val Ser Trp Asn
        145                 150                 155                 160

Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                        180                 185                 190

Ser Leu Gly Thr Gln Thr Tyr Ile Cys Asn Val Asn His Lys Pro Ser
                        195                 200                 205

Asn Thr Lys Val Asp Lys Lys Val Glu Pro Lys Ser Cys Asp Lys Thr
                        210                 215                 220

His Thr Cys Pro Pro Cys Pro Ala Pro Glu Leu Leu Gly Gly Pro Ser
```

```
                225                 230                 235                 240
Val Phe Leu Phe Pro Lys Pro Lys Asp Thr Leu Met Ile Ser Arg
                    245                 250                 255

Thr Pro Glu Val Thr Cys Val Val Asp Val Ser His Glu Asp Pro
                    260                 265                 270

Glu Val Lys Phe Asn Trp Tyr Val Asp Gly Val Glu Val His Asn Ala
                    275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                    420                 425                 430

Leu His Asn His Tyr Thr Gln Lys Ser Leu Ser Leu Ser Pro Gly Lys
                435                 440                 445

<210> SEQ ID NO 153
<211> LENGTH: 214
<212> TYPE: PRT
<213> ORGANISM: artificial
<220> FEATURE:
<223> OTHER INFORMATION: 122A2-VKha-CL

<400> SEQUENCE: 153

Asp Ile Gln Met Thr Gln Ser Thr Ser Ser Leu Ser Ala Ser Leu Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Thr Gly Val Pro Ser Arg Phe Ser Gly
        50                  55                  60

Ser Gly Ser Gly Thr Asp Tyr Ser Leu Thr Ile Ser Asn Leu Asp Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 154
<211> LENGTH: 214
<212> TYPE: PRT
<213> ORGANISM: artificial
<220> FEATURE:
<223> OTHER INFORMATION: 122A2-VKhb-CL

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Thr Gly Val Pro Ser Arg Phe Ser Gly
        50                  55                  60

Ser Gly Ser Gly Thr Asp Tyr Ser Leu Thr Ile Ser Asn Leu Asp Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
                    100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 155
<211> LENGTH: 214
<212> TYPE: PRT
<213> ORGANISM: artificial
<220> FEATURE:
<223> OTHER INFORMATION: 122A2-VKhc-CL

<400> SEQUENCE: 155

Asp Ile Gln Met Thr Gln Ser Thr Ser Ser Leu Ser Ala Ser Leu Gly
1               5                   10                  15
```

Asp Arg Val Thr Ile Thr Cys Gln Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Thr Gly Val Pro Ser Arg Phe Ser Gly
    50                  55                  60

Ser Gly Ser Gly Thr Asp Tyr Ser Leu Thr Ile Ser Asn Leu Gln Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 156
<211> LENGTH: 214
<212> TYPE: PRT
<213> ORGANISM: artificial
<220> FEATURE:
<223> OTHER INFORMATION: 122A2-VKhd-CL

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Thr Gly Val Pro Ser Arg Phe Ser Gly
    50                  55                  60

Ser Gly Ser Gly Thr Asp Tyr Ser Leu Thr Ile Ser Asn Leu Gln Gln
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 157
<211> LENGTH: 451
<212> TYPE: PRT
<213> ORGANISM: artificial
<220> FEATURE:
<223> OTHER INFORMATION: 102E9-VHha-CH

<400> SEQUENCE: 157

Gln Ile His Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Met His Trp Val Lys Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 158
<211> LENGTH: 451
<212> TYPE: PRT
<213> ORGANISM: artificial
<220> FEATURE:
<223> OTHER INFORMATION: 102E9-VHhb-CH

<400> SEQUENCE: 158

Gln Ile His Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Gln Asp Phe
    50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                85                  90                  95

Thr Arg Asn Gly Tyr Tyr Val Gly Tyr Tyr Ala Met Asp Tyr Trp Gly
                100                 105                 110

Gln Gly Thr Ser Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
    195                 200                 205
```

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 159
<211> LENGTH: 451
<212> TYPE: PRT
<213> ORGANISM: artificial
<220> FEATURE:
<223> OTHER INFORMATION: 102E9-VHhc-CH

<400> SEQUENCE: 159

Gln Ile His Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Gln Asp Phe
    50                  55                  60

Lys Gly Arg Phe Val Phe Ser Leu Asp Thr Ser Val Ser Thr Ala Tyr
65                  70                  75                  80

Leu Gln Ile Asn Ser Leu Lys Asn Glu Asp Thr Ser Thr Tyr Tyr Cys
                85                  90                  95

Thr Arg Asn Gly Tyr Tyr Val Gly Tyr Tyr Ala Met Asp Tyr Trp Gly
            100                 105                 110

Gln Gly Thr Ser Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 160
<211> LENGTH: 213
<212> TYPE: PRT
<213> ORGANISM: artificial
<220> FEATURE:
<223> OTHER INFORMATION: 102E9-VKha-CL

<400> SEQUENCE: 160

Gln Ile Gln Leu Thr Gln Ser Pro Ser Phe Leu Ser Ala Ser Pro Gly
1               5                   10                  15

Glu Arg Val Thr Ile Thr Cys Ser Ala Ser Ser Ser Val Ile Tyr Ile
            20                  25                  30

His Trp Phe Gln Gln Lys Pro Gly Lys Ala Pro Lys Leu Trp Ile Tyr
            35                  40                  45

Ser Thr Ser Tyr Leu Ala Ser Gly Val Pro Ser Arg Phe Ser Gly Ser
 50                  55                  60

Gly Ser Gly Thr Glu Tyr Thr Leu Thr Ile Ser Ser Met Glu Ala Glu
 65                  70                  75                  80

Asp Phe Ala Thr Tyr Tyr Cys Gln Gln Arg Arg Ser Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
 130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 161
<211> LENGTH: 213
<212> TYPE: PRT
<213> ORGANISM: artificial
<220> FEATURE:
<223> OTHER INFORMATION: 102E9-VKhb-CL

<400> SEQUENCE: 161

Gln Ile Gln Leu Thr Gln Ser Pro Ser Phe Leu Ser Ala Ser Pro Gly
 1               5                  10                  15

Glu Arg Val Thr Ile Thr Cys Ser Ala Ser Ser Ser Val Ile Tyr Ile
            20                  25                  30

His Trp Phe Gln Gln Lys Pro Gly Thr Ala Pro Lys Leu Trp Ile Tyr
            35                  40                  45

Ser Thr Ser Tyr Leu Ala Ser Gly Val Pro Ser Arg Phe Ser Gly Ser
 50                  55                  60

Gly Ser Gly Thr Ser Tyr Thr Leu Thr Ile Ser Arg Met Glu Ala Glu
 65                  70                  75                  80

Asp Phe Ala Thr Tyr Tyr Cys Gln Gln Arg Arg Ser Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
 130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                        165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 162
<211> LENGTH: 213
<212> TYPE: PRT
<213> ORGANISM: artificial
<220> FEATURE:
<223> OTHER INFORMATION: 102E9-VKhc-CL

<400> SEQUENCE: 162

Gln Ile Gln Leu Thr Gln Ser Pro Ser Phe Leu Ser Ala Ser Pro Gly
1               5                   10                  15

Asp Arg Val Thr Ile Thr Cys Ser Ala Ser Ser Val Ile Tyr Ile
            20                  25                  30

His Trp Phe Gln Gln Lys Pro Gly Lys Ala Pro Lys Leu Trp Ile Tyr
        35                  40                  45

Ser Thr Ser Tyr Leu Ala Ser Gly Val Pro Ser Arg Phe Ser Gly Ser
    50                  55                  60

Gly Ser Gly Thr Glu Tyr Thr Leu Thr Ile Ser Ser Met Gln Ala Glu
65                  70                  75                  80

Asp Phe Ala Thr Tyr Tyr Cys Gln Gln Arg Arg Ser Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 163
<211> LENGTH: 466
<212> TYPE: PRT
<213> ORGANISM: artificial
<220> FEATURE:
<223> OTHER INFORMATION: MB7-VH-CH-122A2

<400> SEQUENCE: 163

Met Arg Trp Ser Trp Ile Phe Leu Leu Leu Leu Ser Ile Thr Ser Ala
1               5                   10                  15

Asn Ala Gln Val Gln Leu Gln Gln Ser Gly Ala Glu Leu Val Arg Pro
            20                  25                  30

```
Gly Val Ser Val Lys Ile Ser Cys Lys Gly Ser Gly Tyr Thr Phe Thr
            35                  40                  45

Asp Tyr Ser Met His Trp Val Lys Gln Ser His Ala Lys Ser Leu Glu
    50                  55                  60

Trp Ile Gly Val Ile Ser Thr Tyr Tyr Gly Asp Ser Asn Tyr Asn Gln
65                  70                  75                  80

Lys Phe Lys Gly Lys Ala Thr Met Thr Val Asp Lys Ser Ser Thr Thr
                85                  90                  95

Ala Tyr Met Glu Leu Ala Arg Leu Thr Ser Glu Asp Ser Ala Ile Tyr
            100                 105                 110

Tyr Cys Ala Arg Asn Gly Asn Phe Tyr Val Met Asp Tyr Trp Gly Gln
            115                 120                 125

Gly Thr Ser Val Thr Val Ser Ser Ala Ser Thr Lys Gly Pro Ser Val
            130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445
```

<210> SEQ ID NO 164
<211> LENGTH: 469
<212> TYPE: PRT
<213> ORGANISM: artificial
<220> FEATURE:
<223> OTHER INFORMATION: MB7-VH-CH-102E9

<400> SEQUENCE: 164

```
Glu Ala Leu His Asn His Tyr Thr Gln Lys Ser Leu Ser Leu Ser Pro
    450                 455                 460
Gly Lys
465
```

```
Met Arg Trp Ser Trp Ile Phe Leu Leu Leu Ser Ile Thr Ser Ala
1               5                   10                  15

Asn Ala Gln Ile His Leu Val Gln Ser Gly Pro Asp Leu Lys Lys Pro
                20                  25                  30

Gly Glu Thr Val Lys Ile Ser Cys Lys Ala Ser Gly Tyr Thr Phe Thr
            35                  40                  45

Asp Tyr Ser Met His Trp Val Lys Gln Ala Pro Gly Lys Gly Leu Lys
        50                  55                  60

Trp Met Gly Trp Ile Asn Thr Glu Thr Gly Glu Pro Thr Tyr Ala Asp
65                  70                  75                  80

Asp Phe Lys Gly Arg Phe Ala Phe Ser Leu Glu Ser Ser Ala Ser Thr
                85                  90                  95

Ala Phe Leu Gln Ile Asn Asn Leu Lys Asn Glu Asp Thr Ser Thr Tyr
                100                 105                 110

Phe Cys Thr Arg Asn Gly Tyr Tyr Val Gly Tyr Tyr Ala Met Asp Tyr
            115                 120                 125

Trp Gly Gln Gly Thr Ser Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335
```

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465

<210> SEQ ID NO 165
<211> LENGTH: 466
<212> TYPE: PRT
<213> ORGANISM: artificial
<220> FEATURE:
<223> OTHER INFORMATION: MB7-VH-CH-104C12

<400> SEQUENCE: 165

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Leu Val Gly Pro
                20                  25                  30

Gly Val Ser Val Lys Ile Ser Cys Lys Gly Ser Gly Tyr Thr Phe Thr
            35                  40                  45

Asp Tyr Ser Met His Trp Val Lys Gln Ser His Ala Lys Ser Leu Glu
    50                  55                  60

Trp Ile Gly Val Ile Ser Pro Tyr Tyr Gly Asp Thr Asn Tyr Asn Gln
65                  70                  75                  80

Lys Phe Lys Gly Lys Ala Thr Met Thr Val Asp Lys Ser Ser Ser Thr
                85                  90                  95

Ala Tyr Met Glu Leu Ala Ser Leu Thr Ser Glu Asp Ser Ala Ile Tyr
                100                 105                 110

Phe Cys Ala Arg Asn Asp Asp Tyr Tyr Arg Phe Ala Tyr Trp Gly Gln
            115                 120                 125

Gly Thr Leu Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

```
Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 166
<211> LENGTH: 469
<212> TYPE: PRT
<213> ORGANISM: artificial
<220> FEATURE:
<223> OTHER INFORMATION: MB7-VH-CH-114D11

<400> SEQUENCE: 166

Met Arg Trp Ser Trp Ile Phe Leu Leu Leu Ser Ile Thr Ser Ala
1               5                   10                  15

Asn Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asp Ser Ser Met His Trp Val Gln Gln Ala Pro Asn Lys Gly Leu Lys
    50                  55                  60

Trp Met Gly Trp Ile Asn Thr Glu Thr Gly Pro Thr Tyr Ala Asp
65                  70                  75                  80

Asp Phe Lys Gly Arg Phe Ala Phe Ser Leu Glu Thr Ser Ala Arg Thr
                85                  90                  95

Ala Tyr Leu Gln Ile Asn Asn Leu Lys Asn Glu Asp Thr Ala Thr Tyr
            100                 105                 110
```

-continued

Phe Cys Ala Arg Asn Gly Tyr Tyr Val Gly Tyr Tyr Ala Leu Asp Tyr
            115                 120                 125

Trp Gly Gln Gly Thr Ser Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 167
<211> LENGTH: 469
<212> TYPE: PRT
<213> ORGANISM: artificial
<220> FEATURE:
<223> OTHER INFORMATION: MB7-VH-CH-104E10

<400> SEQUENCE: 167

-continued

```
Met Arg Trp Ser Trp Ile Phe Leu Leu Leu Leu Ser Ile Thr Ser Ala
1               5                   10                  15

Asn Ala Gln Ile Gln Leu Val Gln Ser Gly Pro Glu Leu Lys Lys Pro
                20                  25                  30

Gly Glu Thr Val Lys Ile Ser Cys Lys Ala Ser Gly Tyr Thr Phe Thr
                35                  40                  45

Asp Tyr Ser Met His Trp Val Lys Gln Ala Pro Gly Lys Gly Leu Lys
            50                  55                  60

Trp Met Gly Trp Ile Asn Thr Glu Thr Gly Glu Pro Thr Tyr Ala Asp
65                  70                  75                  80

Asp Phe Lys Gly Arg Phe Ala Phe Ser Leu Glu Thr Ser Ala Thr Thr
                85                  90                  95

Ala Tyr Leu Gln Ile Asn Asn Phe Lys Asn Glu Asp Thr Ala Thr Tyr
                100                 105                 110

Phe Cys Ala Arg Asn Gly Tyr Tyr Val Gly Tyr Tyr Ala Met Asp Tyr
                115                 120                 125

Trp Gly Gln Gly Thr Ser Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
```

-continued

```
                  420                 425                 430
Thr Val Asp Lys Ser Arg Trp Gln Gln Gly Asn Val Phe Ser Cys Ser
            435                 440                 445
Val Met His Glu Ala Leu His Asn His Tyr Thr Gln Lys Ser Leu Ser
    450                 455                 460
Leu Ser Pro Gly Lys
465

<210> SEQ ID NO 168
<211> LENGTH: 466
<212> TYPE: PRT
<213> ORGANISM: artificial
<220> FEATURE:
<223> OTHER INFORMATION: 122A2-MB7-VHha-CH

<400> SEQUENCE: 168

Met Arg Trp Ser Trp Ile Phe Leu Leu Leu Ser Ile Thr Ser Ala
1               5                   10                  15

Asn Ala Gln Val Gln Leu Gln Gln Ser Gly Ala Glu Val Val Lys Pro
            20                  25                  30

Gly Ala Ser Val Lys Ile Ser Cys Lys Gly Ser Gly Tyr Thr Phe Thr
        35                  40                  45

Asp Tyr Ser Met His Trp Val Lys Gln Ala His Ala Lys Ser Leu Glu
    50                  55                  60

Trp Ile Gly Val Ile Ser Thr Tyr Tyr Gly Asp Ser Asn Tyr Asn Gln
65                  70                  75                  80

Lys Phe Lys Gly Lys Val Thr Met Thr Val Asp Lys Ser Ser Ser Thr
                85                  90                  95

Ala Tyr Met Glu Leu Ser Arg Leu Thr Ser Asp Asp Thr Ala Val Tyr
            100                 105                 110

Tyr Cys Ala Arg Asn Gly Asn Phe Tyr Val Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
```

```
            305                 310                 315                 320
Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Asp Glu Leu Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
            450                 455                 460

Gly Lys
465

<210> SEQ ID NO 169
<211> LENGTH: 466
<212> TYPE: PRT
<213> ORGANISM: artificial
<220> FEATURE:
<223> OTHER INFORMATION: 122A2-MB7-VHhb-CH

<400> SEQUENCE: 169

Met Arg Trp Ser Trp Ile Phe Leu Leu Leu Leu Ser Ile Thr Ser Ala
1               5                   10                  15

Asn Ala Gln Val Gln Leu Gln Gln Ser Gly Ala Glu Val Val Lys Pro
                20                  25                  30

Gly Ala Ser Val Lys Ile Ser Cys Lys Gly Ser Gly Tyr Thr Phe Thr
            35                  40                  45

Asp Tyr Ser Met His Trp Val Arg Gln Ala His Ala Lys Ser Leu Glu
        50                  55                  60

Trp Ile Gly Val Ile Ser Thr Tyr Tyr Gly Asp Ser Asn Tyr Asn Gln
65                  70                  75                  80

Lys Phe Lys Gly Lys Val Thr Met Thr Val Asp Thr Ser Ser Ser Thr
                85                  90                  95

Ala Tyr Met Glu Leu Ser Arg Leu Arg Ser Asp Asp Thr Ala Val Tyr
            100                 105                 110

Tyr Cys Ala Arg Asn Gly Asn Phe Tyr Val Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
```

```
                195                 200                 205
Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 170
<211> LENGTH: 466
<212> TYPE: PRT
<213> ORGANISM: artificial
<220> FEATURE:
<223> OTHER INFORMATION: 122A2-MB7-VHhc-CH

<400> SEQUENCE: 170

Met Arg Trp Ser Trp Ile Phe Leu Leu Leu Leu Ser Ile Thr Ser Ala
1               5                   10                  15

Asn Ala Gln Val Gln Leu Gln Gln Ser Gly Ala Glu Val Val Lys Pro
            20                  25                  30

Gly Ala Ser Val Lys Ile Ser Cys Lys Gly Ser Gly Tyr Thr Phe Thr
        35                  40                  45

Asp Tyr Ser Met His Trp Val Arg Gln Ala Pro Gly Gln Gly Leu Glu
    50                  55                  60

Trp Ile Gly Val Ile Ser Thr Tyr Tyr Gly Asp Ser Asn Tyr Asn Gln
65                  70                  75                  80

Lys Phe Lys Gly Lys Val Thr Met Thr Val Asp Lys Ser Ser Ser Thr
```

```
                    85                  90                  95
Ala Tyr Met Glu Leu Ser Arg Leu Thr Ser Asp Asp Thr Ala Val Tyr
                100                 105                 110

Tyr Cys Ala Arg Asn Gly Asn Phe Tyr Val Met Asp Tyr Trp Gly Gln
                115                 120                 125

Gly Thr Leu Val Thr Val Ser Ser Ala Ser Thr Lys Gly Pro Ser Val
            130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
                210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
                275                 280                 285

Asp Pro Glu Val Lys Phe Asn Trp Tyr Val Asp Gly Val Glu Val His
                290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Asp Glu Leu Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
                450                 455                 460

Gly Lys
465

<210> SEQ ID NO 171
<211> LENGTH: 232
<212> TYPE: PRT
<213> ORGANISM: artificial
```

<220> FEATURE:
<223> OTHER INFORMATION: 122A2-MB7-VKha-CL

<400> SEQUENCE: 171

Met Arg Trp Ser Trp Ile Phe Leu Leu Leu Ser Ile Thr Ser Ala
1               5                   10                  15

Asn Ala Asp Ile Gln Met Thr Gln Ser Thr Ser Ser Leu Ser Ala Ser
                20                  25                  30

Leu Gly Asp Arg Val Thr Ile Thr Cys Gln Ala Ser Gln Asp Ile Ser
            35                  40                  45

Asn Tyr Leu Asn Trp Tyr Gln Gln Lys Pro Asp Gly Thr Val Lys Leu
        50                  55                  60

Leu Ile Tyr Tyr Thr Ser Arg Leu His Thr Gly Val Pro Ser Arg Phe
65                  70                  75                  80

Ser Gly Ser Gly Ser Gly Thr Asp Tyr Ser Leu Thr Ile Ser Asn Leu
                85                  90                  95

Asp Gln Glu Asp Ile Ala Thr Tyr Tyr Cys Gln Gln Gly Asn Thr Leu
                100                 105                 110

Pro Trp Thr Phe Gly Gly Gly Thr Lys Leu Glu Ile Lys Arg Thr Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 172
<211> LENGTH: 232
<212> TYPE: PRT
<213> ORGANISM: artificial
<220> FEATURE:
<223> OTHER INFORMATION: 122A2-MB7-VKhb-CL

<400> SEQUENCE: 172

Met Arg Trp Ser Trp Ile Phe Leu Leu Leu Ser Ile Thr Ser Ala
1               5                   10                  15

Asn Ala Asp Ile Gln Met Thr Gln Ser Pro Ser Ser Leu Ser Ala Ser
                20                  25                  30

Val Gly Asp Arg Val Thr Ile Thr Cys Gln Ala Ser Gln Asp Ile Ser
            35                  40                  45

Asn Tyr Leu Asn Trp Tyr Gln Gln Lys Pro Asp Gly Thr Val Lys Leu
        50                  55                  60

Leu Ile Tyr Tyr Thr Ser Arg Leu His Thr Gly Val Pro Ser Arg Phe
65                  70                  75                  80

Ser Gly Ser Gly Ser Gly Thr Asp Tyr Ser Leu Thr Ile Ser Asn Leu
                85                  90                  95

Asp Gln Glu Asp Ile Ala Thr Tyr Tyr Cys Gln Gln Gly Asn Thr Leu

```
                100             105             110
Pro Trp Thr Phe Gly Gly Thr Lys Leu Glu Ile Lys Arg Thr Val
            115             120             125

Ala Ala Pro Ser Val Phe Ile Phe Pro Pro Ser Asp Glu Gln Leu Lys
            130             135             140

Ser Gly Thr Ala Ser Val Val Cys Leu Leu Asn Asn Phe Tyr Pro Arg
145             150             155             160

Glu Ala Lys Val Gln Trp Lys Val Asp Asn Ala Leu Gln Ser Gly Asn
            165             170             175

Ser Gln Glu Ser Val Thr Glu Gln Asp Ser Lys Asp Ser Thr Tyr Ser
            180             185             190

Leu Ser Ser Thr Leu Thr Leu Ser Lys Ala Asp Tyr Glu Lys His Lys
            195             200             205

Val Tyr Ala Cys Glu Val Thr His Gln Gly Leu Ser Ser Pro Val Thr
            210             215             220

Lys Ser Phe Asn Arg Gly Glu Cys
225             230
```

<210> SEQ ID NO 173
<211> LENGTH: 232
<212> TYPE: PRT
<213> ORGANISM: artificial
<220> FEATURE:
<223> OTHER INFORMATION: 122A2-MB7-VKhc-CL

<400> SEQUENCE: 173

```
Met Arg Trp Ser Trp Ile Phe Leu Leu Leu Leu Ser Ile Thr Ser Ala
1               5                   10                  15

Asn Ala Asp Ile Gln Met Thr Gln Ser Thr Ser Ser Leu Ser Ala Ser
            20                  25                  30

Leu Gly Asp Arg Val Thr Ile Thr Cys Gln Ala Ser Gln Asp Ile Ser
            35                  40                  45

Asn Tyr Leu Asn Trp Tyr Gln Gln Lys Pro Asp Gly Thr Val Lys Leu
    50                  55                  60

Leu Ile Tyr Tyr Thr Ser Asn Leu His Thr Gly Val Pro Ser Arg Phe
65                  70                  75                  80

Ser Gly Ser Gly Ser Gly Thr Asp Tyr Ser Leu Thr Ile Ser Asn Leu
            85                  90                  95

Gln Gln Glu Asp Ile Ala Thr Tyr Tyr Cys Gln Gln Gly Asn Thr Leu
            100                 105                 110

Pro Trp Thr Phe Gly Gly Gly Thr Lys Leu Glu Ile Lys Arg Thr Val
            115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145             150                 155                 160

Glu Ala Lys Val Gln Trp Lys Val Asp Asn Ala Leu Gln Ser Gly Asn
            165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
            210                 215                 220

Lys Ser Phe Asn Arg Gly Glu Cys
```

```
                    225                 230

<210> SEQ ID NO 174
<211> LENGTH: 232
<212> TYPE: PRT
<213> ORGANISM: artificial
<220> FEATURE:
<223> OTHER INFORMATION: 122A2-MB7-VKhd-CL

<400> SEQUENCE: 174

Met Arg Trp Ser Trp Ile Phe Leu Leu Leu Ser Ile Thr Ser Ala
1               5                   10                  15

Asn Ala Asp Ile Gln Met Thr Gln Ser Pro Ser Ser Leu Ser Ala Ser
            20                  25                  30

Val Gly Asp Arg Val Thr Ile Thr Cys Gln Ala Ser Gln Asp Ile Ser
        35                  40                  45

Asn Tyr Leu Asn Trp Tyr Gln Gln Lys Pro Asp Gly Thr Val Lys Leu
    50                  55                  60

Leu Ile Tyr Tyr Thr Ser Asn Leu His Thr Gly Val Pro Ser Arg Phe
65                  70                  75                  80

Ser Gly Ser Gly Ser Gly Thr Asp Tyr Ser Leu Thr Ile Ser Asn Leu
                85                  90                  95

Gln Gln Glu Asp Ile Ala Thr Tyr Tyr Cys Gln Gln Gly Asn Thr Leu
            100                 105                 110

Pro Trp Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 175
<211> LENGTH: 469
<212> TYPE: PRT
<213> ORGANISM: artificial
<220> FEATURE:
<223> OTHER INFORMATION: 102E9-MB7-VHha-CH

<400> SEQUENCE: 175

Met Arg Trp Ser Trp Ile Phe Leu Leu Leu Ser Ile Thr Ser Ala
1               5                   10                  15

Asn Ala Gln Ile His Leu Val Gln Ser Gly Pro Glu Leu Lys Lys Pro
            20                  25                  30

Gly Glu Ser Val Lys Ile Ser Cys Lys Ala Ser Gly Tyr Thr Phe Thr
        35                  40                  45

Asp Tyr Ser Met His Trp Val Lys Gln Ala Pro Gly Gln Gly Leu Lys
    50                  55                  60
```

```
Trp Met Gly Trp Ile Asn Thr Glu Thr Gly Glu Pro Thr Tyr Ala Asp
 65                  70                  75                  80

Asp Phe Lys Gly Arg Phe Val Phe Ser Leu Asp Thr Ser Val Ser Thr
             85                  90                  95

Ala Tyr Leu Gln Ile Asn Ser Leu Lys Asn Glu Asp Thr Ser Thr Tyr
            100                 105                 110

Tyr Cys Thr Arg Asn Gly Tyr Val Gly Tyr Tyr Ala Met Asp Tyr
            115                 120                 125

Trp Gly Gln Gly Thr Ser Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465
```

<210> SEQ ID NO 176
<211> LENGTH: 469
<212> TYPE: PRT
<213> ORGANISM: artificial
<220> FEATURE:
<223> OTHER INFORMATION: 102E9-MB7-VHhb-CH

<400> SEQUENCE: 176

```
Met Arg Trp Ser Trp Ile Phe Leu Leu Leu Ser Ile Thr Ser Ala
1               5                   10                  15

Asn Ala Gln Ile His Leu Val Gln Ser Gly Pro Glu Leu Lys Lys Pro
            20                  25                  30

Gly Glu Ser Val Lys Ile Ser Cys Lys Ala Ser Gly Tyr Thr Phe Thr
        35                  40                  45

Asp Tyr Ser Met His Trp Val Arg Gln Ala Pro Gly Gln Gly Leu Lys
    50                  55                  60

Trp Met Gly Trp Ile Asn Thr Glu Thr Gly Glu Pro Thr Tyr Ala Gln
65                  70                  75                  80

Asp Phe Lys Gly Arg Phe Val Phe Ser Leu Asp Thr Ser Val Ser Thr
                85                  90                  95

Ala Tyr Leu Gln Ile Asn Ser Leu Lys Asn Glu Asp Thr Ser Thr Tyr
            100                 105                 110

Tyr Cys Thr Arg Asn Gly Tyr Tyr Val Gly Tyr Tyr Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
```

```
            370                 375                 380
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys
465
```

<210> SEQ ID NO 177
<211> LENGTH: 469
<212> TYPE: PRT
<213> ORGANISM: artificial
<220> FEATURE:
<223> OTHER INFORMATION: 102E9-MB7-VHhc-CH

<400> SEQUENCE: 177

```
Met Arg Trp Ser Trp Ile Phe Leu Leu Leu Ser Ile Thr Ser Ala
1               5                   10                  15

Asn Ala Gln Ile His Leu Val Gln Ser Gly Ser Glu Leu Lys Lys Pro
                20                  25                  30

Gly Glu Ser Val Lys Ile Ser Cys Lys Ala Ser Gly Tyr Thr Phe Thr
            35                  40                  45

Asp Tyr Ser Met His Trp Val Arg Gln Ala Pro Gly Gln Gly Leu Lys
        50                  55                  60

Trp Met Gly Trp Ile Asn Thr Glu Thr Gly Glu Pro Thr Tyr Ala Gln
65                  70                  75                  80

Asp Phe Lys Gly Arg Phe Val Phe Ser Leu Asp Thr Ser Val Ser Thr
                85                  90                  95

Ala Tyr Leu Gln Ile Asn Ser Leu Lys Asn Glu Asp Thr Ser Thr Tyr
            100                 105                 110

Tyr Cys Thr Arg Asn Gly Tyr Tyr Val Gly Tyr Tyr Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
```

```
                260                 265                 270
Leu Met Ile Ser Arg Thr Pro Glu Val Thr Cys Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 178
<211> LENGTH: 231
<212> TYPE: PRT
<213> ORGANISM: artificial
<220> FEATURE:
<223> OTHER INFORMATION: 102E9-MB7-VKha-CL

<400> SEQUENCE: 178

Met Arg Trp Ser Trp Ile Phe Leu Leu Leu Leu Ser Ile Thr Ser Ala
1               5                   10                  15

Asn Ala Gln Ile Gln Leu Thr Gln Ser Pro Ser Phe Leu Ser Ala Ser
            20                  25                  30

Pro Gly Glu Arg Val Thr Ile Thr Cys Ser Ala Ser Ser Ser Val Ile
        35                  40                  45

Tyr Ile His Trp Phe Gln Gln Lys Pro Gly Lys Ala Pro Lys Leu Trp
    50                  55                  60

Ile Tyr Ser Thr Ser Tyr Leu Ala Ser Gly Val Pro Ser Arg Phe Ser
65                  70                  75                  80

Gly Ser Gly Ser Gly Thr Glu Tyr Thr Leu Thr Ile Ser Ser Met Glu
                85                  90                  95

Ala Glu Asp Phe Ala Thr Tyr Tyr Cys Gln Gln Arg Arg Ser Tyr Pro
            100                 105                 110

Phe Thr Phe Gly Gly Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
```

```
145                 150                 155                 160
Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 179
<211> LENGTH: 231
<212> TYPE: PRT
<213> ORGANISM: artificial
<220> FEATURE:
<223> OTHER INFORMATION: 102E9-MB7-VKhb-CL

<400> SEQUENCE: 179

Met Arg Trp Ser Trp Ile Phe Leu Leu Leu Leu Ser Ile Thr Ser Ala
1               5                   10                  15

Asn Ala Gln Ile Gln Leu Thr Gln Ser Pro Ser Phe Leu Ser Ala Ser
            20                  25                  30

Pro Gly Glu Arg Val Thr Ile Thr Cys Ser Ala Ser Ser Ser Val Ile
        35                  40                  45

Tyr Ile His Trp Phe Gln Gln Lys Pro Gly Thr Ala Pro Lys Leu Trp
    50                  55                  60

Ile Tyr Ser Thr Ser Tyr Leu Ala Ser Gly Val Pro Ser Arg Phe Ser
65                  70                  75                  80

Gly Ser Gly Ser Gly Thr Ser Tyr Thr Leu Thr Ile Ser Arg Met Glu
                85                  90                  95

Ala Glu Asp Phe Ala Thr Tyr Tyr Cys Gln Gln Arg Arg Ser Tyr Pro
            100                 105                 110

Phe Thr Phe Gly Gly Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 180
<211> LENGTH: 231
<212> TYPE: PRT
<213> ORGANISM: artificial
<220> FEATURE:
<223> OTHER INFORMATION: 102E9-MB7-VKhc-CL
```

<400> SEQUENCE: 180

| | | | | | | | | | | | | | | |
|---|---|---|---|---|---|---|---|---|---|---|---|---|---|---|
|Met|Arg|Trp|Ser|Trp|Ile|Phe|Leu|Leu|Leu|Ser|Ile|Thr|Ser|Ala|
|1| | |derive 5| | | | | |10| | | | |15|

Asn Ala Gln Ile Gln Leu Thr Gln Ser Pro Ser Phe Leu Ser Ala Ser
          20            25            30

Pro Gly Asp Arg Val Thr Ile Thr Cys Ser Ala Ser Ser Val Ile
     35            40            45

Tyr Ile His Trp Phe Gln Gln Lys Pro Gly Lys Ala Pro Lys Leu Trp
50            55            60

Ile Tyr Ser Thr Ser Tyr Leu Ala Ser Gly Val Pro Ser Arg Phe Ser
65          70            75          80

Gly Ser Gly Ser Gly Thr Glu Tyr Thr Leu Thr Ile Ser Ser Met Gln
         85            90          95

Ala Glu Asp Phe Ala Thr Tyr Tyr Cys Gln Gln Arg Arg Ser Tyr Pro
        100          105         110

Phe Thr Phe Gly Gly Gly Thr Lys Leu Glu Ile Lys Arg Thr Val Ala
     115          120         125

Ala Pro Ser Val Phe Ile Phe Pro Pro Ser Asp Glu Gln Leu Lys Ser
130            135           140

Gly Thr Ala Ser Val Val Cys Leu Leu Asn Asn Phe Tyr Pro Arg Glu
145          150          155         160

Ala Lys Val Gln Trp Lys Val Asp Asn Ala Leu Gln Ser Gly Asn Ser
        165          170         175

Gln Glu Ser Val Thr Glu Gln Asp Ser Lys Asp Ser Thr Tyr Ser Leu
        180          185         190

Ser Ser Thr Leu Thr Leu Ser Lys Ala Asp Tyr Glu Lys His Lys Val
     195          200         205

Tyr Ala Cys Glu Val Thr His Gln Gly Leu Ser Ser Pro Val Thr Lys
210          215           220

Ser Phe Asn Arg Gly Glu Cys
225          230

<210> SEQ ID NO 181
<211> LENGTH: 354
<212> TYPE: DNA
<213> ORGANISM: artificial
<220> FEATURE:
<223> OTHER INFORMATION: 122A2-VHha

<400> SEQUENCE: 181

```
caggtccagc tgcagcagtc tggcgccgaa gtggtcaagc ctggcgcctc cgtgaagatc    60
agctgcaagg gcagcggcta caccttcacc gactacagca tgcactgggt caagcaggcc   120
cacgccaaga gcctggaatg gatcggcgtg atcagcacct actacggcga cagcaactac   180
aaccagaagt tcaagggcaa agtcaccatg accgtggaca gagcagctc caccgcctac   240
atggaactga gcaggctgac cagcgacgac accgccgtgt actactgcgc cagaaacggc   300
aacttctacg tgatggacta ctggggccag ggcaccctgg tcaccgtgtc atct          354
```

<210> SEQ ID NO 182
<211> LENGTH: 354
<212> TYPE: DNA
<213> ORGANISM: artificial
<220> FEATURE:
<223> OTHER INFORMATION: 122A2-VHhb

<400> SEQUENCE: 182

```
caggtccagc tgcagcagtc tggcgccgaa gtggtcaagc ctggcgcctc cgtgaagatc      60
agctgcaagg gcagcggcta caccttcacc gactacagca tgcactgggt ccgacaggcc     120
cacgccaaga gcctggaatg gatcggcgtg atcagcacct actacggcga cagcaactac     180
aaccagaagt tcaagggcaa agtcaccatg accgtggaca ccagcagctc caccgcctac     240
atggaactga gcaggctgag aagcgacgac accgccgtgt actactgcgc cagaaacggc     300
aacttctacg tgatggacta ctggggccag ggcaccctgg tcaccgtgtc atct           354
```

<210> SEQ ID NO 183
<211> LENGTH: 354
<212> TYPE: DNA
<213> ORGANISM: artificial
<220> FEATURE:
<223> OTHER INFORMATION: 122A2-VHhc

<400> SEQUENCE: 183

```
caggtccagc tgcagcagtc tggcgccgaa gtggtcaagc ctggcgcctc cgtgaagatc      60
agctgcaagg gcagcggcta caccttcacc gactacagca tgcactgggt ccgacaggcc     120
cctggacagg gcctggaatg gatcggcgtg atcagcacct actacggcga cagcaactac     180
aaccagaagt tcaagggcaa agtcaccatg accgtggaca agagcagctc caccgcctac     240
atggaactga gcaggctgac cagcgacgac accgccgtgt actactgcgc cagaaacggc     300
aacttctacg tgatggacta ctggggccag ggcaccctgg tcaccgtgtc atct           354
```

<210> SEQ ID NO 184
<211> LENGTH: 321
<212> TYPE: DNA
<213> ORGANISM: artificial
<220> FEATURE:
<223> OTHER INFORMATION: 122A2-VKha

<400> SEQUENCE: 184

```
gacatccaga tgacccagag caccagcagc ctgagcgcct ctctgggcga cagagtgacc      60
atcacctgtc aggccagcca ggacatcagc aactacctga actggtatca gcagaaaccc     120
gacggcaccg tgaagctgct gatctactac accagcaggc tgcacaccgg cgtgcccagc     180
agattctctg gctctggcag cggcaccgac tacagcctga ccatctccaa cctggaccag     240
gaagatattg ccacctacta ctgccagcag ggcaacaccc tgccctggac attcggcgga     300
ggcaccaagc tggaaatcaa g                                                321
```

<210> SEQ ID NO 185
<211> LENGTH: 321
<212> TYPE: DNA
<213> ORGANISM: artificial
<220> FEATURE:
<223> OTHER INFORMATION: 122A2-VKhb

<400> SEQUENCE: 185

```
gacatccaga tgacccagag ccctagcagc ctgagcgcct ctgtgggcga cagagtgacc      60
atcacctgtc aggccagcca ggacatcagc aactacctga actggtatca gcagaaaccc     120
gacggcaccg tgaagctgct gatctactac accagcaggc tgcacaccgg cgtgcccagc     180
agattctctg gctctggcag cggcaccgac tacagcctga ccatctccaa cctggaccag     240
gaagatattg ccacctacta ctgccagcag ggcaacaccc tgccctggac attcggcgga     300
ggcaccaagc tggaaatcaa g                                                321
```

<210> SEQ ID NO 186
<211> LENGTH: 321
<212> TYPE: DNA
<213> ORGANISM: artificial
<220> FEATURE:
<223> OTHER INFORMATION: 122A2-VKhc

<400> SEQUENCE: 186

```
gacatccaga tgacccagag caccagcagc ctgagcgcct ctctgggcga cagagtgacc      60
atcacctgtc aggccagcca ggacatcagc aactacctga actggtatca gcagaaaccc     120
gacggcaccg tgaagctgct gatctactac accagcaacc tgcacaccgg cgtgcccagc     180
agattcagcg gctctggctc tggcaccgac tacagcctga ccatctccaa cctccagcag     240
gaagatattg ccacctacta ctgccagcag ggcaacaccc tgccctggac attcggcgga     300
ggcaccaagc tggaaatcaa g                                               321
```

<210> SEQ ID NO 187
<211> LENGTH: 321
<212> TYPE: DNA
<213> ORGANISM: artificial
<220> FEATURE:
<223> OTHER INFORMATION: 122A2-VKhd

<400> SEQUENCE: 187

```
gacatccaga tgacccagag ccctagcagc ctgagcgcct ctgtgggcga cagagtgacc      60
atcacctgtc aggccagcca ggacatcagc aactacctga actggtatca gcagaaaccc     120
gacggcaccg tgaagctgct gatctactac accagcaacc tgcacaccgg cgtgcccagc     180
agattcagcg gctctggctc tggcaccgac tacagcctga ccatctccaa cctccagcag     240
gaagatattg ccacctacta ctgccagcag ggcaacaccc tgccctggac attcggcgga     300
ggcaccaagc tggaaatcaa g                                               321
```

<210> SEQ ID NO 188
<211> LENGTH: 363
<212> TYPE: DNA
<213> ORGANISM: artificial
<220> FEATURE:
<223> OTHER INFORMATION: 102E9-VHha

<400> SEQUENCE: 188

```
cagatccatc tggtgcagag cggccctgag ctgaagaaac ccggcgagag cgtgaagatc      60
agctgcaagg ccagcggcta caccttcacc gactacagca tgcactgggt caagcaggcc     120
ccaggccagg gcctgaagtg gatgggctgg atcaacaccg agacaggcga gcccacctac     180
gccgacgact tcaagggcag attcgtgttc agcctggaca ccagcgtgtc caccgcctac     240
ctgcagatca acagcctgaa gaacgaggac acctccacct actactgcac ccggaacggc     300
tactacgtgg ggtactacgc catggactac tggggccagg gcacctccgt gaccgtgtca     360
tct                                                                  363
```

<210> SEQ ID NO 189
<211> LENGTH: 363
<212> TYPE: DNA
<213> ORGANISM: artificial
<220> FEATURE:
<223> OTHER INFORMATION: 102E9-VHhb

<400> SEQUENCE: 189

```
cagatccatc tggtgcagag cggccctgag ctgaagaaac ccggcgagag cgtgaagatc      60
```

```
agctgcaagg ccagcggcta ccttcacc gactacagca tgcactgggt ccgacaggcc     120
cctggacagg gcctgaagtg gatgggctgg atcaacaccg agacaggcga gcccacctac    180
gcccaggact tcaagggcag attcgtgttc agcctggaca ccagcgtgtc accgcctac     240 ctgcagatca acagcctgaa gaacgaggac acctccacct actactgcac ccggaacggc    300
tactacgtgg ggtactacgc catggactac tggggccagg gcacctccgt gaccgtgtca    360
tct                                                                  363

<210> SEQ ID NO 190
<211> LENGTH: 363
<212> TYPE: DNA
<213> ORGANISM: artificial
<220> FEATURE:
<223> OTHER INFORMATION: 102E9-VHhc

<400> SEQUENCE: 190
cagatccatc tggtgcagag cggcagcgag ctgaagaaac ccggcgagag cgtgaagatc     60
agctgcaagg ccagcggcta ccttcacc gactacagca tgcactgggt ccgacaggcc     120
cctggacagg gcctgaagtg gatgggctgg atcaacaccg agacaggcga gcccacctac    180
gcccaggact tcaagggcag attcgtgttc agcctggaca ccagcgtgtc accgcctac     240 ctgcagatca acagcctgaa gaacgaggac acctccacct actactgcac ccggaacggc    300
tactacgtgg ggtactacgc catggactac tggggccagg gcacctccgt gaccgtgtca    360
tct                                                                  363

<210> SEQ ID NO 191
<211> LENGTH: 318
<212> TYPE: DNA
<213> ORGANISM: artificial
<220> FEATURE:
<223> OTHER INFORMATION: 102E9-VKha

<400> SEQUENCE: 191
cagatccagc tgacccagag ccctagcttc ctgagcgcct ctcctggcga gagagtgacc     60
atcacctgta gcgccagcag ctccgtgatc tacatccact ggttccagca gaagcccggc    120
aaggccccta agctgtggat ctacagcacc agctacctgg ccagcggcgt gccaagcaga    180
ttcagcggct ctggctctgg caccgagtac accctgacca tcagctccat ggaagccgag    240
gacttcgcca cctactactg ccagcagagg cggagctacc ccttcacctt cggcggaggc    300
accaagctgg aaatcaag                                                  318

<210> SEQ ID NO 192
<211> LENGTH: 318
<212> TYPE: DNA
<213> ORGANISM: artificial
<220> FEATURE:
<223> OTHER INFORMATION: 102E9-VKhb

<400> SEQUENCE: 192
cagatccagc tgacccagag ccctagcttc ctgagcgcct ctcctggcga gagagtgacc     60
atcacctgta gcgccagcag ctccgtgatc tacatccact ggttccagca gaagcccggc    120
accgccccta agctgtggat ctacagcacc agctacctgg ccagcggcgt gccaagcaga    180
ttcagcggct ctggcagcgg caccgcctac accctgacca tcagcaggat ggaagccgag    240
gacttcgcca cctactactg ccagcagagg cggagctacc ccttcacctt cggcggaggc    300
```
accaagctgg aaatcaag                                                   318

<210> SEQ ID NO 193
<211> LENGTH: 318
<212> TYPE: DNA
<213> ORGANISM: artificial
<220> FEATURE:
<223> OTHER INFORMATION: 102E9-VKhc

<400> SEQUENCE: 193
cagatccagc tgacccagag ccctagcttc ctgagcgcct ctcctggcga cagagtgacc      60
atcacctgta cgccagcag ctccgtgatc tacatccact ggttccagca gaagcccggc     120
aaggccccta agctgtggat ctacagcacc agctacctgg ccagcggcgt gccaagcaga     180
ttcagcggct ctggctctgg caccgagtac accctgacca tcagctccat gcaggccgag     240
gacttcgcca cctactactg ccagcagagg cggagctacc ccttcacctt cggcggaggc     300
accaagctgg aaatcaag                                                  318

<210> SEQ ID NO 194
<211> LENGTH: 1344
<212> TYPE: DNA
<213> ORGANISM: artificial
<220> FEATURE:
<223> OTHER INFORMATION: 122A2-VHha-CH

<400> SEQUENCE: 194
caggtccagc tgcagcagtc tggcgccgaa gtggtcaagc ctggcgcctc cgtgaagatc      60
agctgcaagg gcagcggcta caccttcacc gactacagca tgcactgggt caagcaggcc     120
cacgccaaga gcctggaatg gatcggcgtg atcagcacct actacggcga cagcaactac     180
aaccagaagt tcaagggcaa agtcaccatg accgtggaca gagcagctc caccgcctac     240 atggaactga gcaggctgac cagcgacgac accgccgtgt actactgcgc cagaaacggc     300
aacttctacg tgatggacta ctggggccag ggcaccctgg tcaccgtgtc atctgcctcc     360
accaagggcc catccgtgtt ccccctggcc ccatccagca gtctacctc cggaggcaca     420 gccgccctgg gctgtctggt gaaggactac ttccccgagc cagtgaccgt gtcctggaac     480
tccggagccc tgacatccgg cgtgcacacc ttccccgccg tgctgcagtc cagcggcctg     540
tactctctgt cttccgtggt gaccgtgcca tccagctccc tgggaaccca gacatacatc     600
tgcaacgtga accacaagcc tagcaacacc aaggtggaca agaaggtgga gcctaagagc     660
tgtgacaaga cacacacatg ccctccttgt ccagcccctg agctgctggg cggcccctcc     720
gtgttcctgt tcccccccaa gcctaaggat accctgatga tcagcagaac ccccgaggtg     780
acctgcgtgg tggtggacgt gtcccacgag gatcccgagg tgaagttcaa ctggtacgtg     840
gacggcgtgg aggtgcacaa cgctaagacc aagcccagag aggagcagta caacagcaca     900
tacagagtgg tgtctgtgct gaccgtgctg caccaggact ggctgaacgg aaggagtac      960 aagtgcaagg tgtccaacaa ggccctgcct gcccctatcg agaagaccat ctctaaggct    1020
aaggggcagc ccgggagcc acaggtgtac accctgccac cagccgcga cgagctgacc     1080 aagaaccagg tgtccctgac atgcctggtg aagggattct accccagcga catcgccgtg     1140
gagtgggaga gcaacggcca gcccgagaac aactacaaga caccccctcc cgtgctggac    1200
agcgatggat ccttcttcct gtactccaag ctgaccgtgg acaagagcag gtggcagcag    1260
ggaaacgtgt tctcttgttc cgtgatgcac gaggctctgc acaaccacta cacccagaag    1320
tccctgagcc tgtctccagg caag                                          1344

<210> SEQ ID NO 195
<211> LENGTH: 1344
<212> TYPE: DNA
<213> ORGANISM: artificial
<220> FEATURE:
<223> OTHER INFORMATION: 122A2-VHhb-CH

<400> SEQUENCE: 195

| | |
|---|---|
| caggtccagc tgcagcagtc tggcgccgaa gtggtcaagc ctggcgcctc cgtgaagatc | 60 |
| agctgcaagg gcagcggcta caccttcacc gactacagca tgcactgggt ccgacaggcc | 120 |
| cacgccaaga gcctggaatg gatcggcgtg atcagcacct actacggcga cagcaactac | 180 |
| aaccagaagt tcaagggcaa agtcaccatg accgtggaca ccagcagctc caccgcctac | 240 |
| atggaactga gcaggctgag aagcgacgac accgccgtgt actactgcgc cagaaacggc | 300 |
| aacttctacg tgatggacta ctggggccag ggcaccctgg tcaccgtgtc atctgcctcc | 360 |
| accaagggcc catccgtgtt ccccctggcc catccagca agtctacctc cggaggcaca | 420 |
| gccgccctgg gctgtctggt gaaggactac ttccccgagc cagtgaccgt gtcctggaac | 480 |
| tccggagccc tgacatccgg cgtgcacacc ttccccgccg tgctgcagtc cagcggcctg | 540 |
| tactctctgt cttccgtggt gaccgtgcca tccagctccc tgggaaccca gacatacatc | 600 |
| tgcaacgtga accacaagcc tagcaacacc aaggtggaca gaaggtgga gcctaagagc | 660 |
| tgtgacaaga cacacacatg ccctccttgt ccagcccctg agctgctggg cggcccctcc | 720 |
| gtgttcctgt tccccccaa gcctaaggat accctgatga tcagcagaac ccccgaggtg | 780 |
| acctgcgtgg tggtggacgt gtcccacgag gatcccgagg tgaagttcaa ctggtacgtg | 840 |
| gacggcgtgg aggtgcacaa cgctaagacc aagcccagag aggagcagta caacagcaca | 900 |
| tacagagtgg tgtctgtgct gaccgtgctg caccaggact ggctgaacgg aaggagtac | 960 |
| aagtgcaagg tgtccaacaa ggccctgcct gcccctatcg agaagaccat ctctaaggct | 1020 |
| aagggcagc cccgggagcc acaggtgtac accctgccac ccagccgcga cgagctgacc | 1080 |
| aagaaccagg tgtccctgac atgcctggtg aagggattct accccagcga catcgccgtg | 1140 |
| gagtgggaga gcaacggcca gcccgagaac aactacaaga caacccctcc cgtgctggac | 1200 |
| agcgatggat ccttcttcct gtactccaag ctgaccgtgg acaagagcag gtggcagcag | 1260 |
| ggaaacgtgt tctcttgttc cgtgatgcac gaggctctgc acaaccacta cacccagaag | 1320 |
| tccctgagcc tgtctccagg caag | 1344 |

<210> SEQ ID NO 196
<211> LENGTH: 1344
<212> TYPE: DNA
<213> ORGANISM: artificial
<220> FEATURE:
<223> OTHER INFORMATION: 122A2-VHhc-CH

<400> SEQUENCE: 196

| | |
|---|---|
| caggtccagc tgcagcagtc tggcgccgaa gtggtcaagc ctggcgcctc cgtgaagatc | 60 |
| agctgcaagg gcagcggcta caccttcacc gactacagca tgcactgggt ccgacaggcc | 120 |
| cctggacagg gcctggaatg gatcggcgtg atcagcacct actacggcga cagcaactac | 180 |
| aaccagaagt tcaagggcaa agtcaccatg accgtggaca gagcagctc caccgcctac | 240 |
| atggaactga gcaggctgac cagcgacgac accgccgtgt actactgcgc cagaaacggc | 300 |
| aacttctacg tgatggacta ctggggccag ggcaccctgg tcaccgtgtc atctgcctcc | 360 |

```
accaagggcc catccgtgtt cccctggcc ccatccagca agtctacctc cggaggcaca    420
gccgccctgg gctgtctggt gaaggactac ttccccgagc cagtgaccgt gtcctggaac    480
tccggagccc tgacatccgg cgtgcacacc ttccccgccg tgctgcagtc cagcggcctg    540
tactctctgt cttccgtggt gaccgtgcca tccagctccc tgggaaccca gacatacatc    600
tgcaacgtga accacaagcc tagcaacacc aaggtggaca agaaggtgga gcctaagagc    660
tgtgacaaga cacacacatg ccctccttgt ccagccctg agctgctggg cggcccctcc    720
gtgttcctgt tccccccaa gcctaaggat accctgatga tcagcagaac cccgaggtg    780 acctgcgtgg tggtggacgt gtcccacgag gatcccgagg tgaagttcaa ctggtacgtg    840
gacggcgtgg aggtgcacaa cgctaagacc aagcccagag aggagcagta caacagcaca    900
tacagagtgg tgtctgtgct gaccgtgctg caccaggact ggctgaacgg gaaggagtac    960
aagtgcaagg tgtccaacaa ggccctgcct gcccctatcg agaagaccat ctctaaggct   1020
aaggggcagc ccgggagcc acaggtgtac accctgccac ccagccgcga cgagctgacc   1080
aagaaccagg tgtccctgac atgcctggtg aagggattct accccagcga catcgccgtg   1140
gagtgggaga gcaacggcca gcccgagaac aactacaaga caaccctcc cgtgctggac   1200 agcgatggat ccttcttcct gtactccaag ctgaccgtgg acaagagcag gtggcagcag   1260
ggaaacgtgt tctcttgttc cgtgatgcac gaggctctgc acaaccacta cacccagaag   1320
tccctgagcc tgtctccagg caag                                           1344

<210> SEQ ID NO 197
<211> LENGTH: 642
<212> TYPE: DNA
<213> ORGANISM: artificial
<220> FEATURE:
<223> OTHER INFORMATION: 122A2-VKha-CL

<400> SEQUENCE: 197
gacatccaga tgacccagag caccagcagc ctgagcgcct ctctgggcga cagagtgacc     60
atcacctgtc aggccagcca ggacatcagc aactacctga actggtatca gcagaaaccc    120
gacggcaccg tgaagctgct gatctactac accagcaggc tgcacaccgg cgtgcccagc    180
agattctctg gctctggcag cggcaccgac tacagcctga ccatctccaa cctggaccag    240
gaagatattg ccacctacta ctgccagcag ggcaacaccc tgcccctgga cattcggcgga    300 ggcaccaagc tggaaatcaa gcgaactgtg gctgcaccaa gtgtcttcat ctttcctccg    360
agtgatgagc agctgaagag cggacagct tctgtggtgt gtctgctgaa taacttctac    420
ccaagagaag caaaggtcca gtggaaggtg gacaacgccc tgcagtctgg caactcacag    480
gagtctgtca ctgagcagga ttccaaggac agcacttaca gcctgtccag caccctcact    540
ctgtccaaag ccgactacga aaagcataag gtgtatgctt gtgaggtgac ccaccaggga    600
ctgagcagcc ctgtgacgaa gtccttcaac cggggcgagt gc                        642

<210> SEQ ID NO 198
<211> LENGTH: 642
<212> TYPE: DNA
<213> ORGANISM: artificial
<220> FEATURE:
<223> OTHER INFORMATION: 122A2-VKhb-CL

<400> SEQUENCE: 198
gacatccaga tgacccagag ccctagcagc ctgagcgcct ctgtgggcga cagagtgacc     60
atcacctgtc aggccagcca ggacatcagc aactacctga actggtatca gcagaaaccc    120
```

```
gacggcaccg tgaagctgct gatctactac accagcaggc tgcacaccgg cgtgcccagc    180
agattctctg gctctggcag cggcaccgac tacagcctga ccatctccaa cctggaccag    240
gaagatattg ccacctacta ctgccagcag ggcaacaccc tgccctggac attcggcgga    300
ggcaccaagc tggaaatcaa gcgaactgtg gctgcaccaa gtgtcttcat ctttcctccg    360
agtgatgagc agctgaagag cgggacagct tctgtggtgt gtctgctgaa taacttctac    420
ccaagagaag caaaggtcca gtggaaggtg gacaacgccc tgcagtctgg caactcacag    480
gagtctgtca ctgagcagga ttccaaggac agcacttaca gcctgtccag caccctcact    540
ctgtccaaag ccgactacga aaagcataag gtgtatgctt gtgaggtgac ccaccaggga    600
ctgagcagcc ctgtgacgaa gtccttcaac cggggcgagt gc                      642
```

<210> SEQ ID NO 199
<211> LENGTH: 642
<212> TYPE: DNA
<213> ORGANISM: artificial
<220> FEATURE:
<223> OTHER INFORMATION: 122A2-VKhc-CL
<400> SEQUENCE: 199

```
gacatccaga tgacccagag caccagcagc ctgagcgcct ctctgggcga cagagtgacc     60
atcacctgtc aggccagcca ggacatcagc aactacctga actggtatca gcagaaaccc    120
gacggcaccg tgaagctgct gatctactac accagcaacc tgcacaccgg cgtgcccagc    180
agattcagcg gctctggctc tggcaccgac tacagcctga ccatctccaa cctccagcag    240
gaagatattg ccacctacta ctgccagcag ggcaacaccc tgccctggac attcggcgga    300
ggcaccaagc tggaaatcaa gcgaactgtg gctgcaccaa gtgtcttcat ctttcctccg    360
agtgatgagc agctgaagag cgggacagct tctgtggtgt gtctgctgaa taacttctac    420
ccaagagaag caaaggtcca gtggaaggtg gacaacgccc tgcagtctgg caactcacag    480
gagtctgtca ctgagcagga ttccaaggac agcacttaca gcctgtccag caccctcact    540
ctgtccaaag ccgactacga aaagcataag gtgtatgctt gtgaggtgac ccaccaggga    600
ctgagcagcc ctgtgacgaa gtccttcaac cggggcgagt gc                      642
```

<210> SEQ ID NO 200
<211> LENGTH: 642
<212> TYPE: DNA
<213> ORGANISM: artificial
<220> FEATURE:
<223> OTHER INFORMATION: 122A2-VKhd-CL
<400> SEQUENCE: 200

```
gacatccaga tgacccagag ccctagcagc ctgagcgcct ctgtgggcga cagagtgacc     60
atcacctgtc aggccagcca ggacatcagc aactacctga actggtatca gcagaaaccc    120
gacggcaccg tgaagctgct gatctactac accagcaacc tgcacaccgg cgtgcccagc    180
agattcagcg gctctggctc tggcaccgac tacagcctga ccatctccaa cctccagcag    240
gaagatattg ccacctacta ctgccagcag ggcaacaccc tgccctggac attcggcgga    300
ggcaccaagc tggaaatcaa gcgaactgtg gctgcaccaa gtgtcttcat ctttcctccg    360
agtgatgagc agctgaagag cgggacagct tctgtggtgt gtctgctgaa taacttctac    420
ccaagagaag caaaggtcca gtggaaggtg gacaacgccc tgcagtctgg caactcacag    480
gagtctgtca ctgagcagga ttccaaggac agcacttaca gcctgtccag caccctcact    540
```

```
ctgtccaaag ccgactacga aaagcataag gtgtatgctt gtgaggtgac ccaccaggga    600
ctgagcagcc ctgtgacgaa gtccttcaac cggggcgagt gc                       642

<210> SEQ ID NO 201
<211> LENGTH: 1353
<212> TYPE: DNA
<213> ORGANISM: artificial
<220> FEATURE:
<223> OTHER INFORMATION: 102E9-VHha-CH

<400> SEQUENCE: 201
cagatccatc tggtgcagag cggccctgag ctgaagaaac ccggcgagag cgtgaagatc    60
agctgcaagg ccagcggcta caccttcacc gactacagca tgcactgggt caagcaggcc   120
ccaggccagg gcctgaagtg gatgggctgg atcaacaccg agacaggcga gcccacctac   180
gccgacgact tcaagggcag attcgtgttc agcctggaca ccagcgtgtc caccgcctac   240
ctgcagatca acagcctgaa gaacgaggac acctccacct actactgcac ccggaacggc   300
tactacgtgg ggtactacgc catggactac tggggccagg gcacctccgt gaccgtgtca   360
tctgcctcca ccaagggccc atccgtgttc cccctggccc catccagcaa gtctacctcc   420
ggaggcacag ccgccctggg ctgtctggtg aaggactact cccccgagcc agtgaccgtg   480
tcctggaact ccggagccct gacatccggc gtgcacacct tccccgccgt gctgcagtcc   540
agcggcctgt actctctgtc ttccgtggtg accgtgccat ccagctccct gggaacccag   600
acatacatct gcaacgtgaa ccacaagcct agcaacacca aggtggacaa gaaggtggag   660
cctaagagct gtgacaagac acacacatgc cctccttgtc cagcccctga gctgctgggc   720
ggcccctccg tgttcctgtt ccccccaaag cctaaggata ccctgatgat cagcagaacc   780
cccgaggtga cctgcgtggt ggtggacgtg tcccacgagg atcccgaggt gaagttcaac   840
tggtacgtgg acggcgtgga ggtgcacaac gctaagacca gcccagagga ggagcagtac   900
aacagcacat acagagtggt gtctgtgctg accgtgctgc accaggactg gctgaacggg   960
aaggagtaca agtgcaaggt gtccaacaag gccctgcctg cccctatcga aaagaccatc  1020
tctaaggcta aggggcagcc ccgggagcca caggtgtaca ccctgccacc cagccgcgac  1080
gagctgacca agaaccaggt gtccctgaca tgcctggtga agggattcta ccccagcgac  1140
atcgccgtgg agtgggagag caacggccag cccgagaaca actacaagac aaccccctcc  1200
gtgctggaca gcgatggatc cttcttcctg tactccaagc tgaccgtgga caagagcagg  1260
tggcagcagg gaaacgtgtt ctcttgttcc gtgatgcacg aggctctgca caaccactac  1320
acccagaagt ccctgagcct gtctccaggc aag                               1353

<210> SEQ ID NO 202
<211> LENGTH: 1353
<212> TYPE: DNA
<213> ORGANISM: artificial
<220> FEATURE:
<223> OTHER INFORMATION: 102E9-VHhb-CH

<400> SEQUENCE: 202
cagatccatc tggtgcagag cggccctgag ctgaagaaac ccggcgagag cgtgaagatc    60
agctgcaagg ccagcggcta caccttcacc gactacagca tgcactgggt ccgacaggcc   120
cctggacagg gcctgaagtg gatgggctgg atcaacaccg agacaggcga gcccacctac   180
gcccaggact tcaagggcag attcgtgttc agcctggaca ccagcgtgtc caccgcctac   240
ctgcagatca acagcctgaa gaacgaggac acctccacct actactgcac ccggaacggc   300
```

```
tactacgtgg ggtactacgc catggactac tggggccagg gcacctccgt gaccgtgtca    360
tctgcctcca ccaagggccc atccgtgttc ccctggccc catccagcaa gtctacctcc      420
ggaggcacag ccgccctggg ctgtctggtg aaggactact ccccgagcc agtgaccgtg       480 tcctggaact ccggagccct gacatccggc gtgcacacct ccccgccgt gctgcagtcc       540 agcggcctgt actctctgtc ttccgtggtg accgtgccat ccagctccct gggaacccag     600
acatacatct gcaacgtgaa ccacaagcct agcaacacca aggtggacaa gaaggtggag     660
cctaagagct gtgacaagac acacacatgc cctccttgtc cagcccctga gctgctgggc    720
ggcccctccg tgttcctgtt ccccccaag cctaaggata ccctgatgat cagcagaacc      780
cccgaggtga cctgcgtggt ggtggacgtg tcccacgagg atcccgaggt gaagttcaac    840
tggtacgtgg acggcgtgga ggtgcacaac gctaagacca gcccagaga ggagcagtac     900 aacagcacat acagagtggt gtctgtgctg accgtgctgc accaggactg gctgaacggg    960
aaggagtaca gtgcaaggt gtccaacaag gccctgcctg ccctatcga gaagaccatc       1020 tctaaggcta aggggcagcc ccgggagcca caggtgtaca cctgccacc cagccgcgac      1080 gagctgacca agaaccaggt gtccctgaca tgcctggtga aaggattcta ccccagcgac    1140
atcgccgtgg agtgggagag caacggccag cccgagaaca actacaagac aaccccctccc  1200 gtgctggaca gcgatggatc cttcttcctg tactccaagc tgaccgtgga caagagcagg    1260
tggcagcagg gaaacgtgtt ctcttgttcc gtgatgcacg aggctctgca caaccactac    1320
acccagaagt ccctgagcct gtctccaggc aag                                 1353
```

<210> SEQ ID NO 203
<211> LENGTH: 1353
<212> TYPE: DNA
<213> ORGANISM: artificial
<220> FEATURE:
<223> OTHER INFORMATION: 102E9-VHhc-CH

<400> SEQUENCE: 203

```
cagatccatc tggtgcagag cggcagcgag ctgaagaaac ccggcgagag cgtgaagatc     60
agctgcaagg ccagcggcta caccttcacc gactacagca tgcactgggt ccgacaggcc   120
cctggacagg gcctgaagtg gatgggctgg atcaacaccg agacaggcga gcccacctac   180
gcccaggact tcaagggcag attcgtgttc agcctggaca ccagcgtgtc caccgcctac   240
ctgcagatca acagcctgaa gaacgaggac acctccacct actactgcac ccggaacggc   300
tactacgtgg ggtactacgc catggactac tggggccagg gcacctccgt gaccgtgtca    360
tctgcctcca ccaagggccc atccgtgttc cccctggccc catccagcaa gtctacctcc   420
ggaggcacag ccgccctggg ctgtctggtg aaggactact ccccgagcc agtgaccgtg    480 tcctggaact ccggagccct gacatccggc gtgcacacct ccccgccgt gctgcagtcc    540 agcggcctgt actctctgtc ttccgtggtg accgtgccat ccagctccct gggaacccag   600
acatacatct gcaacgtgaa ccacaagcct agcaacacca aggtggacaa gaaggtggag   660
cctaagagct gtgacaagac acacacatgc cctccttgtc cagcccctga gctgctgggc   720
ggcccctccg tgttcctgtt ccccccaag cctaaggata ccctgatgat cagcagaacc    780
cccgaggtga cctgcgtggt ggtggacgtg tcccacgagg atcccgaggt gaagttcaac   840
tggtacgtgg acggcgtgga ggtgcacaac gctaagacca gcccagaga ggagcagtac   900 aacagcacat acagagtggt gtctgtgctg accgtgctgc accaggactg gctgaacggg   960
```

```
aaggagtaca agtgcaaggt gtccaacaag gccctgcctg cccctatcga aagaccatc    1020 tctaaggcta agggggcagcc ccgggagcca caggtgtaca ccctgccacc cagccgcgac   1080
gagctgacca agaaccaggt gtccctgaca tgcctggtga agggattcta ccccagcgac   1140
atcgccgtgg agtgggagag caacggccag cccgagaaca actacaagac aaccctccc   1200 gtgctggaca gcgatggatc cttcttcctg tactccaagc tgaccgtgga caagagcagg   1260
tggcagcagg gaaacgtgtt ctcttgttcc gtgatgcacg aggctctgca caaccactac   1320
acccagaagt ccctgagcct gtctccaggc aag                                1353
```

<210> SEQ ID NO 204
<211> LENGTH: 639
<212> TYPE: DNA
<213> ORGANISM: artificial
<220> FEATURE:
<223> OTHER INFORMATION: 102E9-VKha-CL

<400> SEQUENCE: 204

```
cagatccagc tgacccagag ccctagcttc ctgagcgcct tcctggcgca gagagtgacc    60
atcacctgta gcgccagcag ctccgtgatc tacatccact ggttccagca gaagcccggc   120
aaggccccta agctgtggat ctacagcacc agctacctgg ccagcggcgt gccaagcaga   180
ttcagcggct ctggctctgg caccgagtac accctgacca tcagctccat ggaagccgag   240
gacttcgcca cctactactg ccagcagagg cggagctacc ccttcacctt cggcggaggc   300
accaagctgg aaatcaagcg aactgtggct gcaccaagtg tcttcatctt cctccgagt    360 gatgagcagc tgaagagcgg acagcttct gtggtgtgtc tgctgaataa cttctaccca    420
agagaagcaa aggtccagtg gaaggtggac aacgccctgc agtctggcaa ctcacaggag   480
tctgtcactg agcaggattc caaggacagc acttacagcc tgtccagcac cctcactctg   540
tccaaagccg actacgaaaa gcataaggtg tatgcttgtg aggtgaccca ccagggactg    600
agcagccctg tgacgaagtc cttcaaccgg ggcgagtgc                          639
```

<210> SEQ ID NO 205
<211> LENGTH: 639
<212> TYPE: DNA
<213> ORGANISM: artificial
<220> FEATURE:
<223> OTHER INFORMATION: 102E9-VKhb-CL

<400> SEQUENCE: 205

```
cagatccagc tgacccagag ccctagcttc ctgagcgcct tcctggcgca gagagtgacc    60
atcacctgta gcgccagcag ctccgtgatc tacatccact ggttccagca gaagcccggc   120
accgccccta agctgtggat ctacagcacc agctacctgg ccagcggcgt gccaagcaga   180
ttcagcggct ctggcagcgg caccctcctac accctgacca tcagcaggat ggaagccgag   240
gacttcgcca cctactactg ccagcagagg cggagctacc ccttcacctt cggcggaggc   300
accaagctgg aaatcaagcg aactgtggct gcaccaagtg tcttcatctt cctccgagt    360 gatgagcagc tgaagagcgg acagcttct gtggtgtgtc tgctgaataa cttctaccca    420
agagaagcaa aggtccagtg gaaggtggac aacgccctgc agtctggcaa ctcacaggag   480
tctgtcactg agcaggattc caaggacagc acttacagcc tgtccagcac cctcactctg   540
tccaaagccg actacgaaaa gcataaggtg tatgcttgtg aggtgaccca ccagggactg    600
agcagccctg tgacgaagtc cttcaaccgg ggcgagtgc                          639
```

<210> SEQ ID NO 206
<211> LENGTH: 639
<212> TYPE: DNA
<213> ORGANISM: artificial
<220> FEATURE:
<223> OTHER INFORMATION: 102E9-VKhc-CL

<400> SEQUENCE: 206

```
cagatccagc tgacccagag ccctagcttc ctgagcgcct ctcctggcga cagagtgacc      60
atcacctgta gcgccagcag ctccgtgatc tacatccact ggttccagca gaagcccggc     120
aaggccccta agctgtggat ctacagcacc agctacctgg ccagcggcgt gccaagcaga     180
ttcagcggct ctggctctgg caccgagtac accctgacca tcagtccat gcaggccgag      240
gacttcgcca cctactactg ccagcagagg cggagctacc ccttcacctt cggcggaggc     300
accaagctgg aaatcaagcg aactgtggct gcaccaagtg tcttcatctt tcctccgagt     360
gatgagcagc tgaagagcgg acagcttct gtggtgtgtc tgctgaataa cttctaccca      420
agagaagcaa aggtccagtg gaaggtggac aacgccctgc agtctggcaa ctcacaggag     480
tctgtcactg agcaggattc caaggacagc acttacagcc tgtccagcac cctcactctg     540
tccaaagccg actacgaaaa gcataaggtg tatgcttgtg aggtgaccca ccagggactg     600
agcagccctg tgacgaagtc cttcaaccgg ggcgagtgc                            639
```

<210> SEQ ID NO 207
<211> LENGTH: 1398
<212> TYPE: DNA
<213> ORGANISM: artificial
<220> FEATURE:
<223> OTHER INFORMATION: 122A2-MB7-VHha-CH

<400> SEQUENCE: 207

```
atgaggtggt cctggatctt cctgctgctg ctgagcatca ccagcgccaa cgcccaggtc      60
cagctgcagc agtctggcgc cgaagtggtc aagcctggcg cctccgtgaa gatcagctgc     120
aagggcagcg gctacacctt caccgactac agcatgcact gggtcaagca ggcccacgcc     180
aagagcctgg aatggatcgg cgtgatcagc acctactacg cgacagcaa ctacaaccag      240
aagttcaagg gcaaagtcac catgaccgtg gacaagagca gctccaccgc ctacatggaa     300
ctgagcaggc tgaccagcga cgacaccgcc gtgtactact gcgccagaaa cggcaacttc     360
tacgtgatgg actactgggg ccagggcacc ctggtcaccg tgtcatctgc ctccaccaag     420
ggcccatccg tgttccccct ggccccatcc agcaagtcta cctccggagg cacagccgcc     480
ctgggctgtc tggtgaagga ctacttcccc gagccagtga ccgtgtcctg gaactccgga     540
gccctgacat ccggcgtgca caccttcccc gccgtgctgc agtccagcgg cctgtactct     600
ctgtcttccg tggtgaccgt gccatccagc tccctgggaa cccagacata catctgcaac     660
gtgaaccaca agcctagcaa caccaaggtg gacaagaagg tggagcctaa gagctgtgac     720
aagacacaca tgccctcc ttgtccagcc cctgagctgc tgggcggcc ctccgtgttc        780
ctgttccccc ccaagcctaa ggatacctg atgatcagca gaaccccga ggtgacctgc       840
gtggtggtgg acgtgtccca cgaggatccc gaggtgaagt tcaactggta cgtggacggc     900
gtggaggtgc acaacgctaa gaccaagccc agagaggagc agtacaacag cacatacaga     960
gtggtgtctg tgctgaccgt gctgcaccag gactggctga acggaagga gtacaagtgc    1020
aaggtgtcca acaaggccct gcctgcccct atcgagaaga ccatctctaa ggctaagggg    1080
cagccccggg agccacaggt gtacaccctg ccacccagcc gcgacgagct gaccaagaac    1140
```

```
caggtgtccc tgacatgcct ggtgaaggga ttctacccca gcgacatcgc cgtggagtgg    1200
gagagcaacg gccagcccga gaacaactac aagacaaccc ctcccgtgct ggacagcgat    1260
ggatccttct tcctgtactc caagctgacc gtggacaaga gcaggtggca gcagggaaac    1320
gtgttctctt gttccgtgat gcacgaggct ctgcacaacc actacaccca gaagtccctg    1380
agcctgtctc caggcaag                                                 1398

<210> SEQ ID NO 208
<211> LENGTH: 1398
<212> TYPE: DNA
<213> ORGANISM: artificial
<220> FEATURE:
<223> OTHER INFORMATION: 122A2-MB7-VHhb-CH

<400> SEQUENCE: 208
atgaggtggt cctggatctt cctgctgctg ctgagcatca ccagcgccaa cgcccaggtc     60
cagctgcagc agtctggcgc cgaagtggtc aagcctggcg cctccgtgaa gatcagctgc    120
aagggcagcg gctacacctt caccgactac agcatgcact gggtccgaca ggcccacgcc    180
aagagcctgg aatggatcgg cgtgatcagc acctactacg gcgacagcaa ctacaaccag    240
aagttcaagg gcaaagtcac catgaccgtg gacaccagcg ctccaccgc ctacatggaa    300 ctgagcaggc tgagaagcga cgacaccgcc gtgtactact gcgccagaaa cggcaacttc    360
tacgtgatgg actactgggg ccagggcacc ctggtcaccg tgtcatctgc ctccaccaag    420
ggcccatccg tgttccccct ggccccatcc agcaagtcta cctccggagg cacagccgcc    480
ctgggctgtc tggtgaagga ctacttcccc gagccagtga ccgtgtcctg gaactccgga    540
gccctgacat ccggcgtgca caccttcccc gccgtgctgc agtccagcgg cctgtactct    600
ctgtcttccg tggtgaccgt gccatccagc tccctgggaa cccagacata catctgcaac    660
gtgaaccaca agcctagcaa caccaaggtg gacaagaagg tggagcctaa gagctgtgac    720
aagacacaca tgccctcc ttgtccagcc cctgagctgc tgggcggccc ctccgtgttc    780
ctgttccccc ccaagcctaa ggatacctg atgatcagca gaaccccga ggtgacctgc    840 gtggtggtgg acgtgtccca cgaggatccc gaggtgaagt tcaactggta cgtggacggc    900
gtggaggtgc acaacgctaa gaccaagccc agagaggagc agtacaacag cacatacaga    960
gtggtgtctg tgctgaccgt gctgcaccag gactggctga acgggaagga gtacaagtgc    1020
aaggtgtcca acaaggccct gcctgcccct atcgagaaga ccatctctaa ggctaagggg    1080
cagccccggg agccacaggt gtacaccctg ccacccagcc gcgacgagct gaccaagaac    1140
caggtgtccc tgacatgcct ggtgaaggga ttctacccca gcgacatcgc cgtggagtgg    1200
gagagcaacg gccagcccga gaacaactac aagacaaccc ctcccgtgct ggacagcgat    1260
ggatccttct tcctgtactc caagctgacc gtggacaaga gcaggtggca gcagggaaac    1320
gtgttctctt gttccgtgat gcacgaggct ctgcacaacc actacaccca gaagtccctg    1380
agcctgtctc caggcaag                                                 1398

<210> SEQ ID NO 209
<211> LENGTH: 1398
<212> TYPE: DNA
<213> ORGANISM: artificial
<220> FEATURE:
<223> OTHER INFORMATION: 122A2-MB7-VHhc-CH

<400> SEQUENCE: 209
atgaggtggt cctggatctt cctgctgctg ctgagcatca ccagcgccaa cgcccaggtc     60
```

| | |
|---|---|
| cagctgcagc agtctggcgc cgaagtggtc aagcctggcg cctccgtgaa gatcagctgc | 120 |
| aagggcagcg gctacacctt caccgactac agcatgcact gggtccgaca ggcccctgga | 180 |
| cagggcctgg aatggatcgg cgtgatcagc acctactacg gcgacagcaa ctacaaccag | 240 |
| aagttcaagg gcaaagtcac catgaccgtg gacaagagca gctccaccgc ctacatggaa | 300 |
| ctgagcaggc tgaccagcga cgacaccgcc gtgtactact gcgccagaaa cggcaacttc | 360 |
| tacgtgatgg actactgggg ccagggcacc ctggtcaccg tgtcatctgc ctccaccaag | 420 |
| ggcccatccg tgttccccct ggccccatcc agcaagtcta cctccggagg cacagccgcc | 480 |
| ctgggctgtc tggtgaagga ctacttcccc gagccagtga ccgtgtcctg gaactccgga | 540 |
| gccctgacat ccggcgtgca caccttcccc gccgtgctgc agtccagcgg cctgtactct | 600 |
| ctgtcttccg tggtgaccgt gccatccagc tccctgggaa cccagacata catctgcaac | 660 |
| gtgaaccaca agcctagcaa caccaaggtg gacaagaagg tggagcctaa agctgtgac | 720 |
| aagacacaca tgccctcc ttgtccagcc cctgagctgc tgggcggccc ctccgtgttc | 780 |
| ctgttccccc ccaagcctaa ggataccctg atgatcagca gaaccccga ggtgacctgc | 840 |
| gtggtggtgg acgtgtccca cgaggatccc gaggtgaagt tcaactggta cgtggacggc | 900 |
| gtggaggtgc acaacgctaa gaccaagccc agagaggagc agtacaacag cacatacaga | 960 |
| gtggtgtctg tgctgaccgt gctgcaccag gactggctga cgggaagga gtacaagtgc | 1020 |
| aaggtgtcca acaaggccct gcctgcccct atcgagaaga ccatctctaa ggctaagggg | 1080 |
| cagccccggg agccacaggt gtacaccctg ccacccagcc gcgacgagct gaccaagaac | 1140 |
| caggtgtccc tgacatgcct ggtgaaggga ttctacccca gcgacatcgc cgtggagtgg | 1200 |
| gagagcaacg gccagcccga gaacaactac aagacaaccc ctcccgtgct ggacagcgat | 1260 |
| ggatccttct tcctgtactc caagctgacc gtggacaaga gcaggtggca gcagggaaac | 1320 |
| gtgttctctt gttccgtgat gcacgaggct ctgcacaacc actacaccca gaagtccctg | 1380 |
| agcctgtctc caggcaag | 1398 |

<210> SEQ ID NO 210
<211> LENGTH: 696
<212> TYPE: DNA
<213> ORGANISM: artificial
<220> FEATURE:
<223> OTHER INFORMATION: 122A2-MB7-VKha-CL

<400> SEQUENCE: 210

| | |
|---|---|
| atgaggtggt cctggatctt cctgctgctg ctgagcatca ccagcgccaa cgccgacatc | 60 |
| cagatgaccc agagcaccag cagcctgagc gcctctctgg gcgacagagt gaccatcacc | 120 |
| tgtcaggcca gccaggacat cagcaactac ctgaactggt atcagcagaa acccgacggc | 180 |
| accgtgaagc tgctgatcta ctacaccagc aggctgcaca ccggcgtgcc cagcagattc | 240 |
| tctggctctg gcagcggcac cgactacagc ctgaccatct ccaacctgga ccaggaagat | 300 |
| attgccacct actactgcca gcagggcaac accctgccct ggacattcgg cggaggcacc | 360 |
| aagctggaaa tcaagcgaac tgtggctgca ccaagtgtct tcatctttcc tccgagtgat | 420 |
| gagcagctga gagcgggac agcttctgtg gtgtgtctgc tgaataactt ctacccaaga | 480 |
| gaagcaaagg tccagtggaa ggtggacaac gccctgcagt ctggcaactc acaggagtct | 540 |
| gtcactgagc aggattccaa ggacagcact tacagcctgt ccagcaccct cactctgtcc | 600 |
| aaagccgact acgaaaagca taaggtgtat gcttgtgagg tgacccacca gggactgagc | 660 | agccctgtga cgaagtcctt caaccggggc gagtgc 696

<210> SEQ ID NO 211
<211> LENGTH: 696
<212> TYPE: DNA
<213> ORGANISM: artificial
<220> FEATURE:
<223> OTHER INFORMATION: 122A2-MB7-VKhb-CL

<400> SEQUENCE: 211
atgaggtggt cctggatctt cctgctgctg ctgagcatca ccagcgccaa cgccgacatc 60
cagatgaccc agagccctag cagcctgagc gcctctgtgg gcgacagagt gaccatcacc 120
tgtcaggcca gccaggacat cagcaactac ctgaactggt atcagcagaa acccgacggc 180
accgtgaagc tgctgatcta ctacaccagc aggctgcaca ccggcgtgcc cagcagattc 240
tctggctctg gcagcggcac cgactacagc ctgaccatct ccaacctgga ccaggaagat 300
attgccacct actactgcca gcagggcaac accctgccct ggacattcgg cggaggcacc 360
aagctggaaa tcaagcgaac tgtggctgca ccaagtgtct tcatctttcc tccgagtgat 420
gagcagctga agagcgggac agcttctgtg gtgtgtctgc tgaataactt ctacccaaga 480
gaagcaaagg tccagtggaa ggtggacaac gccctgcagt ctggcaactc acaggagtct 540
gtcactgagc aggattccaa ggacagcact tacagcctgt ccagcaccct cactctgtcc 600
aaagccgact acgaaaagca taaggtgtat gcttgtgagg tgacccacca gggactgagc 660
agccctgtga cgaagtcctt caaccggggc gagtgc 696

<210> SEQ ID NO 212
<211> LENGTH: 696
<212> TYPE: DNA
<213> ORGANISM: artificial
<220> FEATURE:
<223> OTHER INFORMATION: 122A2-MB7-VKhc-CL

<400> SEQUENCE: 212
atgaggtggt cctggatctt cctgctgctg ctgagcatca ccagcgccaa cgccgacatc 60
cagatgaccc agagccaccag cagcctgagc gcctctctgg gcgacagagt gaccatcacc 120
tgtcaggcca gccaggacat cagcaactac ctgaactggt atcagcagaa acccgacggc 180
accgtgaagc tgctgatcta ctacaccagc aacctgcaca ccggcgtgcc cagcagattc 240
agcggctctg gctctggcac cgactacagc ctgaccatct ccaacctcca gcaggaagat 300
attgccacct actactgcca gcagggcaac accctgccct ggacattcgg cggaggcacc 360
aagctggaaa tcaagcgaac tgtggctgca ccaagtgtct tcatctttcc tccgagtgat 420
gagcagctga agagcgggac agcttctgtg gtgtgtctgc tgaataactt ctacccaaga 480
gaagcaaagg tccagtggaa ggtggacaac gccctgcagt ctggcaactc acaggagtct 540
gtcactgagc aggattccaa ggacagcact tacagcctgt ccagcaccct cactctgtcc 600
aaagccgact acgaaaagca taaggtgtat gcttgtgagg tgacccacca gggactgagc 660
agccctgtga cgaagtcctt caaccggggc gagtgc 696

<210> SEQ ID NO 213
<211> LENGTH: 696
<212> TYPE: DNA
<213> ORGANISM: artificial
<220> FEATURE:
<223> OTHER INFORMATION: 122A2-MB7-VKhd-CL

<400> SEQUENCE: 213

| | |
|---|---|
| atgaggtggt cctggatctt cctgctgctg ctgagcatca ccagcgccaa cgccgacatc | 60 |
| cagatgaccc agagccctag cagcctgagc gcctctgtgg gcgacagagt gaccatcacc | 120 |
| tgtcaggcca gccaggacat cagcaactac ctgaactggt atcagcagaa acccgacggc | 180 |
| accgtgaagc tgctgatcta ctacaccagc aacctgcaca ccggcgtgcc cagcagattc | 240 |
| agcggctctg gctctggcac cgactacagc ctgaccatct ccaacctcca gcaggaagat | 300 |
| attgccacct actactgcca gcagggcaac accctgccct ggacattcgg cggaggcacc | 360 |
| aagctggaaa tcaagcgaac tgtggctgca ccaagtgtct tcatctttcc tccgagtgat | 420 |
| gagcagctga gagcgggac agcttctgtg gtgtgtctgc tgaataactt ctacccaaga | 480 |
| gaagcaaagg tccagtggaa ggtggacaac gccctgcagt ctggcaactc acaggagtct | 540 |
| gtcactgagc aggattccaa ggacagcact tacagcctgt ccagcaccct cactctgtcc | 600 |
| aaagccgact acgaaaagca taaggtgtat gcttgtgagg tgacccacca gggactgagc | 660 |
| agccctgtga cgaagtcctt caaccggggc gagtgc | 696 |

<210> SEQ ID NO 214
<211> LENGTH: 1407
<212> TYPE: DNA
<213> ORGANISM: artificial
<220> FEATURE:
<223> OTHER INFORMATION: 102E9-MB7-VHha-CH

<400> SEQUENCE: 214

| | |
|---|---|
| atgaggtggt cctggatctt cctgctgctg ctgagcatca ccagcgccaa cgcccagatc | 60 |
| catctggtgc agagcggccc tgagctgaag aaacccggcg agagcgtgaa gatcagctgc | 120 |
| aaggccagcg gctacacctt caccgactac agcatgcact gggtcaagca ggccccaggc | 180 |
| cagggcctga agtggatggg ctggatcaac accgagacag gcgagcccac ctacgccgac | 240 |
| gacttcaagg gcagattcgt gttcagcctg gacaccagcg tgtccaccgc ctacctgcag | 300 |
| atcaacagcc tgaagaacga ggacacctcc acctactact gcacccggaa cggctactac | 360 |
| gtggggtact acgccatgga ctactggggc cagggcacct ccgtgaccgt gtcatctgcc | 420 |
| tccaccaagg gcccatccgt gttccccctg gccccatcca gcaagtctac ctccggaggc | 480 |
| acagccgccc tgggctgtct ggtgaaggac tacttccccg agccagtgac cgtgtcctgg | 540 |
| aactccggag ccctgacatc cggcgtgcac accttccccg ccgtgctgca gtccagcggc | 600 |
| ctgtactctc tgtcttccgt ggtgaccgtg ccatccagct ccctgggaac ccagacatac | 660 |
| atctgcaacg tgaaccacaa gcctagcaac accaaggtgg acaagaaggt ggagcctaag | 720 |
| agctgtgaca gacacacac atgccctcct gtccagccc ctgagctgct gggcggcccc | 780 |
| tccgtgttcc tgttcccccc caagcctaag gatacccctga tgatcagcag aaccccgag | 840 |
| gtgacctgcg tggtggtgga cgtgtcccac gaggatcccg aggtgaagtt caactggtac | 900 |
| gtggacggcg tggaggtgca caacgctaag accaagccca gagaggagca gtacaacagc | 960 |
| acatacagag tggtgtctgt gctgaccgtg ctgcaccagg actggctgaa cgggaaggag | 1020 |
| tacaagtgca aggtgtccaa caaggccctg cctgccccta tcgagaagac catctctaag | 1080 |
| gctaagggc agccccggga ccacaggtg tacaccctgc cacccagccg cgacgagctg | 1140 |
| accaagaacc aggtgtccct gacatgcctg gtgaagggat tctaccccag cgacatcgcc | 1200 |
| gtggagtggg agagcaacgg ccagcccgag aacaactaca agacaacccc tcccgtgctg | 1260 |
| gacagcgatg gatccttctt cctgtactcc aagctgaccg tggacaagag caggtggcag | 1320 |

| | |
|---|---|
| cagggaaacg tgttctcttg ttccgtgatg cacgaggctc tgcacaacca ctacacccag | 1380 |
| aagtccctga gcctgtctcc aggcaag | 1407 |

<210> SEQ ID NO 215
<211> LENGTH: 1407
<212> TYPE: DNA
<213> ORGANISM: artificial
<220> FEATURE:
<223> OTHER INFORMATION: 102E9-MB7-VHhb-CH

<400> SEQUENCE: 215

| | |
|---|---|
| atgaggtggt cctggatctt cctgctgctg ctgagcatca ccagcgccaa cgcccagatc | 60 |
| catctggtgc agagcggccc tgagctgaag aaaccggcg agagcgtgaa gatcagctgc | 120 |
| aaggccagcg gctacacctt caccgactac agcatgcact gggtccgaca ggcccctgga | 180 |
| cagggcctga gtggatgggc tggatcaac accgagacag gcgagcccac ctacgcccag | 240 |
| gacttcaagg gcagattcgt gttcagcctg gacaccagcg tgtccaccgc ctacctgcag | 300 |
| atcaacagcc tgaagaacga ggacacctcc acctactact gcaccggaa cggctactac | 360 |
| gtggggtact acgccatgga ctactgggc cagggcacct ccgtgaccgt gtcatctgcc | 420 |
| tccaccaagg gcccatccgt gttccccctg gccccatcca gcaagtctac ctccggaggc | 480 |
| acagccgccc tgggctgtct ggtgaaggac tacttccccg agccagtgac cgtgtcctgg | 540 |
| aactccggag ccctgacatc cggcgtgcac accttcccg ccgtgctgca gtccagcggc | 600 |
| ctgtactctc tgtcttccgt ggtgaccgtg ccatccagct ccctgggaac ccagacatac | 660 |
| atctgcaacg tgaaccacaa gcctagcaac accaaggtgg acaagaaggt ggagcctaag | 720 |
| agctgtgaca agacacacac atgccctcct tgtccagccc ctgagctgct gggcggcccc | 780 |
| tccgtgttcc tgttccccccc caagcctaag gatacccctga tgatcagcag aaccccgag | 840 |
| gtgacctgcg tggtggtgga cgtgtcccac gaggatcccg aggtgaagtt caactggtac | 900 |
| gtggacggcg tggaggtgca caacgctaag accaagccca gagaggagca gtacaacagc | 960 |
| acatacagag tggtgtctgt gctgaccgtg ctgcaccagg actggctgaa cgggaaggag | 1020 |
| tacaagtgca aggtgtccaa caaggccctg cctgcccta tcgagaagac catctctaag | 1080 |
| gctaagggc agccccggga gccacaggtg tacaccctgc acccagccg cgacgagctg | 1140 |
| accaagaacc aggtgtccct gacatgcctg gtgaagggat tctacccag cgacatcgcc | 1200 |
| gtggagtggg agagcaacgg ccagcccgag aacaactaca agacaacccc tcccgtgctg | 1260 |
| gacagcgatg gatccttctt cctgtactcc aagctgaccg tggacaagag caggtggcag | 1320 |
| cagggaaacg tgttctcttg ttccgtgatg cacgaggctc tgcacaacca ctacacccag | 1380 |
| aagtccctga gcctgtctcc aggcaag | 1407 |

<210> SEQ ID NO 216
<211> LENGTH: 1407
<212> TYPE: DNA
<213> ORGANISM: artificial
<220> FEATURE:
<223> OTHER INFORMATION: 102E9-MB7-VHhc-CH

<400> SEQUENCE: 216

| | |
|---|---|
| atgaggtggt cctggatctt cctgctgctg ctgagcatca ccagcgccaa cgcccagatc | 60 |
| catctggtgc agagcggcag cgagctgaag aaaccggcg agagcgtgaa gatcagctgc | 120 |
| aaggccagcg gctacacctt caccgactac agcatgcact gggtccgaca ggcccctgga | 180 |
| cagggcctga gtggatgggc tggatcaac accgagacag gcgagcccac ctacgcccag | 240 |

```
gacttcaagg gcagattcgt gttcagcctg gacaccagcg tgtccaccgc ctacctgcag    300
atcaacagcc tgaagaacga ggacacctcc acctactact gcacccggaa cggctactac    360
gtggggtact acgccatgga ctactggggc cagggcacct ccgtgaccgt gtcatctgcc    420
tccaccaagg gcccatccgt gttccccctg gccccatcca gcaagtctac ctccggaggc    480
acagccgccc tgggctgtct ggtgaaggac tacttccccg agccagtgac cgtgtcctgg    540
aactccggag ccctgacatc cggcgtgcac accttccccg ccgtgctgca gtccagcggc    600
ctgtactctc tgtcttccgt ggtgaccgtg ccatccagct ccctgggaac ccagacatac    660
atctgcaacg tgaaccacaa gcctagcaac accaaggtgg acaagaaggt ggagcctaag    720
agctgtgaca gacacacac atgccctcct tgtccagccc ctgagctgct gggcggcccc    780
tccgtgttcc tgttcccccc caagcctaag gataccctga tgatcagcag aaccccccgag    840 gtgacctgcg tggtggtgga cgtgtcccac gaggatcccg aggtgaagtt caactggtac    900
gtggacggcg tggaggtgca caacgctaag accaagccca gagaggagca gtacaacagc    960
acatacagag tggtgtctgt gctgaccgtg ctgcaccagg actggctgaa cgggaaggag    1020
tacaagtgca aggtgtccaa caaggccctg cctgccccta cgagaagac catctctaag    1080 gctaaggggc agccccggga gccacaggtg tacaccctgc acccagccg cgacgagctg    1140 accaagaacc aggtgtccct gacatgcctg gtgaagggat tctacccag cgacatcgcc    1200 gtggagtggg agagcaacgg ccagcccgag aacaactaca agacaacccc tcccgtgctg    1260
gacagcgatg gatccttctt cctgtactcc aagctgaccg tggacaagag caggtggcag    1320
cagggaaacg tgttctcttg ttccgtgatg cacgaggctc tgcacaacca ctacacccag    1380
aagtccctga gcctgtctcc aggcaag                                         1407

<210> SEQ ID NO 217
<211> LENGTH: 693
<212> TYPE: DNA
<213> ORGANISM: artificial
<220> FEATURE:
<223> OTHER INFORMATION: 102E9-MB7-VKha-CL

<400> SEQUENCE: 217
atgaggtggt cctggatctt cctgctgctg ctgagcatca ccagcgccaa cgcccagatc     60
cagctgaccc agagccctag cttcctgagc gcctctcctg gcgagagagt gaccatcacc    120
tgtagcgcca gcagctccgt gatctacatc cactggttcc agcagaagcc cggcaaggcc    180
cctaagctgt ggatctacag caccagctac tggccagcg gcgtgccaag cagattcagc    240
ggctctggct ctggcaccga gtacaccctg accatcagct ccatggaagc cgaggacttc    300
gccacctact actgccagca gaggcggagc taccccttca ccttcggcgg aggcaccaag    360
ctggaaatca agcgaactgt ggctgcacca agtgtcttca tctttcctcc gagtgatgag    420
cagctgaaga gcgggacagc ttctgtggtg tgtctgctga ataacttcta cccaagagaa    480
gcaaaggtcc agtggaaggt ggacaacgcc ctgcagtctg gcaactcaca ggagtctgtc    540
actgagcagg attccaagga cagcacttac agcctgtcca gcaccctcac tctgtccaaa    600
gccgactacg aaaagcataa ggtgtatgct tgtgaggtga cccaccaggg actgagcagc    660
cctgtgacga agtccttcaa ccggggcgag tgc                                  693

<210> SEQ ID NO 218
<211> LENGTH: 693
<212> TYPE: DNA
```

<213> ORGANISM: artificial
<220> FEATURE:
<223> OTHER INFORMATION: 102E9-MB7-VKhb-CL

<400> SEQUENCE: 218

```
atgaggtggt cctggatctt cctgctgctg ctgagcatca ccagcgccaa cgcccagatc      60
cagctgaccc agagccctag cttcctgagc gcctctcctg gcgagagagt gaccatcacc     120
tgtagcgcca gcagctccgt gatctacatc cactggttcc agcagaagcc cggcaccgcc     180
cctaagctgt ggatctacag caccagctac ctggccagcg gcgtgccaag cagattcagc     240
ggctctggca gcggcaccct ctacaccctg accatcagca ggatggaagc cgaggacttc     300
gccacctact actgccagca gaggcggagc taccccttca ccttcggcgg aggcaccaag     360
ctggaaatca gcgaactgt ggctgcacca agtgtcttca tctttcctcc gagtgatgag      420
cagctgaaga gcggacagc ttctgtggtg tgtctgctga ataacttcta cccaagagaa      480
gcaaggtcc agtggaaggt ggacaacgcc ctgcagtctg gaactcaca ggagtctgtc       540
actgagcagg attccaagga cagcacttac agcctgtcca gcaccctcac tctgtccaaa     600
gccgactacg aaaagcataa ggtgtatgct tgtgaggtga cccaccaggg actgagcagc     660
cctgtgacga agtccttcaa ccggggcgag tgc                                  693
```

<210> SEQ ID NO 219
<211> LENGTH: 693
<212> TYPE: DNA
<213> ORGANISM: artificial
<220> FEATURE:
<223> OTHER INFORMATION: 102E9-MB7-VKhc-CL

<400> SEQUENCE: 219

```
atgaggtggt cctggatctt cctgctgctg ctgagcatca ccagcgccaa cgcccagatc      60
cagctgaccc agagccctag cttcctgagc gcctctcctg gcgacagagt gaccatcacc     120
tgtagcgcca gcagctccgt gatctacatc cactggttcc agcagaagcc cggcaaggcc    180
cctaagctgt ggatctacag caccagctac ctggccagcg gcgtgccaag cagattcagc     240
ggctctggct ctggcaccga gtacaccctg accatcagct ccatgcaggc cgaggacttc     300
gccacctact actgccagca gaggcggagc taccccttca ccttcggcgg aggcaccaag     360
ctggaaatca gcgaactgt ggctgcacca agtgtcttca tctttcctcc gagtgatgag      420
cagctgaaga gcggacagc ttctgtggtg tgtctgctga ataacttcta cccaagagaa      480
gcaaggtcc agtggaaggt ggacaacgcc ctgcagtctg gaactcaca ggagtctgtc       540
actgagcagg attccaagga cagcacttac agcctgtcca gcaccctcac tctgtccaaa     600
gccgactacg aaaagcataa ggtgtatgct tgtgaggtga cccaccaggg actgagcagc     660
cctgtgacga agtccttcaa ccggggcgag tgc                                  693
```

<210> SEQ ID NO 220
<211> LENGTH: 306
<212> TYPE: DNA
<213> ORGANISM: artificial
<220> FEATURE:
<223> OTHER INFORMATION: enhancer du virus hCMVe

<400> SEQUENCE: 220

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
```

| | |
|---|---|
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatgg | 306 |

<210> SEQ ID NO 221
<211> LENGTH: 352
<212> TYPE: DNA
<213> ORGANISM: artificial
<220> FEATURE:
<223> OTHER INFORMATION: region promotrice de la cycline dependante des kinases 9 (CDK9)

<400> SEQUENCE: 221

| | |
|---|---|
| catgcagcgg gacgcgccac cccgagcccc agctccggcg ccccggctcc ccgcgccccc | 60 |
| gatcggggcc gccgctagta gtggcggcgg cggaggcggg ggcagcggcg gcggcggcgg | 120 |
| aggcgcctct gcagctccgg ctcccccTgg cctctcggga actacaagtc ccaggggggcc | 180 |
| tggcggtggg cggcgggcgg aagaggcggg gtcggcgccg cgaggccgga agtggccgtg | 240 |
| gaggcggaag tggcgcggcc gcggaggggc ctggagtgcg gcggcggcgg gacccggagc | 300 |
| aggagcggcg gcagcagcga ctgggggcgg cggcggcgcg ttggaggcgg cc | 352 |

<210> SEQ ID NO 222
<211> LENGTH: 267
<212> TYPE: DNA
<213> ORGANISM: artificial
<220> FEATURE:
<223> OTHER INFORMATION: region LTR du virus HTLV-1

<400> SEQUENCE: 222

| | |
|---|---|
| ggctcgcatc tctccttcac gcgcccgccg ccctacctga ggccgccatc cacgccggtt | 60 |
| gagtcgcgtt ctgccgcctc ccgcctgtgg tgcctcctga actgcgtccg ccgtctaggt | 120 |
| aagtttaaag ctcaggtcga gaccgggcct tgtccggcg ctcccttgga gcctacctag | 180 |
| actcagccgg ctctccacgc tttgcctgac cctgcttgct caactctacg tctttgtttc | 240 |
| gttttctgtt ctgcgccgtt acagatc | 267 |

<210> SEQ ID NO 223
<211> LENGTH: 653
<212> TYPE: DNA
<213> ORGANISM: artificial
<220> FEATURE:
<223> OTHER INFORMATION: region 5' UTR du gene NRF

<400> SEQUENCE: 223

| | |
|---|---|
| cagagtaatg acatggttcc ttccatcctc caaaggtgac caataatagt ttgtaagtat | 60 |
| cattatgaac taatgaattt tcaacatatt tgatatattt caatccattg ccatcattgt | 120 |
| tcttatcgat atttgagttg gctcactttg ccagtaagag tctattcaaa ttggcttctg | 180 |
| agtccatttg acacaacacc tttgatcttt gacagtttcc ttggttttag gtgctagatg | 240 |
| atttctcagg ctcaccttag acatttcctg ccacagactt agaatcagcc atttctctaa | 300 |
| ggaccctgat tccatttcat gagaaatgat agagaccaca atcaaaacaa gtcatgaatt | 360 |
| tatactgata ttttcaattc aaattaaaga tgaggttttt gctaaatttt tttgagttta | 420 |
| tatttgtatg tcttatgctg aaaaatcttg tttcctaatt agtaacataa ttattcattt | 480 |
| gatgggtaaa tattttaggg ccgattcttt ggttttatag ccaagatacc ctgttgataa | 540 |
| agtcttgtgg gagcaattat aagactggct tattttgaag cttttttaaaa aagacatcct | 600 |

| | |
|---|---|
| tacctgtttt aactgtagat tatattaact taaataggta cagcccacgc ttg | 653 |

<210> SEQ ID NO 224
<211> LENGTH: 314
<212> TYPE: DNA
<213> ORGANISM: artificial
<220> FEATURE:
<223> OTHER INFORMATION: region 5' UTR du gene eIF4GI

<400> SEQUENCE: 224

| | |
|---|---|
| gctggtgggt agggatgagg gagggagggg cattgtgatg tacagggctg ctctgtgaga | 60 |
| tcaagggtct cttaagggtg ggagctgggg cagggactac gagagcagcc agatgggctg | 120 |
| aaagtggaac tcaaggggtt tctggcacct acctacctgc ttcccgctgg ggggtgggga | 180 |
| gttggcccag agtcttaaga ttggggcagg gtggagaggg gggctcttcc tgcttcccac | 240 |
| tcatcttata gctttctttc cccagatccg aattcgagat ccaaaccaag gaggaaagga | 300 |
| tatcacagag gaga | 314 |

<210> SEQ ID NO 225
<211> LENGTH: 939
<212> TYPE: DNA
<213> ORGANISM: artificial
<220> FEATURE:
<223> OTHER INFORMATION: intron du gene EF1a

<400> SEQUENCE: 225

| | |
|---|---|
| gtaagtgccg tgtgtggttc ccgcgggcct ggcctcttta cgggttatgg cccttgcgtg | 60 |
| ccttgaatta cttccacctg gctgcagtac gtgattcttg atcccgagct tcgggttgga | 120 |
| agtgggtggg agagttcgag gccttgcgct taaggagccc cttcgcctcg tgcttgagtt | 180 |
| gaggcctggc ctgggcgctg gggccgccgc gtgcgaatct ggtggcacct tcgcgcctgt | 240 |
| ctcgctgctt tcgataagtc tctagccatt taaaatttt gatgacctgc tgcgacgctt | 300 |
| ttttttctggc aagatagtct tgtaaatgcg ggccaagatc tgcacactgg tatttcggtt | 360 |
| tttgggcccg cggcggcga cggggcccgt gcgtcccagc gcacatgttc ggcgaggcgg | 420 |
| ggcctgcgag cgcggccacc gagaatcgga cgggggtagt ctcaagctgg ccggcctgct | 480 |
| ctggtgcctg gcctcgcgcc gccgtgtatc gccccgccct gggcggcaag gctggcccgg | 540 |
| tcggcaccag ttgcgtgagc ggaaagatgg ccgcttcccg gccctgctgc agggagctca | 600 |
| aaatggagga cgcggcgctc gggagagcgg gcgggtgagt cacccacaca aaggaaaagg | 660 |
| gcctttccgt cctcagccgt cgcttcatgt gactccacgg agtaccgggc gccgtccagg | 720 |
| cacctcgatt agttctcgag cttttggagt acgtcgtctt taggttgggg ggagggtttt | 780 |
| tatgcgatgg agtttcccca cactgagtgg gtggagactg aagttaggcc agcttggcac | 840 |
| ttgatgtaat tctccttgga atttgccctt tttgagtttg gatcttggtt cattctcaag | 900 |
| cctcagacag tggttcaaag ttttttttctt ccatttcag | 939 |

<210> SEQ ID NO 226
<211> LENGTH: 351
<212> TYPE: DNA
<213> ORGANISM: artificial
<220> FEATURE:
<223> OTHER INFORMATION: intron murin ROSA

<400> SEQUENCE: 226

| | |
|---|---|
| gtaggggatc gggactctgg cgggagggcg gcttggtgcg tttgcgggga tgggcggccg | 60 |

```
cggcaggccc tccgagcgtg gtggagccgt tctgtgagac agccgggtac gagtcgtgac    120
gctggaaggg gcaagcgggt ggtgggcagg aatgcggtcc gccctgcagc aaccggaggg    180
ggagggagaa gggagcggaa aagtctccac cggacgcggc catggctcgg ggggggggg     240 gcagcggagg agcgcttccg gccgacgtct cgtcgctgat tggcttcttt tcctcccgcc    300
gtgtgtgaaa acacaattgt actaaccttc ttctctttcc tctcctgaca g             351

<210> SEQ ID NO 227
<211> LENGTH: 288
<212> TYPE: DNA
<213> ORGANISM: artificial
<220> FEATURE:
<223> OTHER INFORMATION: intron 5'LTR du virus HTLV-1

<400> SEQUENCE: 227
ggctcgcatc tctccttcac gcgcccgccg ccctacctga ggccgccatc cacgccggtt     60
gagtcgcgtt ctgccgcctc ccgcctgtgg tgcctcctga actgcgtccg ccgtctaggt    120
aagtttaaag ctcaggtcga gaccgggcct ttgtccggcg ctcccttgga gcctacctag    180
actcagccgg ctctccacgc tttgcctgac cctgcttgct caactctacg tctttgtttc    240
gttttctgtt ctgcgccgtt acagatccaa gctgtgaccg gcgcctac                 288

<210> SEQ ID NO 228
<211> LENGTH: 133
<212> TYPE: DNA
<213> ORGANISM: artificial
<220> FEATURE:
<223> OTHER INFORMATION: intron pcineo

<400> SEQUENCE: 228
gtaagtatca aggttacaag acaggtttaa ggagaccaat agaaactggg cttgtcgaga     60
cagagaagac tcttgcgttt ctgataggca cctattggtc ttactgacat ccactttgcc    120
tttctctcca cag                                                      133

<210> SEQ ID NO 229
<211> LENGTH: 812
<212> TYPE: DNA
<213> ORGANISM: artificial
<220> FEATURE:
<223> OTHER INFORMATION: intron du gene ubiquitine

<400> SEQUENCE: 229
gtgagtagcg ggctgctggg ctggccgggg ctttcgtggc cgccgggccg ctcggtggga     60
cggaagcgtg tggagagacc gccaagggct gtagtctggg tccgcgagca aggttgccct    120
gaactggggg ttggggggag cgcagcaaaa tggcggctgt tcccgagtct tgaatggaag    180
acgcttgtga ggcgggctgt gaggtcgttg aaacaaggtg gggggcatgg tgggcggcaa    240
gaacccaagg tcttgaggcc ttcgctaatg cgggaaagct cttattcggg tgagatgggc    300
tggggcacca tctgggacc ctgacgtgaa gtttgtcact gactgagaa ctcggtttgt      360 cgtctgttgc gggggcggca gttatggcgg tgccgttggg cagtgcaccc gtacctttgg    420
gagcgcgcgc cctcgtcgtg tcgtgacgtc acccgttctg ttggcttata atgcagggtg    480
gggccacctg ccggtaggtg tgcggtaggc ttttctccgt cgcaggacgc agggttcggg    540
cctagggtag gctctcctga atcgacaggc gccggacctc tggtgagggg agggataagt    600
gaggcgtcag tttctttggt cggttttatg tacctatctt cttaagtagc tgaagctccg    660
gttttgaact atgcgctcgg ggttggcgag tgtgttttgt gaagttttt aggcacctttt     720
```

| | |
|---|---|
| tgaaatgtaa tcatttgggt caatatgtaa ttttcagtgt tagactagta aattgtccgc | 780 |
| taaattctgg ccgtttttgg cttttttgtt ag | 812 |

<210> SEQ ID NO 230
<211> LENGTH: 1217
<212> TYPE: DNA
<213> ORGANISM: artificial
<220> FEATURE:
<223> OTHER INFORMATION: intron humain ROSA

<400> SEQUENCE: 230

| | |
|---|---|
| gtaggggagc ggaactctgg tgggagggga ggtgcggtgc actgggggga tgggtggcta | 60 |
| ggggggccgt ctggtggctt gcggggggttg cctttcccgt gggaagtcgg gaacataatg | 120 |
| tttgttacgt tgggagggaa aggggtggct ggatgcaggc ggggagggagg cccgccctgc | 180 |
| ggcaaccgga gggggaggga aagggagcg gaaaatgctc gaaaccggac ggagccattg | 240 |
| ctctcgcaga ggggaggagcg cttccggcta gcctcttgtc gccgattggc cgtttctcct | 300 |
| cccgccgtgt gtgaaaacac aaatggcgta ttctggttgg agtaaagctc ctgtcagtta | 360 |
| caccgtcggg agtacgcagc cgcttagcga ctctcgcgtt gccccctggg tggggcgggt | 420 |
| aggtaggtgg ggtgtagaga tgctgggtgt gcgggcgcgg ccggcctcct gcggcgggag | 480 |
| gggagggtca gtgaaattgg ctctggcgcg ggcgtcctcc caccctcccc ttccttcggg | 540 |
| ggagtcggtt tacccgccgc ctgcttgtct tcgacacctg attggctgtc gaagctgtgg | 600 |
| gaccgggccc ttgctactgg ctcgagtctc acatgagcga aaccactgcg cggggcgcgg | 660 |
| gggtggcggg gaggcgggcg ttggtacggt cctccccgag gccgagcgcc gcagtgtctg | 720 |
| gccccgcgcc cctgcgcaac gtggcaggaa gcgcgcgctg gaggcggggg cgggctgccg | 780 |
| gccgagactt ctggatggcg gcggccgcgg ctccgccccg ggttcccacc gcctgaaggg | 840 |
| cgagacaagc ccgacctgct acaggcactc gtggggggtgg gggaggagcg ggggtcggtc | 900 |
| cggctggttt gtgggtggga ggcgcttgtt ctccaaaaac cggcgcgagc tgcaatcctg | 960 |
| agggagctgc ggtggaggag gtggagagaa ggccgcaccc ttctgggcag ggggagggga | 1020 |
| gtgccgcaat acctttatgg gagttctttg ctgcctcccg tcttgtaagg accgccctgg | 1080 |
| gcctggaaga agccctccct cctttcctcc tcgcgtgatc tcgtcatcgc ctccatgtcg | 1140 |
| agtcgcttct cgattatggg cgggattctt ttgcctagac aattgtacta accttcttct | 1200 |
| ctttcctctc ctgacag | 1217 |

<210> SEQ ID NO 231
<211> LENGTH: 1964
<212> TYPE: DNA
<213> ORGANISM: artificial
<220> FEATURE:
<223> OTHER INFORMATION: sequence unite transcription

<400> SEQUENCE: 231

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccag ctccggcgcc | 360 |

```
ccggctcccc gcgccccga tcggggccgc cgctagtagt ggcggcggcg gaggcggggg    420
cagcggcggc ggcggcggag gcgcctctgc agctccggct ccccctggcc tctcgggaac    480
tacaagtccc aggggccctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt    660
ggaggcggcc ggatccgttt aacgctggtg ggtagggatg agggagggag gggcattgtg    720
atgtacaggg ctgctctgtg agatcaaggg tctcttaagg gtgggagctg gggcagggac    780
tacgagagca gccagatggg ctgaaagtgg aactcaaggg gtttctggca cctacctacc    840
tgcttcccgc tgggggtgg ggagttggcc cagagtctta agattgggc agggtggaga    900
ggtgggctct tcctgcttcc cactcatctt atagctttct ttccccagat ccgaattcga    960
gatccaaacc aaggaggaaa ggatatcaca gaggagagct agtcgggttt gccgccagaa   1020
cacaggtaag tgccgtgtgt ggttcccgcg ggcctggcct cttttacgggt tatggccctt   1080
gcgtgccttg aattacttcc acctggctgc agtacgtgat tcttgatccc gagcttcggg   1140
ttggaagtgg gtgggagagt tcgaggcctt gcgcttaagg agccccttcg cctcgtgctt   1200
gagttgaggc ctggcctggg cgctggggcc gccgcgtgcg aatctggtgg caccttcgcg   1260
cctgtctcgc tgcttttcgat aagtctctag ccatttaaaa ttttgatga cctgctgcga   1320
cgcttttttt ctggcaagat agtcttgtaa atgcgggcca agatctgcac actggtattt   1380
cggttttttgg ggccgcgggc ggcgacgggg cccgtgcgtc ccagcgcaca tgttcggcga   1440
ggcggggcct gcgagcgcgg ccaccgagaa tcggacgggg gtagtctcaa gctggccggc   1500
ctgctctggt gcctggcctc gcgccgccgt gtatcgcccc gccctgggcg gcaaggctgg   1560
cccggtcggc accagttgcg tgagcggaaa gatggccgct tcccggccct gctgcaggga   1620
gctcaaaatg gaggacgcgg cgctcgggag agcgggcggg tgagtcaccc acacaaagga   1680
aaagggcctt tccgtcctca gccgtcgctt catgtgactc cacggagtac cgggcgccgt   1740
ccaggcacct cgattagttc tcgagctttt ggagtacgtc gtctttaggt tgggggagg   1800
ggttttatgc gatggagttt ccccacactg agtgggtgga gactgaagtt aggccagctt   1860
ggcacttgat gtaattctcc ttggaatttg cccttttga gtttggatct tggttcattc   1920
tcaagcctca gacagtggtt caaagttttt ttcttccatt tcag                    1964
```

<210> SEQ ID NO 232
<211> LENGTH: 306
<212> TYPE: DNA
<213> ORGANISM: artificial
<220> FEATURE:
<223> OTHER INFORMATION: enhancer du virus hCMVie

<400> SEQUENCE: 232

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatgg                                                               306
```

<210> SEQ ID NO 233
<211> LENGTH: 283

```
<212> TYPE: DNA
<213> ORGANISM: artificial
<220> FEATURE:
<223> OTHER INFORMATION: region promotrice de la beta-actine

<400> SEQUENCE: 233
catggtcgag gtgagcccca cgttctgctt cactctcccc atctcccccc cctcccacc      60 cccaattttg tatttattta ttttttaatt attttgtgca gcgatggggg cggggggggg    120
gggggggcgc gcgccaggcg gggcggggcg gggcgagggg cggggcgggg cgaggcggag    180
aggtgcggcg gcagccaatc agagcggcgc gctccgaaag tttccttttta tggcgaggcg    240 gcggcggcgg cggccctata aaaagcgaag cgcgcggcgg gcg                       283

<210> SEQ ID NO 234
<211> LENGTH: 267
<212> TYPE: DNA
<213> ORGANISM: artificial
<220> FEATURE:
<223> OTHER INFORMATION: region regulatrice R du 5' Long Terminal Repeat
      (LTR) du virus HTLV-1

<400> SEQUENCE: 234
ggctcgcatc tctccttcac gcgcccgccg ccctacctga ggccgccatc cacgccggtt     60
gagtcgcgtt ctgccgcctc ccgcctgtgg tgcctcctga actgcgtccg ccgtctaggt   120
aagtttaaag ctcaggtcga gaccgggcct tgtccggcg ctcccttgga gcctacctag    180
actcagccgg ctctccacgc tttgcctgac cctgcttgct caactctacg tctttgtttc   240
gttttctgtt ctgcgccgtt acagatc                                        267

<210> SEQ ID NO 235
<211> LENGTH: 653
<212> TYPE: DNA
<213> ORGANISM: artificial
<220> FEATURE:
<223> OTHER INFORMATION: region 5' UTR du gene NRF

<400> SEQUENCE: 235
cagagtaatg acatggttcc ttccatcctc caaaggtgac caataatagt ttgtaagtat    60
cattatgaac taatgaattt tcaacatatt tgatatattt caatccattg ccatcattgt   120
tcttatcgat atttgagttg gctcactttg ccagtaagag tctattcaaa ttggcttctg   180
agtccatttg acacaacacc tttgatctttt gacagtttcc ttggttttag gtgctagatg   240
atttctcagg ctcaccttag acatttcctg ccacagactt agaatcagcc atttctctaa    300
ggaccctgat tccatttcat gagaaatgat agagaccaca atcaaaacaa gtcatgaatt    360
tatactgata ttttcaattc aaattaaaga tgaggttttt gctaaatttt tttgagttta    420
tatttgtatg tcttatgctg aaaaatcttg tttcctaatt agtaacataa ttattcattt    480
gatgggtaaa tatttagggt ccgattcttt ggttttatag ccaagatacc ctgttgataa    540
agtcttgtgg gagcaattat aagactggct tattttgaag ctttttaaaa aagcatcct    600 tacctgttttt aactgtagat tatattaact taaataggta cagcccacgc ttg          653

<210> SEQ ID NO 236
<211> LENGTH: 314
<212> TYPE: DNA
<213> ORGANISM: artificial
<220> FEATURE:
<223> OTHER INFORMATION: region 5' UTR du gene eIF4GI

<400> SEQUENCE: 236
```

```
gctggtgggt agggatgagg gagggagggg cattgtgatg tacagggctg ctctgtgaga      60
tcaagggtct cttaagggtg ggagctgggg cagggactac gagagcagcc agatgggctg     120
aaagtggaac tcaagggtt tctggcacct acctacctgc ttcccgctgg ggggtgggga     180
gttggcccag agtcttaaga ttggggcagg gtggagaggg gggctcttcc tgcttcccac     240
tcatcttata gctttctttc cccagatccg aattcgagat ccaaaccaag gaggaaagga     300
tatcacagag gaga                                                        314

<210> SEQ ID NO 237
<211> LENGTH: 939
<212> TYPE: DNA
<213> ORGANISM: artificial
<220> FEATURE:
<223> OTHER INFORMATION: intron du gene Elongation Factor 1a (EF1a)

<400> SEQUENCE: 237
gtaagtgccg tgtgtggttc ccgcgggcct ggcctcttta cgggttatgg cccttgcgtg      60
ccttgaatta cttccacctg ctgcagtac gtgattcttg atcccgagct tcgggttgga     120
agtgggtggg agagttcgag gccttgcgct taaggagccc cttcgcctcg tgcttgagtt     180
gaggcctggc ctgggcgctg gggccgccgc gtgcgaatct ggtggcacct tcgcgcctgt     240
ctcgctgctt tcgataagtc tctagccatt taaaattttt gatgacctgc tgcgacgctt     300 ttttttctggc aagatagtct tgtaaatgcg ggccaagatc tgcacactgg tatttcggtt     360
tttggggccg cggcggcga cggggcccgt gcgtcccagc gcacatgttc ggcgaggcgg     420
ggcctgcgag cgcggccacc gagaatcgga cgggggtagt ctcaagctgg ccggcctgct     480
ctggtgcctg gcctcgcgcc gccgtgtatc gccccgccct gggcggcaag gctggcccgg     540
tcggcaccag ttgcgtgagc ggaaagatgg ccgcttcccg gccctgctgc agggagctca     600
aaatggagga cgcggcgctc gggagagcgg gcgggtgagt cacccacaca aggaaaagg     660 gcctttccgt cctcagccgt cgcttcatgt gactccacgg agtaccgggc gccgtccagg     720
cacctcgatt agttctcgag ctttttggagt acgtcgtctt taggttgggg ggaggggttt     780
tatgcgatgg agtttcccca cactgagtgg gtggagactg aagttaggcc agcttggcac     840
ttgatgtaat ctccttgga atttgccctt tttgagtttg gatcttggtt cattctcaag     900
cctcagacag tggttcaaag ttttttttctt ccatttcag                           939

<210> SEQ ID NO 238
<211> LENGTH: 351
<212> TYPE: DNA
<213> ORGANISM: artificial
<220> FEATURE:
<223> OTHER INFORMATION: intron murin ROSA

<400> SEQUENCE: 238 gtagggatc gggactctgg cgggagggcg gcttggtgcg tttgcgggga tgggcggccg      60
cggcaggccc tccgagcgtg gtggagccgt tctgtgagac agccgggtac gagtcgtgac     120
gctggaaggg gcaagcgggt ggtgggcagg aatgcggtcc gccctgcagc aaccggaggg     180
ggagggagaa gggagcggaa aagtctccac cggacgcggc catggctcgg ggggggggg     240 gcagcggagg agcgcttccg gccgacgtct cgtcgctgat tggcttcttt tcctcccgcc     300
gtgtgtgaaa acacaattgt actaaccttc ttctcttttcc tctcctgaca g             351

<210> SEQ ID NO 239
```

<211> LENGTH: 1217
<212> TYPE: DNA
<213> ORGANISM: artificial
<220> FEATURE:
<223> OTHER INFORMATION: intron humain ROSA

<400> SEQUENCE: 239

```
gtaggggagc ggaactctgg tgggagggga ggtgcggtgc actgggggga tgggtggcta      60
ggggggccgt ctggtggctt gcggggttg cctttcccgt gggaagtcgg gaacataatg     120
tttgttacgt tgggagggaa aggggtggct ggatgcaggc gggagggagg cccgccctgc     180
ggcaaccgga gggggaggga gaagggagcg gaaaatgctc gaaaccggac ggagccattg     240
ctctcgcaga gggaggagcg cttccggcta gcctcttgtc gccgattggc cgtttctcct     300
cccgccgtgt gtgaaaacac aaatggcgta ttctggttgg agtaaagctc ctgtcagtta     360
caccgtcggg agtacgcagc cgcttagcga ctctcgcgtt gccccctggg tggggcgggt     420
aggtaggtgg ggtgtagaga tgctgggtgt gcgggcgcgg ccggcctcct gcggcgggag     480
gggagggtca gtgaaattgg ctctggcgcg ggcgtcctcc caccctcccc ttccttcggg     540
ggagtcggtt tacccgccgc ctgcttgtct tcgacacctg attggctgtc gaagctgtgg     600
gacccgggccc ttgctactgg ctcgagtctc acatgagcga aaccactgcg cggggcgcgg     660
gggtggcggg gaggcgggcg ttggtacggt cctccccgag gccgagcgcc gcagtgtctg     720
gccccgcgcc cctgcgcaac gtggcaggaa gcgcgcgctg gaggcggggg cgggctgccg     780
gccgagactt ctggatggcg gcggccgcgg ctccgccccg ggttcccacc gcctgaaggg     840
cgagacaagc ccgacctgct acaggcactc gtggggtgg gggaggagcg ggggtcggtc     900
cggctggttt gtgggtggga ggcgcttgtt ctccaaaaac cggcgcgagc tgcaatcctg     960
agggagctgc ggtggaggag gtggagagaa ggccgcaccc ttctgggcag ggggaggggga    1020
gtgccgcaat acctttatgg gagttcttttg ctgcctcccg tcttgtaagg accgccctgg    1080
gcctggaaga agccctccct cctttcctcc tcgcgtgatc tcgtcatcgc ctccatgtcg    1140
agtcgcttct cgattatggg cgggattctt ttgcctagac aattgtacta accttcttct    1200
ctttcctctc ctgacag                                                    1217
```

<210> SEQ ID NO 240
<211> LENGTH: 1205
<212> TYPE: DNA
<213> ORGANISM: artificial
<220> FEATURE:
<223> OTHER INFORMATION: sequence unite transcription

<400> SEQUENCE: 240

```
gcgttacata acttacggta atggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tggtcgaggt gagcccacg ttctgcttca ctctcccccat     360
ctccccccccc tccccacccc caattttgta tttatttatt ttttaattat tttgtgcagc     420
gatggggggcg gggggggggg gggggcgcgc gccaggcggg gcggggcggg gcgaggggcg     480
gggcggggcg aggcggagag gtgcggcggc agccaatcag agcggcgcgc tccgaaagtt     540
tccttttatg gcgaggcggc ggcggcggcg gccctataaa aagcgaagcg cgcggcgggc     600
```

```
ggatccgttt aaacggctcg catctctcct tcacgcgccc gccgccctac ctgaggccgc    660
catccacgcc ggttgagtcg cgttctgccg cctcccgcct gtggtgcctc ctgaactgcg    720
tccgccgtct aggtaagttt aaagctcagg tcgagaccgg gcctttgtcc ggcgctccct    780
tggagcctac ctagactcag ccggctctcc acgctttgcc tgaccctgct tgctcaactc    840
tacgtctttg tttcgttttc tgttctgcgc cgttacagat cactagttaa cgctggtggg    900
tagggatgag ggagggaggg gcattgtgat gtacagggct gctctgtgag atcaagggtc    960
tcttaagggt gggagctggg gcagggacta cgagagcagc cagatgggct gaaagtggaa   1020
ctcaaggggt ttctggcacc tacctacctg cttcccgctg gggggtgggg agttggccca   1080
gagtcttaag attggggcag ggtggagagg tgggctcttc ctgcttccca ctcatcttat   1140
agctttcttt ccccagatcc gaattcgaga tccaaaccaa ggaggaaagg atatcacaga   1200
ggaga                                                               1205
```